US011708401B2

(12) United States Patent
Emtage et al.

(10) Patent No.: US 11,708,401 B2
(45) Date of Patent: Jul. 25, 2023

(54) CHIMERIC TRANSMEMBRANE PROTEINS AND USES THEREOF

(71) Applicant: Kite Pharma, Inc., Santa Monica, CA (US)

(72) Inventors: Peter Emtage, Lafayette, CA (US); Gabrielle Romain, Berkeley, CA (US); Rosa Vincent, New York, NY (US); Sarah Wyman, Oakland, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 978 days.

(21) Appl. No.: 16/449,089

(22) Filed: Jun. 21, 2019

(65) Prior Publication Data

US 2020/0002402 A1 Jan. 2, 2020

Related U.S. Application Data

(60) Provisional application No. 62/688,810, filed on Jun. 22, 2018.

(51) Int. Cl.

| | |
|---|---|
| ***C07K 14/715*** | (2006.01) |
| ***A61K 35/17*** | (2015.01) |
| ***C07K 14/705*** | (2006.01) |
| ***C07K 14/54*** | (2006.01) |
| ***C07K 14/725*** | (2006.01) |
| ***C07K 16/28*** | (2006.01) |
| ***C07K 16/30*** | (2006.01) |
| *A61K 38/00* | (2006.01) |

(52) U.S. Cl.

CPC .......... *C07K 14/7155* (2013.01); *A61K 35/17* (2013.01); *C07K 14/5443* (2013.01); *C07K 14/7051* (2013.01); *C07K 14/70517* (2013.01); *C07K 14/70521* (2013.01); *C07K 14/70578* (2013.01); *C07K 16/2803* (2013.01); *C07K 16/30* (2013.01); *A61K 38/00* (2013.01); *C07K 2317/522* (2013.01); *C07K 2317/524* (2013.01); *C07K 2317/526* (2013.01); *C07K 2317/53* (2013.01); *C07K 2317/56* (2013.01); *C07K 2319/02* (2013.01); *C07K 2319/03* (2013.01); *C07K 2319/30* (2013.01); *C07K 2319/33* (2013.01)

(58) Field of Classification Search

CPC ........................ C07K 14/7051; C07K 14/7155

See application file for complete search history.

(56) References Cited

U.S. PATENT DOCUMENTS

| | | | |
|---|---|---|---|
| 5,219,740 | A | 6/1993 | Miller et al. |
| 6,207,453 | B1 | 3/2001 | Maass et al. |
| 9,926,377 | B2 | 3/2018 | Polakis et al. |
| 2003/0125251 | A1 | 7/2003 | Wakefield et al. |
| 2012/0177595 | A1 | 7/2012 | Wong et al. |
| 2015/0359853 | A1 | 12/2015 | Felber et al. |
| 2016/0108123 | A1 | 4/2016 | Freeman et al. |
| 2018/0066057 | A1 | 3/2018 | Govindappa et al. |
| 2019/0151362 | A1 | 5/2019 | Li et al. |

FOREIGN PATENT DOCUMENTS

| | | | |
|---|---|---|---|
| CN | 105949324 | A | 9/2016 |
| JP | 2013-541335 | A | 11/2013 |
| JP | 2015-536935 | A | 12/2015 |
| JP | 2017-536099 | A | 12/2017 |
| WO | 9309228 | A1 | 5/1993 |
| WO | 9409815 | A1 | 5/1994 |
| WO | 03000883 | A1 | 1/2003 |
| WO | 04022597 | A1 | 3/2004 |
| WO | 11109789 | A2 | 9/2011 |
| WO | 12145469 | A1 | 10/2012 |
| WO | 13070468 | A1 | 5/2013 |
| WO | 13181543 | A1 | 12/2013 |
| WO | WO-2014/127261 | A1 | 8/2014 |
| WO | WO-2014/134165 | A1 | 9/2014 |
| WO | 14180306 | A1 | 11/2014 |
| WO | 15027082 | A1 | 2/2015 |
| WO | WO-2015/142675 | A2 | 9/2015 |
| WO | WO-2015/150526 | A2 | 10/2015 |
| WO | 16036973 | A1 | 3/2016 |
| WO | 16049459 | A1 | 3/2016 |
| WO | 16113203 | A1 | 7/2016 |
| WO | 16115482 | A1 | 7/2016 |
| WO | 18018958 | A1 | 2/2018 |
| WO | 2018044866 | A1 | 3/2018 |
| WO | WO-2018/038945 | A1 | 3/2018 |
| WO | 2018111763 | A1 | 6/2018 |
| WO | 18131586 | A1 | 7/2018 |
| WO | 18200586 | A1 | 11/2018 |
| WO | 18204594 | A1 | 11/2018 |
| WO | 19094482 | A1 | 5/2019 |
| WO | 2019109980 | A1 | 6/2019 |

OTHER PUBLICATIONS

Shum et al., Cancer Discov 7(11):1238-47 (Year: 2017).*

Office Action, issued in TW Application No. 108121854, dated Nov. 3, 2020.

Hurton et al., "Tethered IL-15 augments antitumor activity and promotes a stem-cell memory subset in tumor-specific T cells", Proc. Natl Acad Sci USA 113(48): E7788-E7797, (2016).

Shochat et al., "Novel activating mutations lacking cysteine in type I cytokine receptors in acute lymphoblastic leukemia", Blood, 124(1): 106-110, (2014).

Palmer et al., "Interleukin-7 receptor signaling network: an integrated systems perspective", Cell. Mol. Immunol. 5(2):79-89, 2008.

(Continued)

*Primary Examiner* — Jessica H Roark

(57) ABSTRACT

Provided herein are chimeric transmembrane proteins and proteins, nucleic acids encoding these chimeric transmembrane proteins or proteins, and mammalian cells containing these nucleic acids, and methods of making and using these mammalian cells.

20 Claims, 18 Drawing Sheets

Specification includes a Sequence Listing.

(56) References Cited

OTHER PUBLICATIONS

Fedorov et al., "PD-1- and CTLA-4-based inhibitory chimeric antigen receptors (iCARs) divert off-target immunotherapy responses", Sci Transl Med (2013) 5(215):215ra172.
Glienke et al., "Advantages and applications of CAR-expressing natural killer cells", Front Pharmacol (2015) 6:21.
Kakarla et al., "CAR T cells for solid tumors: armed and ready to go?", Cancer J (2014) 20(2):151-5.
Riddell et al., "Adoptive therapy with chimeric antigen receptor-modified T cells of defined subset composition," Cancer J (2014) 20(2):141-4.
Pegram et al., "CD28z CARS and armored CARS," Cancer J (2014) 20(2):127-33.
Cheadle et al., "CAR T cells: driving the road from the laboratory to the clinic", Immunol Rev (2014) 257(1):91-106.
Barrett et al., "Chimeric antigen receptor therapy for cancer", Annu Rev Med (2014) 65:333-47.
Sadelain et al., "The basic principles of chimeric antigen receptor design", Cancer Discov (2013) 3(4):388-98.
Cartellieri et al., "Chimeric antigen receptor-engineered T cells for immunotherapy of cancer" J Biomed Biotechnol (2010) 956304.
Kershaw et al., "Supernatural T cells: genetic modification of T cells for cancer therapy", Nature Reviews Immunol. 5(12):928-940, 2005.
Eshhar et al., "Specific activation and targeting of cytotoxic lymphocytes through chimeric single chains consisting of antibody-binding domains and the gamma or zeta subunits of the immunoglobulin and T-cell receptors" Proc. Natl. Acad. Sci. U.S.A. 90(2):720-724, 1993.
Chen et al., "Molecular mechanisms of T cell co-stimulation and co-inhibition", Nature Reviews Immunol. 13:227-242, 2013.
Sadelain et al., "The promise and potential pitfalls of chimeric antigen receptors.", Curr. Opin. Immunol. 21(2): 215-223, 2009.
Ranganathan, "Pinpointing the putative heparin/sialic acid-binding residues in the 'sushi' domain 7 of factor H: a molecular modeling study", Pac. Symp Biocomput. 20 2000:155-67.
Carlens et al., "Ex vivo T lymphocyte expansion for retroviral transduction", Exp. Hematol. 28(10):1137-1146, 2000.
Park et al., "Treating cancer with genetically engineered T cells", Trends Biotechnol. 29(11):550-557, 2011.
Alonso-Camino et al., "CARbodies: Human Antibodies Against Cell Surface Tumor Antigens Selected From Repertoires Displayed on T Cell Chimeric Antigen Receptors" Mol. Ther. Nucleic Acids 2:e93, 2013.
Miller et al., "Improved retroviral vectors for gene transfer and expression", BioTechniques 7:980-990, 1989.
Miller, "Retrovirus packaging cells" Human Gene Therapy 1:5-14, 25 1990.
Scarpa et al., "Characterization of recombinant helper retroviruses from Moloney-based vectors in ecotropic and amphotropic packaging cell lines." Virology 180:849-852, 1991.
Burns et al., "Vesicular stomatitis virus G glycoprotein pseudotyped retroviral vectors: concentration to very high titer and efficient gene transfer into mammalian and nonmammalian cells" Proc. Natl. Acad. Sci. U.S.A. 90:8033-8037, 1993.
Boris-Lawrie et al., "Recent Advances in Retrovirus Vector Technology", Cur. Opin. Genet. Develop. 3:102-109, 1993.
Wang et al., "Phenotypic and Functional Attributes of Lentivirus Modified CD19-specific Human CD8+ Central Memory T Cells Manufactured at Clinical Scale", J. Immunother. 35(9):689-701, 2003.
Cooper et al., "T-cell clones can be rendered specific for CD19: toward the selective augmentation of the graft-versus-B-lineage leukemia effect", Blood 101:1637-1644, 2003.
Verhoeyen et al., "Lentiviral vector gene transfer into human T cells", Methods Mol. Biol. 506:97-114, 2009.
Cavalieri et al., "Human T lymphocytes transduced by lentiviral vectors in the absence of TCR activation maintain an intact immune competence", Blood 30 102(2):497-505, 2003.
Gao et al., Clin Cancer Res. 20(24):6418-28 (2014).
Li et al., Hum Gene Ther. 28(5):437-48 (2017).
Wieser et al., Molecular and Cellular Biology 13(12): 7239-7247 (1993).
Bollard et al., Blood. 99(9):3179-3187 (2002).
Yu et al., "Development of GPC3-Specific Chimeric Antigen Receptor-Engineered Natural Killer Cells for the Treatment of Hepatocellular Carcinoma," Molecular Therapy, vol. 26, No. 2, (2017), pp. 366-378.
International Search Report, issued in PCT/US2020/070157, dated Jan. 18, 2021.
Shochat, C. et al. (2011) "Gain-of-function mutations in interleukin-7 receptor-$\alpha$ (IL7R) in childhood acute lymphoblastic leukemias" J Exp Med 208(5):901-908.
Office Action dated May 16, 2023 for Japanese Appl. No. 2020-570911.

* cited by examiner

IL7Rα TMD Mutatlons

Homodimerization of IL7Rα mutants induces phosphorylation of STAT5 through Tyrosine region and STAT3 through BOX1 motif pSTAT5 induced through T region of IL17Rα and through IL15/IL15Rα interaction with IL2RB and Yc SFFV
IL7Ra
T2A
GFP
EF1a
1928z

CHIMERIC TRANSMEMBRANE PROTEINS AND USES THEREOF

CROSS-REFERENCE TO RELATED APPLICATION

This application claims priority to U.S. Provisional Patent Application Ser. No. 62/688,810, filed on Jun. 22, 2018; the entire contents of which are herein incorporated by reference.

SEQUENCE LISTING

The instant application contains a Sequence Listing which has been submitted electronically in ASCII format and is hereby incorporated by reference in its entirety. Said ASCII copy, created on Jun. 21, 2019, is named CDL-700_PC-43159-0072001_SL.txt and is 175,261 bytes in size.

TECHNICAL FIELD

The present disclosure relates to the field of biotechnology, and more specifically, to chimeric transmembrane proteins and uses thereof.

BACKGROUND

Interleukin-7 (IL-7) receptor is expressed on the cell surface (either temporary or permanent) of various cell types, including naïve and memory T-cells. Upon binding to IL-7, the IL-7 receptor transduces a signal into the cell via activation of the Janus kinases—JAK1 and JAK3 (Palmer et al., *Cell. Mol. Immunol.* 5(2):79-89, 2008).

While many improvements have been made to generate a secondary proliferative signal in second generation chimeric antigen receptor (CAR) T-cells (through the inclusion of co-stimulatory signaling domains such as CD28 and 4-1 BB in chimeric antigen receptors), this signal remains antigen-dependent often does not have sufficient co-stimulatory activity in solid tumors that have low tumor associated antigen levels.

In another attempt to provide sufficient co-stimulatory activity in CAR T-cells, co-administration of cytokines belonging to the common gamma (γc) chain receptor family have been used. However, prolonged usage of recombinant, pro-proliferative cytokines, such as IL-2, is often associated with severe side effects, limiting the duration and dosage of administration. In view of the above, alternative, improved methods of providing a co-stimulatory signal to CAR T-cells are desired.

SUMMARY

The present disclosure is based, at least in part, on the discovery that a protein that includes a transmembrane domain of an alpha chain of interleukin-7 receptor that includes the sequence of PILLTISILSFFSVALLVILACVLW (SEQ ID NO: 1) with one or more (e.g., two, three, or four) of the following modifications: (i) alanine-leucine-leucine at amino acids positions 15 through 17 in SEQ ID NO: 1 has been replaced with glutamic acid-lysine-valine or glutamic acid-lysine-alanine; (ii) a to cysteine-proline-threonine has been inserted between amino acid positions 5 and 6 in SEQ ID NO: 1; and (iii) a proline-proline-cysteine-leucine has been inserted between amino acid positions 4 and 5 in SEQ ID NO: 1, demonstrates increased downstream signaling as compared to a corresponding protein that includes a wildtype transmembrane domain of an alpha chain of interleukin-7 receptor or a corresponding protein that includes the sequence of SEQ ID NO: 1. Representative modified transmembrane domains have a sequence of SEQ ID NO: 2, 4, 6 or 8.

The present disclosure is also based, at least in part, on the discovery that a chimeric transmembrane protein that includes an extracellular interleukin-15 domain; an extracellular sushi domain from an alpha chain of interleukin-15 receptor; and a transmembrane domain from an alpha chain of interleukin-7 receptor provide for antigen-independent co-stimulation of a chimeric antigen receptor (CAR) T-cell.

In view of this discovery, provided herein are chimeric transmembrane proteins that include an extracellular IL-15 domain, an extracellular sushi domain from an alpha chain of interleukin-15 receptor, and a transmembrane domain of an alpha chain of interleukin-7 receptor. Also provided are proteins that include a transmembrane domain of an alpha chain of interleukin-7 receptor that includes the sequence of PILLTISILSFFSVALLVILACVLW (SEQ ID NO: 1) with one or more (e.g., two, three, or four) of the following modifications: (i) alanine-leucine-leucine at amino acids positions 15 through 17 in SEQ ID NO: 1 has been replaced with glutamic acid-lysine-valine or glutamic acid-lysine-alanine (ii) a cysteine-proline-threonine has been inserted between amino acid positions 5 and 6 in SEQ ID NO: 1; and (iii) a proline-proline-cysteine-leucine has been inserted between amino acid positions 4 and 5 in SEQ ID NO: 1. Representative modified transmembrane domains have a sequence of SEQ ID NO: 2, 4, 6 or 8.

Also provided are nucleic acids encoding these chimeric transmembrane proteins or these proteins, vectors including any of these nucleic acids, and mammalian cells that include any of these nucleic acids or vectors. Also provided herein are methods of treating a cancer, methods of inducing cell death in a cancer cell (e.g., apoptosis and/or necrosis), and methods of decreasing the risk of developing a metastasis or an additional metastasis in a subject in need thereof that include administering any of the mammalian cells described herein to the subject.

In some embodiments, provided herein is a protein that includes a transmembrane domain of an alpha chain of interleukin-7 receptor, wherein the transmembrane domain includes the sequence of PILLTISILSFFSVALLVILACVLW (SEQ ID NO: 1) with one or more of the following modifications: (i) alanine-leucine-leucine at amino acids positions 15 through 17 in SEQ ID NO: 1 has been replaced with glutamic acid-lysine-valine or glutamic acid-lysine-alanine; (ii) a cysteine-proline-threonine has been inserted between amino acid positions 5 and 6 in SEQ ID NO: 1; and (iii) a proline-proline-cysteine-leucine has been inserted between amino acid positions 4 and 5 in SEQ ID NO: 1. Representative modified transmembrane domains have a sequence of SEQ ID NO: 2, 4, 6 or 8.

In some embodiments, the protein further includes an intracellular domain of an alpha chain of interleukin-7 receptor (e.g., a wildtype alpha chain of interleukin-7 receptor such as, without limitation, a wildtype human alpha chain of interleukin-7 receptor). In some embodiments, the protein further includes an intracellular domain that includes a sequence of SEQ ID NO: 45 or a sequence that is at least 80% identical to the sequence of an intracellular domain of a wildtype alpha chain of interleukin-7 receptor (e.g., a wildtype human alpha chain of interleukin-7 receptor, e.g., SEQ ID NO: 45). In some embodiments, the intracellular domain is at least 90% or 95% identical to SEQ ID NO: 45. In some embodiments, the protein further includes an intracellular domain of a wildtype alpha chain of interleukin-7 receptor having one or both of: (i) one to ten amino acids deleted from the N-terminus of the sequence of the intracellular domain of the wildtype alpha chain of interleukin-7 receptor (e.g., wildtype human alpha chain of interleukin-7 receptor, e.g., SEQ ID NO: 45) and (ii) one to ten amino acids deleted from the C-terminus of the sequence of the intracellular domain of the wildtype alpha chain of interleukin-7 receptor (e.g., wildtype human alpha chain of interleukin-7 receptor, e.g., SEQ ID NO: 45).

In some embodiments, the protein further includes an extracellular domain of an alpha chain of interleukin-7 receptor (e.g., a wildtype alpha chain of interleukin-7 receptor such as, without limitation, a wildtype human alpha chain of interleukin-7 receptor). In some embodiments, the protein further includes an extracellular domain that includes a sequence of SEQ ID NO: 11 or a sequence that is at least 80% identical to the sequence of an extracellular domain of a wildtype alpha chain of interleukin-7 receptor (e.g., a wildtype human alpha chain of interleukin-7 receptor, e.g., SEQ ID to NO: 11). In some embodiments, the extracellular domain is at least 90% or 95% identical to SEQ ID NO: 11. In some embodiments, the protein further includes an extracellular domain of a wildtype alpha chain of interleukin-7 receptor having one or both of: (i) one to ten amino acids deleted from the N-terminus of the sequence of the extracellular domain of the wildtype alpha chain of interleukin-7 receptor (e.g., wildtype human alpha chain of interleukin-7 receptor, e.g., SEQ ID NO: 11) and (ii) one to ten amino acids deleted from the C-terminus of the sequence of the extracellular domain of the wildtype alpha chain of interleukin-7 receptor (e.g., wildtype human alpha chain of interleukin-7 receptor, e.g., SEQ ID NO: 11).

Also provided herein are nucleic acids encoding any of the variety of proteins described herein. Also provided herein are vectors that include any of the nucleic acids encoding any of the variety of proteins described herein. In some embodiments, vectors that include any of the nucleic acids encoding any of the variety of proteins described herein include a promoter operably linked to the nucleic acid, and optionally, an enhancer sequence operably linked to the nucleic acid. In some embodiments, vectors that include any of the nucleic acids encoding any of the variety of proteins described herein include a poly(A) sequence operably linked to the nucleic acid. In some embodiments, vectors that include any of the nucleic acids encoding any of the variety of proteins described herein are lentiviral or adenoviral vectors.

In some embodiments, vectors that include any of the nucleic acids encoding any of the variety of proteins described herein include a sequence encoding a chimeric antigen receptor. In some embodiments, the chimeric antigen receptor binds specifically to a tumor antigen (e.g., a tumor antigen is selected from the group consisting of: glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin). In some embodiments, the chimeric antigen receptor comprises one or more co-stimulatory signaling domains selected from the group consisting of: 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, B7-H3, DAP-10, and DAP-12.

Also provided herein are mammalian cells that include any of the variety of nucleic acids encoding any of the variety of proteins described herein or vectors that include such nucleic acids described herein. In some embodiments, the mammalian cell is an immune cell. In some embodiments, the immune cell is selected from the group consisting of: a CD4+ T cell, a CD8+ T cell, a B cell, a monocyte, a natural killer cell, a dendritic cell, a macrophage, a regulatory T cell, and a helper T cell. In some embodiments, the mammalian cell was previously obtained from a subject or is a daughter cell of a mammalian cell that was previously obtained from the subject. In some embodiments, the mammalian cell is a human cell.

Also provided herein are pharmaceutical compositions that include any of the variety of vectors that include any of the nucleic acids encoding any of the variety of proteins described herein and a pharmaceutically acceptable carrier. Also provided herein are pharmaceutical compositions that include any of the variety of mammalian cells that include vectors that include any of the nucleic acids encoding any of the variety of proteins described herein.

Also provided herein are sets of vectors that include a first vector that includes any of the nucleic acids encoding any of the variety of proteins described herein, and a second vector that includes a sequence encoding a chimeric antigen receptor. In some embodiments of such sets of vectors, the chimeric antigen receptor binds specifically to a tumor antigen (e.g., a tumor antigen is selected from the group consisting of: glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin). In some embodiments of such sets of vectors, the chimeric antigen receptor comprises one or more co-stimulatory signaling domains selected from the group consisting of: 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, B7-H3, DAP-10, and DAP-12. In some embodiments of such sets of vectors, both of the first vector and the second vector is a lentiviral or adenoviral vector. In some embodiments of sets of vectors provided herein, the second vector further includes a promoter operably linked to the sequence encoding the chimeric antigen receptor, and optionally, an enhancer operably linked to the sequence encoding the chimeric antigen receptor. In some embodiments of such sets of vectors, the second vector further comprises a poly(A) sequence operably linked to the sequence encoding the chimeric antigen receptor.

Also provided herein are mammalian cells that include any of the variety of sets of vectors provided herein that include a first vector that includes any of the nucleic acids encoding any of the variety of proteins described herein, and a second vector that includes a sequence encoding a chimeric antigen receptor. In some embodiments, the mammalian cell is an immune cell. In some embodiments, the immune cell is selected from the group consisting of: a CD4+ T cell, a CD8+ T cell, a B cell, a monocyte, a natural killer cell, a dendritic cell, a macrophage, a regulatory T cell, and a helper T cell. In some embodiments, the mammalian cell was previously obtained from a subject or is a daughter cell of a mammalian cell that was previously obtained from the subject. In some embodiments, the mammalian cell is a human cell.

Also provided herein are pharmaceutical compositions that include any of the variety of sets of vectors provided herein (e.g., sets of vectors that include a first vector that includes any of the nucleic acids encoding any of the variety of proteins described herein, and a second vector that includes a sequence encoding a chimeric antigen receptor) and a pharmaceutically acceptable carrier. Also provided herein are pharmaceutical compositions that include any of the variety of mammalian cells that include such sets of vectors.

Also provided herein are chimeric transmembrane proteins that include: an extracellular interleukin-15 domain; an extracellular sushi domain from an alpha chain of interleukin-15 receptor; and a transmembrane domain from an alpha chain of interleukin-7 receptor. In some embodiments, the extracellular interleukin-15 domain includes a sequence of a wildtype interleukin-15 protein. In some embodiments, a wildtype interleukin-15 protein is a wildtype human interleukin-15 protein (e.g., a wildtype human interleukin-15 protein having a sequence of SEQ ID NO: 22 or SEQ ID NO: 24). In some embodiments, the extracellular interleukin-15 domain comprises a sequence that is at least 80% identical to the sequence of a wildtype interleukin-15 protein (e.g., a wildtype human interleukin-15 protein such as, without limitation, a wildtype human interleukin-15 protein having a sequence of SEQ ID NO: 22 or SEQ ID NO: 24). In some embodiments, the extracellular interleukin-15 domain comprises a sequence that is at least 95% identical to the sequence of a wildtype interleukin-15 protein (e.g., a wildtype human interleukin-15 protein such as, without limitation, a wildtype human interleukin-15 protein having a sequence of SEQ ID NO: 22 or SEQ ID NO: 24). In some embodiments, the extracellular interleukin-15 domain is a sequence of a wildtype interleukin-15 protein having one or both of (i) one to ten amino acids removed from the N-terminus of the sequence of the wildtype interleukin-15 protein (e.g., a wildtype human interleukin-15 protein such as, without limitation, a wildtype human interleukin-15 protein having a sequence of SEQ ID NO: 22 or SEQ ID NO: 24), and (ii) one to ten amino acids removed from the C-terminus of the sequence of the wildtype interleukin-15 protein (e.g., a wildtype human interleukin-15 protein such as, without limitation, a wildtype human interleukin-15 protein having a sequence of SEQ ID NO: 22 or SEQ ID NO: 24).

In some embodiments, the chimeric transmembrane protein further includes a linker sequence positioned between the extracellular interleukin-15 domain and the extracellular sushi domain. In some embodiments, the linker sequence is about 2 amino acids to about 50 amino acids. In some embodiments, the linker sequence is about 4 amino acids to about 40 amino acids. In some embodiments, the linker is a naturally-occurring amino acid sequence. In some embodiments, the linker sequence is not a naturally-occurring amino acid sequence. In some embodiments, the linker sequence includes a sequence of SEQ ID NO: 92. In some embodiments, the linker sequence consists of a sequence of SEQ ID NO: 92.

In some embodiments, the chimeric transmembrane protein further includes an additional linker sequence between the extracellular sushi domain and the transmembrane domain. In some embodiments, the additional linker sequence is about 2 amino acids to about 50 amino acids. In some embodiments, the additional linker sequence is about 4 amino acids to about 40 amino acids. In some embodiments, the additional linker is a naturally-occurring amino acid sequence. In some embodiments, the additional linker sequence is not a naturally-occurring amino acid sequence.

In some embodiments of chimeric transmembrane proteins having an extracellular sushi domain, the extracellular sushi domain includes a sushi domain from a wildtype alpha chain of interleukin-15 receptor. In some embodiments, the wildtype alpha chain of interleukin-15 receptor is wildtype human alpha chain of interleukin-15 receptor. In some embodiments, the extracellular sushi domain of the wildtype human alpha chain of interleukin-15 receptor includes SEQ ID NO: 36 or SEQ ID NO: 37. In some embodiments, the extracellular sushi domain is at least 80% identical to a sequence of an extracellular sushi domain of a wildtype alpha chain of interleukin-15 receptor (e.g., a wildtype human alpha chain of interleukin-15 receptor such as, without limitation, a wildtype human alpha chain of interleukin-15 receptor having a sequence of SEQ ID NO: 36 or SEQ ID NO: 37). In some embodiments, the extracellular sushi domain is at least 95% identical to a sequence of an extracellular sushi domain of a wildtype alpha chain of interleukin-15 receptor (e.g., a wildtype human alpha chain of interleukin-15 receptor such as, without limitation, a wildtype human alpha chain of interleukin-15 receptor having a sequence of SEQ ID NO: 36 or SEQ ID NO: 37). In some embodiments, the extracellular sushi domain is a sequence of an extracellular sushi domain of a wildtype alpha chain of interleukin-15 receptor having one or both of (i) one to five amino acids removed from the N-terminus of the sequence of the extracellular sushi domain of the wildtype alpha chain of interleukin-15 receptor (e.g., a wildtype human alpha chain of interleukin-15 receptor such as, without limitation, a wildtype human alpha chain of interleukin-15 receptor having a sequence of SEQ ID NO: 36 or SEQ ID NO: 37), and (ii) one to five amino acids removed from the C-terminus of the sequence of the extracellular sushi domain of the wildtype alpha chain of interleukin-15 receptor (e.g., a wildtype human alpha chain of interleukin-15 receptor such as, without limitation, a wildtype human alpha chain of interleukin-15 receptor having a sequence of SEQ ID NO: 36 or SEQ ID NO: 37).

In some embodiments of chimeric transmembrane proteins having a transmembrane domain from an alpha chain of interleukin-7 receptor, the transmembrane domain includes a transmembrane domain from a wildtype alpha chain of interleukin-7 receptor. In some embodiments, the wildtype alpha chain of the interleukin-7 receptor is a wildtype alpha chain of a human interleukin-7 receptor. In some embodiments, the transmembrane domain of the wild-type alpha chain of a human interleukin-7 receptor includes a sequence of PILLTISILSFFSVALLVILACVLW (SEQ ID NO: 1). In some embodiments, the transmembrane domain of the wildtype alpha chain of a human interleukin-7 receptor includes a sequence of PILLTISILSFFSVALLVI-LACVLW (SEQ ID NO: 1) with one or more of the following modifications: (i) alanine-leucine-leucine at amino acids positions 15 through 17 in SEQ ID NO: 1 has been replaced with glutamic acid-lysine-valine or glutamic acid-lysine-alanine; (ii) a cysteine-proline-threonine has been inserted between amino acid positions 5 and 6 in SEQ ID NO: 1; and (iii) a proline-proline-cysteine-leucine has been inserted between amino acid positions 4 and 5 in SEQ ID NO: 1. Representative modified transmembrane domains have a sequence of SEQ ID NO: 2, 4, 6 or 8. In some embodiments, the transmembrane domain is at least 80% identical to a sequence of a transmembrane domain of a wildtype alpha chain of interleukin-7 receptor (e.g., a transmembrane domain of a wildtype alpha chain interleukin-7 receptor such as, without limitation, a transmembrane domain of a wildtype alpha chain of a human interleukin-7 receptor having a sequence of SEQ ID NO: 1). In some embodiments, the transmembrane domain is at least 95% identical to a sequence of a transmembrane domain of a wildtype alpha chain of interleukin-7 receptor (e.g., a transmembrane domain of a wildtype alpha chain interleukin-7 receptor such as, without limitation, a transmembrane domain of a wildtype alpha chain of a human interleukin-7 receptor having a sequence of SEQ ID NO: 1). In some embodiments, the transmembrane domain is a sequence of a transmembrane domain of a wildtype alpha chain of interleukin-7 receptor having one or both of (i) one to three amino acids removed from the N-terminus of the sequence of the transmembrane domain of the wildtype alpha chain of interleukin-2 receptor (e.g., a transmembrane domain of a wildtype alpha chain interleukin-7 receptor such as, without limitation, a transmembrane domain of a wildtype alpha chain of a human interleukin-7 receptor having a sequence of SEQ ID NO: 1), and (ii) one to three amino acids removed from the C-terminus of the sequence of the transmembrane domain of the wildtype alpha chain of interleukin-7 receptor (e.g., a transmembrane domain of a wildtype alpha chain interleukin-7 receptor such as, without limitation, a transmembrane domain of a wildtype alpha chain of a human interleukin-7 receptor having a sequence of SEQ ID NO: 1).

In some embodiments of chimeric transmembrane proteins provided herein, the chimeric transmembrane protein further includes an intracellular domain of an alpha chain of interleukin-7 receptor. In some embodiments, the alpha chain of interleukin-7 receptor is a wildtype alpha chain of interleukin-7 receptor. In some embodiments, the wildtype alpha chain of interleukin-7 receptor is a wildtype human alpha chain of interleukin-7 receptor. In some embodiments, the intracellular domain includes a sequence of SEQ ID NO: 45. In some embodiments, the intracellular domain includes a sequence that is at least 80% identical to the sequence of an intracellular domain of a wildtype alpha chain of interleukin-7 receptor (e.g., a wildtype human alpha chain of interleukin-7 receptor, e.g., SEQ ID NO: 45). In some embodiments, the intracellular domain is at least 90% or 95% identical to SEQ ID NO: 45. In some embodiments, the intracellular domain is a sequence of an intracellular domain of a wildtype alpha chain of interleukin-7 receptor having one or both of: (i) one to ten amino acids deleted from the N-terminus of the sequence of the intracellular domain of the wildtype alpha chain of interleukin-7 receptor (e.g., a wildtype human alpha chain of interleukin-7 receptor, e.g., SEQ ID NO: 45) and (ii) one to ten amino acids deleted from the C-terminus of the sequence of the intracellular domain of the wildtype alpha chain of interleukin-7 receptor (e.g., a wildtype human alpha chain of interleukin-7 receptor, e.g., SEQ ID NO: 45).

Also provided herein are nucleic acids encoding any of the variety of chimeric transmembrane proteins described herein. Also provided herein are vectors that include any of the nucleic acids encoding any of the variety of chimeric transmembrane proteins described herein. In some embodiments, vectors that include any of the nucleic acids encoding any of the variety of chimeric transmembrane proteins described herein include a promoter operably linked to the nucleic acid, and optionally, an enhancer sequence operably linked to the nucleic acid. In some embodiments, vectors that include any of the nucleic acids encoding any of the variety of chimeric transmembrane proteins described herein include a poly(A) sequence operably linked to the nucleic acid. In some embodiments, vectors that include any of the nucleic acids encoding any of the variety of chimeric transmembrane proteins described herein are lentiviral or adenoviral vectors.

In some embodiments, vectors that include any of the nucleic acids encoding any of the variety of chimeric transmembrane proteins described herein include a sequence encoding a chimeric antigen receptor. In some embodiments, the chimeric antigen receptor binds specifically to a tumor antigen (e.g., a tumor antigen is selected from the group consisting of: glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TN-FRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin $\alpha5\beta1$, integrin $\alpha v\beta3$, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin). In some embodiments, the chimeric antigen receptor comprises one or more co-stimulatory signaling domains selected from the group consisting of: 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, B7-H3, DAP-10, and DAP-12.

Also provided herein are mammalian cells that include any of the variety of nucleic acids encoding any of the variety of chimeric transmembrane proteins described herein or vectors that include such nucleic acids described herein. In some embodiments, the mammalian cell is an immune cell. In some embodiments, the immune cell is selected from the group consisting of: a CD4+ T cell, a CD8+ T cell, a B cell, a monocyte, a natural killer cell, a dendritic cell, a macrophage, a regulatory T cell, and a helper T cell. In some embodiments, the mammalian cell was previously obtained from a subject or is a daughter cell of a mammalian cell that was previously obtained from the subject. In some embodiments, the mammalian cell is a human cell.

Also provided herein are pharmaceutical compositions that include any of the variety of vectors that include any of the nucleic acids encoding any of the variety of chimeric transmembrane proteins described herein and a pharmaceutically acceptable carrier. Also provided herein are pharmaceutical compositions that include any of the variety of mammalian cells that include vectors that include any of the nucleic acids encoding any of the variety of chimeric transmembrane proteins described herein.

Also provided herein are sets of vectors that include a first vector that is any of the vectors that include any of the nucleic acids encoding any of the variety of chimeric transmembrane proteins described herein, and a second vector that includes a sequence encoding a chimeric antigen receptor. In some embodiments of sets of such vectors, the chimeric antigen receptor binds specifically to a tumor antigen (e.g., a tumor antigen is selected from the group consisting of: glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin $\alpha5\beta1$, integrin $\alpha v\beta3$, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-$\beta$, TRAIL-R1, TRAIL-R2, tumor antigen CTAA16.88, VEGF-A, VEGFR-1, VEGFR2, and vimentin). In some embodiments of such sets of vectors, the chimeric antigen receptor comprises one or more co-stimulatory signaling domains selected from the group consisting of: 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, B7-H3, DAP-10, and DAP-12. In some embodiments of such sets of vectors, both of the first vector and the second vector is a lentiviral or adenoviral vector. In some embodiments of such sets of vectors, the second vector further includes a promoter operably linked to the sequence encoding the chimeric antigen receptor, and optionally, an enhancer operably linked to the sequence encoding the chimeric antigen receptor. In some embodiments of such sets of vectors, the second vector further comprises a poly (A) sequence operably linked to the sequence encoding the chimeric antigen receptor.

Also provided herein are mammalian cells that include any of the variety of sets of vectors described herein that include a first vector that includes any of the nucleic acids encoding any of the variety of chimeric transmembrane proteins described herein, and a second vector that includes a sequence encoding a chimeric antigen receptor. In some embodiments, the mammalian cell is an immune cell. In some embodiments, the immune cell is selected from the group consisting of: a CD4+ T cell, a CD8+ T cell, a B cell, a monocyte, a natural killer cell, a dendritic cell, a macrophage, a regulatory T cell, and a helper T cell. In some embodiments, the mammalian cell was previously obtained from a subject or is a daughter cell of a mammalian cell that was previously obtained from the subject. In some embodiments, the mammalian cell is a human cell.

Also provided herein are pharmaceutical compositions that include any of the variety of sets of vectors described herein (e.g., sets of vectors that include a first vector that includes any of the nucleic acids encoding any of the variety of chimeric transmembrane proteins described herein, and a second vector that includes a sequence encoding a chimeric antigen receptor) and a pharmaceutically acceptable carrier. Also provided herein are pharmaceutical compositions that include any of the variety of mammalian cells that include such sets of vectors.

Also provided herein are kits that include any of the variety of pharmaceutical compositions described herein (e.g., pharmaceutical compositions that include any of the variety of vectors or sets of vectors described herein).

Also provided herein are methods of treating a cancer in a subject in need thereof, the methods including: administering a therapeutically effective amount of any of the variety of mammalian cells described herein (e.g., mammalian cells that include any of the variety of nucleic acids, vectors, or sets of vectors described herein). In some embodiments, the subject is a human and the mammalian cell is human. In some embodiments, the mammalian cell was previously obtained from the subject or is a daughter cell of a cell previously obtained from the subject.

Also provided herein are methods of reducing the volume of a solid tumor in a subject in need thereof, the methods including: administering a therapeutically effective amount of any of the variety of mammalian cells described herein (e.g., mammalian cells that include any of the variety of nucleic acids, vectors, or sets of vectors described herein). In some embodiments, the subject is a human and the mammalian cell is human. In some embodiments, the mammalian cell was previously obtained from the subject or is a daughter cell of a cell previously obtained from the subject.

Also provided herein are methods of inducing cell death in a cancer cell in a subject in need thereof, the methods including: administering a therapeutically effective amount of any of the variety of mammalian cells described herein (e.g., mammalian cells that include any of the variety of nucleic acids, vectors, or sets of vectors described herein). In some embodiments, the subject is a human and the mammalian cell is human. In some embodiments, the mammalian cell was previously obtained from the subject or is a daughter cell of a cell previously obtained from the subject.

Also provided herein are methods of decreasing the risk of developing a metastasis or an additional metastasis in a subject having a cancer, the methods including: administering a therapeutically effective amount of any of the variety of mammalian cells described herein (e.g., mammalian cells that include any of the variety of nucleic acids, vectors, or sets of vectors described herein). In some embodiments, the subject is a human and the mammalian cell is human. In some embodiments, the mammalian cell was previously obtained from the subject or is a daughter cell of a cell previously obtained from the subject.

Also provided herein are methods of activating STATS signaling in an immune cell, the methods including introducing into the immune cell any of the variety of nucleic acids described herein (e.g., nucleic acids encoding any of the variety of proteins or chimeric transmembrane proteins described herein). In some embodiments, the immune cell is obtained from the subject. In some embodiments, the subject has been identified as having a cancer. In some embodiments, the immune cell is selected from the group consisting of: a CD4+ T cell, a CD8+ T cell, a B cell, a monocyte, a natural killer cell, a dendritic cell, a macrophage, a regulatory T cell, and a helper T cell.

The use of the term "a" before a noun is meant "one or more" of the particular noun. For example, the phrase "a mammalian cell" means "one or more mammalian cell." In some examples, the term "a" can mean a single unit of the particular noun.

The terms "chimeric antigen receptor" and "CAR" are used interchangeably herein, and refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. CAR molecules and derivatives thereof (e.g., CAR variants) are described, e.g., in PCT Application No. US2014/016527; Fedorov et al., *Sci Transl Med* (2013) 5(215):215ra172; Glienke et al., *Front Pharmacol* (2015) 6:21; Kakarla & Gottschalk, *Cancer J* (2014) 20(2):151-5; Riddell et al., *Cancer J* (2014) 20(2):141-4; Pegram et al., *Cancer J* (2014) 20(2):127-33; Cheadle et al., *Immunol Rev* (2014) 257(1):91-106; Barrett et al., *Annu Rev Med* (2014) 65:333-47; Sadelain et al., *Cancer Discov* (2013) 3(4):388-98; Cartellieri et al., *J Biomed Biotechnol* (2010) 956304; the disclosures of which are incorporated herein by reference in their entirety. A CAR can be a single-chain chimeric antigen receptor or a multi-chain chimeric antigen receptor.

The term "transmembrane domain" means a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The term "antigen-binding domain" means a domain that binds specifically to a target antigen. In some examples, an antigen-binding domain can be formed from the amino acids present within a single-chain polypeptide. In other examples, an antigen-binding domain can be formed from amino acids present within a first single-chain polypeptide and the amino acids present in one or more additional single-chain polypeptides (e.g., a second single-chain polypeptide). Non-limiting examples of antigen-binding domains are described herein, including, without limitation, scFvs, or ligand-binding domains (LBDs) of growth factors. Additional examples of antigen-binding domains are known in the art.

As used herein, the term "antigen" refers generally to a binding partner specifically recognized by an antigen-binding domain described herein. Exemplary antigens include different classes of molecules, such as, but not limited to, polypeptides and peptide fragments thereof, small molecules, lipids, carbohydrates, and nucleic acids. Non-limiting examples of antigen or antigens that can be specifically bound by any of the antigen-binding domains are described herein. Additional examples of antigen or antigens that can be specifically bound by any of the antigen-binding domains are known in the art.

The term "intracellular signaling domain" means an intracellular signaling domain from an endogenous signaling transmembrane polypeptide expressed in an immune cell (e.g., a T lymphocyte) that promotes downstream immune cell signaling (e.g., T-cell receptor signaling) and/or immune cell activation (e.g., T cell activation). Non-limiting examples of intracellular signaling domains are described herein. Additional examples of intracellular signaling domains are known in the art. See, e.g., Chen et al., *Nature Reviews Immunol.* 13:227-242, 2013.

The term "immunoreceptor tyrosine-based activation motif" or "ITAM" means an amino acid motif that includes a four amino-acid consensus sequence of a tyrosine separated from a leucine or an isoleucine by two other amino acids (YxxL/I). The tyrosine residue in the four-amino acid consensus sequence becomes phosphorylated following interaction of a signaling pathway kinase (e.g., a lymphocyte signaling pathway kinase). Non-limiting examples of ITAMs are described herein. Additional examples of ITAMs are known in the art.

The phrase "treatment of cancer" means a reduction in the number, frequency, or severity of one or more (e.g., two, three, four, or five) symptoms of a cancer in a subject having a cancer, a reduction in the number of cancer cells and/or tumors present in a subject, and/or a reduction in the size of one or more solid tumors present in a subject.

As used herein, "extracellular domain" describes a portion of a polypeptide (e.g., a domain) that is present in the extracellular space when the polypeptide is expressed in a mammalian cell (e.g., a human cell).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIGS. 11A and 11B show that CAR T-cells expressing IL7Rα mutants demonstrate superior expansion compared to control CAR upon serial exposure to antigen at a 1:1 ratio effector to target (E:T) ratio.

FIGS. 14A and 14B show that CAR T-cells expressing IL7Rα mutants demonstrate superior expansion to control CAR upon a single exposure to target.

DETAILED DESCRIPTION

Figure 1:
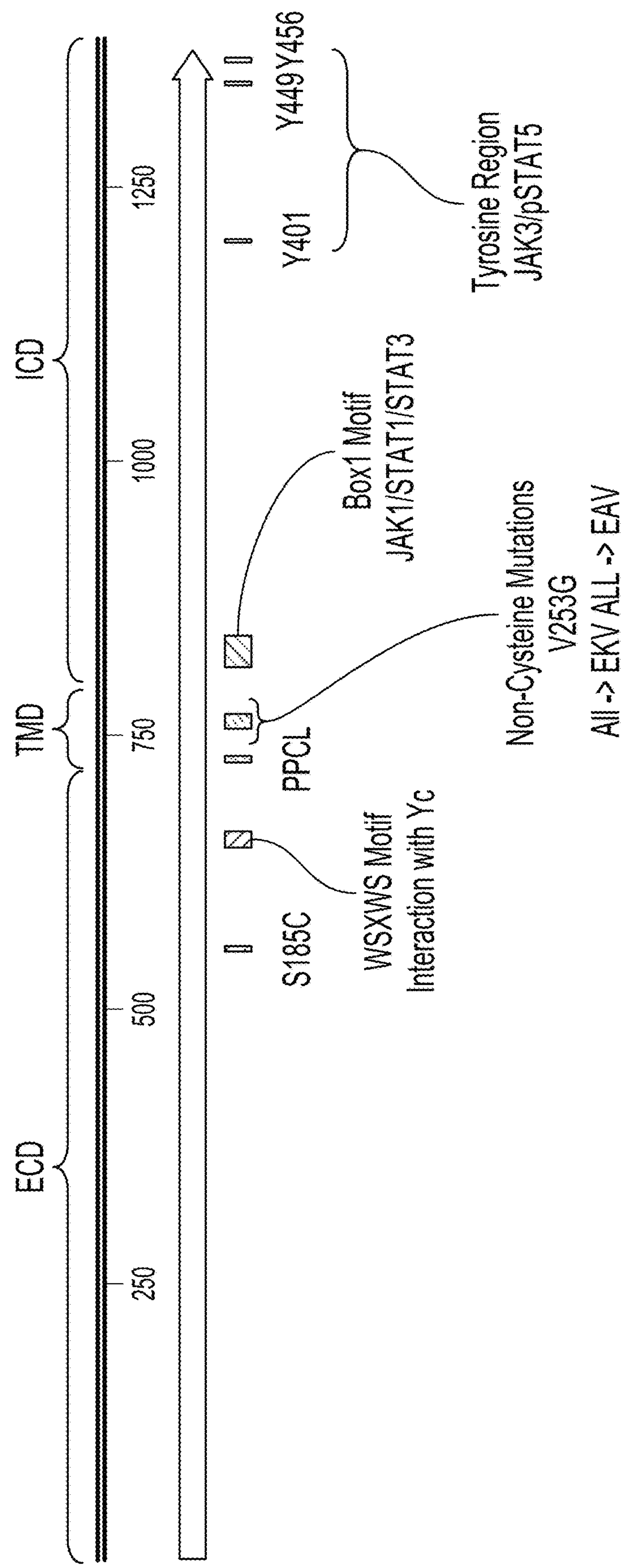
FIG. 1 is a schematic diagram of IL7Rα. ECD=extracellular domain. TMD=transmembrane domain. ICD=intracellular domain. Relevant regions, motifs, and amino acid modifications are indicated.
Figure 2:
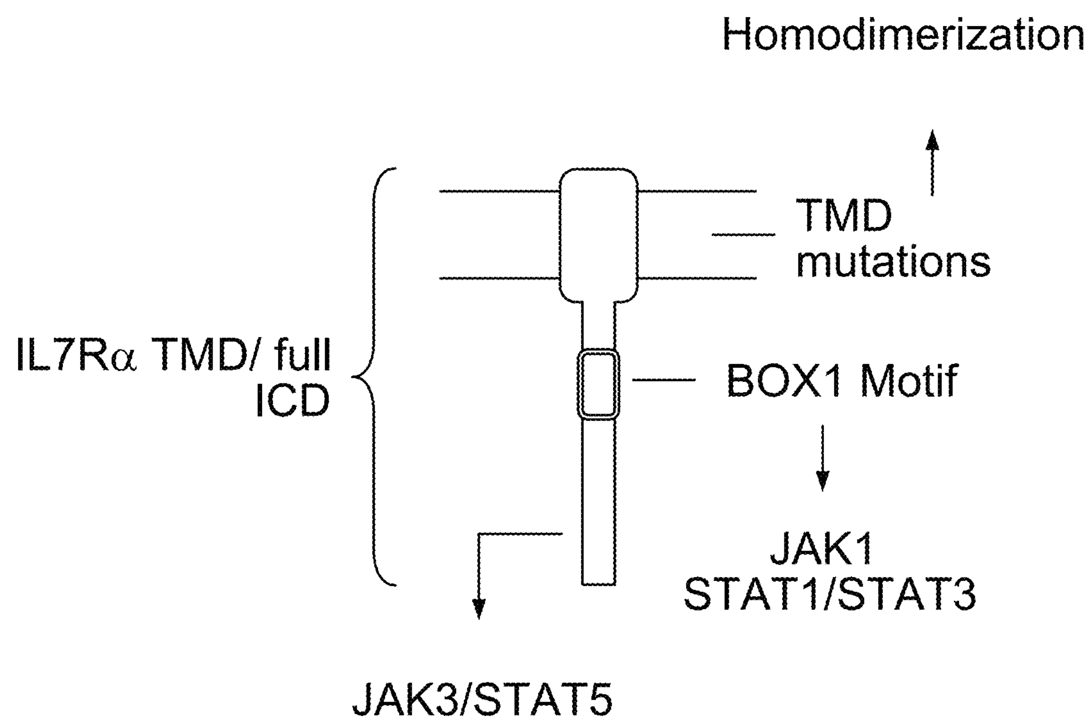
FIG. 2 is a schematic diagram of IL7Rα, showing relevant motifs, and mechanisms of signaling activation.

Provided herein are proteins that include a transmembrane domain of an alpha chain of interleukin-7 receptor, where the transmembrane domain includes the sequence of PILLTISILSFFSVALLVILACVLW (SEQ ID NO: 1) with one or more (e.g., two, three, or four) of the following modifications: (i) alanine-leucine-leucine at amino acids positions 15 through 17 in SEQ ID NO: 1 has been replaced with glutamic acid-lysine-valine or glutamic acid-lysine-alanine; (ii) a cysteine-proline-threonine has been inserted between amino acid positions 5 and 6 in SEQ ID NO: 1; and (iii) a proline-proline-cysteine-leucine has been inserted between amino acid positions 4 and 5 in SEQ ID NO: 1. Representative modified transmembrane domains have a sequence of SEQ ID NO: 2, 4, 6 or 8.

Also provided herein are chimeric transmembrane proteins that include an extracellular IL-15 domain, an extracellular sushi domain from an alpha chain of interleukin-15 receptor, and a transmembrane domain of an alpha chain of interleukin-7 receptor.

Also provided are nucleic acids encoding any of these chimeric transmembrane proteins and proteins, vectors including any of these nucleic acids, and mammalian cells that include any of these nucleic acids or vectors. Also provided herein are methods of treating a cancer, methods of inducing cell death in a cancer cell (e.g., apoptosis and/or necrosis), and methods of decreasing the risk of developing a metastasis or an additional metastasis in a subject in need thereof that include administering any of the mammalian cells described herein to the subject.

The chimeric transmembrane proteins and proteins provided herein can be used to maintain CAR T-cells in the absence of exogenous cytokine support or antigen stimulation, thus providing for the T-cell stimulatory effects without the dose-limiting toxicities associated with prolonged administration of a cytokine, e.g., soluble, recombinant IL-2.

Non-limiting aspects of the chimeric transmembrane proteins, nucleic acids, vectors, mammalian cells, and methods provided herein are described below, and can be used in any combination without limitation. Additional aspects of these chimeric transmembrane proteins, nucleic acids, vectors, mammalian cells, and methods are known in the art.

Proteins Including a Transmembrane Domain of an Alpha Chain of Interleukin-7 Receptor Provided herein are proteins that include a transmembrane domain of an alpha chain of interleukin-7 receptor, where the transmembrane domain includes the sequence of PILLTISILSFFSVALLVILACVLW (SEQ ID NO: 1) with one or more (e.g., one, two, three, or four) of the following modifications: (i) alanine-leucine-leucine at amino acids positions 15 through 17 in SEQ ID NO: 1 has been replaced with a different three-amino acid sequence (e.g., has been replaced with glutamic acid-lysine-valine or glutamic acid-lysine-alanine); (ii) one to three (e.g., one, two, or three) amino acids (e.g., cysteine-proline-threonine) has been inserted between amino acid positions 5 and 6 in SEQ ID NO: 1; and (iii) one to four (e.g., one, two, three, or four) amino acids (e.g., proline-proline-cysteine-leucine) has been inserted between amino acid positions 4 and 5 in SEQ ID NO: 1. Representative modified transmembrane domains have a sequence of SEQ ID NO: 2, 4, 6 or 8.

In some embodiments, the transmembrane domain includes the sequence of SEQ ID NO: 1 with the alanine-leucine-leucine at amino acid positions 15 through 17 in SEQ ID NO: 1 replaced with glutamic acid-lysine-valine or glutamic acid-lysine-alanine. In some embodiments, the transmembrane domain includes the sequence of SEQ ID NO: 1 with cysteine-proline-threonine inserted between amino acid positions 5 and 6 in SEQ ID NO: 1. In some embodiments, the transmembrane domain includes the sequence of SEQ ID NO: 1 with a proline-proline-cysteine-leucine inserted between amino acid positions 4 and 5 in SEQ ID NO: 1.

In some embodiments, the proteins provided herein (e.g., mature or precursor protein) can be, e.g., about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 250 amino acids, about 40 amino acids to about 200 amino acids, about 40 amino acids to about 180 amino acids, about 40 amino acids to about 160 amino acids, about 40 amino acids to about 140 amino acids, about 40 amino acids to about 120 amino acids, about 40 amino acids to about 100 amino acids, about 40 amino acids to about 80 amino acids, about 40 amino acids to about 60 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 250 amino acids, about 60 amino acids to about 200 amino acids, about 60 amino acids to about 180 amino acids, about 60 amino acids to about 160 amino acids, about 60 amino acids to about 140 amino acids, about 60 amino acids to about 120 amino acids, about 60 amino acids to about 100 amino acids, about 60 amino acids to about 80 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 250 amino acids, about 80 amino acids to about 200 amino acids, about 80 amino acids to about 180 amino acids, about 80 amino acids to about 160 amino acids, about 80 amino acids to about 140 amino acids, about 80 amino acids to about 120 amino acids, about 80 amino acids to about 100 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 180 amino acids, about 100 amino acids to about 160 amino acids, about 100 amino acids to about 140 amino acids, about 100 amino acids to about 120 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 250 amino acids, about 120 amino acids to about 200 amino acids, about 120 amino acids to about 180 amino acids, about 120 amino acids to about 160 amino acids, about 120 amino acids to about 140 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 250 amino acids, about 140 amino acids to about 200 amino acids, about 140 amino acids to about 180 amino acids, about 140 amino acids to about 160 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 250 amino acids, about 160 amino acids to about 200 amino acids, about 160 amino acids to about 180 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 250 amino acids, about 180 amino acids to about 200 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 800 amino acids, about 250 amino acids to about 750 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 800 amino acids, about 600 amino acids to about 750 amino acids, about 600 amino acids to about 700 amino acids, about 600 amino acids to about 650 amino acids, about 650 amino acids to about 800 amino acids, about 650 amino acids to about 750 amino acids, about 650 amino acids to about 700 amino acids, about 700 amino acids to about 800 amino acids, about 700 amino acids to about 750 amino acids, or about 750 amino acids to about 800 amino acids.

In some embodiments, the protein comprises or is SEQ ID NO: 2 (shown below).

```
Exemplary Protein (SEQ ID NO: 2) (IL7RA EKA
Protein, EKA sequence is underlined)
PILLTISILSFFSVEKAVILACVLW

Nucleic Acid Encoding IL7RA EKA (SEQ ID NO: 3,
nucleic acid sequence encoding the EKA sequence is
underlined)
cccatcctgctgaccatcagcatcctgagcttcttcagcgtg

gagaaggtggtgatcctggcctgcgtgctgtgg
```

In some embodiments, the protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 2. In some embodiments, a protein includes a sequence that differs from SEQ ID NO: 2 by one to twenty amino acids (e.g., 1, 2, 3, 4, 5, 6, 7, 8, 9, 10, 11, 12, 13, 14, 15, 16, 17, 18, 19, or 20 amino acids). In some embodiments, any of the proteins provided herein can further include one or more additional amino acids (e.g., 1 amino acid to 300 amino acids, 1 amino acid to about 250 amino acids, 1 amino acid to about 200 amino acids, 1 amino acid to about 150 amino acids, 1 amino acid to about 100 amino acids, 1 amino acid to about 50 amino acids, about 5 amino acids to about 300 amino acids, about 5 amino acids to about 250 amino acids, about 5 amino acids to about 200 amino acids, about 5 amino acids to about 150 amino acids, about 5 amino acids to about 100 amino acids, about 5 amino acids to about 50 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, or about 10 amino acids to about 50 amino acids), e.g., in addition to SEQ ID NO: 2. Additionally or alternatively, a protein can lack one to twenty amino acids (e.g., 1, 2, 3, 4, 5, 6, 7, 8, 9, 10, 11, 12, 13, 14, 15, 16, 17, 18, 19, or 20) from the N-terminus of SEQ ID NO: 2 and/or lack one to twenty amino acids (e.g., 1, 2, 3, 4, 5, 6, 7, 8, 9, 10, 11, 12, 13, 14, 15, 16, 17, 18, 19, or 20) from the C-terminus of SEQ ID NO: 2.

In some embodiments, a nucleic acid encoding the protein comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 3. In some embodiments, a nucleic acid encoding the protein includes a sequence that differs from SEQ ID NO: 3 by one to sixty nucleotides (e.g., 1 to 60 nucleotides, 1 to 55 nucleotides, 1 to 50 nucleotides, 1 to 45 nucleotides, 1 to 40 nucleotides, 1 to 35 nucleotides, 1 to 30 nucleotides, 1 to 25 nucleotides, 1 to 20 nucleotides, 1 to 15 nucleotides, 1 to 10 nucleotides, or 1 to 5 nucleotides). In some embodiments, a nucleic acid encoding the protein can further includes one or more additional nucleotides (e.g., 1 to about 900 nucleotides, 1 to about 850 nucleotides, 1 to about 800 nucleotides, 1 to about 750 nucleotides, 1 to about 700 nucleotides, 1 to about 650 nucleotides, 1 to about 600 nucleotides, 1 to about 550 nucleotides, 1 to about 500 nucleotides, 1 to about 450 nucleotides, 1 to about 400 nucleotides, 1 to about 350 nucleotides, 1 to about 300 nucleotides, 1 to about 250 nucleotides, 1 to about 200 nucleotides, 1 to about 150 nucleotides, 1 to about 100 nucleotides, or 1 to about 50 nucleotides), e.g., in addition to SEQ ID NO: 3. Additionally or alternatively, a nucleic acid encoding the protein can lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 3 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 3.

In some embodiments, the protein comprises or is SEQ ID NO: 4 (shown below).

```
Exemplary Protein (SEQ ID NO: 4) (IL7RA EKV
Protein, EKV sequence is underlined)
PILLTISILSFFSVEKVVILACVLW

Nucleic Acid Encoding IL7RA EKV (SEQ ID NO: 5,
nucleic acid sequence encoding EKV sequence
is underlined)
cccatcctgctgaccatcagcatcctgagcttcttcagcgtg

gagaaggtggtgatcctggcctgcgtgctgtgg
```

In some embodiments, the protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 4. In some embodiments, a protein includes a sequence that differs from SEQ ID NO: 4 by one to twenty amino acids (e.g., 1, 2, 3, 4, 5, 6, 7, 8, 9, 10, 11, 12, 13, 14, 15, 16, 17, 18, 19, or 20 amino acids). In some embodiments, any of the proteins provided herein can further include one or more additional amino acids (e.g., 1 amino acid to 300 amino acids, 1 amino acid to about 250 amino acids, 1 amino acid to about 200 amino acids, 1 amino acid to about 150 amino acids, 1 amino acid to about 100 amino acids, 1 amino acid to about 50 amino acids, about 5 amino acids to about 300 amino acids, about 5 amino acids to about 250 amino acids, about 5 amino acids to about 200 amino acids, about 5 amino acids to about 150 amino acids, about 5 amino acids to about 100 amino acids, about 5 amino acids to about 50 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, or about 10 amino acids to about 50 amino acids), e.g., in addition to SEQ ID NO: 4. Additionally or alternatively, a protein can lack one to twenty amino acids (e.g., 1, 2, 3, 4, 5, 6, 7, 8, 9, 10, 11, 12, 13, 14, 15, 16, 17, 18, 19, or 20) from the N-terminus of SEQ ID NO: 4 and/or lack one to twenty amino acids (e.g., 1, 2, 3, 4, 5, 6, 7, 8, 9, 10, 11, 12, 13, 14, 15, 16, 17, 18, 19, or 20) from the C-terminus of SEQ ID NO: 4.

In some embodiments, a nucleic acid encoding the protein comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 5. In some embodiments, a nucleic acid encoding the protein includes a sequence that differs from SEQ ID NO: 5 by one to sixty nucleotides (e.g., 1 to 60 nucleotides, 1 to 55 nucleotides, 1 to 50 nucleotides, 1 to 45 nucleotides, 1 to 40 nucleotides, 1 to 35 nucleotides, 1 to 30 nucleotides, 1 to 25 nucleotides, 1 to 20 nucleotides, 1 to 15 nucleotides, 1 to 10 nucleotides, or 1 to 5 nucleotides). In some embodiments, a nucleic acid encoding the protein can further includes one or more additional nucleotides (e.g., 1 to about 900 nucleotides, 1 to about 850 nucleotides, 1 to about 800 nucleotides, 1 to about 750 nucleotides, 1 to about 700 nucleotides, 1 to about 650 nucleotides, 1 to about 600 nucleotides, 1 to about 550 nucleotides, 1 to about 500 nucleotides, 1 to about 450 nucleotides, 1 to about 400 nucleotides, 1 to about 350 nucleotides, 1 to about 300 nucleotides, 1 to about 250 nucleotides, 1 to about 200 nucleotides, 1 to about 150 nucleotides, 1 to about 100 nucleotides, or 1 to about 50 nucleotides), e.g., in addition to SEQ ID NO: 5. Additionally or alternatively, a nucleic acid encoding the protein can lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 5 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 5.

In some embodiments, the protein comprises or is SEQ ID NO: 6 (shown below).

```
Exemplary Protein (SEQ ID NO: 6) (IL7RA CPT
insert Protein, CPT sequence is underlined)
PILLTCPTISILSFFSVALLVILACVLW

Nucleic Acid Encoding IL7RA CPT insert
(SEQ ID NO: 7, nucleic acid sequence encoding
the CPT sequence is underlined)
cccatcctgctgacctgccccaccatcagcatcctgagcttcttca

gcgtggccctgctggtgatcctggcctgcgtgctgtgg
```

In some embodiments, the protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 6. In some embodiments, a protein includes a sequence that differs from SEQ ID NO: 6 by one to twenty amino acids (e.g., 1, 2, 3, 4, 5, 6, 7, 8, 9, 10, 11, 12, 13, 14, 15, 16, 17, 18, 19, or 20 amino acids). In some embodiments, any of the proteins provided herein can further include one or more additional amino acids (e.g., 1 amino acid to 300 amino acids, 1 amino acid to about 250 amino acids, 1 amino acid to about 200 amino acids, 1 amino acid to about 150 amino acids, 1 amino acid to about 100 amino acids, 1 amino acid to about 50 amino acids, about 5 amino acids to about 300 amino acids, about 5 amino acids to about 250 amino acids, about 5 amino acids to about 200 amino acids, about 5 amino acids to about 150 amino acids, about 5 amino acids to about 100 amino acids, about 5 amino acids to about 50 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, or about 10 amino acids to about 50 amino acids), e.g., in addition to SEQ ID NO: 6. Additionally or alternatively, a protein can lack one to twenty amino acids (e.g., 1, 2, 3, 4, 5, 6, 7, 8, 9, 10, 11, 12, 13, 14, 15, 16, 17, 18, 19, or 20) from the N-terminus of SEQ ID NO: 6 and/or lack one to twenty amino acids (e.g., 1, 2, 3, 4, 5, 6, 7, 8, 9, 10, 11, 12, 13, 14, 15, 16, 17, 18, 19, or 20) from the C-terminus of SEQ ID NO: 6.

In some embodiments, a nucleic acid encoding the protein comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 7. In some embodiments, a nucleic acid encoding the protein includes a sequence that differs from SEQ ID NO: 7 by one to sixty nucleotides (e.g., 1 to 60 nucleotides, 1 to 55 nucleotides, 1 to 50 nucleotides, 1 to 45 nucleotides, 1 to 40 nucleotides, 1 to 35 nucleotides, 1 to 30 nucleotides, 1 to 25 nucleotides, 1 to 20 nucleotides, 1 to 15 nucleotides, 1 to 10 nucleotides, or 1 to 5 nucleotides). In some embodiments, a nucleic acid encoding the protein can further includes one or more additional nucleotides (e.g., 1 to about 900 nucleotides, 1 to about 850 nucleotides, 1 to about 800 nucleotides, 1 to about 750 nucleotides, 1 to about 700 nucleotides, 1 to about 650 nucleotides, 1 to about 600 nucleotides, 1 to about 550 nucleotides, 1 to about 500 nucleotides, 1 to about 450 nucleotides, 1 to about 400 nucleotides, 1 to about 350 nucleotides, 1 to about 300 nucleotides, 1 to about 250 nucleotides, 1 to about 200 nucleotides, 1 to about 150 nucleotides, 1 to about 100 nucleotides, or 1 to about 50 nucleotides), e.g., in addition to SEQ ID NO: 7. Additionally or alternatively, a nucleic acid encoding the protein can lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 7 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 7.

In some embodiments, the protein comprises or is SEQ ID NO: 8 (shown below).

```
Exemplary Protein (SEQ ID NO: 8) (IL7RA PPCL
insert Protein, PPCL sequence is underlined)
PILLPPCLTISILSFFSVALLVILACVLW

Nucleic Acid Encoding IL7RA PPCL insert
(SEQ ID NO: 9, nucleic acid sequence encoding
the PPCL sequence is underlined)
cccatcctgctgccaccctgtttaaccatcagcatcctgagctt

cttcagcgtggccctgctggtgatcctggcctgcgtgctgtgg
```

In some embodiments, the protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 8. In some embodiments, a protein includes a sequence that differs from SEQ ID NO: 8 by one to twenty amino acids (e.g., 1, 2, 3, 4, 5, 6, 7, 8, 9, 10, 11, 12, 13, 14, 15, 16, 17, 18, 19, or 20 amino acids). In some embodiments, any of the proteins provided herein can further include one or more additional amino acids (e.g., 1 amino acid to 300 amino acids, 1 amino acid to about 250 amino acids, 1 amino acid to about 200 amino acids, 1 amino acid to about 150 amino acids, 1 amino acid to about 100 amino acids, 1 amino acid to about 50 amino acids, about 5 amino acids to about 300 amino acids, about 5 amino acids to about 250 amino acids, about 5 amino acids to about 200 amino acids, about 5 amino acids to about 150 amino acids, about 5 amino acids to about 100 amino acids, about 5 amino acids to about 50 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, or about 10 amino acids to about 50 amino acids), e.g., in addition to SEQ ID NO: 8. Additionally or alternatively, a protein can lack one to twenty amino acids (e.g., 1, 2, 3, 4, 5, 6, 7, 8, 9, 10, 11, 12, 13, 14, 15, 16, 17, 18, 19, or 20) from the N-terminus of SEQ ID NO: 8 and/or lack one to twenty amino acids (e.g., 1, 2, 3, 4, 5, 6, 7, 8, 9, 10, 11, 12, 13, 14, 15, 16, 17, 18, 19, or 20) from the C-terminus of SEQ ID NO: 8.

In some embodiments, a nucleic acid encoding the protein comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 9. In some embodiments, a nucleic acid encoding the protein includes a sequence that differs from SEQ ID NO: 9 by one to sixty nucleotides (e.g., 1 to 60 nucleotides, 1 to 55 nucleotides, 1 to 50 nucleotides, 1 to 45 nucleotides, 1 to 40 nucleotides, 1 to 35 nucleotides, 1 to 30 nucleotides, 1 to 25 nucleotides, 1 to 20 nucleotides, 1 to 15 nucleotides, 1 to 10 nucleotides, or 1 to 5 nucleotides). In some embodiments, a nucleic acid encoding the protein can further includes one or more additional nucleotides (e.g., 1 to about 900 nucleotides, 1 to about 850 nucleotides, 1 to about 800 nucleotides, 1 to about 750 nucleotides, 1 to about 700 nucleotides, 1 to about 650 nucleotides, 1 to about 600 nucleotides, 1 to about 550 nucleotides, 1 to about 500 nucleotides, 1 to about 450 nucleotides, 1 to about 400 nucleotides, 1 to about 350 nucleotides, 1 to about 300 nucleotides, 1 to about 250 nucleotides, 1 to about 200 nucleotides, 1 to about 150 nucleotides, 1 to about 100 nucleotides, or 1 to about 50 nucleotides), e.g., in addition to SEQ ID NO: 9. Additionally or alternatively, a nucleic acid encoding the protein can lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 9 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 9.

In some embodiments, the protein comprises or is SEQ ID NO: 79 (shown below).

Exemplary Protein (SEQ ID NO: 79) (IL7RA MCP insert Protein, MCP sequence is underlined)
PILLTMCPISILSFFSVALLVILACVLW Nucleic Acid Encoding IL7RA MCP insert (SEQ ID NO: 80, nucleic acid sequence encoding the MCP sequence is underlined)
cccatcctgctgaccatgtgccccatcagcatcctgagcttcttcag cgtggccctgctggtgatcctggcctgcgtgctgtgg In some embodiments, the protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 79. In some embodiments, a protein includes a sequence that differs from SEQ ID NO: 79 by one to twenty amino acids (e.g., 1, 2, 3, 4, 5, 6, 7, 8, 9, 10, 11, 12, 13, 14, 15, 16, 17, 18, 19, or 20 amino acids). In some embodiments, any of the proteins provided herein can further include one or more additional amino acids (e.g., 1 amino acid to 300 amino acids, 1 amino acid to about 250 amino acids, 1 amino acid to about 200 amino acids, 1 amino acid to about 150 amino acids, 1 amino acid to about 100 amino acids, 1 amino acid to about 50 amino acids, about 5 amino acids to about 300 amino acids, about 5 amino acids to about 250 amino acids, about 5 amino acids to about 200 amino acids, about 5 amino acids to about 150 amino acids, about 5 amino acids to about 100 amino acids, about 5 amino acids to about 50 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, or about 10 amino acids to about 50 amino acids), e.g., in addition to SEQ ID NO: 79. Additionally or alternatively, a protein can lack one to twenty amino acids (e.g., 1, 2, 3, 4, 5, 6, 7, 8, 9, 10, 11, 12, 13, 14, 15, 16, 17, 18, 19, or 20) from the N-terminus of SEQ ID NO: 79 and/or lack one to twenty amino acids (e.g., 1, 2, 3, 4, 5, 6, 7, 8, 9, 10, 11, 12, 13, 14, 15, 16, 17, 18, 19, or 20) from the C-terminus of SEQ ID NO: 79.

In some embodiments, a nucleic acid encoding the protein comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 80. In some embodiments, a nucleic acid encoding the protein includes a sequence that differs from SEQ ID NO: 80 by one to sixty nucleotides (e.g., 1 to 60 nucleotides, 1 to 55 nucleotides, 1 to 50 nucleotides, 1 to 45 nucleotides, 1 to 40 nucleotides, 1 to 35 nucleotides, 1 to 30 nucleotides, 1 to 25 nucleotides, 1 to 20 nucleotides, 1 to 15 nucleotides, 1 to 10 nucleotides, or 1 to 5 nucleotides). In some embodiments, a nucleic acid encoding the protein can further includes one or more additional nucleotides (e.g., 1 to about 900 nucleotides, 1 to about 850 nucleotides, 1 to about 800 nucleotides, 1 to about 750 nucleotides, 1 to about 700 nucleotides, 1 to about 650 nucleotides, 1 to about 600 nucleotides, 1 to about 550 nucleotides, 1 to about 500 nucleotides, 1 to about 450 nucleotides, 1 to about 400 nucleotides, 1 to about 350 nucleotides, 1 to about 300 nucleotides, 1 to about 250 nucleotides, 1 to about 200 nucleotides, 1 to about 150 nucleotides, 1 to about 100 nucleotides, or 1 to about 50 nucleotides), e.g., in addition to SEQ ID NO: 80. Additionally or alternatively, a nucleic acid encoding the protein can lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 80 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 80.

Some embodiments of any of the proteins described herein can further include an intracellular domain of an alpha chain of interleukin-7 receptor (e.g., any of the exemplary intracellular domains of an alpha chain of interleukin-7 receptor described herein or known in the art).

Some embodiments of any of the proteins described herein can further include an extracellular domain of an alpha chain of interleukin-7 receptor (e.g., any of the exemplary extracellular domains of an alpha chain of interleukin-7 receptor described herein or known in the art).

Some embodiments of any of the proteins described herein can further include a linker sequence (e.g., any of the exemplary linker sequences described herein or known in the art) positioned between the transmembrane domain of an alpha chain of interleukin-7 receptor and the extracellular domain of an alpha chain of interleukin-7 receptor (e.g., any of the exemplary extracellular domains of an alpha chain of interleukin-7 receptor described herein or known in the art).

Some embodiments of any of the proteins described herein can further include an additional linker sequence (e.g., any of the exemplary additional linker sequences described herein or known in the art) positioned between the transmembrane domain of an alpha chain of interleukin-7 receptor and the intracellular domain of an alpha chain of interleukin-7 receptor (e.g., any of the exemplary intracellular domains of an alpha chain of interleukin-7 receptor described herein or known in the art).

In some embodiments, the protein further comprises a signal sequence at its N-terminus. In some embodiments, the signal sequence comprises or is the sequence MLLLVTSLLLCELPHPAFLLIP (SEQ ID NO: 10). In some embodiments, the nucleic acid encoding the signal sequence comprises or is the sequence atgctcctgctcgtgacttcacttcttctctgtgaactcccacaccccgcgtttttgcttatccct (SEQ ID NO: 81). Additional examples of signal sequences are known in the art. For example, a signal sequence can be about 5 amino acids to about 30 amino acids, about 5 amino acids to about 28 amino acids, about 5 amino acids to about 26 amino acids, about 5 amino acids to about 24 amino acids, about 5 amino acids to about 22 amino acids, about 5 amino acids to about 20 amino acids, about 5 amino acids to about 18 amino acids, about 5 amino acids to about 16 amino acids, about 5 amino acids to about 14 amino acids, about 5 amino acids to about 12 amino acids, about 5 amino acids to about 10 amino acids, about 5 amino acids to about 8 amino acids, about 6 amino acids to about 30 amino acids, about 6 amino acids to about 28 amino acids, about 6 amino acids to about 26 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 30 amino acids, about 8 amino acids to about 28 amino acids, about 8 amino acids to about 26 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 30 amino acids, about 10 amino acids to about 28 amino acids, about 10 amino acids to about 26 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 30 amino acids, about 12 amino acids to about 28 amino acids, about 12 amino acids to about 26 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 30 amino acids, about 14 amino acids to about 28 amino acids, about 14 amino acids to about 26 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 30 amino acids, about 16 amino acids to about 28 amino acids, about 16 amino acids to about 26 amino acids, about 16 amino acids to about 24 amino acids, about 16 amino acids to about 22 amino acids, about 16 amino acids to about 20 amino acids, about 16 amino acids to about 18 amino acids, about 18 amino acids to about 30 amino acids, about 18 amino acids to about 28 amino acids, about 18 amino acids to about 26 amino acids, about 18 amino acids to about 24 amino acids, about 18 amino acids to about 22 amino acids, about 18 amino acids to about 20 amino acids, about 20 amino acids to about 30 amino acids, about 20 amino acids to about 28 amino acids, about 20 amino acids to about 26 amino acids, about 20 amino acids to about 24 amino acids, about 20 amino acids to about 22 amino acids, about 22 amino acids to about 30 amino acids, about 22 amino acids to about 28 amino acids, about 22 amino acids to about 26 amino acids, about 22 amino acids to about 24 amino acids, about 24 amino acids to about 30 amino acids, about 24 amino acids to about 28 amino acids, about 24 amino acids to about 26 amino acids, about 26 amino acids to about 30 amino acids, about 26 amino acids to about 28 amino acids, or about 28 amino acids to about 30 amino acids, in length.

In some embodiments, the protein can further include a peptide tag. For example, a tag can be used to help facilitate purification, production, and/or identification of the chimeric transmembrane protein. In some embodiments, the tag is a histidine tag comprising at least six histidine residues. Additional examples of tags are known in the art.

Non-limiting aspects of any of the proteins provided herein are described below.

Extracellular Domains of an Alpha Chain of Interleukin-7 Receptor

Some embodiments of the proteins described herein can further include an extracellular domain of an alpha chain of interleukin-7 receptor (e.g., any of the exemplary domains of an alpha chain of interleukin-7 receptor described herein). For example, proteins described herein can include an extracellular domain of a wildtype alpha chain of interleukin-7 receptor, from a human, a mouse, a rat, a monkey, a chimpanzee, a pig, a dog, a cat, or any other appropriate species. Non-limiting examples of extracellular domains of wildtype alpha chains of interleukin-7 receptors are described below. Additional examples of extracellular domains of wildtype alpha chains of interleukin-7 receptors are known in the art.

In some embodiments, the extracellular domain of an alpha chain of interleukin-7 receptor is or comprises an extracellular domain of a wildtype alpha chain of interleukin-7 receptor. For example, the extracellular domain of an alpha chain of interleukin-7 receptor comprises or is an extracellular domain of a wildtype to human alpha chain of interleukin-7 receptor (e.g., SEQ ID NO: 11, SEQ ID NO: 13, or SEQ ID NO: 15).

```
Exemplary Extracellular Domain of a Wildtype
Human Alpha Chain of Interleukin-7 Receptor
                                    (SEQ ID NO: 11)
GESGYAQNGDLEDAELDDYSFSCYSQLEVNGSQHSLTCAFEDPDVNITN

LEFEICGALVEVKCLNFRKLQEIYFIETKKFLLIGKSNICVKVGEKSLTC

KKIDLTTIVKPEAPFDLSVVYREGANDFVVTFNTSHLQKKYVKVLMHDVA

YRQEKDENKWTHVNLSSTKLTLLQRKLQPAAMYEIKVRSIPDHYFKGFW

SEWSPSYYFRTPEINNSSGEMD
```

```
Nucleic Acid Encoding the Wildtype Human
Extracellular Domain of an Alpha Chain of
Interleukin-7 Receptor
                                    (SEQ ID NO: 12)
ggcgagagcggctacgcccagaacggcgacctggaggacgccgagctgg

acgactacagcttcagctgctacagccagctggaggtgaacggcagccag

cacagcctgacctgcgccttcgaggaccccgacgtgaacatcaccaacct

ggagttcgagatctgcggcgccctggtggaggtgaagtgcctgaacttca

ggaagctgcaggagatctacttcatcgagaccaagaagttcctgctgatc

ggcaagagcaacatctgcgtgaaggtgggcgagaagagcctgacctgca

agaagatcgacctgaccaccatcgtgaagcccgaggccccttcgacct

gagcgtggtgtacagggagggcgccaacgacttcgtggtgaccttcaa

caccagccacctgcagaagaagtacgtgaaggtgctgatgcacgacgtg

gcctacaggcaggagaaggacgagaacaagtggacccacgtgaacctga

gcagcaccaagctgaccctgctgcagaggaagctgcagcccgccgccatg

tacgagatcaaggtgaggagcatccccgaccactacttcaagggcttctg

gagcgagtggagccccagctactacttcaggacccccgagatcaacaac

agcagcggcgagatggac
```

In some embodiments, an extracellular domain of an alpha chain of interleukin-7 receptor comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to a sequence of an extracellular domain of a wildtype alpha chain of interleukin-7 receptor (e.g., a sequence of an extracellular domain of a wildtype human alpha chain of interleukin-7 receptor, e.g., SEQ ID NO: 11). In some embodiments, an extracellular domain of an alpha chain of interleukin-7 receptor includes a sequence that differs from SEQ ID NO: 11 by one to forty amino acids (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids). In some embodiments, an extracellular domain of an alpha chain of interleukin-7 receptor can further includes one to about 250 additional amino acids (e.g., 1 to about 200 amino acids, 1 to about 150 amino acids, 1 to about 100 amino acids, 1 to about 50 amino acids, about 5 to about 250 amino acids, about 5 to about 200 amino acids, about 5 to about 150 amino acids, about 5 to about 100 amino acids, about 5 to about 50 amino acids, about 10 to about 250 amino acids, about 10 to about 200 amino acids, about 10 to about 150 amino acids, about 10 to about 100 amino acids, or about 10 to about 50 amino acids), e.g., in addition to SEQ ID NO: 11. Additionally or alternatively, an extracellular domain of an alpha chain of interleukin-7 receptor is a sequence of an extracellular domain of a wildtype alpha chain of interleukin-7 receptor (e.g., a sequence of an extracellular domain of a wildtype human alpha chain of interleukin-7 receptor, e.g., SEQ ID NO: 11) having one or both of: one to ten amino acids (e.g., 1, 2, 3, 4, 5, 6, 7, 8, 9, or 10 amino acids) deleted from the N-terminus of the sequence of the extracellular domain of the wildtype alpha chain of interleukin-7 receptor and (ii) one to ten amino acids (e.g., 1, 2, 3, 4, 5, 6, 7, 8, 9, or 10) deleted from the C-terminus of the sequence of the extracellular domain of the wildtype alpha chain of interleukin-7 receptor.

In some embodiments, a nucleic acid encoding the extracellular domain of an alpha chain of interleukin-7 receptor comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 12. In some embodiments, a nucleic acid encoding the extracellular domain of an alpha chain of interleukin-7 receptor includes a sequence that differs from SEQ ID NO: 12 by one to sixty nucleotides (e.g., 1 to 55 nucleotides, 1 to 50 nucleotides, 1 to 45 nucleotides, 1 to 40 nucleotides, 1 to 35 nucleotides, 1 to 30 nucleotides, 1 to 25 nucleotides, 1 to 20 nucleotides, 1 to 15 nucleotides, 1 to 10 nucleotides, or 1 to 5 nucleotides). In some embodiments, a nucleic acid encoding the extracellular domain of an alpha chain of interleukin-7 receptor can further include one or more additional nucleotides (e.g., 1 to about 900 nucleotides, 1 to about 850 nucleotides, 1 to about 800 nucleotides, 1 to about 750 nucleotides, 1 to about 700 nucleotides, 1 to about 650 nucleotides, 1 to about 600 nucleotides, 1 to about 550 nucleotides, 1 to about 500 nucleotides, 1 to about 450 nucleotides, 1 to about 400 nucleotides, 1 to about 350 nucleotides, 1 to about 300 nucleotides, 1 to about 250 nucleotides, 1 to about 200 nucleotides, 1 to about 150 nucleotides, 1 to about 100 nucleotides, or 1 to about 50 nucleotides), e.g., in addition to SEQ ID NO: 12. Additionally or alternatively, a nucleic acid encoding the extracellular domain of an alpha chain of interleukin-7 receptor can lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 12 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 12.

Additional exemplary extracellular domains of wildtype alpha chains of interleukin-7 receptors are provided below.

Exemplary Wildtype Mouse Extracellular Domain of an Alpha Chain of Interleukin-7 Receptor Isoform 1
(SEQ ID NO: 13)

```
ESGNAQDGDLEDADADDHSFWCHSQLEVDGSQHLLTCAFNDSDINTANLE

FQICGALLRVKCLTLNKLQDIYFIKTSEFLLIGSSNICVKLGQKNLTCKN

MAINTIVKAEAPSDLKVVYRKEANDFLVTFNAPHLKKKYLKKVKHDVAYR

PARGESNWTHVSLFHTRTTIPQRKLRPKAMYEIKVRSIPHNDYFKGFWSE

WSPSSTFETPEPKNQGGWD
```

Nucleic Acid Encoding the Wildtype Mouse Extracellular Domain of an Alpha Chain of Interleukin-7 Receptor Isoform 1
(SEQ ID NO: 14)

```
gaaagtggaaatgcccaggatggagacctagaagatgcagacgcggacga

tcactccttctggtgccacagccagttggaagtggatggaagtcaacatt

tattgacttgtgcttttaatgactcagacatcaacacagctaatctggaa

tttcaaatatgtggggctcttttacgagtgaaatgcctaactcttaacaa

gctgcaagatatatattttataaagacatcagaattcttactgattggta

gcagcaatatatgtgtgaagcttggacaaaagaatttaacttgcaaaaat

atggctataaacacaatagttaaagccgaggctccctctgacctgaaagt

cgtttatcgcaaagaagcaaatgatttttttggtgacatttaatgcacctc

acttgaaaaagaaatatttaaaaaaagtaaagcatgatgtggcctaccgc

ccagcaaggggtgaaagcaactggacgcatgtatctttattccacacaag

aacaacaatcccacagagaaaactacgaccaaaagcaatgtatgaaatca

aagtccgatccattccccataacgattacttcaaaggcttctggagcgag

tggagtccaagttctaccttcgaaactccagaacccaagaatcaaggagg

atgggat
```

Exemplary Wildtype Mouse Extracellular Domain of an Alpha Chain of Interleukin-7 Receptor Isoform 2
(SEQ ID NO: 15)

```
ESGNAQDGDLEDADADDHSFWCHSQLEVDGSQHLLTCAFNDSDINTANLE

FQICGALLRVKCLTLNKLQDIYFIKTSEFLLIGSSNICVKLGQKNLTCKN

MAINTIVKAEAPSDLKVVYRKEANDFLVTFNAPHLKKKYLKKVKHDVAYR

PARGESNWTHVSLFHTRTTIPQRKLRPKAMYEIKVRSIPHNDYFKGFWSE

WSPSSTFETPEPKNQGGWD
```

Nucleic Acid Encoding the Wildtype Mouse Extracellular Domain of an Alpha Chain of Interleukin-7 Receptor Variant 2
(SEQ ID NO: 16)

```
gaaagtggaaatgcccaggatggagacctagaagatgcagacgcggacga

tcactccttctggtgccacagccagttggaagtggatggaagtcaacatt

tattgacttgtgcttttaatgactcagacatcaacacagctaatctggaa

tttcaaatatgtggggctcttttacgagtgaaatgcctaactcttaacaa
```

-continued

```
gctgcaagatatatattttataaagacatcagaattcttactgattggta

gcagcaatatatgtgtgaagcttggacaaaagaatttaacttgcaaaaat

atggctataaacacaatagttaaagccgaggctccctctgacctgaaagt

cgtttatcgcaaagaagcaaatgatttttttggtgacatttaatgcacctc

acttgaaaaagaaatatttaaaaaaagtaaagcatgatgtggcctaccgc

ccagcaaggggtgaaagcaactggacgcatgtatctttattccacacaag

aacaacaatcccacagagaaaactacgaccaaaagcaatgtatgaaatca

aagtccgatccattccccataacgattacttcaaaggcttctggagcgag

tggagtccaagttctaccttcgaaactccagaacccaagaatcaaggagg

atgggat
```

In some embodiments, the extracellular domain of an alpha chain of interleukin-7 receptor is a sequence of a wildtype extracellular domain of an alpha chain of interleukin-7 receptor (e.g., a mature wildtype extracellular domain of an alpha chain of interleukin-7 receptor, e.g., any of the mature wildtype extracellular domains of an alpha chain of interleukin-7 receptor described herein, e.g., SEQ ID NO: 11, SEQ ID NO: 13, or SEQ ID NO: 15) having one to ten (e.g., one, two, three, four, five, six, seven, eight, nine, or ten) amino acids removed from the N-terminus of the sequence of the wildtype extracellular domain of an alpha chain of interleukin-7 receptor. In some embodiments, the extracellular domain of an alpha chain of interleukin-7 receptor is a sequence of a wildtype extracellular domain of an alpha chain of interleukin-7 receptor (e.g., a mature wildtype extracellular domain of an alpha chain of interleukin-7 receptor, e.g., any of the mature wildtype extracellular domains of an alpha chain of interleukin-7 receptor described herein, e.g., SEQ ID NO: 11, SEQ ID NO: 13, or SEQ ID NO: 15) having one to ten (e.g., one, two, three, four, five, six, seven, eight, nine, or ten) amino acids removed from the C-terminus of the sequence of the wildtype extracellular domain of an alpha chain of interleukin-7 receptor. In some embodiments, the extracellular domain of an alpha chain of interleukin-7 receptor is a sequence of a wildtype extracellular domain of an alpha chain of interleukin-7 receptor (e.g., a mature wildtype extracellular domain of an alpha chain of interleukin-7 receptor, e.g., any of the mature wildtype extracellular domains of an alpha chain of interleukin-7 receptor described herein, e.g., SEQ ID NO: 11, SEQ ID NO: 13, or SEQ ID NO: 15) having both one to ten amino (e.g., one, two, three, four, five, six, seven, eight, nine, or ten) acids removed from the N-terminus of the sequence of the wildtype extracellular domain of an alpha chain of interleukin-7 receptor and one to ten (e.g., one, two, three, four, five, six, seven, eight, nine, or ten) amino acids removed from the C-terminus of the sequence of the wildtype extracellular domain of an alpha chain of interleukin-7 receptor.

As will be appreciated by those of ordinary skill in the art, when a nucleic acid encoding an extracellular domain of an alpha chain of interleukin-7 receptor includes or lacks one or more additional nucleotides as compared to SEQ ID NO: 12, SEQ ID NO: 14, or SEQ ID NO: 16, the translational reading frame should still be maintained such that a nonsense codon is not introduced and the full protein can be translated (e.g., a nucleic acid encoding an extracellular domain of an alpha chain of interleukin-7 receptor can include or lack three nucleotides, or multiples thereof).

As one skilled in the art can appreciate, when amino acids that are not conserved between extracellular domains of alpha chains of interleukin-7 receptors from different species are mutated (e.g., substituted with a different amino acid) they are less likely to cause a decrease in the level of one or more activities of an extracellular domain of an alpha chain of interleukin-7 receptor. In contrast, when amino acids that are conserved between extracellular domains of alpha chains of interleukin-7 receptors from different species are mutated (e.g., substituted with a different amino acid) they are more likely to cause a decrease in the level of one or more activities of an extracellular domain of an alpha chain of interleukin-7 receptor. In view of this knowledge, one skilled in the art can select which amino acid positions in an extracellular domain of an alpha chain of interleukin-7 receptor (e.g., the non-conserved amino acids) can be substituted without decreasing the activity of the extracellular domain of an alpha chain of interleukin-7 receptor.

Chimeric Transmembrane Proteins

Provided herein are chimeric transmembrane proteins that include an extracellular IL-15 domain (e.g., any of the exemplary extracellular IL-15 domains described herein or known in the art), an extracellular sushi domain from an alpha chain of interleukin-15 receptor (e.g., one or more of any of the exemplary extracellular sushi domains from an alpha chain of interleukin-15 receptor described herein or known in the art), and a transmembrane domain of an alpha chain of interleukin-7 receptor (e.g., any of the exemplary transmembrane domains of an alpha chain of interleukin-7 receptor described herein or known in the art). In some embodiments, the chimeric transmembrane protein comprises a linker sequence positioned between the extracellular IL-15 domain and the extracellular sushi domain from an alpha chain of interleukin-15 receptor (e.g., any of the exemplary linker sequences described herein or known in the art). In some embodiments, the chimeric transmembrane protein further comprises an additional linker positioned between the extracellular sushi domain from an alpha chain of interleukin-15 receptor and the transmembrane domain of the alpha chain of the interleukin-7 receptor (e.g., any of the exemplary linker sequences described herein or known in the art). In some embodiments, the chimeric transmembrane protein can further include an intracellular domain of an alpha chain of interleukin-7 receptor (e.g., any of the exemplary intracellular domains of an alpha chain of interleukin-7 receptor described herein or known in the art).

In some embodiments, the chimeric transmembrane protein comprises or is SEQ ID NO: 17 (shown below).

```
Exemplary Chimeric Transmembrane Protein
                                        (SEQ ID NO: 17)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSSGGGSGGGGSGGGGSGGGGSGGGSLQITCPPPMSVE

HADIWVKSYSLYSRERYICNSGFKRKAGTSSLTECVLNKATNVAHWTTPS

LKCIRDPALVHQRPAPPSTVTTAGVTPQPESLSPSGKEPAASSPSSNNTA

ATTAAIVPGSQLMPSKSPSTGTTEISSHESSHGTPSQTTAKNWELTASAS

HQPPGVYPQGHSDTTPILLTISLLSFFSVALLVILACVLWKKRIKPIVWP

SLPDHKKTLEHLCKKPRKNLNVSFNPESFLDCQIHRVDDIQARDEVEGFL

QDTFPQQLEESEKQRLGGDVQSPNCPSEDVVITPESFGRDSSLTCLAGNV
```

-continued

```
SACDAPILSSSRSLDCRESGKNGPHVYQDLLLSLGTTNSTLPPPFSLQSG

ILTLNPVAQGQPILTSLGSNQEEAYVTMSSFYQNQ
```

```
Nucleic Acid Encoding Chimeric Transmembrane
Protein
                                        (SEQ ID NO: 18)
aactgggtgaatgtgatcagcgacctgaagaagatcgaggatctgatcca

gagcatgcacattgatgccaccctgtacacagaatctgatgtgcacccta

gctgtaaagtgaccgccatgaagtgttttctgctggagctgcaggtgatt

tctctggaaagcggagatgcctctatccacgacacagtggagaatctgat

catcctggccaacaatagcctgagcagcaatggcaatgtgacagagtctg

gctgtaaggagtgtgaggagctggaggagaagaacatcaaggagtttctg

cagagctttgtgcacatcgtgcagatgttcatcaatacaagcagcggtgg

gggctcaggcggaggaggctctggcggaggcggaagcgggggagggggct

caggcggcgggtccttgcagattacatgccctcctccaatgtctgtggag

cacgccgatatttgggtgaagtcctacagcctgtacagcagagagagata

catctgcaacagcggctttaagagaaaggccggcacctcttctctgacag

agtgcgtgctgaataaggccacaaatgtggcccactggacaacacctagc

ctgaagtgcattagagatcctgccctggtccaccagaggcctgcccctcc

atctacagtgacaacagccggagtgacacctcagcctgaatctctgagcc

cttctggaaaagaacctgccgccagctctcctagctctaataataccgcc

gccacaacagccgccattgtgcctggatctcagctgatgcctagcaagtc

tcctagcacaggcacaacagagatcagcagccacgaatcttctcacggaa

caccttctcagaccaccgccaagaattgggagctgacagcctctgcctct

caccagcctccaggagtgtatcctcagggccactctgatacaacacccat

cctgctgaccatcagcatcctgagcttcttcagcgtggccctgctggtga

tcctggcctgcgtgctgtggaagaagaggatcaagcccatcgtgtggccc

agcctgcccgaccacaagaagaccctggagcacctgtgtaagaagcccag

gaagaacctgaacgtgagcttcaaccccgagagcttcctggactgccaga

tccacagggtggacgacatccaggccagggacgaggtggagggcttcctg

caggacaccttcccccagcagctggaggagagcgagaagcagaggctggg

cggcgacgtgcagagccccaactgccccagcgaggacgtggtgatcaccc

ccgagagcttcggcagggacagcagcctgacctgcctggccggcaacgtg

agcgcctgcgacgcccccatcctgagcagcagcaggagcctggactgcag

ggagagcggcaagaacggcccccacgtgtaccaggacctgctgctgagcc

tgggcaccaccaacagcaccctgccacccccccttcagcctgcagagcggc

atcctgaccctgaaccccgtggcccagggccagcccatcctgaccagcct

gggcagcaaccaggaggaggcctacgtgaccatgagcagcttctaccaga

accag
```

In some embodiments, the chimeric transmembrane protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 17. In some embodiments, a chimeric transmembrane protein includes a sequence that differs from SEQ ID NO: 17 by one to about 100 amino acids (e.g., 1 to about 95 amino acids, 1 to about 90 amino acids, 1 to about 80 amino acids, 1 to about 75 amino acids, 1 to about 70 amino acids, 1 to about 65 amino acids, 1 to about 60 amino acids, 1 to about 55 amino acids, 1 to about 50 amino acids, 1 to about 45 amino acids, 1 to about 40 amino acids, 1 to about 35 amino acids, 1 to about 30 amino acids, 1 to about 25 amino acids, 1 to about 20 amino acids, 1 to about 15 amino acids, 1 to about 10 amino acids, 1 to about 5 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, or about 5 amino acids to about 10 amino acids). In some embodiments, a chimeric transmembrane protein includes 1 to about 300 additional amino acids (e.g., 1 to about 250 amino acids, 1 to about 200 amino acids, 1 to about 150 amino acids, 1 to about 100 amino acids, 1 to about 50 amino acids, 1 to about 25 amino acids, about 5 to about 300 amino acids, about 5 to about 250 amino acids, about 5 to about 200 amino acids, about 5 to about 150 amino acids, about 5 to about 100 amino acids, about 5 to about 50 amino acids, about 10 to about 300 amino acids, about 10 to about 250 amino acids, about 10 to about 200 amino acids, about 10 to about 150 amino acids, about 10 to about 100 amino acids, or about 10 to about 50 amino acids), e.g., in addition to the sequence of SEQ ID NO: 17. In some embodiments, the chimeric transmembrane protein comprises a sequence of SEQ ID NO: 17 having one to twenty amino acids (e.g., 1, 2, 3, 4, 5, 6, 7, 8, 9, 10, 11, 12, 13, 14, 15, 16, 17, 18, 19, or 20 amino acids) removed from the N-terminus of SEQ ID NO: 17 and/or one to twenty amino acids (e.g., 1, 2, 3, 4, 5, 6, 7, 8, 9, 10, 11, 12, 13, 14, 15, 16, 17, 18, 19, or 20 amino acids) removed from the C-terminus of SEQ ID NO: 17.

In some embodiments, a nucleic acid encoding a chimeric transmembrane protein comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 18. In some embodiments, a nucleic acid encoding a chimeric transmembrane protein includes a sequence that differs from SEQ ID NO: 18 by 1 to about 300 nucleotides (e.g., 1 to about 250 nucleotides, 1 to about 200 nucleotides, 1 to about 150 nucleotides, 1 to about 100 nucleotides, 1 to about 50 nucleotides, about 5 nucleotides to about 300 nucleotides, about 5 nucleotides to about 250 nucleotides, about 5 nucleotides to about 200 nucleotides, about 5 nucleotides to about 150 nucleotides, about 5 nucleotides to about 100 nucleotides, about 5 nucleotides to about 50 nucleotides, about 10 nucleotides to about 300 nucleotides, about 10 nucleotides to about 250 nucleotides, about 10 nucleotides to about 200 nucleotides, about 10 nucleotides to about 150 nucleotides, about 10 nucleotides to about 100 nucleotides, or about 10 nucleotides to about 50 nucleotides). In some embodiments, a nucleic acid encoding a chimeric transmembrane protein includes one or more additional nucleotides (e.g., 1 to about 900 nucleotides, 1 to about 850 nucleotides, 1 to about 800 nucleotides, 1 to about 750 nucleotides, 1 to about 700 nucleotides, 1 to about 650 nucleotides, 1 to about 600 nucleotides, 1 to about 550 nucleotides, 1 to about 500 nucleotides, 1 to about 450 nucleotides, 1 to about 400 nucleotides, 1 to about 350 nucleotides, 1 to about 300 nucleotides, 1 to about 250 nucleotides, 1 to about 200 nucleotides, 1 to about 150 nucleotides, 1 to about 100 nucleotides, or 1 to about 50 nucleotides), e.g., in addition to SEQ ID NO: 18. Additionally or alternatively, a nucleic acid encoding the chimeric transmembrane protein can lack one to sixty nucleotides (e.g., 1 to about 60 to nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 18 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 18.

In some embodiments, the chimeric transmembrane protein comprises or is one of SEQ ID NO: 19, 83, 85, 87, or 89 (shown below).

```
Exemplary Chimeric Transmembrane Protein
                                        (SEQ ID NO: 19)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSSGGGSGGGGSGGGGSGGGGSGGGSLQITCPPPMSVE

HADIWVKSYSLYSRERYICNSGFKRKAGTSSLTECVLNKATNVAHWTTPS

LKCIRDPALVHQRPAPPSTVTTAGVTPQPESLSPSGKEPAASSPSSNNTA

ATTAAIVPGSQLMPSKSPSTGTTEISSHESSHGTPSQTTAKNWELTASAS

HQPPGVYPQGHSDTTPILLPPCLTISILSFFSVALLVILACVLWKKRIKP

IVWPSLPDHKKTLEHLCKKPRKNLNVSFNPESFLDCQIHRVDDIQARDEV

EGFLQDTFPQQLEESEKQRLGGDVQSPNCPSEDVVITPESFGRDSSLTCL

AGNVSACDAPILSSSRSLDCRESGKNGPHVYQDLLLSLGTTNSTLPPPFS

LQSGILTLNPVAQGQPILTSLGSNQEEAYVTMSSFYQNQ

Nucleic Acid Encoding Exemplary Chimeric
Transmembrane Protein
                                        (SEQ ID NO: 20)
aactgggtgaatgtgatcagcgacctgaagaagatcgaggatctgatcca

gagcatgcacattgatgccaccctgtacacagaatctgatgtgcacccta

gctgtaaagtgaccgccatgaagtgttttctgctggagctgcaggtgatt

tctctggaaagcggagatgcctctatccacgacacagtggagaatctgat

catcctggccaacaatagcctgagcagcaatggcaatgtgacagagtctg

gctgtaaggagtgtgaggagctggaggagaagaacatcaaggagtttctg
```

-continued cagagctttgtgcacatcgtgcagatgttcatcaatacaagcagcggtgg
gggctcaggcggaggaggctctggcggaggcggaagcgggggagggggct
caggcggcgggtccttgcagattacatgccctcctccaatgtctgtggag
cacgccgatatttgggtgaagtcctacagcctgtacagcagagagagata
catctgcaacagcggctttaagagaaaggccggcacctcttctctgacag
agtgcgtgctgaataaggccacaaatgtggcccactggacaacacctagc
ctgaagtgcattagagatcctgccctggtccaccagaggcctgcccctcc
atctacagtgacaacagccggagtgacacctcagcctgaatctctgagcc
cttctggaaaagaacctgccgccagctctcctagctctaataataccgcc
gccacaacagccgccattgtgcctggatctcagctgatgcctagcaagtc
tcctagcacaggcacaacagagatcagcagccacgaatcttctcacggaa
caccttctcagaccaccgccaagaattgggagctgacagcctctgcctct
caccagcctccaggagtgtatcctcagggccactctgatacaacacccat
cctgctgccaccctgtttaaccatcagcatcctgagcttcttcagcgtgg
ccctgctggtgatcctggcctgcgtgctgtggaagaagaggatcaagccc
atcgtgtggcccagcctgcccgaccacaagaagaccctggagcacctgtg
taagaagcccaggaagaacctgaacgtgagcttcaaccccgagagcttcc
tggactgccagatccacagggtggacgacatccaggccagggacgaggtg
gagggcttcctgcaggacaccttcccccagcagctggaggagagcgagaa
gcagaggctgggcggcgacgtgcagagccccaactgccccagcgaggacg
tggtgatcacccccgagagcttcggcagggacagcagcctgacctgcctg
gccggcaacgtgagcgcctgcgacgcccccatcctgagcagcagcaggag
cctggactgcagggagagcggcaagaacggcccccacgtgtaccaggacc
tgctgctgagcctgggcaccaccaacagcaccctgccacccccccttcagc
ctgcagagcggcatcctgaccctgaaccccgtggcccagggccagcccat
cctgaccagcctgggcagcaaccaggaggaggcctacgtgaccatgagca
gcttctaccagaaccag Exemplary Chimeric Transmembrane Protein (SEQ ID NO: 83)

NWVNVISDLKKIEDLIQSMHIDATLYTESDVHPSCKVTAMKCFLLELQVI
SLESGDASIHDTVENLIILANNSLSSNGNVTESGCKECEELEEKNIKEFL
QSFVHIVQMFINTSSGGGSGGGGSGGGGSGGGGSGGGSLQITCPPPMSVE
HADIWVKSYSLYSRERYICNSGFKRKAGTSSLTECVLNKATNVAHWTTPS
LKCIRDPALVHQRPAPPSTVTTAGVTPQPESLSPSGKEPAASSPSSNNTA
ATTAAIVPGSQLMPSKSPSTGTTEISSHESSHGTPSQTTAKNWELTASAS
HQPPGVYPQGHSDTTPILLTCPTISILSFFSVALLVILACVLWKKRIKPI
VWPSLPDHKKTLEHLCKKPRKNLNVSFNPESFLDCQIHRVDDIQARDEVE
GFLQDTFPQQLEESEKQRLGGDVQSPNCPSEDVVITPESFGRDSSLTCLA
GNVSACDAPILSSSRSLDCRESGKNGPHVYQDLLLSLGTTNSTLPPPFSL
QSGILTLNPVAQGQPILTSLGSNQEEAYVTMSSFYQNQ

-continued

Nucleic Acid Encoding Exemplary Chimeric Transmembrane Protein (SEQ ID NO: 84)

aactgggtgaatgtgatcagcgacctgaagaagatcgaggatctgatcca
gagcatgcacattgatgccaccctgtacacagaatctgatgtgcaccccta
gctgtaaagtgaccgccatgaagtgttttctgctggagctgcaggtgatt
tctctggaaagcggagatgcctctatccacgacacagtggagaatctgat
catcctggccaacaatagcctgagcagcaatggcaatgtgacagagtctg
gctgtaaggagtgtgaggagctggaggagaagaacatcaaggagtttctg
cagagctttgtgcacatcgtgcagatgttcatcaatacaagcagcggtgg
gggctcaggcggaggaggctctggcggaggcggaagcgggggagggggct
caggcggcgggtccttgcagattacatgccctcctccaatgtctgtggag
cacgccgatatttgggtgaagtcctacagcctgtacagcagagagagata
catctgcaacagcggctttaagagaaaggccggcacctcttctctgacag
agtgcgtgctgaataaggccacaaatgtggcccactggacaacacctagc
ctgaagtgcattagagatcctgccctggtccaccagaggcctgcccctcc
atctacagtgacaacagccggagtgacacctcagcctgaatctctgagcc
cttctggaaaagaacctgccgccagctctcctagctctaataataccgcc
gccacaacagccgccattgtgcctggatctcagctgatgcctagcaagtc
tcctagcacaggcacaacagagatcagcagccacgaatcttctcacggaa
caccttctcagaccaccgccaagaattgggagctgacagcctctgcctct
caccagcctccaggagtgtatcctcagggccactctgatacaacacccat
cctgctgacctgccccaccatcagcatcctgagcttcttcagcgtggccc
tgctggtgatcctggcctgcgtgctgtggaagaagaggatcaagcccatc
gtgtggcccagcctgcccgaccacaagaagaccctggagcacctgtgtaa
gaagcccaggaagaacctgaacgtgagcttcaaccccgagagcttcctgg
actgccagatccacagggtggacgacatccaggccagggacgaggtggag
ggcttcctgcaggacaccttcccccagcagctggaggagagcgagaagca
gaggctgggcggcgacgtgcagagccccaactgccccagcgaggacgtgg
tgatcacccccgagagcttcggcagggacagcagcctgacctgcctggcc
ggcaacgtgagcgcctgcgacgcccccatcctgagcagcagcaggagcct
ggactgcagggagagcggcaagaacggcccccacgtgtaccaggacctgc
tgctgagcctgggcaccaccaacagcaccctgccacccccccttcagcctg
cagagcggcatcctgaccctgaaccccgtggcccagggccagcccatcct
gaccagcctgggcagcaaccaggaggaggcctacgtgaccatgagcagct
tctaccagaaccag Exemplary Chimeric Transmembrane Protein (SEQ ID NO: 85)

NWVNVISDLKKIEDLIQSMHIDATLYTESDVHPSCKVTAMKCFLLELQVI
SLESGDASIHDTVENLIILANNSLSSNGNVTESGCKECEELEEKNIKEFL
QSFVHIVQMFINTSSGGGSGGGGSGGGGSGGGGSGGGSLQITCPPPMSVE
HADIWVKSYSLYSRERYICNSGFKRKAGTSSLTECVLNKATNVAHWTTPS
LKCIRDPALVHQRPAPPSTVTTAGVTPQPESLSPSGKEPAASSPSSNNTA

-continued

ATTAAIVPGSQLMPSKSPSTGTTEISSHESSHGTPSQTTAKNWELTASAS

HQPPGVYPQGHSDTTPILLMCPTISILSFFSVALLVILACVLWKKRIKPI

VWPSLPDHKKTLEHLCKKPRKNLNVSFNPESFLDCQIHRVDDIQARDEVE

GFLQDTFPQQLEESEKQRLGGDVQSPNCPSEDVVITPESFGRDSSLTCLA

GNVSACDAPILSSSRSLDCRESGKNGPHVYQDLLLSLGTTNSTLPPPFSL

QSGILTLNPVAQGQPILTSLGSNQEEAYVTMSSFYQNQ

Nucleic Acid Encoding Exemplary Chimeric Transmembrane Protein (SEQ ID NO: 86)

aactgggtgaatgtgatcagcgacctgaagaagatcgaggatctgatcca gagcatgcacattgatgccaccctgtacacagaatctgatgtgcacccta gctgtaaagtgaccgccatgaagtgttttctgctggagctgcaggtgatt tctctggaaagcggagatgcctctatccacgacacagtggagaatctgat catcctggccaacaatagcctgagcagcaatggcaatgtgacagagtctg gctgtaaggagtgtgaggagctggaggagaagaacatcaaggagtttctg cagagctttgtgcacatcgtgcagatgttcatcaatacaagcagcggtgg gggctcaggcggaggaggctctggcggaggcggaagcgggggagggggct caggcggcgggtccttgcagattacatgccctcctccaatgtctgtggag cacgccgatatttgggtgaagtcctacagcctgtacagcagagagagata catctgcaacagcggctttaagagaaaggccggcacctcttctctgacag agtgcgtgctgaataaggccacaaatgtggcccactggacaacacctagc ctgaagtgcattagagatcctgccctggtccaccagaggcctgcccctcc atctacagtgacaacagccggagtgacacctcagcctgaatctctgagcc cttctggaaaagaacctgccgccagctctcctagctctaataataccgcc gccacaacagccgccattgtgcctggatctcagctgatgcctagcaagtc tcctagcacaggcacaacagagatcagcagccacgaatcttctcacggaa caccttctcagaccaccgccaagaattgggagctgacagcctctgcctct caccagcctccaggagtgtatcctcagggccactctgatacaacacccat cctgctgatgtgccccaccatcagcatcctgagcttcttcagcgtggccc tgctggtgatcctggcctgcgtgctgtggaagaagaggatcaagcccatc gtgtggcccagcctgcccgaccacaagaagaccctggagcacctgtgtaa gaagcccaggaagaacctgaacgtgagcttcaaccccgagagcttcctgg actgccagatccacagggtggacgacatccaggccagggacgaggtggag ggcttcctgcaggacaccttcccccagcagctggaggagagcgagaagca gaggctgggcggcgacgtgcagagccccaactgccccagcgaggacgtgg tgatcacccccgagagcttcggcagggacagcagcctgacctgcctggcc ggcaacgtgagcgcctgcgacgcccccatcctgagcagcagcaggagcct ggactgcagggagagcggcaagaacggcccccacgtgtaccaggacctgc tgctgagcctgggcaccaccaacagcaccctgccaccccccttcagcctg cagagcggcatcctgaccctgaaccccgtggcccagggccagcccatcct gaccagcctgggcagcaaccaggaggaggcctacgtgaccatgagcagct tctaccagaaccag Exemplary Chimeric Transmembrane Protein (SEQ ID NO: 87)

NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSSGGGSGGGGSGGGGSGGGGSGGGSLQITCPPPMSVE

HADIWVKSYSLYSRERYICNSGFKRKAGTSSLTECVLNKATNVAHWTTPS

LKCIRDPALVHQRPAPPSTVTTAGVTPQPESLSPSGKEPAASSPSSNNTA

ATTAAIVPGSQLMPSKSPSTGTTEISSHESSHGTPSQTTAKNWELTASAS

HQPPGVYPQGHSDTTPILLTISILSFFSVEKAVILACVLWKKRIKPIVWP

SLPDHKKTLEHLCKKPRKNLNVSFNPESFLDCQIHRVDDIQARDEVEGFL

QDTFPQQLEESEKQRLGGDVQSPNCPSEDVVITPESFGRDSSLTCLAGNV

SACDAPILSSSRSLDCRESGKNGPHVYQDLLLSLGTTNSTLPPPFSLQSG

ILTLNPVAQGQPILTSLGSNQEEAYVTMSSFYQNQ

Nucleic Acid Encoding Exemplary Chimeric Transmembrane Protein (SEQ ID NO: 88)

aactgggtgaatgtgatcagcgacctgaagaagatcgaggatctgatcca gagcatgcacattgatgccaccctgtacacagaatctgatgtgcacccta gctgtaaagtgaccgccatgaagtgttttctgctggagctgcaggtgatt tctctggaaagcggagatgcctctatccacgacacagtggagaatctgat catcctggccaacaatagcctgagcagcaatggcaatgtgacagagtctg gctgtaaggagtgtgaggagctggaggagaagaacatcaaggagtttctg cagagctttgtgcacatcgtgcagatgttcatcaatacaagcagcggtgg gggctcaggcggaggaggctctggcggaggcggaagcgggggagggggct caggcggcgggtccttgcagattacatgccctcctccaatgtctgtggag cacgccgatatttgggtgaagtcctacagcctgtacagcagagagagata catctgcaacagcggctttaagagaaaggccggcacctcttctctgacag agtgcgtgctgaataaggccacaaatgtggcccactggacaacacctagc ctgaagtgcattagagatcctgccctggtccaccagaggcctgcccctcc atctacagtgacaacagccggagtgacacctcagcctgaatctctgagcc cttctggaaaagaacctgccgccagctctcctagctctaataataccgcc gccacaacagccgccattgtgcctggatctcagctgatgcctagcaagtc tcctagcacaggcacaacagagatcagcagccacgaatcttctcacggaa caccttctcagaccaccgccaagaattgggagctgacagcctctgcctct caccagcctccaggagtgtatcctcagggccactctgatacaacacccat cctgctgaccatcagcatcctgagcttcttcagcgtggagaaggccgtga tcctggcctgcgtgctgtggaagaagaggatcaagcccatcgtgtggccc agcctgcccgaccacaagaagaccctggagcacctgtgtaagaagcccag gaagaacctgaacgtgagcttcaaccccgagagcttcctggactgccaga tccacagggtggacgacatccaggccagggacgaggtggagggcttcctg caggacaccttcccccagcagctggaggagagcgagaagcagaggctggg cggcgacgtgcagagccccaactgccccagcgaggacgtggtgatcaccc ccgagagcttcggcagggacagcagcctgacctgcctggccggcaacgtg -continued

```
agcgcctgcgacgcccccatcctgagcagcagcaggagcctggactgcag

ggagagcggcaagaacggcccccacgtgtaccaggacctgctgctgagcc

tgggcaccaccaacagcaccctgccaccccccttcagcctgcagagcggc

atcctgaccctgaaccccgtggcccagggccagcccatcctgaccagcct

gggcagcaaccaggaggaggcctacgtgaccatgagcagcttctaccaga

accag
```

Exemplary Chimeric Transmembrane Protein (SEQ ID NO: 89)

```
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSSGGGSGGGGSGGGGSGGGGSGGGSLQITCPPPMSVE

HADIWVKSYSLYSRERYICNSGFKRKAGTSSLTECVLNKATNVAHWTTPS

LKCIRDPALVHQRPAPPSTVTTAGVTPQPESLSPSGKEPAASSPSSNNTA

ATTAAIVPGSQLMPSKSPSTGTTEISSHESSHGTPSQTTAKNWELTASAS

HQPPGVYPQGHSDTTPILLTISILSFFSVEKVVILACVLWKKRIKPIVWP

SLPDHKKTLEHLCKKPRKNLNVSFNPESFLDCQIHRVDDIQARDEVEGFL

QDTFPQQLEESEKQRLGGDVQSPNCPSEDVVITPESFGRDSSLTCLAGNV

SACDAPILSSSRSLDCRESGKNGPHVYQDLLLSLGTTNSTLPPPFSLQSG

ILTLNPVAQGQPILTSLGSNQEEAYVTMSSFYQNQ
```

Nucleic Acid Encoding Exemplary Chimeric Transmembrane Protein (SEQ ID NO: 90)

```
aactgggtgaatgtgatcagcgacctgaagaagatcgaggatctgatcca

gagcatgcacattgatgccaccctgtacacagaatctgatgtgcacccta

gctgtaaagtgaccgccatgaagtgttttctgctggagctgcaggtgatt

tctctggaaagcggagatgcctctatccacgacacagtggagaatctgat

catcctggccaacaatagcctgagcagcaatggcaatgtgacagagtctg

gctgtaaggagtgtgaggagctggaggagaagaacatcaaggagtttctg

cagagctttgtgcacatcgtgcagatgttcatcaatacaagcagcggtgg

gggctcaggcggaggaggctctggcggaggcggaagcgggggaggggggct

caggcggcgggtccttgcagattacatgccctcctccaatgtctgtggag

cacgccgatatttgggtgaagtcctacagcctgtacagcagagagagata

catctgcaacagcggctttaagagaaaggccggcacctcttctctgacag

agtgcgtgctgaataaggccacaaatgtggcccactggacaacacctagc

ctgaagtgcattagagatcctgccctggtccaccagaggcctgcccctcc

atctacagtgacaacagccggagtgacacctcagcctgaatctctgagcc

cttctggaaaagaacctgccgccagctctcctagctctaataataccgcc

gccacaacagccgccattgtgcctggatctcagctgatgcctagcaagtc

tcctagcacaggcacaacagagatcagcagccacgaatcttctcacggaa

caccttctcagaccaccgccaagaattgggagctgacagcctctgcctct

caccagcctccaggagtgtatcctcagggccactctgatacaacacccat

cctgctgaccatcagcatcctgagcttcttcagcgtggagaaggtggtga

tcctggcctgcgtgctgtggaagaagaggatcaagcccatcgtgtggccc

agcctgcccgaccacaagaagaccctggagcacctgtgtaagaagcccag

gaagaacctgaacgtgagcttcaaccccgagagcttcctggactgccaga

tccacagggtggacgacatccaggccagggacgaggtggagggcttcctg

caggacaccttcccccagcagctggaggagagcgagaagcagaggctggg

cggcgacgtgcagagccccaactgccccagcgaggacgtggtgatcaccc

ccgagagcttcggcagggacagcagcctgacctgcctggccggcaacgtg

agcgcctgcgacgcccccatcctgagcagcagcaggagcctggactgcag

ggagagcggcaagaacggcccccacgtgtaccaggacctgctgctgagcc

tgggcaccaccaacagcaccctgccaccccccttcagcctgcagagcggc

atcctgaccctgaaccccgtggcccagggccagcccatcctgaccagcct

gggcagcaaccaggaggaggcctacgtgaccatgagcagcttctaccaga

accag
```

In some embodiments, the chimeric transmembrane protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 19, 83, 85, 87, or 89. In some embodiments, a chimeric transmembrane protein includes a sequence that differs from SEQ ID NO: 19, 83, 85, 87, or 89 by one to about 100 amino acids (e.g., 1 to about 95 amino acids, 1 to about 90 amino acids, 1 to about 80 amino acids, 1 to about 75 amino acids, 1 to about 70 amino acids, 1 to about 65 amino acids, 1 to about 60 amino acids, 1 to about 55 amino acids, 1 to about 50 amino acids, 1 to about 45 amino acids, 1 to about 40 amino acids, 1 to about 35 amino acids, 1 to about 30 amino acids, 1 to about 25 amino acids, 1 to about 20 amino acids, 1 to about 15 amino acids, 1 to about 10 amino acids, 1 to about 5 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, or about 5 amino acids to about 10 amino acids). In some embodiments, a chimeric transmembrane protein includes 1 to about 300 additional amino acids (e.g., 1 to about 250 amino acids, 1 to about 200 amino acids, 1 to about 150 amino acids, 1 to about 100 amino acids, 1 to about 50 amino acids, 1 to about 25 amino acids, about 5 to about 300 amino acids, about 5 to about 250 amino acids, about 5 to about 200 amino acids, about 5 to about 150 amino acids, about 5 to about 100 amino acids, about 5 to about 50 amino acids, about 10 to about 300 amino acids, about 10 to about 250 amino acids, about 10 to about 200 amino acids, about 10 to about 150 amino acids, about 10 to about 100 amino acids, or about 10 to about 50 amino acids), e.g., in addition to the sequence of SEQ ID NO: 19, 83, 85, 87, or 89. In some embodiments, the chimeric transmembrane protein comprises a sequence of SEQ ID NO: 19, 83, 85, 97, or 89 having one to twenty amino acids (e.g., 1, 2, 3, 4, 5, 6, 7, 8, 9, 10, 11, 12, 13, 14, 15, 16, 17, 18, 19, or 20 amino acids) removed from the N-terminus of SEQ ID NO: 19, 83, 85, 87, or 89 and/or one to twenty amino acids (e.g., 1, 2, 3, 4, 5, 6, 7, 8, 9, 10, 11, 12, 13, 14, 15, 16, 17, 18, 19, or 20 amino acids) removed from the C-terminus of SEQ ID NO: 19, 83, 85, 87, or 89.

In some embodiments, a nucleic acid encoding a chimeric transmembrane protein comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 20, 84, 86, 88, or 90. In some embodiments, a nucleic acid encoding a chimeric transmembrane protein includes a sequence that differs from SEQ ID NO: 20, 84, 86, 88, or 90 by 1 to about 300 nucleotides (e.g., 1 to about 250 nucleotides, 1 to about 200 nucleotides, 1 to about 150 nucleotides, 1 to about 100 nucleotides, 1 to about 50 nucleotides, about 5 nucleotides to about 300 nucleotides, about 5 nucleotides to about 250 nucleotides, about 5 nucleotides to about 200 nucleotides, about 5 nucleotides to about 150 nucleotides, about 5 nucleotides to about 100 nucleotides, about 5 nucleotides to about 50 nucleotides, about 10 nucleotides to about 300 nucleotides, about 10 nucleotides to about 250 nucleotides, about 10 nucleotides to about 200 nucleotides, about 10 nucleotides to about 150 nucleotides, about 10 nucleotides to about 100 nucleotides, or about 10 nucleotides to about 50 nucleotides). In some embodiments, a nucleic acid encoding a chimeric transmembrane protein includes one or more additional nucleotides (e.g., 1 to about 900 nucleotides, 1 to about 850 nucleotides, 1 to about 800 nucleotides, 1 to about 750 nucleotides, 1 to about 700 nucleotides, 1 to about 650 nucleotides, 1 to about 600 nucleotides, 1 to about 550 nucleotides, 1 to about 500 nucleotides, 1 to about 450 nucleotides, 1 to about 400 nucleotides, 1 to about 350 nucleotides, 1 to about 300 nucleotides, 1 to about 250 nucleotides, 1 to about 200 nucleotides, 1 to about 150 nucleotides, 1 to about 100 nucleotides, or 1 to about 50 nucleotides), e.g., in addition to SEQ ID NO: 20, 84, 86, 88, or 90. Additionally or alternatively, a nucleic acid encoding the chimeric transmembrane protein can lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 20, 84, 86, 88, or 90 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 20, 84, 86, 88, or 90.

In some embodiments, the chimeric transmembrane protein (e.g., mature or precursor protein) can be about 210 amino acids to about 650 amino acids, about 210 amino acids to about 640 amino acids, about 210 amino acids to about 620 amino acids, about 210 amino acids to about 600 amino acids, about 210 amino acids to about 580 amino acids, about 210 amino acids to about 560 amino acids, about 210 amino acids to about 540 amino acids, about 210 amino acids to about 520 amino acids, about 210 amino acids to about 500 amino acids, about 210 amino acids to about 480 amino acids, about 210 amino acids to about 460 amino acids, about 210 amino acids to about 440 amino acids, about 210 amino acids to about 420 amino acids, about 210 amino acids to about 400 amino acids, about 210 amino acids to about 380 amino acids, about 210 amino acids to about 360 amino acids, about 210 amino acids to about 340 amino acids, about 210 amino acids to about 320 amino acids, about 210 amino acids to about 300 amino acids, about 210 amino acids to about 280 amino acids, about 210 amino acids to about 260 amino acids, about 210 amino acids to about 240 amino acids, about 220 amino acids to about 650 amino acids, about 220 amino acids to about 640 amino acids, about 220 amino acids to about 620 amino acids, about 220 amino acids to about 600 amino acids, about 220 amino acids to about 580 amino acids, about 220 amino acids to about 560 amino acids, about 220 amino acids to about 540 amino acids, about 220 amino acids to about 520 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 650 amino acids, about 240 amino acids to about 640 amino acids, about 240 amino acids to about 620 amino acids, about 240 amino acids to about 600 amino acids, about 240 amino acids to about 580 amino acids, about 240 amino acids to about 560 amino acids, about 240 amino acids to about 540 amino acids, about 240 amino acids to about 520 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 650 amino acids, about 260 amino acids to about 640 amino acids, about 260 amino acids to about 620 amino acids, about 260 amino acids to about 600 amino acids, about 260 amino acids to about 580 amino acids, about 260 amino acids to about 560 amino acids, about 260 amino acids to about 540 amino acids, about 260 amino acids to about 520 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 650 amino acids, about 280 amino acids to about 640 amino acids, about 280 amino acids to about 620 amino acids, about 280 amino acids to about 600 amino acids, about 280 amino acids to about 580 amino acids, about 280 amino acids to about 560 amino acids, about 280 amino acids to about 540 amino acids, about 280 amino acids to about 520 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 650 amino acids, about 300 amino acids to about 640 amino acids, about 300 amino acids to about 620 amino acids, about 300 amino acids to about 600 amino acids, about 300 amino acids to about 580 amino acids, about 300 amino acids to about 560 amino acids, about 300 amino acids to about 540 amino acids, about 300 amino acids to about 520 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 650 amino acids, about 320 amino acids to about 640 amino acids, about 320 amino acids to about 620 amino acids, about 320 amino acids to about 600 amino acids, about 320 amino acids to about 580 amino acids, about 320 amino acids to about 560 amino acids, about 320 amino acids to about 540 amino acids, about 320 amino acids to about 520 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 650 amino acids, about 340 amino acids to about 640 amino acids, about 340 amino acids to about 620 amino acids, about 340 amino acids to about 600 amino acids, about 340 amino acids to about 580 amino acids, about 340 amino acids to about 560 amino acids, about 340 amino acids to about 540 amino acids, about 340 amino acids to about 520 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 650 amino acids, about 360 amino acids to about 640 amino acids, about 360 amino acids to about 620 amino acids, about 360 amino acids to about 600 amino acids, about 360 amino acids to about 580 amino acids, about 360 amino acids to about 560 amino acids, about 360 amino acids to about 540 amino acids, about 360 amino acids to about 520 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 650 amino acids, about 380 amino acids to about 640 amino acids, about 380 amino acids to about 620 amino acids, about 380 amino acids to about 600 amino acids, about 380 amino acids to about 580 amino acids, about 380 amino acids to about 560 amino acids, about 380 amino acids to about 540 amino acids, about 380 amino acids to about 520 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 650 amino acids, about 400 amino acids to about 640 amino acids, about 400 amino acids to about 620 amino acids, about 400 amino acids to about 600 amino acids, about 400 amino acids to about 580 amino acids, about 400 amino acids to about 560 amino acids, about 400 amino acids to about 540 amino acids, about 400 amino acids to about 520 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 650 amino acids, about 420 amino acids to about 640 amino acids, about 420 amino acids to about 620 amino acids, about 420 amino acids to about 600 amino acids, about 420 amino acids to about 580 amino acids, about 420 amino acids to about 560 amino acids, about 420 amino acids to about 540 amino acids, about 420 amino acids to about 520 amino acids, about 420 amino acids to about 500 amino acids, about 420 amino acids to about 480 amino acids, about 420 amino acids to about 460 amino acids, about 420 amino acids to about 440 amino acids, about 440 amino acids to about 650 amino acids, about 440 amino acids to about 640 amino acids, about 440 amino acids to about 620 amino acids, about 440 amino acids to about 600 amino acids, about 440 amino acids to about 580 amino acids, about 440 amino acids to about 560 amino acids, about 440 amino acids to about 540 amino acids, about 440 amino acids to about 520 amino acids, about 440 amino acids to about 500 amino acids, about 440 amino acids to about 480 amino acids, about 440 amino acids to about 460 amino acids, about 460 amino acids to about 650 amino acids, about 460 amino acids to about 640 amino acids, about 460 amino acids to about 620 amino acids, about 460 amino acids to about 600 amino acids, about 460 amino acids to about 580 amino acids, about 460 amino acids to about 560 amino acids, about 460 amino acids to about 540 amino acids, about 460 amino acids to about 520 amino acids, about 460 amino acids to about 500 amino acids, about 460 amino acids to about 480 amino acids, about 480 amino acids to about 650 amino acids, about 480 amino acids to about 640 amino acids, about 480 amino acids to about 620 amino acids, about 480 amino acids to about 600 amino acids, about 480 amino acids to about 580 amino acids, about 480 amino acids to about 560 amino acids, about 480 amino acids to about 540 amino acids, about 480 amino acids to about 520 amino acids, about 480 amino acids to about 500 amino acids, about 500 amino acids to about 650 amino acids, about 500 amino acids to about 640 amino acids, about 500 amino acids to about 620 amino acids, about 500 amino acids to about 600 amino acids, about 500 amino acids to about 580 amino acids, about 500 amino acids to about 560 amino acids, about 500 amino acids to about 540 amino acids, about 500 amino acids to about 520 amino acids, about 520 amino acids to about 650 amino acids, about 520 amino acids to about 640 amino acids, about 520 amino acids to about 620 amino acids, about 520 amino acids to about 600 amino acids, about 520 amino acids to about 580 amino acids, about 520 amino acids to about 560 amino acids, about 520 amino acids to about 540 amino acids, about 540 amino acids to about 650 amino acids, about 540 amino acids to about 640 amino acids, about 540 amino acids to about 620 amino acids, about 540 amino acids to about 600 amino acids, about 540 amino acids to about 580 amino acids, about 540 amino acids to about 560 amino acids, about 560 amino acids to about 650 amino acids, about 560 amino acids to about 640 amino acids, about 560 amino acids to about 620 amino acids, about 560 amino acids to about 600 amino acids, about 560 amino acids to about 580 amino acids, about 580 amino acids to about 650 amino acids, about 580 amino acids to about 640 amino acids, about 580 amino acids to about 620 amino acids, about 580 amino acids to about 600 amino acids, about 600 amino acids to about 650 amino acids, about 600 amino acids to about 640 amino acids, about 600 amino acids to about 620 amino acids, about 620 amino acids to about 650 amino acids, about 620 amino acids to about 640 amino acids, or about 630 amino acids to about 650 amino acids, in length.

In some embodiments, the chimeric transmembrane protein further comprises a signal sequence at its N-terminus. In some embodiments, the signal sequence comprises or is the sequence of MDWTWILFLVAAATRVHS (SEQ ID NO: 21). In some embodiments, the nucleic acid encoding the signal sequence comprises or is the sequence atggattggacctggattctgtttctggtggccgctgccacaagagtgcacagc (SEQ ID NO: 91). Additional examples of signal sequences are known in the art. For example, a signal sequence can be about 5 amino acids to about 30 amino acids, about 5 amino acids to about 28 amino acids, about 5 amino acids to about 26 amino acids, about 5 amino acids to about 24 amino acids, about 5 amino acids to about 22 amino acids, about 5 amino acids to about 20 amino acids, about 5 amino acids to about 18 amino acids, about 5 amino acids to about 16 amino acids, about 5 amino acids to about 14 amino acids, about 5 amino acids to about 12 amino acids, about 5 amino acids to about 10 amino acids, about 5 amino acids to about 8 amino acids, about 6 amino acids to about 30 amino acids, about 6 amino acids to about 28 amino acids, about 6 amino acids to about 26 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 30 amino acids, about 8 amino acids to about 28 amino acids, about 8 amino acids to about 26 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 30 amino acids, about 10 amino acids to about 28 amino acids, about 10 amino acids to about 26 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 30 amino acids, about 12 amino acids to about 28 amino acids, about 12 amino acids to about 26 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 30 amino acids, about 14 amino acids to about 28 amino acids, about 14 amino acids to about 26 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 30 amino acids, about 16 amino acids to about 28 amino acids, about 16 amino acids to about 26 amino acids, about 16 amino acids to about 24 amino acids, about 16 amino acids to about 22 amino acids, about 16 amino acids to about 20 amino acids, about 16 amino acids to about 18 amino acids, about 18 amino acids to about 30 amino acids, about 18 amino acids to about 28 amino acids, about 18 amino acids to about 26 amino acids, about 18 amino acids to about 24 amino acids, about 18 amino acids to about 22 amino acids, about 18 amino acids to about 20 amino acids, about 20 amino acids to about 30 amino acids, about 20 amino acids to about 28 amino acids, about 20 amino acids to about 26 amino acids, about 20 amino acids to about 24 amino acids, about 20 amino acids to about 22 amino acids, about 22 amino acids to about 30 amino acids, about 22 amino acids to about 28 amino acids, about 22 amino acids to about 26 amino acids, about 22 amino acids to about 24 amino acids, about 24 amino acids to about 30 amino acids, about 24 amino acids to about 28 amino acids, about 24 amino acids to about 26 amino acids, about 26 amino acids to about 30 amino acids, about 26 amino acids to about 28 amino acids, or about 28 amino acids to about 30 amino acids, in length.

In some embodiments, the chimeric transmembrane protein can further include a peptide tag. For example, a tag can be used to help facilitate purification, production, and/or identification of the chimeric transmembrane protein. In some embodiments, the tag is a histidine tag comprising at least six histidine residues. Additional examples of tags are known in the art.

Non-limiting aspects of any of the chimeric transmembrane proteins provided herein are described below.

Extracellular IL-15 Domains

In some embodiments of any of the chimeric transmembrane proteins described herein, the extracellular IL-15 domain comprises or is a sequence of a wildtype IL-15 protein (e.g., a mature wildtype IL-15 protein). For example, the wildtype IL-15 protein can be a wildtype human IL-15 protein (e.g., a mature wildtype human IL-2 protein), a wildtype mouse IL-15 protein (e.g., a mature wildtype mouse IL-15 protein), a wildtype chimpanzee IL-15 protein (e.g., a mature wildtype chimpanzee IL-15 protein), or a wildtype monkey IL-15 protein (e.g., a mature wildtype monkey IL-15 protein). Non-limiting examples of wildtype IL-15 protein sequences and nucleic acids encoding these exemplary IL-15 protein sequences are provided below.

Exemplary Human IL-15 Isoform 1
(SEQ ID NO: 22)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Nucleic Acid Encoding Human IL-15 Isoform 1
(SEQ ID NO: 23)
aactgggtgaatgtaataagtgatttgaaaaaaattgaagatcttattca atctatgcatattgatgctactttatatacggaaagtgatgttcacccca gttgcaaagtaacagcaatgaagtgctttctcttggagttacaagttatt tcacttgagtccggagatgcaagtattcatgatacagtagaaaatctgat catcctagcaaacaacagtttgtcttctaatgggaatgtaacagaatctg gatgcaaagaatgtgaggaactggaggaaaaaaatattaaagaatttttg cagagttttgtacatattgtccaaatgttcatcaacacttct Exemplary Human IL-15 Isoform 2
(SEQ ID NO: 24)
MVLGTIDLCSCFSAGLPKTEANWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS

Nucleic Acid Encoding Human IL-15 Isoform 2
(SEQ ID NO: 25)
atggtattgggaaccatagatttgtgcagctgtttcagtgcagggcttcc taaaacagaagccaactgggtgaatgtaataagtgatttgaaaaaaattg aagatcttattcaatctatgcatattgatgctactttatatacggaaagt gatgttcaccccagttgcaaagtaacagcaatgaagtgctttctcttgga gttacaagttatttcacttgagtccggagatgcaagtattcatgatacag tagaaaatctgatcatcctagcaaacaacagtttgtcttctaatgggaat gtaacagaatctggatgcaaagaatgtgaggaactggaggaaaaaaatat taaagaatttttgcagagttttgtacatattgtccaaatgttcatcaaca cttcttga Exemplary Mouse IL-15 Variant A
(SEQ ID NO: 26)
NWIDVRYDLEKIESLIQSIHIDTTLYTDSDFHPSCKVTAMNCFLLELQVI

LHEYSNMTLNETVRNVLYLANSTLSSNKNVAESGCKECEELEEKTFTEFL

QSFIRIVQMFINTS

Nucleic Acid Encoding Mouse IL-15 Variant A
(SEQ ID NO: 27)
aactggatagatgtaagatatgacctggagaaaattgaaagccttattca atctattcatattgacaccactttatacactgacagtgactttcatccca gttgcaaagttactgcaatgaactgctttctcctggaattgcaggttatt ttacatgagtacagtaacatgactcttaatgaaacagtaagaaacgtgct ctaccttgcaaacagcactctgtcttctaacaagaatgtagcagaatctg gctgcaaggaatgtgaggagctggaggagaaaaccttcacagagtttttg caaagctttatacgcattgtccaaatgttcatcaacacgtcc -continued Exemplary Mouse IL-15 Variant B
(SEQ ID NO: 28)
NWIDVRYDLEKIESLIQSIHIDTTLYTDSDFHPSCKVTAMNCFLLELQVI

LHEYSNMTLNETVRNVLYLANSTLSSNKNVAESGCKECEELEEKTFTEFL

QSFIRIVQMFINTS

Nucleic Acid Encoding Mouse IL-15 Variant B
(SEQ ID NO: 29)
aactggatagatgtaagatatgacctggagaaaattgaaagccttattca atctattcatattgacaccactttatacactgacagtgactttcatccca gttgcaaagttactgcaatgaactgctttctcctggaattgcaggttatt ttacatgagtacagtaacatgactcttaatgaaacagtaagaaacgtgct ctaccttgcaaacagcactctgtcttctaacaagaatgtagcagaatctg gctgcaaggaatgtgaggagctggaggagaaaaccttcacagagtttttg caaagctttatacgcattgtccaaatgttcatcaacacgtcc In some embodiments, the extracellular IL-15 domain comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to a wildtype IL-15 protein (e.g., a wildtype mature IL-15 protein, e.g., SEQ ID NO: 22, 24, 26, or 28). In some embodiments, an extracellular IL-15 domain includes a sequence that differs from SEQ ID NO: 22, 24, 26, or 28 by one to 25 amino acids (e.g., 1, 2, 3, 4, 5, 6, 7, 8, 9, 10, 11, 12, 13, 14, 15, 16, 17, 18, 19, 20, 21, 22, 23, 24, or 25 amino acids). In some embodiments, an extracellular IL-15 domain includes one or more additional amino acids (e.g., 1 to about 100 amino acids, 1 to about 80 amino acids, 1 to about 60 amino acids, 1 to about 40 amino acids, 1 to about 20 amino acids, 1 to about 10 amino acids, about 5 to about 100 amino acids, about 5 to about 80 amino acids, about 5 to about 60 amino acids, about 5 to about 40 amino acids, about 5 to about 20 amino acids, about 10 to about 100 amino acids, about 10 to about 80 amino acids, about 10 to about 60 amino acids, about 10 to about 40 amino acids, or about 10 to about 20 amino acids), e.g., in addition to the sequence of SEQ ID NO: 22, 24, 26, or 28. Additionally or alternatively, an extracellular IL-15 domain can lack one to about 25 amino acids (e.g., 1, 2, 3, 4, 5, 6, 7, 8, 9, 10, 11, 12, 13, 14, 15, 16, 17, 18, 19, 20, 21, 22, 23, 24, or 25 amino acids) as compared to the sequence of SEQ ID NO: 22, 24, 26, or 28.

In some embodiments, a nucleic acid encoding an extracellular IL-15 domain comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 23, 25, 27, or 29. In some embodiments, a nucleic acid encoding an extracellular IL-15 domain includes a sequence that differs from SEQ ID NO: 23, 25, 27, or 29 by one to about 75 nucleotides (e.g., 1 to about 70 nucleotides, 1 to about 60 nucleotides, 1 to about 50 nucleotides, 1 to about 40 nucleotides, 1 to about 30 nucleotides, 1 to about 20 nucleotides, 1 to about 10 nucleotides, about 5 nucleotides to about 75 nucleotides, about 5 nucleotides to about 70 nucleotides, about 5 nucleotides to about 60 nucleotides, about 5 nucleotides to about 50 nucleotides, about 5 nucleotides to about 40 nucleotides, about 5 nucleotides to about 30 nucleotides, about 5 nucleotides to about 20 nucleotides, about 5 nucleotides to about 10 nucleotides). In some embodiments, a nucleic acid encoding an extracellular IL-15 domain includes one or more additional nucleotides (e.g., 1 to about 300 nucleotides, 1 to about 250 nucleotides, 1 to about 200 nucleotides, 1 to about 150 nucleotides, 1 to about 100 nucleotides, 1 to about 50 nucleotides, about 5 nucleotides to about 300 nucleotides, about 5 nucleotides to about 250 nucleotides, about 5 nucleotides to about 200 nucleotides, about 5 nucleotides to about 150 nucleotides, about 5 nucleotides to about 100 nucleotides, or about 5 nucleotides to about 50 nucleotides), e.g., in addition to the sequence of SEQ ID NO: 23, 25, 27, or 29. Additionally or alternatively, a nucleic acid encoding the extracellular IL-15 domain can lack one to 75 nucleotides (e.g., 1 to about 70 nucleotides, 1 to about 65 nucleotides, 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 5'-end of SEQ ID NO: 23, 25, 27, or 29 and/or lack one to sixty nucleotides (e.g., 1 to about 60 nucleotides, 1 to about 55 nucleotides, 1 to about 50 nucleotides, 1 to about 45 nucleotides, 1 to 40 nucleotides, 1 to about 35 nucleotides, 1 to about 30 nucleotides, 1 to about 25 nucleotides, 1 to about 20 nucleotides, 1 to about 15 nucleotides, 1 to about 10 nucleotides, or 1 to about 5 nucleotides) from the 3'-end of SEQ ID NO: 23, 25, 27, or 29.

As one skilled in the art can appreciate, when amino acids that are not conserved between wildtype IL-15 proteins from different species are mutated (e.g., substituted with a different amino acid) they are less likely to cause a decrease in the level of one or more activities of an IL-15 protein. In contrast, when amino acids that are conserved between wildtype IL-15 proteins from different species are mutated (e.g., substituted with a different amino acid) they are more likely to cause a decrease in the level of one or more activities of an IL-15 protein. In view of this knowledge, one skilled in the art can select which amino acid positions in a wildtype IL-15 protein (e.g., the non-conserved amino acids) can be substituted without decreasing the activity of the IL-15 protein.

In some embodiments, the extracellular IL-15 domain is a sequence of a wildtype IL-15 protein (e.g., a mature wildtype IL-15 protein, e.g., any of the mature wildtype IL-15 proteins described herein, e.g., SEQ ID NO: 22, SEQ ID NO: 24, SEQ ID NO: 26, or SEQ ID NO: 28) having one to ten (e.g., one, two, three, four, five, six, seven, eight, nine, or ten) amino acids removed from the N-terminus of the sequence of the wildtype IL-15 protein. In some embodiments, the extracellular IL-15 domain is a sequence of a wildtype IL-15 protein (e.g., a mature wildtype IL-15 protein, e.g., any of the mature wildtype IL-15 proteins described herein, e.g., mature wildtype human IL-15 protein, SEQ ID NO: 22, SEQ ID NO: 24, SEQ ID NO: 26, or SEQ ID NO: 28) having one to ten (e.g., one, two, three, four, five, six, seven, eight, nine, or ten) amino acids removed from the C-terminus of the sequence of the wildtype IL-15 protein. In some embodiments, the extracellular IL-15 domain is a sequence of a wildtype IL-15 protein (e.g., a mature wildtype IL-15 protein, e.g., any of the mature wildtype IL-15 proteins described herein, e.g., mature wildtype human IL-15 protein, e.g., SEQ ID NO: 22, SEQ ID NO: 24, SEQ ID NO: 26, or SEQ ID NO: 28) having both one to ten amino (e.g., one, two, three, four, five, six, seven, eight, nine, or ten) acids removed from the N-terminus of the sequence of the wildtype IL-15 protein and one to ten (e.g., one, two, three, four, five, six, seven, eight, nine, or ten) amino acids removed from the C-terminus of the sequence of the wildtype IL-15 protein.

As will be appreciated by those of ordinary skill in the art, when a nucleic acid encoding a chimeric transmembrane protein having an extracellular IL-15 domain includes or lacks one or more additional nucleotides as compared to SEQ ID NO: 23, SEQ ID NO: 25, SEQ ID NO: 27, or SEQ ID NO: 29, the translational reading frame should still be maintained such that a nonsense codon is not introduced and the full protein can be translated (e.g., a nucleic acid encoding a chimeric transmembrane protein having an extracellular IL-15 domain can include or lack three nucleotides, or multiples thereof, within the extracellular IL-15 portion of the chimeric transmembrane protein).

Alpha Chain of an IL-7 Receptor

Some embodiments of the chimeric transmembrane proteins described herein can further include a sequence of an alpha chain of an IL-7 receptor protein, or a portion thereof. For example, chimeric transmembrane proteins described herein can include a sequence of a wildtype alpha chain of an IL-7 receptor protein from a human, a mouse, a rat, a monkey, a chimpanzee, a pig, a dog, a cat, or any other appropriate species, or a portion thereof. Non-limiting examples of wildtype alpha chains of IL-7 receptors are described below. Additional examples of alpha chains of IL-7 receptors are known in the art. In some embodiments, chimeric transmembrane proteins including a sequence of an alpha chain of an IL-7 receptor, or a portion thereof, include a transmembrane domain of an alpha chain of an IL-7 receptor (e.g., any of the transmembrane domains of an alpha chain of an IL-7 receptor described herein).

```
Exemplary Wildtype Human IL-7 Receptor Alpha Chain
                                        (SEQ ID NO: 30)
ESGYAQNGDLEDAELDDYSFSCYSQLEVNGSQHSLTCAFEDPDVNITNLE

FEICGALVEVKCLNFRKLQEIYFIETKKFLLIGKSNICVKVGEKSLTCKK

IDLTTIVKPEAPFDLSVVYREGANDFVVTFNTSHLQKKYVKVLMHDVAYR

QEKDENKWTHVNLSSTKLTLLQRKLQPAAMYEIKVRSIPDHYFKGFWSEW

SPSYYFRTPEINNSSGEMDPILLTISILSFFSVALLVILACVLWKKRIKP

IVWPSLPDHKKTLEHLCKKPRKNLNVSFNPESFLDCQIHRVDDIQARDEV

EGFLQDTFPQQLEESEKQRLGGDVQSPNCPSEDVVITPESFGRDSSLTCL

AGNVSACDAPILSSSRSLDCRESGKNGPHVYQDLLLSLGTTNSTLPPPFS

LQSGILTLNPVAQGQPILTSLGSNQEEAYVTMSSFYQNQ

Nucleic Acid Encoding Wildtype Human IL-7
Receptor Alpha Chain
                                        (SEQ ID NO: 31)
gaaagtggctatgctcaaaatggagacttggaagatgcagaactggatga

ctactcattctcatgctatagccagttggaagtgaatggatcgcagcact

cactgacctgtgcttttgaggacccagatgtcaacatcaccaatctggaa

tttgaaatatgtggggccctcgtggaggtaaagtgcctgaatttcaggaa

actacaagagatatatttcatcgagacaaagaaattcttactgattggaa
```

-continued agagcaatatatgtgtgaaggttggagaaaagagtctaacctgcaaaaaa atagacctaaccactatagttaaacctgaggctccttttgacctgagtgt cgtctatcgggaaggagccaatgactttgtggtgacatttaatacatcac acttgcaaaagaagtatgtaaaagttttaatgcacgatgtagcttaccgc caggaaaaggatgaaaacaaatggacgcatgtgaatttatccagcacaaa gctgacactcctgcagagaaagctccaaccggcagcaatgtatgagatta aagttcgatccatccctgatcactattttaaaggcttctggagtgaatgg agtccaagttattacttcagaactccagagatcaataatagctcagggga gatggatcctatcttactaaccatcagcattttgagtttttttctctgtcg ctctgttggtcatcttggcctgtgtgttatggaaaaaaaggattaagcct atcgtatggcccagtctccccgatcataagaagactctggaacatctttg taagaaaccaagaaaaaatttaaatgtgagtttcaatcctgaaagtttcc tggactgccagattcatagggtggatgacattcaagctagagatgaagtg gaaggttttctgcaagatacgtttcctcagcaactagaagaatctgagaa gcagaggcttggaggggatgtgcagagccccaactgcccatctgaggatg tagtcatcactccagaaagctttggaagagattcatccctcacatgcctg gctgggaatgtcagtgcatgtgacgcccctattctctcctcttccaggtc cctagactgcagggagagtggcaagaatgggcctcatgtgtaccaggacc tcctgcttagccttgggactacaaacagcacgctgccccctccatttct ctccaatctggaatcctgacattgaacccagttgctcagggtcagcccat tcttacttccctgggatcaaatcaagaagaagcatatgtcaccatgtcca gcttctaccaaaaccag Exemplary Wildtype Mouse IL-7 Receptor Alpha Chain Variant 1

(SEQ ID NO: 32)

ESGNAQDGDLEDADADDHSFWCHSQLEVDGSQHLLTCAFNDSDINTANLE

FQICGALLRVKCLTLNKLQDIYFIKTSEFLLIGSSNICVKLGQKNLTCKN

MAINTIVKAEAPSDLKVVYRKEANDFLVTFNAPHLKKKYLKKVKHDVAYR

PARGESNWTHVSLFHTRTTIPQRKLRPKAMYEIKVRSIPHNDYFKGFWSE

WSPSSTFETPEPKNQGGWDPVLPSVTILSLFSVFLLVILAHVLWKKRIKP

VVWPSLPDHKKTLEQLCKKPKTSLNVSFNPESFLDCQIHEVKGVEARDEV

ESFLPNDLPAQPEELETQGHRAAVHSANRSPETSVSPPETVRRESPLRCL

ARNLSTCNAPPLLSSRSPDYRDGDRNRPPVYQDLLPNSGNTNVPVPVPQP

LPFQSGILIPVSQRQPISTSSVLNQEEAYVTMSSFYQNK

Nucleic Acid Encoding Wildtype Mouse IL-7 Receptor Alpha Chain Variant 1

(SEQ ID NO: 33)

gaaagtggaaatgcccaggatggagacctagaagatgcagacgcggacga tcactccttctggtgccacagccagttggaagtggatggaagtcaacatt tattgacttgtgcttttaatgactcagacatcaacacagctaatctggaa tttcaaatatgtggggctcttttacgagtgaaatgcctaactcttaacaa gctgcaagatatatattttataaagacatcagaattcttactgattggta gcagcaatatatgtgtgaagcttggacaaaagaatttaacttgcaaaaat atggctataaacacaatagttaaagccgaggctccctctgacctgaaagt -continued cgtttatcgcaaagaagcaaatgatttttttggtgacatttaatgcacctc acttgaaaaagaaatatttaaaaaaagtaaagcatgatgtggcctaccgc ccagcaaggggtgaaagcaactggacgcatgtatctttattccacacaag aacaacaatcccacagagaaaactacgaccaaaagcaatgtatgaaatca aagtccgatccattccccataacgattacttcaaaggcttctggagcgag tggagtccaagttctaccttcgaaactccagaacccaagaatcaaggagg atgggatcctgtcttgccaagtgtcaccattctgagtttgttctctgtgt ttttgttggtcatcttagcccatgtgctatggaaaaaaaggattaaacct gtcgtatggcctagtctccccgatcataagaaaactctggaacaactatg taagaagccaaaaacgagtctgaatgtgagtttcaatcccgaaagtttcc tggactgccagattcatgaggtgaaaggcgttgaagccagggacgaggtg gaaagttttctgcccaatgatcttcctgcacagccagaggagttggagac acagggacacagagccgctgtacacagtgcaaaccgctcgcctgagactt cagtcagcccaccagaaacagttagaagagagtcacccttaagatgcctg gctagaaatctgagtacctgcaatgcccctccactcctttcctctaggtc ccctgactacagagatggtgacagaaataggcctcctgtgtatcaagact tgctgccaaactctggaaacacaaatgtccctgtccctgtccctcaacca ttgcctttccagtcgggaatcctgataccagtttctcagagacagcccat ctccacttcctcagtactgaatcaagaagaagcgtatgtcaccatgtcta gtttttaccaaaacaaa Exemplary Wildtype Mouse IL-7 Receptor Alpha Chain Variant 2

(SEQ ID NO: 34)

ESGNAQDGDLEDADADDHSFWCHSQLEVDGSQHLLTCAFNDSDINTANLE

FQICGALLRVKCLTLNKLQDIYFIKTSEFLLIGSSNICVKLGQKNLTCKN

MAINTIVKAEAPSDLKVVYRKEANDFLVTFNAPHLKKKYLKKVKHDVAYR

PARGESNWTHVSLFHTRTTIPQRKLRPKAMYEIKVRSIPHNDYFKGFWSE

WSPSSTFETPEPKNQGGWDPVLPSVTILSLFSVFLLVILAHVLWKKRIKP

VVWPSLPDHKKTLEQL

Nucleic Acid Encoding Mouse IL-7 Receptor Alpha Chain Variant 2

(SEQ ID NO: 35)

atgatggctctgggtagagctttcgctatagttttctgcttaattcaagc tgtttctggagaaagtggaaatgcccaggatggagacctagaagatgcag acgcggacgatcactccttctggtgccacagccagttggaagtggatgga agtcaacatttattgacttgtgcttttaatgactcagacatcaacacagc taatctggaatttcaaatatgtggggctcttttacgagtgaaatgcctaa ctcttaacaagctgcaagatatatattttataaagacatcagaattctta ctgattggtagcagcaatatatgtgtgaagcttggacaaaagaatttaac ttgcaaaaatatggctataaacacaatagttaaagccgaggctccctctg acctgaaagtcgtttatcgcaaagaagcaaatgatttttttggtgacattt aatgcacctcacttgaaaaagaaatatttaaaaaaagtaaagcatgatgt ggcctaccgcccagcaaggggtgaaagcaactggacgcatgtatctttat -continued

```
tccacacaagaacaacaatcccacagagaaaactacgaccaaaagcaatg

tatgaaatcaaagtccgatccattccccataacgattacttcaaaggctt

ctggagcgagtggagtccaagttctaccttcgaaactccagaacccaaga

atcaaggaggatgggatcctgtcttgccaagtgtcaccattctgagtttg

ttctctgtgtttttgttggtcatcttagcccatgtgctatggaaaaaaag

gattaaacctgtcgtatggcctagtctccccgatcataagaaaactctgg

aacaactatag
```

Some embodiments of any of the chimeric transmembrane proteins provided herein can include, e.g., a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to SEQ ID NO: 30, 32 or 34, or a portion thereof. Some embodiments of any of the chimeric transmembrane proteins provided herein can include, e.g., a sequence that differs from SEQ ID NO: 30, 32 or 34 by one to 60 amino acids (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids). Some embodiments of any of the chimeric transmembrane proteins described herein can further include, e.g., a sequence that differs from SEQ ID NO: 30, 32 or 34 by lacking one to 60 amino acids (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids).

In some embodiments, a nucleic acid encoding an alpha chain of an IL-7 receptor comprises or is a sequence that is at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 31, 33, or 35. In some embodiments, a nucleic acid encoding an alpha chain of an IL-7 receptor includes a sequence that differs from SEQ ID NO: 31, 33, or 35 by one or more nucleotides (e.g., 1 to about 180 nucleotides, 1 to about 160 nucleotides, 1 to about 140 nucleotides, 1 to about 120 nucleotides, 1 to about 100 nucleotides, 1 to about 80 nucleotides, 1 to about 60 nucleotides, 1 to about 40 nucleotides, 1 to about 20 nucleotides, about 5 to about 180 nucleotides, about 5 to about 180 nucleotides, about 5 to about 160 nucleotides, about 5 to about 160 nucleotides, about 5 to about 140 nucleotides, about 5 to about 120 nucleotides, about 5 to about 100 nucleotides, about 5 to about 80 nucleotides, about 5 to about 60 nucleotides, about 5 to about 40 nucleotides, or about 5 to about 20 nucleotides). Additionally or alternatively, a nucleic acid encoding an alpha chain of an IL-7 receptor can lack one or more nucleotides (e.g., 1 to about 180 nucleotides, 1 to about 160 nucleotides, 1 to about 140 nucleotides, 1 to about 120 nucleotides, 1 to about 100 nucleotides, 1 to about 80 nucleotides, 1 to about 60 nucleotides, 1 to about 40 nucleotides, 1 to about 20 nucleotides, about 5 to about 180 nucleotides, about 5 to about 180 nucleotides, about 5 to about 160 nucleotides, about 5 to about 160 nucleotides, about 5 to about 140 nucleotides, about 5 to about 120 nucleotides, about 5 to about 100 nucleotides, about 5 to about 80 nucleotides, about 5 to about 60 nucleotides, about 5 to about 40 nucleotides, or about 5 to about 20 nucleotides) as compared to the sequence of SEQ ID NO: 31, 33, or 35.

As one skilled in the art can appreciate, when amino acids that are not conserved between wildtype alpha chains of IL-7 receptor proteins from different species are mutated (e.g., substituted with a different amino acid) they are less likely to cause a decrease in the level of one or more activities of an alpha chain of an IL-7 receptor protein. In contrast, when amino acids that are conserved between wildtype alpha chains of alpha chains of IL-7 receptor proteins from different species are mutated (e.g., substituted with a different amino acid) they are more likely to cause a decrease in the level of one or more activities of an alpha chain of an alpha chain of an IL-7 receptor protein. In view of this knowledge, one skilled in the art can select which amino acid positions in a wildtype alpha chain of an alpha chain of an IL-7 receptor protein (e.g., the non-conserved amino acids) can be substituted without decreasing the activity of the alpha chain of an alpha chain of an IL-7 receptor protein.

Some embodiments of any of the chimeric transmembrane proteins described herein can include the sequence of a wildtype alpha chain of IL-7 receptor protein (e.g., a mature wildtype alpha chain of IL-7 receptor protein, e.g., any of the mature wildtype alpha chains of IL-7 receptor described herein, e.g., mature wildtype human alpha chain of IL-7 receptor protein, e.g., SEQ ID NO: 30) having one to ten (e.g., one, two, three, four, five, six, seven, eight, nine, or ten) amino acids removed from the N-terminus of the sequence of the wildtype alpha chain of IL-7 receptor protein. Some embodiments of any of the chimeric transmembrane proteins described herein can include the sequence of a wildtype alpha chain of IL-7 receptor protein (e.g., a mature wildtype alpha chain of IL-7 receptor protein, e.g., any of the mature wildtype alpha chains of IL-7 receptor described herein, e.g., mature wildtype human alpha chain of IL-7 receptor protein, e.g., SEQ ID NO: 30) having one to ten (e.g., one, two, three, four, five, six, seven, eight, nine, or ten) amino acids removed from the C-terminus of the sequence of the wildtype alpha chain of IL-7 receptor protein. Some embodiments of any of the chimeric transmembrane proteins described herein can include the sequence of a wildtype alpha chain of IL-7 receptor protein (e.g., a mature wildtype alpha chain of IL-7 receptor protein, e.g., any of the mature wildtype alpha chains of IL-7 receptor described herein, e.g., mature wildtype human alpha chain of IL-7 receptor protein, e.g., SEQ ID NO: 30) having both one to ten amino (e.g., one, two, three, four, five, six, seven, eight, nine, or ten) acids removed from the N-terminus of the sequence of the wildtype alpha chain of IL-7 receptor protein and one to ten (e.g., one, two, three, four, five, six, seven, eight, nine, or ten) amino acids removed from the C-terminus of the sequence of the wildtype alpha chain of IL-7 receptor protein.

As will be appreciated by those of ordinary skill in the art, when a nucleic acid encoding a chimeric transmembrane protein having an alpha chain of an IL-7 receptor protein domain includes or lacks one or more additional nucleotides as compared to SEQ ID NO: 31, SEQ ID NO: 33, or SEQ ID NO: 35, the translational reading frame should still be maintained such that a nonsense codon is not introduced and the full protein can be translated (e.g., a nucleic acid encoding a chimeric transmembrane protein having a domain encoding an alpha chain of an IL-7 receptor protein can include or lack three nucleotides, or multiples thereof, within the domain encoding the alpha chain of the IL-7 receptor).

Extracellular Sushi Domain of an Alpha Chain of IL-15 Receptor

In some embodiments, the chimeric transmembrane receptors described herein can include one or more (e.g., one, two, three, or four) sushi domains from an alpha chain of IL-15 receptor. For example, chimeric transmembrane proteins described herein can include a sushi domain from a wildtype alpha chain of a IL-15 receptor (e.g., a wildtype human alpha chain of a IL-15 receptor, a wildtype mouse alpha chain of a IL-15 receptor, a wildtype rat alpha chain of a IL-15 receptor, a wildtype monkey alpha chain of an IL-15 receptor, a wildtype chimpanzee alpha chain of an IL-15 receptor, a wildtype pig alpha chain of an IL-15 receptor, a wildtype dog alpha chain of an IL-15 receptor, or a wildtype cat alpha chain of an IL-15 receptor). Non-limiting examples of sushi domains from IL-15 receptors are described below. Additional examples of sushi domains from IL-15 receptors are known in the art.

A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, *Pac. Symp Biocomput.* 2000:155-67). The first cysteine can form a disulfide bond with the third cysteine, and the second cysteine can form a disulfide bridge with the fourth cysteine.

In some embodiments, a sushi domain can be about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 90 amino acids, about 70 amino acids to about 85 amino acids, about 70 amino acids to about 80 amino acids, about 70 amino acids to about 75 amino acids, about 75 amino acids to about 90 amino acids, about 75 amino acids to about 85 amino acids, about 75 amino acids to about 80 amino acids, about 80 amino acids to about 90 amino acids, about 80 amino acids to about 85 amino acids, or about 85 amino acids to about 90 amino acids, in length.

In some embodiments, an extracellular sushi domain comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to an extracellular portion of a mature wildtype alpha chain of IL-2 receptor, e.g., a mature wildtype human alpha chain of IL-2 receptor, e.g., SEQ ID NO: 36 or 37.

```
Sushi Domain from Wildtype Human Alpha
Chain of IL-15 Isoform 1
                                        (SEQ ID NO: 36)
CPPPMSVEHADIWVKSYSLYSRERYICNSGFKRKAGTSSLTECVLNKATN

VAHWTTPSLKCI

Sushi Domain from Wildtype Human Alpha
Chain of IL-15 Isoform 2
                                        (SEQ ID NO: 37)
CPPPMSVEHADIWVKSYSLYSRERYICNSGFKRKAGTSSLTECVLNKATN

VAHWTTPSLKCI
```

-continued

Sushi Domain from Wildtype Mouse Alpha Chain of IL-15 Isoform 1

(SEQ ID NO: 38)

CPPPVSIEHADIRVKNYSVNSRERYVCNSGFKRKAGTSTLIECVINKNTN

VAHWTTPSLKCI

Sushi Domain from Wildtype Mouse Alpha Chain of IL-15 Isoform 4

(SEQ ID NO: 39)

CPPPVSIEHADIRVKNYSVNSRERYVCNSGFKRKAGTSTLIECVINKNTN

VAHWTTPSLKCI

Sushi Domain from Wildtype Chicken Alpha Chain of IL-15 Protein (SEQ ID NO: 40

CPRLSTTEFADVAAETYPLKTKLRYECDSGYRRRSGNTLTIRCQNVSGTA

SWVHDELVC

Extracellular Portion from Wildtype Human Alpha Chain of IL-15 Isoform 1

(SEQ ID NO: 41)

ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEP

AASSPSSNNTAATTAAIVPGSQLMPSKSPSTGTTEISSHESSHGTPSQTT

AKNWELTASASHQPPGVYPQGHSDTT

In some embodiments, an extracellular sushi domain is an extracellular portion of a mature wildtype alpha chain of IL-15 receptor (e.g., an extracellular portion of a mature wildtype human alpha chain of IL-15 receptor, e.g., SEQ ID NO: 41). In some embodiments, an extracellular sushi domain is sequence that is at least 80%, at least 82%, at least 84%, at least 85%, at least 86%, at least 88%, at least 90%, at least 92%, at least 94%, at least 95%, at least 96%, at least 98%, at least 99%, or 100% identical to an extracellular portion of a mature wildtype alpha chain of IL-15 receptor (e.g., SEQ ID NO: 41). In some embodiments, an extracellular sushi domain is a sequence of an extracellular portion of a mature wildtype alpha chain of IL-15 receptor (e.g., SEQ ID NO: 41) having one to twenty (e.g., 1, 2, 3, 4, 5, 6, 7, 8, 9, 10, 11, 12, 13, 14, 15, 16, 17, 18, 19, or 20) amino acids removed from the N-terminus of the sequence of the extracellular portion of the mature wildtype alpha chain of IL-15 receptor In some embodiments, an extracellular sushi domain is a sequence of an extracellular portion of a mature wildtype alpha chain of IL-15 receptor (e.g., SEQ ID NO: 41) having one to twenty (e.g., 1, 2, 3, 4, 5, 6, 7, 8, 9, 10, 11, 12, 13, 14, 15, 16, 17, 18, 19, or 20) amino acids removed from the C-terminus of the sequence of the extracellular portion of the mature wildtype alpha chain of IL-15 receptor. In some embodiments, an extracellular sushi domain is a sequence of an extracellular portion of a mature wildtype alpha chain of IL-15 receptor (e.g., SEQ ID NO: 41) having one to twenty (e.g., 1, 2, 3, 4, 5, 6, 7, 8, 9, 10, 11, 12, 13, 14, 15, 16, 17, 18, 19, or 20) amino acids removed from the N-terminus of the sequence of the extracellular portion of the mature wildtype alpha chain of IL-15 receptor and one to twenty (e.g., 1, 2, 3, 4, 5, 6, 7, 8, 9, 10, 11, 12, 13, 14, 15, 16, 17, 18, 19, or 20) amino acids removed from the C-terminus of the sequence of the extracellular portion of the mature wildtype alpha chain of IL-15 receptor.

In some embodiments, an extracellular sushi domain comprises or is a sequence of a sushi domain from a wildtype alpha-chain of IL-15 receptor (e.g., any of the sushi domains from wildtype alpha-chains of IL-15 receptor described herein, e.g., a sushi domain from wildtype human alpha-chain of IL-15 receptor, e.g., a sequence comprising one or both of SEQ ID NO: 36 or 37).

In some embodiments, the extracellular sushi domain of the chimeric transmembrane protein comprises a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to a sushi domain of a wildtype alpha chain of IL-15 receptor (e.g., SEQ ID NO: 36, 37, 38, 39, or 40).

As one skilled in the art can appreciate, when amino acids that are not conserved between sushi domains from wildtype alpha chains of IL-15 receptor protein from different species are mutated (e.g., substituted with a different amino acid) they are less likely to cause a decrease in the level of IL-15 binding activity of the sushi domain from an alpha chain of IL-15 receptor protein. In contrast, when amino acids that are conserved between the sushi domains from wildtype alpha chains of IL-15 receptor protein from different species are mutated (e.g., substituted with a different amino acid) they are more likely to cause a decrease in the level of IL-15 binding activity of the sushi domain from an alpha chain of IL-15 receptor protein. In view of this knowledge, one skilled in the art can select which amino acid positions in a sushi domain of an alpha chain of an IL-15 receptor protein (e.g., the non-conserved amino acids) can be substituted without decreasing the activity of the sushi domain of the alpha chain of an IL-15 receptor protein.

In some embodiments, the extracellular sushi domain of the chimeric transmembrane protein is a sequence of a sushi domain from a wildtype alpha chain of an IL-15 receptor (e.g., any of SEQ ID NO: 36, 37, 38, 39, or 40) having one to five (e.g., one, two, three, four, or five) amino acids removed from the N-terminus of the sushi domain from the wildtype alpha chain of an IL-15 receptor. In some embodiments, the extracellular sushi domain of the chimeric transmembrane protein is a sequence of a sushi domain from a wildtype alpha chain of an IL-15 receptor (e.g., any of SEQ ID NO: 36, 37, 38, 39, or 40) having one to five (e.g., one, two, three, four, or five) amino acids removed from the C-terminus of the sushi domain from the wildtype alpha chain of an IL-15 receptor. In some embodiments, the extracellular sushi domain of the chimeric transmembrane protein is a sequence of a sushi domain from a wildtype alpha chain of an IL-15 receptor (e.g., any of SEQ ID NO: 36, 37, 38, 39, or 40) having one to five (e.g., one, two, three, four, or five) amino acids removed from the N-terminus of the sushi domain from the wildtype alpha chain of an IL-15 receptor, and one to five (e.g., one, two, three, four, or five) amino acids removed from the C-terminus of the sushi domain from the wildtype alpha chain of an IL-15 receptor.

In some embodiments, the chimeric transmembrane protein comprises two to sushi domains. In some embodiments, each of the sushi domains can independently be any of the sushi domains described herein.

Transmembrane Domains of an Alpha-Chain of an IL-7 Receptor

Chimeric transmembrane proteins described herein can include a transmembrane domain of a wildtype alpha chain of an IL-7 receptor from a human, a mouse, a rat, a monkey, a chimpanzee, a pig, a dog, a cat, or any other appropriate species. Non-limiting examples of transmembrane domains of alpha chains of IL-7 receptors are described below. Additional examples of transmembrane domains of alpha chain of IL-7 receptors are known in the art.

```
Transmembrane Domain of Wildtype Human
Alpha Chain of IL-7 Receptor
                                    (SEQ ID NO: 1)
PILLTISILSFFSVALLVILACVLW

Transmembrane Domain of Wildtype Mouse Alpha
Chain of IL-7 Receptor Isoform 1
                                   (SEQ ID NO: 42)
PVLPSVTILSLFSVFLLVILAHVLW

Transmembrane Domain of Wildtype Mouse Alpha
Chain of IL-7 Receptor Isoform 2
                                   (SEQ ID NO: 42)
PVLPSVTILSLFSVFLLVILAHVLW

Transmembrane Domain of Wildtype Macaca
fascicularis Alpha Chain of IL-7 Receptor
                                   (SEQ ID NO: 44)
PILLTISLLSFFSVALLVILACVLW
```

In some embodiments, the transmembrane domain from an alpha chain of an IL-2 receptor protein can be about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 22 amino acids, about 10 amino acids to about 20 amino acids, about 10 amino acids to about 18 amino acids, about 10 amino acids to about 15 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 22 amino acids, about 15 amino acids to about 20 amino acids, about 15 amino acids to about 18 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 22 amino acids, about 18 amino acids to about 20 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 22 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 50 amino acids, about 30 amino acids to about 45 amino acids, about 30 amino acids to about 40 amino acids, about 30 amino acids to about 35 amino acids, about 35 amino acids to about 50 amino acids, about 35 amino acids to about 45 amino acids, about 35 amino acids to about 40 amino acids, about 40 amino acids to about 50 amino acids, about 40 amino acids to about 45 amino acids, or about 45 amino acids to about 50 amino acids, in length.

In some embodiments of any of the chimeric transmembrane proteins described herein, the transmembrane domain of an alpha chain of an IL-7 receptor can be a transmembrane domain from a wildtype alpha chain of an IL-7 receptor (e.g., a transmembrane domain of a wildtype human alpha chain of an IL-7 receptor, e.g., SEQ ID NO: 1) (e.g., any of the exemplary transmembrane domains of a wildtype alpha chain of an IL-7 receptor listed below or known in the art, e.g., SEQ ID NO: 1, 42, 43, or 44).

In some embodiments, the transmembrane domain of an alpha chain of IL-7 receptor comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to a transmembrane domain from a wildtype alpha chain of IL-7 receptor (e.g., any one of SEQ ID NO: 1, 42, 43, or 44). In some embodiments, a transmembrane domain of an alpha chain of an IL-7 receptor includes a sequence that differs from a transmembrane domain of a wildtype alpha chain of IL-7 receptor (e.g., any one of SEQ ID NO: 1, 42, 43, or 44) by one to five amino acids (e.g., 1, 2, 3, 4, or 5 amino acids). In some embodiments, a transmembrane domain of an alpha chain of an IL-7 receptor includes one or twenty additional amino acids (e.g., 1, 2, 3, 4, 5, 6, 7, 8, 9, 10, 11, 12, 13, 14, 15, 16, 17, 18, 19, or 20 amino acids), e.g., in addition to the sequence of SEQ ID NO: 1, 42, 43, or 44. In some embodiments, a transmembrane domain of an alpha chain of an IL-7 receptor can have a sequence of any one of SEQ ID NOs: 1, 42, 43, or 44, but lack one to five amino acids (e.g., 1, 2, 3, 4, or 5 amino acids).

As one skilled in the art can appreciate, when amino acids that are not conserved between transmembrane domains from wildtype alpha chains of IL-7 receptor protein from different species are mutated (e.g., substituted with a different amino acid) they are less likely to cause a decrease in the activity of the transmembrane domain from an alpha chain of IL-7 receptor protein. In contrast, when amino acids that are conserved between the transmembrane domains from wildtype alpha chains of IL-7 receptor protein from different species are mutated (e.g., substituted with a different amino acid) they are more likely to cause a decrease in the activity of the transmembrane domain from an alpha chain of IL-7 receptor protein. In view of this knowledge, one skilled in the art can select which amino acid positions in a transmembrane domain of an alpha chain of an IL-7 receptor protein (e.g., the non-conserved amino acids) can be substituted without decreasing the activity of the transmembrane domain from the alpha chain of an IL-7 receptor protein.

In some embodiments, the transmembrane domain of an alpha chain of an IL-7 receptor protein is a sequence of a transmembrane domain of a wildtype alpha chain of IL-7 receptor protein (e.g., SEQ ID NO: 1, 42, 43, or 44) having one to five (e.g., one, two, three, four, or five) amino acids removed from the N-terminus of the transmembrane domain of the alpha chain of the IL-7 receptor protein. In some embodiments, the transmembrane domain of an alpha chain of an IL-7 receptor protein is a sequence of a transmembrane domain of a wildtype alpha chain of an IL-7 receptor protein (e.g., SEQ ID NO: 1, 42, 43, or 44) having one to five (e.g., one, two, three, four, or five) amino acids removed from the C-terminus of the transmembrane domain of the alpha chain of the IL-7 receptor protein. In some embodiments, the transmembrane domain of an alpha chain of an IL-7 receptor protein is a sequence of a transmembrane domain of a wildtype alpha chain of IL-7 receptor protein (e.g., a transmembrane domain of a wildtype human alpha chain of IL-7 receptor protein, e.g., SEQ ID NO: 1, 42, 43, or 44) having one to five (e.g., one, two, three, four, or five) amino acids removed from the N-terminus of the transmembrane domain of the alpha chain of the IL-7 receptor protein, and one to five (e.g., one, two, three, four, or five) amino acids removed from the C-terminus of the transmembrane domain of the alpha chain of the IL-7 receptor protein.

In some embodiments of any of the chimeric transmembrane proteins described herein, the transmembrane domain of an alpha chain of interleukin-7 receptor includes the sequence of PILLTISILSFFSVALLVILACVLW (SEQ ID NO: 1) with one or more (e.g., one, two, three, or four) of the following modifications: (i) alanine-leucine-leucine at amino acids positions 15 through 17 in SEQ ID NO: 1 has been replaced with a different three-amino acid sequence (e.g., has been replaced with glutamic acid-lysine-valine or glutamic acid-lysine-alanine); (ii) one to three (e.g., one, two, or three) amino acids (e.g., cysteine-proline-threonine) has been inserted between amino acid positions 5 and 6 in SEQ ID NO: 1; and (iii) one to four (e.g., one, two, three, or four) amino acids (e.g., proline-proline-cysteine-leucine) has been inserted between amino acid positions 4 and 5 in SEQ ID NO: 1. In some embodiments, the transmembrane domain is modified to have a sequence of SEQ ID NO: 2, 4, 6 or 8.

In some embodiments, the transmembrane domain includes the sequence of SEQ ID NO: 1 with the alanine-leucine-leucine at amino acid positions 15 through 17 in SEQ ID NO: 1 replaced with glutamic acid-lysine-valine or glutamic acid-lysine-alanine. In some embodiments, the transmembrane domain includes the sequence of SEQ ID NO: 1 with cysteine-proline-threonine inserted between amino acid positions 5 and 6 in SEQ ID NO: 1. In some embodiments, the transmembrane domain includes the sequence of SEQ ID NO: 1 with a proline-proline-cysteine-leucine inserted between amino acid positions 4 and 5 in SEQ ID NO: 1. In some embodiments, the transmembrane domain is modified to have a sequence of SEQ ID NO: 2, 4, 6 or 8.

Intracellular Domains of an Alpha Chain of IL-7 Receptor

Some embodiments of the chimeric transmembrane proteins described herein can further include an intracellular domain of an alpha chain of an IL-7 receptor, or a portion thereof. For example, chimeric transmembrane proteins described herein can include an intracellular domain of a wildtype alpha chain of an IL-7 receptor from a human, a mouse, a rat, a monkey, a chimpanzee, a pig, a dog, a cat, or any other appropriate species. Non-limiting examples of intracellular domains of alpha chains of IL-7 receptors are described below. Additional examples of intracellular domains of alpha chain of IL-7 receptors are known in the art.

Any of the chimeric transmembrane proteins described herein can comprise an intracellular domain of an alpha chain of an interleukin-7 receptor (e.g., any of the alpha chains of an interleukin-7 receptor described herein). In some embodiments, the intracellular domain of an alpha chain of an interleukin-7 receptor can be about 100 amino acids to about 225 amino acids, about 100 amino acids to about 200 amino acids, about 100 amino acids to about 180 amino acids, about 100 amino acids to about 160 amino acids, about 100 amino acids to about 140 amino acids, about 100 amino acids to about 120 amino acids, about 120 amino acids to about 225 amino acids, about 120 amino acids to about 200 amino acids, about 120 amino acids to about 180 amino acids, about 120 amino acids to about 160 amino acids, about 120 amino acids to about 140 amino acids, about 140 amino acids to about 225 amino acids, about 140 amino acids to about 200 amino acids, about 140 amino acids to about 180 amino acids, about 140 amino acids to about 160 amino acids, about 160 amino acids to about 225 amino acids, about 160 amino acids to about 200 amino acids, about 160 amino acids to about 180 amino acids, about 180 amino acids to about 225 amino acids, about 180 amino acids to about 200 amino acids, or about 200 amino acids to about 225 amino acids, in length.

Any of the chimeric transmembrane proteins described herein can comprise an intracellular domain of an alpha chain of interleukin-7 receptor (e.g., an intracellular domain of a wildtype alpha chain of interleukin-7 receptor (e.g., an intracellular domain of a wildtype human alpha chain of interleukin-7 receptor, e.g., SEQ ID NO: 45) (e.g., an intracellular domain of a wildtype human alpha chain of interleukin-7 of SEQ ID NO: 46).

Intracellular Domain of Wildtype Human Alpha Chain of IL-7 Receptor (SEQ ID NO: 45, the BOX1 motif is underlined, the tyrosines that are phosphorylated are in large bold font)

KKRIKPIVWPSLPDHKKTLEHLCKKPRKNLNVSFNPESFLDCQIHRVDDI

QARDEVEGFLQDTFPQQLEESEKQRLGGDVQSPNCPSEDVVITPESFGRD

SSLTCLAGNVSACDAPILSSSRSLDCRESGKNGPHVYQDLLLSLGTTNST

LPPPFSLQSGILTLNPVAQGQPILTSLGSNQEEAYVTMSSFYQNQ

Nucleic Acid Encoding an Intracellular Domain of Wildtype Human Alpha Chain of IL-7 Receptor (SEQ ID NO: 82, nucleic acid sequence encoding the BOX1 motif is underlined)

aagaagaggatcaagcccatcgtgtggcccagcctgcccgaccacaagaa gaccctggagcacctgtgtaagaagcccaggaagaacctgaacgtgagct tcaaccccgagagcttcctggactgccagatccacagggtggacgacatc caggccagggacgaggtggagggcttcctgcaggacaccttcccccagca gctggaggagagcgagaagcagaggctgggcggcgacgtgcagagcccca actgccccagcgaggacgtggtgatcacccccgagagcttcggcagggac agcagcctgacctgcctggccggcaacgtgagcgcctgcgacgcccccat cctgagcagcagcaggagcctggactgcagggagagcggcaagaacggcc cccacgtgtaccaggacctgctgctgagcctgggcaccaccaacagcacc ctgccaccccccttcagcctgcagagcggcatcctgaccctgaaccccgt ggcccagggccagcccatcctgaccagcctgggcagcaaccaggaggagg cctacgtgaccatgagcagcttctaccagaaccag Intracellular Domain of Wildtype Mouse Alpha Chain of IL-7 Receptor Isoform 1

(SEQ ID NO: 46)

KKRIKPVVWPSLPDHKKTLEQLCKKPKTSLNVSFNPESFLDCQIHEVKGV

EARDEVESFLPNDLPAQPEELETQGHRAAVHSANRSPETSVSPPETVRRE

SPLRCLARNLSTCNAPPLLSSRSPDYRDGDRNRPPVYQDLLPNSGNTNVP

VPVPQPLPFQSGILIPVSQRQPISTSSVLNQEEAYVTMSSFYQNK

In some embodiments, the intracellular domain of an alpha chain of IL-7 receptor comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the intracellular domain of a wildtype alpha chain of IL-7 receptor (e.g., SEQ ID NO: 45 or 46). In some embodiments, an intracellular domain of an alpha chain of an IL-7 receptor includes a sequence that differs the sequence of an intracellular domain of a wildtype alpha chain of IL-7 receptor (e.g., SEQ ID NO: 45 or 46) by one to 40 amino acids (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids). In some embodiments, an intracellular domain of an alpha chain of an IL-7 receptor includes one or more additional amino acids (e.g., 1 to about 100 amino acids, 1 to about 95 amino acids, 1 to about 90 amino acids, 1 to about 85 amino acids, 1 to about 80 amino acids, 1 to about 75 amino acids, 1 to about 70 amino acids, 1 to about 65 amino acids, 1 to about 60 amino acids, 1 to about 55 amino acids 1 to about 50 amino acids, 1 to about 45 amino acids, 1 to about 40 amino acids, 1 to about 35 amino acids, 1 to about 30 amino acids, 1 to about 25 amino acids, 1 to about 20 amino acids, 1 to about 15 amino acids, 1 to about 10 amino acids, or 1 to about 5 amino acids), e.g., in addition to the sequence of SEQ ID NO: 45 or 46. In some embodiments, an intracellular domain of an alpha chain of an IL-7 receptor can have a sequence of any one of SEQ ID NOs: 45 or 46, but lack one to forty amino acids (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids).

As one skilled in the art can appreciate, when amino acids that are not conserved between intracellular domains from wildtype alpha chains of IL-7 receptor protein from different species are mutated (e.g., substituted with a different amino acid) they are less likely to cause a decrease in the activity of the intracellular domain from an alpha chain of IL-7 receptor protein. In contrast, when amino acids that are conserved between the intracellular domains from wildtype alpha chains of IL-7 receptor protein from different species are mutated (e.g., substituted with a different amino acid) they are more likely to cause a decrease in the activity of the intracellular domain from an alpha chain of IL-7 receptor protein. In view of this knowledge, one skilled in the art can select which amino acid positions in an intracellular domain of an alpha chain of an IL-7 receptor protein (e.g., the non-conserved amino acids) can be substituted without decreasing the activity of the intracellular domain from the alpha chain of an IL-7 receptor protein.

In some embodiments, the intracellular domain of an alpha chain of an IL-7 receptor protein is a sequence of an intracellular domain of a wildtype alpha chain of IL-7 receptor protein (e.g., SEQ ID NO: 45 or 46) having one to three (e.g., one, two, or three) amino acids removed from the N-terminus of the intracellular domain of the alpha chain of the IL-7 receptor protein. In some embodiments, the intracellular domain of an alpha chain of an IL-7 receptor protein is a sequence of an intracellular domain of a wildtype alpha chain of an IL-7 receptor protein (e.g., SEQ ID NO: 45 or 46) having one to three (e.g., one, two, or three) amino acids removed from the C-terminus of the intracellular domain of the alpha chain of the IL-7 receptor protein. In some embodiments, the intracellular domain of an alpha chain of an IL-7 receptor protein is a sequence of an intracellular domain of a wildtype alpha chain of IL-7 receptor protein (e.g., SEQ ID NO: 45 or 46) having one to three (e.g., one, two, or three) amino acids removed from the N-terminus of the intracellular domain of the alpha chain of the IL-7 receptor protein, and one to three (e.g., one, two, or three) amino acids removed from the C-terminus of the intracellular domain of the alpha chain of the IL-7 receptor protein.

Linker Sequences

In some embodiments, the chimeric transmembrane protein comprises a linker sequence positioned between the extracellular IL-15 domain and the extracellular sushi domain. In some embodiments, the chimeric transmembrane protein comprises an additional linker sequence positioned between extracellular sushi domain and the transmembrane domain of an alpha chain of an IL-15 receptor. When the chimeric transmembrane protein comprises a linker sequence and an additional linker sequence, each the linker sequences can be the same or different from each other.

In some embodiments, the linker sequence or the additional linker sequence is 1 amino acid to about 50 amino acids, 1 amino acid to about 48 amino acids, 1 amino acid to about 46 amino acids, 1 amino acid to about 44 amino acids, 1 amino acid to about 42 amino acids, 1 amino acid to about 40 amino acids, 1 amino acid to about 38 amino acids, 1 amino acid to about 36 amino acids, 1 amino acid to about 34 amino acids, 1 amino acid to about 32 amino acids, 1 amino acid to about 30 amino acids, 1 amino acid to about 28 amino acids, 1 amino acid to about 26 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, 1 amino acid to about 3 amino acids, about 2 amino acids to about 50 amino acids, about 2 amino acids to about 48 amino acids, about 2 amino acids to about 46 amino acids, about 2 amino acids to about 44 amino acids, about 2 amino acids to about 42 amino acids, about 2 amino acids to about 40 amino acids, about 2 amino acids to about 38 amino acids, about 2 amino acids to about 36 amino acids, about 2 amino acids to about 34 amino acids, about 2 amino acids to about 32 amino acids, about 2 amino acids to about 30 amino acids, about 2 amino acids to about 28 amino acids, about 2 amino acids to about 26 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 50 amino acids, about 4 amino acids to about 48 amino acids, about 4 amino acids to about 46 amino acids, about 4 amino acids to about 44 amino acids, about 4 amino acids to about 42 amino acids, about 4 amino acids to about 40 amino acids, about 4 amino acids to about 38 amino acids, about 4 amino acids to about 36 amino acids, about 4 amino acids to about 34 amino acids, about 4 amino acids to about 32 amino acids, about 4 amino acids to about 30 amino acids, about 4 amino acids to about 28 amino acids, about 4 amino acids to about 26 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 50 amino acids, about 6 amino acids to about 48 amino acids, about 6 amino acids to about 46 amino acids, about 6 amino acids to about 44 amino acids, about 6 amino acids to about 42 amino acids, about 6 amino acids to about 40 amino acids, about 6 amino acids to about 38 amino acids, about 6 amino acids to about 36 amino acids, about 6 amino acids to about 34 amino acids, about 6 amino acids to about 32 amino acids, about 6 amino acids to about 30 amino acids, about 6 amino acids to about 28 amino acids, about 6 amino acids to about 26 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 50 amino acids, about 8 amino acids to about 48 amino acids, about 8 amino acids to about 46 amino acids, about 8 amino acids to about 44 amino acids, about 8 amino acids to about 42 amino acids, about 8 amino acids to about 40 amino acids, about 8 amino acids to about 38 amino acids, about 8 amino acids to about 36 amino acids, about 8 amino acids to about 34 amino acids, about 8 amino acids to about 32 amino acids, about 8 amino acids to about 30 amino acids, about 8 amino acids to about 28 amino acids, about 8 amino acids to about 26 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 50 amino acids, about 10 amino acids to about 48 amino acids, about 10 amino acids to about 46 amino acids, about 10 amino acids to about 44 amino acids, about 10 amino acids to about 42 amino acids, about 10 amino acids to about 40 amino acids, about 10 amino acids to about 38 amino acids, about 10 amino acids to about 36 amino acids, about 10 amino acids to about 34 amino acids, about 10 amino acids to about 32 amino acids, about 10 amino acids to about 30 amino acids, about 10 amino acids to about 28 amino acids, about 10 amino acids to about 26 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 50 amino acids, about 12 amino acids to about 48 amino acids, about 12 amino acids to about 46 amino acids, about 12 amino acids to about 44 amino acids, about 12 amino acids to about 42 amino acids, about 12 amino acids to about 40 amino acids, about 12 amino acids to about 38 amino acids, about 12 amino acids to about 36 amino acids, about 12 amino acids to about 34 amino acids, about 12 amino acids to about 32 amino acids, about 12 amino acids to about 30 amino acids, about 12 amino acids to about 28 amino acids, about 12 amino acids to about 26 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 50 amino acids, about 14 amino acids to about 48 amino acids, about 14 amino acids to about 46 amino acids, about 14 amino acids to about 44 amino acids, about 14 amino acids to about 42 amino acids, about 14 amino acids to about 40 amino acids, about 14 amino acids to about 38 amino acids, about 14 amino acids to about 36 amino acids, about 14 amino acids to about 34 amino acids, about 14 amino acids to about 32 amino acids, about 14 amino acids to about 30 amino acids, about 14 amino acids to about 28 amino acids, about 14 amino acids to about 26 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 50 amino acids, about 16 amino acids to about 48 amino acids, about 16 amino acids to about 46 amino acids, about 16 amino acids to about 44 amino acids, about 16 amino acids to about 42 amino acids, about 16 amino acids to about 40 amino acids, about 16 amino acids to about 38 amino acids, about 16 amino acids to about 36 amino acids, about 16 amino acids to about 34 amino acids, about 16 amino acids to about 32 amino acids, about 16 amino acids to about 30 amino acids, about 16 amino acids to about 28 amino acids, about 16 amino acids to about 26 amino acids, about 16 amino acids to about 24 amino acids, about 16 amino acids to about 22 amino acids, about 16 amino acids to about 20 amino acids, about 16 amino acids to about 18 amino acids, about 18 amino acids to about 50 amino acids, about 18 amino acids to about 48 amino acids, about 18 amino acids to about 46 amino acids, about 18 amino acids to about 44 amino acids, about 18 amino acids to about 42 amino acids, about 18 amino acids to about 40 amino acids, about 18 amino acids to about 38 amino acids, about 18 amino acids to about 36 amino acids, about 18 amino acids to about 34 amino acids, about 18 amino acids to about 32 amino acids, about 18 amino acids to about 30 amino acids, about 18 amino acids to about 28 amino acids, about 18 amino acids to about 26 amino acids, about 18 amino acids to about 24 amino acids, about 18 amino acids to about 22 amino acids, about 18 amino acids to about 20 amino acids, about 20 amino acids to about 50 amino acids, about 20 amino acids to about 48 amino acids, about 20 amino acids to about 46 amino acids, about 20 amino acids to about 44 amino acids, about 20 amino acids to about 42 amino acids, about 20 amino acids to about 40 amino acids, about 20 amino acids to about 38 amino acids, about 20 amino acids to about 36 amino acids, about 20 amino acids to about 34 amino acids, about 20 amino acids to about 32 amino acids, about 20 amino acids to about 30 amino acids, about 20 amino acids to about 28 amino acids, about 20 amino acids to about 26 amino acids, about 20 amino acids to about 24 amino acids, about 20 amino acids to about 22 amino acids, about 22 amino acids to about 50 amino acids, about 22 amino acids to about 48 amino acids, about 22 amino acids to about 46 amino acids, about 22 amino acids to about 44 amino acids, about 22 amino acids to about 42 amino acids, about 22 amino acids to about 40 amino acids, about 22 amino acids to about 38 amino acids, about 22 amino acids to about 36 amino acids, about 22 amino acids to about 34 amino acids, about 22 amino acids to about 32 amino acids, about 22 amino acids to about 30 amino acids, about 22 amino acids to about 28 amino acids, about 22 amino acids to about 26 amino acids, about 22 amino acids to about 24 amino acids, about 24 amino acids to about 50 amino acids, about 24 amino acids to about 48 amino acids, about 24 amino acids to about 46 amino acids, about 24 amino acids to about 44 amino acids, about 24 amino acids to about 42 amino acids, about 24 amino acids to about 40 amino acids, about 24 amino acids to about 38 amino acids, about 24 amino acids to about 36 amino acids, about 24 amino acids to about 34 amino acids, about 24 amino acids to about 32 amino acids, about 24 amino acids to about 30 amino acids, about 24 amino acids to about 28 amino acids, about 24 amino acids to about 26 amino acids, about 26 amino acids to about 50 amino acids, about 26 amino acids to about 48 amino acids, about 26 amino acids to about 46 amino acids, about 26 amino acids to about 44 amino acids, about 26 amino acids to about 42 amino acids, about 26 amino acids to about 40 amino acids, about 26 amino acids to about 38 amino acids, about 26 amino acids to about 36 amino acids, about 26 amino acids to about 34 amino acids, about 26 amino acids to about 32 amino acids, about 26 amino acids to about 30 amino acids, about 26 amino acids to about 28 amino acids, about 28 amino acids to about 50 amino acids, about 28 amino acids to about 48 amino acids, about 28 amino acids to about 46 amino acids, about 28 amino acids to about 44 amino acids, about 28 amino acids to about 42 amino acids, about 28 amino acids to about 40 amino acids, about 28 amino acids to about 38 amino acids, about 28 amino acids to about 36 amino acids, about 28 amino acids to about 34 amino acids, about 28 amino acids to about 32 amino acids, about 28 amino acids to about 30 amino acids, about 30 amino acids to about 50 amino acids, about 30 amino acids to about 48 amino acids, about 30 amino acids to about 46 amino acids, about 30 amino acids to about 44 amino acids, about 30 amino acids to about 42 amino acids, about 30 amino acids to about 40 amino acids, about 30 amino acids to about 38 amino acids, about 30 amino acids to about 36 amino acids, about 30 amino acids to about 34 amino acids, about 30 amino acids to about 32 amino acids, about 32 amino acids to about 50 amino acids, about 32 amino acids to about 48 amino acids, about 32 amino acids to about 46 amino acids, about 32 amino acids to about 44 amino acids, about 32 amino acids to about 42 amino acids, about 32 amino acids to about 40 amino acids, about 32 amino acids to about 38 amino acids, about 32 amino acids to about 36 amino acids, about 32 amino acids to about 34 amino acids, about 34 amino acids to about 50 amino acids, about 34 amino acids to about 48 amino acids, about 34 amino acids to about 46 amino acids, about 34 amino acids to about 44 amino acids, about 34 amino acids to about 42 amino acids, about 34 amino acids to about 40 amino acids, about 34 amino acids to about 38 amino acids, about 34 amino acids to about 36 amino acids, about 36 amino acids to about 50 amino acids, about 36 amino acids to about 48 amino acids, about 36 amino acids to about 46 amino acids, about 36 amino acids to about 44 amino acids, about 36 amino acids to about 42 amino acids, about 36 amino acids to about 40 amino acids, about 36 amino acids to about 38 amino acids, about 38 amino acids to about 50 amino acids, about 38 amino acids to about 48 amino acids, about 38 amino acids to about 46 amino acids, about 38 amino acids to about 44 amino acids, about 38 amino acids to about 42 amino acids, about 38 amino acids to about 40 amino acids, about 40 amino acids to about 50 amino acids, about 40 amino acids to about 48 amino acids, about 40 amino acids to about 46 amino acids, about 40 amino acids to about 44 amino acids, about 40 amino acids to about 42 amino acids, about 42 amino acids to about 50 amino acids, about 42 amino acids to about 48 amino acids, about 42 amino acids to about 46 amino acids, about 42 amino acids to about 44 amino acids, about 44 amino acids to about 50 amino acids, about 44 amino acids to about 48 amino acids, about 44 amino acids to about 46 amino acids, about 46 amino acids to about 50 amino acids, about 46 amino acids to about 48 amino acids, or about 48 amino acids to about 50 amino acids.

In some embodiments, the linker sequence and/or the additional linker sequence comprises a sequence of $(SG)_n$, where n can be 1, 2, 3, 4, 5, 6, 7, 8, 9, 10, 11, 12, 13, 14, 15, 16, 17, 18, 19, 20, 21, 22, 23, 24, or 25. In some embodiments, the linker sequence and/or the additional linker sequence comprises a sequence of $(GS)_n$, where n can be 1, 2, 3, 4, 5, 6, 7, 8, 9, 10, 11, 12, 13, 14, 15, 16, 17, 18, 19, 20, 21, 22, 23, 24, or 25.

In some embodiments, the linker sequence and/or the additional linker sequence comprises a sequence of $(SGGS)_n$ [SGGS=SEQ ID NO: 47], where n can be 1, 2, 3, 4, 5, 6, 7, 8, 9, 10, 11, 12, or 13. In some embodiments, the linker sequence and/or the additional linker sequence comprises a sequence of $(SGGGS)_n$ [SGGGS=SEQ ID NO: 48], where n can be 1, 2, 3, 4, 5, 6, 7, 8, 9, or 10. In some embodiments, the linker sequence and/or the additional linker sequence comprises a sequence of $(SGGGGS)_n$ [SGGGGS=SEQ ID NO: 49], where n can be 1, 2, 3, 4, 5, 6, 7, 8, or 9.

In some embodiments, the linker sequence and/or the additional linker sequence can be or include the sequence of SGGGGSGGGGSGGGG (SEQ ID NO: 50). In some embodiments, the linker sequence and/or the additional linker sequence can be or include the sequence of ASTKGPSVFPLAPSSSGSG (SEQ ID NO: 51). In some embodiments, the linker sequence and/or the additional linker sequence can be or include the sequence of GGGGSGGGGSGGGGS (SEQ ID NO: 52). In some embodiments, the linker sequence and/or the additional linker sequence can be or include the sequence of GGGSGGGGSGGGGSGGGGSGGGS (SEQ ID NO: 53). In some embodiments, the linker sequence and/or the additional linker sequence can be or include the sequence of SGGGSGGGGSGGGGSGGGGSGGGSLQ (SEQ ID NO: 92).

In some embodiments, the linker sequence and/or the additional linker sequence can be a Whitlow linker. In some embodiments, the Whitlow linker has the amino acid sequence of GSTSGSGKPGSGEGSTKG (SEQ ID NO: 54) or the nucleotide sequence encoding the Whitlow linker sequence is

```
                                          (SEQ ID NO: 55)
ggcagcaccagcggcagcggcaaaccgggcagcggcgaaggcagcaccaa

aggc.
```

In some embodiments, the linker sequence and/or the additional linker sequence can be a $(G_4S)_5$ linker. In some embodiments, the $(G_4S)_5$ linker has the amino acid sequence of GGGGSGGGGSGGGGSGGGGSGGGGS (SEQ ID NO: 56) or the nucleotide sequence encoding the $(G_4S)_5$ linker sequence is

```
                                          (SEQ ID NO: 57)
ggcggtggtggttctggaggcggtggcagcggtggaggtggctcaggagg

aggaggtagcggcggcggagggagt.
```

In some embodiments, the linker sequence and/or the additional linker sequence can be or can include one or more of an IgG1, IgG2, IgG3, or IgG4 CH1, CH2, and CH3 domain. In some embodiments, the linker sequence and/or the additional linker sequence can be or can include CH2-CH3 human IgG1 domains. In some embodiments, the CH2-CH3 human IgG1 domains have a sequence of:

```
                                          (SEQ ID NO: 58)
AEPKSPDKTHTCPPCPAPPVAGPSVFLFPPKPKDTLMIARTPEVTCWVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGKKD.
```

In some embodiments, the linker sequence and/or the additional linker sequence can be or include a portion of the human CD8 extracellular sequence that is proximal to the human CD8 transmembrane domain. For example, the linker sequence and/or the additional linker sequence can be or include human CD8 sequence of: TTTPAPRPPTPAPTIASQPLSLRPEACRPAAGGAVHTRGLDFACDI (SEQ ID NO: 59).

In some embodiments, the linker sequence and/or the additional linker sequence can be or include a human IgG1 hinge sequence. In some embodiments, the human IgG1 hinge sequence is AEPKSPDKTHTCPPCPKDPK (SEQ ID NO: 60).

In some embodiments, the linker sequence and/or the additional linker sequence has an alpha helix structure. In some embodiments, the linker sequence and/or the additional linker sequence is a coiled coil domain.

In some embodiments, the linker sequence and/or the additional linker sequence is a naturally-occurring amino acid sequence. In some embodiments, the linker sequence and/or the additional linker sequence is not a naturally-occurring amino acid sequence. In some embodiments, the linker sequence and/or the additional linker sequence comprises a sequence of SEQ ID NO: 92. In some embodiments, the linker sequence and/or the additional linker sequence consists of a sequence of SEQ ID NO: 92. Additional aspects and examples of linkers are known in the art.

Chimeric Antigen Receptors

A chimeric antigen receptor (CAR) is a protein that includes an extracellular antigen-binding domain (e.g., any of the antigen-binding domains described herein or known in the art), a transmembrane domain (e.g., any of the transmembrane domains described herein or known in the art), a costimulatory domain (e.g., any of the costimulatory domains described herein or known in the art), and an immunoreceptor tyrosine-based activation motif (ITAM). In some embodiments, a CAR comprises additional sequences such as, without limitation an extracellular stalk sequence (e.g., a CD28 stalk sequence). In some embodiments of a CAR comprising an extracellular stalk sequence (e.g., a CD28 stalk sequence), the stalk sequence is coterminal with the transmembrane domain. In some embodiments of a CAR comprising an extracellular stalk sequence (e.g., a CD28 stalk sequence), the extracellular stalk sequence is from the same protein as the transmembrane domain. In some embodiments of a CAR comprising an extracellular stalk sequence (e.g., a CD28 stalk sequence), the extracellular stalk sequence is from a different protein as the transmembrane domain. Non-limiting aspects of chimeric antigen receptors are described in, e.g., Kershaw et al., *Nature Reviews Immunol.* 5(12):928-940, 2005; Eshhar et al., *Proc. Natl. Acad. Sci. U.S.A.* 90(2):720-724, 1993; Sadelain et al., *Curr. Opin. Immunol.* 21(2): 215-223, 2009; WO 2015/142675; WO 2015/150526; and WO 2014/134165, the disclosures of each of which are incorporated herein by reference in their entirety.

In some embodiments, a chimeric antigen receptor can include one or more (e.g., two, three, four, or five) costimulatory domain(s) (e.g., any combination of any of the exemplary costimulatory domains described herein or known in the art). Some embodiments of these chimeric antigen receptors include one or both of a 4-1 BB costimulatory domain and a CD28 costimulatory domain.

In some embodiments, a chimeric antigen receptor can include one or more (e.g., two, three, four, or five) ITAMs (e.g., any of the ITAMs described herein or known in the art). In some embodiments of these chimeric antigen receptors, the ITAM includes a cytoplasmic signaling sequence from CD3 (e.g., human CD3).

In some embodiments, one or more amino acids between the extracellular antigen-binding domain and the transmembrane domain is a sequence from the same endogenous single-chain polypeptide from which the transmembrane domain is derived. In some embodiments, one or more amino acids between the extracellular antigen-binding domain and the transmembrane domain is or includes a hinge region sequence of an antibody such as, without limitation, a human antibody (e.g., IgG1, IgG2, IgG3, or IgG4). In some embodiments, one or more amino acids between the extracellular antigen-binding domain and the transmembrane domain is or comprises a linker sequence (e.g., a non-naturally occurring linker sequence, e.g., GS or any of the other linker sequences described herein).

In some examples of any of the CARs described herein, going in the N-terminal to the C-terminal direction, the intracellular portion of the CAR includes a co-stimulatory domain and an intracellular signaling domain. In some examples of any of the CARs described herein, going in the N-terminal to the C-terminal direction, the intracellular portion of the CAR includes an intracellular signaling domain and a co-stimulatory domain.

In some examples of any of the CARs described herein, going in the C-terminal to the N-terminal direction, the intracellular portion of the CAR includes a co-stimulatory domain and an intracellular signaling domain. In some examples of any of the CARs described herein, going in the C-terminal to the N-terminal direction, the intracellular portion of the CAR includes an intracellular signaling domain and a co-stimulatory domain.

In some embodiments of any of the CARs described herein, the transmembrane domain is or includes a transmembrane domain of CD28, CD3 epsilon, CD4, CD5, CD6, CD8a, CD9, CD16, CD22, CD33, CD37, CD45, CD64, CD80, CD86, CD134, 4-1BB, or CD154. Additional examples and aspects of transmembrane domains are described herein.

In some embodiments of any of the CARs described herein, the co-stimulatory domain is or includes the co-stimulatory domain of 4-1BB, CD28, CD2, CD4 or CD8. Additional examples and aspects of co-stimulatory domains are described herein.

In some embodiments of any of the CARs described herein, the CAR is generated from a CAR precursor, which CAR precursor include a signal peptide sequence for targeting the CAR to the cell membrane. In some embodiments, a CAR signal peptide comprises or is a sequence of SEQ ID NO: 93:

Exemplary CAR Signal Sequence Peptide (SEQ ID NO: 93)

MLLLVTSLLLCELPHPAFLLIP

Exemplary Nucleic Acid Sequence Encoding an Exemplary CAR Signal Sequence Peptide (SEQ ID NO: 94)

atgcttctcctggtgacaagccttctgctctgtgagttaccacacccagc attcctcctgattcct

In some embodiments, a CAR signal peptide comprises a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the polypeptide sequence of SEQ ID NO: 93. In some embodiments, a nucleic acid sequence encoding a CAR signal peptide comprises a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the nucleic acid sequence of SEQ ID NO: 94.

A variety of methods that can be used to determine the $K_D$ values of any of the CARs described herein are known in the art (e.g., an electrophoretic mobility shift assay, a filter binding assay, surface plasmon resonance, and a biomolecular binding kinetics assay, etc.).

Some embodiments of any of the chimeric antigen receptors described herein can further include a dimerization domain and/or a peptide tag.

Antigen-Binding Domains

In some embodiments of chimeric antigen receptors, the antigen-binding domain can be selected from a scFv, a scFv-Fc, a VHH domain, a VNAR domain, a $(scFv)_2$, and a BiTE. Additional examples of antigen-binding domains that can be used with chimeric antigen receptors described herein are known in the art.

A single-chain Fv or scFv fragment includes a $V_H$ domain and a $V_L$ domain in a single polypeptide chain. The $V_H$ and $V_L$ are generally linked by a peptide linker. In other examples, the linker can be a single amino acid. In some examples, the linker can be a chemical bond. See, e.g., Pluckthun, Antibodies from *E. coli*. In Rosenberg M. & Moore G P. (Eds.), The Pharmacology of Monoclonal Antibodies, Vol. 113, pp. 269-315, Spinger-Verlag, New York, 1994.

ScFv-Fc fragments include an scFv attached to an Fc domain. For example, an Fc domain can be attached, e.g., to the C-terminus of the scFv. The Fc domain can follow the $V_L$ or $V_H$, depending on the orientation of the variable domains in the scFv. The Fc domain can be any Fc domain known in the art. In some examples, the Fc domain is an IgG1, IgG2, IgG3, or IgG4 Fc domain (e.g., a human IgG1, IgG2, IgG3, or IgG4 Fc domain).

BiTEs are antigen-binding domains that include two $V_L$ and two $V_H$ in a single polypeptide that together form two scFvs, which can each bind to different epitopes on the same antigen or each bind to different antigens. See, e.g., Baeuerle et al., *Curr. Opin. Mol. Ther.* 11:22-30, 2009; Wolf et al., *Drug Discovery Today* 10:1237-1244, 2005; and Huehls et al., *Immunol. Cell Biol.* 93:290-296, 2015.

A $V_H$H domain is a single monomeric variable antibody domain found in camelids, and a VNAR domain is a single monomeric variable antibody domain found in cartilaginous fish. $V_H$H domains and $V_{NAR}$ domains are described in, e.g., Van Audenhove et al., *EBioMedicine* 8:40-48, 2016; Krah et al., *Immunopharmacol. Immunotoxicol.* 38:21-28, 2016; Cromie et al., *Curr. Top. Med. Chem.* 15:2543-2557, 2016; Kijanka et al., *Nanomedicine* 10:161-174, 2015; Kovaleva et al., *Expert. Opin. Biol. Ther* 14:1527-1539, 2014; De Meyer et al., *Trends Biotechnol.* 32:263-270, 2014; Mujic-Delic et al., *Trends Pharmacol. Sci.* 35:247-255, 2014; *Muyldermans, Ann. Rev. Biochem.* 82:775-797, 2013; Vincke et al., *Methods Mol. Biol.* 911:15-26, 2012; Rahbarizadeh et al., *Immunol. Invest.* 40:299-338, 2011; Van Bockstaele et al., *Curr. Opin. Investig. Drugs* 10:1212-1224, 2009; Wesolowski et al., *Med. Microbiol. Immunol.* 198:157-174, 2009; De Genst et al., *Dev. Comp. Immunol.* 30:187-198, 2006; Muyldermans, *J. Biotechnol.* 74:277-302, 2001; and Muyldermans et al., *Trends Biochem. Sci.* 26:230-235, 2001.

In some embodiments, an antigen-binding domain of a CAR is a sequence that comprises or is SEQ ID NO: 95:

Exemplary anti-CD19 Antigen Binding Domain (SEQ ID NO: 95)

DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEITGGGGSGGGGSGGGGSEVKLQESGPGLVAPSQSLSVTCTVSGVS

LPDYGVSWIRQPPRKGLEWLGVIWGSETTYYNSALKSRLTIIKDNSKSQV

FLKMNSLQTDDTAIYYCAKHYYYGGSYAMDYWGQGTSVTVSS

Nucleic Acid Encoding an Exemplary anti-CD19 Antigen Binding Domain (SEQ ID NO: 96)

Gacatccagatgacccagaccaccagcagcctgagcgccagcctgggcga tagagtgaccatcagctgcagagccagccaggacatcagcaagtacctga actggtatcagcagaaacccgacggcaccgtgaagctgctgatctaccac accagcagactgcacagcggcgtgcccagcagattttctggcagcggctc cggcaccgactacagcctgaccatctccaacctggaacaggaagatatcg ctacctacttctgtcagcaaggcaacaccctgccctacaccttcggcgga ggcaccaagctggaaatcacaggcggcggaggatctggcggaggcggaag tggcggagggggatctgaagtgaaactgcaggaaagcggccctggcctgg tggccccatctcagtctctgagcgtgacctgtaccgtgtccggcgtgtcc ctgcctgactatggcgtgtcctggatcagacagcccccagaaagggcct ggaatggctgggagtgatctggggcagcgagacaacctactacaacagcg ccctgaagtcccggctgaccatcatcaaggacaactccaagagccaggtg ttcctgaagatgaacagcctgcagaccgacgacaccgccatctactactg cgccaagcactactactacggcggcagctacgccatggactactggggcc agggcacaagcgtgaccgtgtctagc In some embodiments, an antigen binding domain comprises a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the polypeptide sequence of SEQ ID NO: 95. In some embodiments, a nucleic acid sequence encoding an antigen binding domain comprises a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the nucleic acid sequence of SEQ ID NO: 96.

Any of the antigen-binding domains described herein can bind to an antigen with a dissociation equilibrium constant ($K_D$) of less than $1\times10^{-7}$ M, less than $1\times10^{-8}$ M, less than $1\times10^{-9}$ M, less than $1\times10^{-19}$M, less than $1\times10^{-11}$ M, less than $1\times10^{-12}$ M, or less than $1\times10^{-13}$ M. In some embodiments, the antigen-binding protein complexes provided herein can bind to a first and/or second antigen with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive). A variety of different methods known in the art can be used to determine the $K_D$ value of an antigen-binding domain (e.g., an electrophoretic mobility shift assay, a filter binding assay, surface plasmon resonance, and a biomolecular binding kinetics assay, etc.).

Antigens

In some embodiments, a chimeric antigen receptor described herein can bind to a single antigen (e.g., any of the exemplary antigens described herein or known in the art). In some embodiments, an antigen-binding domain described herein can bind to two or more different antigens (e.g., two or more of any of the exemplary antigens described herein or known in the art). Non-limiting examples of antigens include: glypican-3, HER2, A33 antigen, 9-O-acetyl-GD3, CA19-9 marker, BhCC; CA-125 marker, carboanhydrase IX (MN/CA IX), calreticulin, CCR5, CCR8, CD2, CD3, CD5, CD16, CD19, CD20, CD22, CD24, CD25, CD27, CD28, CD30, CD33, CD38, CD40L, CD44, CD44V6, CD63, CD70, CD84, CD96, CD100, CC123, CD133, CD137, CD138, CD150, CD152 (CTLA-4), CD160, CRTAM, CS1 (CD319), DNAM-1 (CD226), CD229, CD244, CD272 (BTLA), CD274 (PDL-1, B7H1), CD279 (PD-1), CD319, CD352, CRTAM (CD355), CD358, DR3, GITR (TNFRSF 18), HVEM, ICOS, LIGHT, LTBR, OX40, activating forms of KIR, NKG2C, NKG2D, NKG2E, one or more natural cytotoxicity receptors, NTB-A, PEN-5, carcinoma embryonic antigen (CEA; CD66e), desmoglein 4, E-cadherin neoepitope, endosialin, ephrin A2 (EphA2), epidermal growth factor receptor (EGFR), epithelial cell adhesion molecule (EpCAM), fucosyl GM1, GD2, GD3, GM2, ganglioside GM3, Globo H, glycoprotein 100, HER2/neu, HER3, HER4, insulin-like growth factor receptor 1, Lewis-Y, LG, Ly-6, melanoma-specific chondroitin-sulfate proteoglycan (MCSCP), mesothelin, MUC1, MUC2, MUC3, MUC4, MUC5AC, $MUC5_b$, MUC7, MUC16, Mullerian inhibitory substance (MIS) receptor type II, plasma cell antigen, poly SA, PSCA, PSMA, sonic hedgehog (SHH), SAS, STEAP, sTn antigen, TNF-α precursor, 2B4 (CD244), β2-integrins, KIR, KIR2DL1, KIR2DL2, KIR2DL3, KIR3DL2, KIR-L, KLRGI, LAIR-1, NKG2A, NKR-P IA, Siglec-3, Siglec-7, Siglec-9, TCRa, TCRB, TCR5K, TIM1, LAG3, LAIR1, PD-1H, TIGIT, TIM2, and TIM3. Additional examples of antigens are known in the art.

CAR Transmembrane Domains

In some embodiments, a chimeric antigen receptor includes a transmembrane domain, or portion thereof, from an endogenous polypeptide, where the endogenous polypeptide is selected from the group of: an α chain of a T cell receptor, a β chain of the T cell receptor, a ζ chain of the T cell receptor, CD28 (also known as Tp44), CD3ε, CD3δ, CD3γ, CD33, CD37 (also known as GP52-40 or TSPAN26), CD64 (also known as FCGR1A), CD80 (also known as B7, B7-1, B7.1, BB1, CD28LG, CD28LG1, and LAB7), CD45 (also known as PTPRC, B220, CD45R, GP180, L-CA, LCA, LY5, T200, and protein tyrosine phosphatase, receptor type C), CD4, CD5 (also known as LEU1 and T1), CD8a (also known as Leu2, MAL, and p32), CD9 (also known as BTCC-1, DRAP-27, MIC3, MRP-1, TSPAN-29, and TSPAN29), CD16 (also known as FCGR3 andFCG3), CD22 (also known as SIGLEC-2 and SIGLEC2), CD86 (also known as B7-2, B7.2, B70, CD28LG2, and LAB72), CD134 (also known as TNFRSF4, ACT35, RP5-902P8.3, IMD16, OX40, TXGP1L, and tumor necrosis factor receptor superfamily member 4), CD137 (also known as TNFRSF9, 4-1BB, CDw137, ILA, and tumor necrosis factor receptor superfamily member 9), CD27 (also known as 5152, S152.LPFS2, T14, TNFRSF7, and Tp55), CD152 (also known as CTLA4, ALPS5, CELIAC3, CTLA-4, GRD4, GSE, IDDM12, and cytotoxic T-lymphocyte associated protein 4), PD1 (also known as PDCD1, CD279, PD-1, SLEB2, hPD-1, hPD-1, hSLE1, and Programmed cell death 1), ICOS (also known as AILIM, CD278, and CVID1), CD272 (also known as BTLA and BTLA1), CD30 (also known as TNFRSF8, D1S166E, and Ki-1), GITR (also known as TNFRSF18, RP5-902P8.2, AITR, CD357, and GITR-D), HVEM (also known as TNFRSF14, RP3-395M20.6, ATAR, CD270, HVEA, HVEM, LIGHTR, and TR2), DAP10, and CD154 (also known as CD40LG, CD40L, HIGM1, IGM, IMD3, T-BAM, TNFSF5, TRAP, gp39, hCD40L, and CD40 ligand). The letters "CD" is the previous sentence stand for "Cluster of Differentiation." E.g., CD3 stands for "Cluster of Differentiation 3." In some embodiments, a chimeric antigen receptor includes a transmembrane domain, or portion thereof, from an endogenous mammalian (e.g., human) polypeptide (e.g., a mammalian or human homolog of any of the polypeptides listed above).

Any transmembrane domain, or portion thereof, that serves to anchor an endogenous polypeptide in a lipid bilayer (e.g., plasma membrane) of a mammalian cell is suitable for use in accordance with compositions and methods disclosed herein. In some embodiments, a chimeric antigen receptor includes a transmembrane domain, or portion thereof, from human CD28, e.g., GenBank Accession No. P01747, e.g., amino acids 153 to 179 of SEQ ID NO: 61. In some embodiments, a chimeric antigen receptor includes a transmembrane domain that is at least 80% (e.g., at least 82%, at least 84%, at least 85%, at least 86%, at least 88%, at least 90%, at least 92%, at least 94%, at least 95%, at least 96%, at least 98%, or at least 99% identical) to amino acids 153 to 179 of SEQ ID NO: 61, or a portion thereof.

SEQ ID NO: 61

```
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPG

PTRKHYQPYAPPRDFAAYRS
```

In some embodiments, a CAR comprises a transmembrane domain and extracellular stalk domain having the sequence of SEQ ID NO: 97. In some embodiments, a chimeric antigen receptor includes transmembrane domain and extracellular stalk domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to SEQ ID NO: 97.

Exemplary Polypeptide Sequence for CD28 Stalk and TMD (SEQ ID NO: 97)

```
LDNEKSNGTIIHVKGKHLCPSPLFPGPSKPFWVLVVVGGVLACYSLLVTV

AFIIFWV
```

In some embodiments, a nucleic acid encoding a CAR comprises a nucleic acid sequence encoding a transmembrane domain and extracellular stalk domain having the sequence of SEQ ID NO: 98. In some embodiments, a nucleic acid encoding a chimeric antigen receptor includes a nucleic acid encoding a transmembrane domain and extracellular stalk domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to SEQ ID NO: 98.

Exemplary Nucleic Acid Sequence Encoding a Polypeptide Sequence for CD28 Stalk and TMD (SEQ ID NO: 98)

```
ctagacaatgagaagagcaatggaaccattatccatgtgaaagggaaaca

cctttgtccaagtcccctatttcccggaccttctaagcccttttgggtgc

tggtggtggttggtggagtcctggcttgctatagcttgctagtaacagtg

gcctttattattttctgggtg
```

In some embodiments, a chimeric antigen receptor includes a transmembrane domain, or portion thereof, from human CD3, e.g., GenBank Accession No. P20963, e.g., amino acids 31 to 51 of SEQ ID NO: 62. In some embodiments, a chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to amino acids 31 to 51 of SEQ ID NO: 62.

SEQ ID NO: 62

```
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP
```

-continued

```
QRRKNPQEGLYNELQKDKMAEAYSEIGMKGERRRGKGHDGLYQGLSTATK

DTYDALHMQALPPR
```

In some embodiments, a chimeric antigen receptor includes a transmembrane domain, or portion thereof, of any one of SEQ ID NOs. 63-69.

```
(SEQ ID NO: 63)
LGLLVAGVLVLLVSLGVAIHLCC;

(SEQ ID NO: 64)
VAAILGLGLVLGLLGPLAILLALYLL;

(SEQ ID NO: 65)
ALIVLGGVAGLLLFIGLGIFFCVRC;

(SEQ ID NO: 66)
LCYLLDGILFIYGVILTALFLRV;

(SEQ ID NO: 67)
WVLVVVGGVLACYSLLVTVAFIIFWV;

(SEQ ID NO: 68)
IYIWAPLAGTCGVLLLSLVITLYC;
and

(SEQ ID NO: 69)
ALPAALAVISFLLGLGLGVACVLA.
```

In some embodiments, a chimeric antigen receptor includes a transmembrane domain that is or includes a sequence that is at least 80% (e.g., at least 82%, at least 84%, at least 85%, at least 86%, at least 88%, at least 90%, at least 92%, at least 94%, to at least 95%, at least 96%, at least 98%, or at least 99% identical) to any one of SEQ ID NOs. 63-69.

As will be appreciated by those of ordinary skill in the art, certain endogenous polypeptides have two or more isoforms that differ at least in their primary polypeptide sequence. A chimeric antigen receptor disclosed herein can include a transmembrane domain that includes a sequence of amino acids from any isoform of an endogenous transmembrane protein (e.g., an endogenous mammalian, e.g., human, transmembrane protein) including, e.g., an isoform (e.g., a human isoform) of: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, CD27, CD152, PD1, or CD154.

In some embodiments, a transmembrane domain, or portion thereof, of a chimeric antigen receptor includes a sequence of amino acids that exhibits at least 85%, 86%, 87%, 88%, 89%, 90%, 91%, 92%, 93%, 94%, 95%, 96%, 97%, 98%, 99% or more sequence identity to the transmembrane domains from one or more of the following endogenous mammalian (e.g., human) transmembrane proteins: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, CD27, CD152, PD1, or CD154. In some embodiments, a transmembrane domain, or portion thereof, of a chimeric antigen receptor includes a sequence of amino acids having one or more amino acid substitutions, deletions, or additions as compared to the transmembrane domain of an endogenous mammalian (e.g., human) transmembrane protein: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, CD27, CD152, PD1, or CD154.

In some embodiments, a chimeric antigen receptor includes a synthetic transmembrane domain. In some cases, a synthetic transmembrane domain can include predominantly hydrophobic residues such as, without limitation, leucine and valine. In some embodiments, a synthetic transmembrane domain includes a triplet of phenylalanine, tryptophan, and valine at each end of the domain.

In some embodiments, a chimeric antigen receptor includes a transmembrane domain that is a chimeric transmembrane domain having portions of a transmembrane to domain from two or more endogenous mammalian (e.g., human) transmembrane polypeptides such as, without limitation, an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, CD27, CD152, PD1, and CD154, such that the two or more portions of transmembrane domains together constitute a functional transmembrane domain. In some embodiments, such a portion of a chimeric transmembrane domain can include one or more amino acid substitutions, deletions, or additions as compared to a corresponding portion of a wild type transmembrane domain.

A transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Additional examples and features of transmembrane domains are known in the art.

Costimulatory Domains

In normal lymphocytes, T cell activation is mediated by two classes of intracellular signaling domains. Primary signaling is initiated via MHC-mediated antigen-dependent activation via the T cell receptor (e.g., a TCR/CD3 complex). A secondary or costimulatory signal is provided by a different receptor that includes a costimulatory signaling domain, which acts in an antigen-independent manner. Signals generated through the signaling domain of the TCR alone are insufficient for complete T cell activation; a co-stimulatory signal is also required.

In some embodiments, a chimeric antigen receptor includes a costimulatory to domain, or portion thereof, from an endogenous mammalian (e.g., human) transmembrane polypeptide selected from the group of: CD27 (also known as S152, S152.LPFS2, T14, TNFRSF7, and Tp55), CD28 (also known as Tp44), 4-1BB (also known as TNFRSF9, CD137, CDw137, ILA, and tumor necrosis factor receptor superfamily member 9), OX40 (also known as TNFRSF4, ACT35, RP5-902P8.3, IMD16, CD134, TXGP1L, and tumor necrosis factor receptor superfamily member 4), CD30 (also known as TNFRSF8, D1S166E, and Ki-1), CD40L (also known as CD40LG, CD154, HIGM1, IGM, IMD3, T-BAM, TNFSF5, TRAP, gp39, hCD40L, and CD40 ligand), CD40 (also known as Bp50, CDW40, TNFRSF5, p50, CD40 (protein), and CD40 molecule), PD-1 (also known as PDCD1, CD279, PD-1, SLEB2, hPD-1, hPD-1, hSLE1, and Programmed cell death 1), PD-L1 (also known as CD274, B7-H, B7H1, PD-L1, PDCD1L1, PDCD1LG1, PDL1, CD274 molecule, and Programmed cell death 1 ligand 1), ICOS (also known as AILIM, CD278, and CVID1), LFA-1 (also known as Lymphocyte function-associated antigen 1), CD2 (also known as LFA-2, SRBC, T11, and CD2 molecule), CD7 (also known as GP40, LEU-9, TP41, Tp40, and CD7 molecule), CD160 (also known as BY55, NK1, NK28, and CD160 molecule), LIGHT (also known as TNFSF14, CD258, HVEML, LIGHT, LTg, TR2, TNLG1D, and tumor necrosis factor superfamily member 14), BTLA (also known as CD272 and BTLA1), TIM3 (also known as HAVCR2, HAVcr-2, KIM-3, TIM3, TIMD-3, TIMD3, Tim-3, CD366, and hepatitis A virus cellular receptor 2), CD244 (also known as 2B4, NAIL, NKR2B4, Nmrk, SLAMF4, and CD244 molecule), CD80 (also known as B7, B7-1, B7.1, BB1, CD28LG, CD28LG1, LAB7, and CD80 molecule), LAG3 (also known as CD223 and lymphocyte activating 3), NKG2C (also known as CD314, D12S2489E, KLR, NKG2-D, NKG2D, and killer cell lectin like receptor K1), GITR (also known as TNFRSF18, RP5-902P8.2, AITR, CD357, and GITR-D), HVEM (also known as TNFRSF14, RP3-395M20.6, ATAR, CD270, HVEA, HVEM, LIGHTR, and TR2), TLR1, TLR2, TLR3, TLR4, TLR5, TLR6, TLR7, TLR8, TLR9, TLRIO, CARD' 1, CD54 (ICAM), CD83, DAP10, LAT, SLP76, TRIM, ZAP70, and B7-H3 (also known as CD276, 4Ig-B7-H3, B7H3, B7RP-2, and CD276 molecule). In some embodiments, a single-chain chimeric polypeptide, a single-chain chimeric antigen receptor, or a multi-chain chimeric antigen receptor includes a costimulatory domain, or portion thereof, from an endogenous mammalian (e.g., human) transmembrane polypeptide (e.g., a mammalian or human homolog of any of the polypeptides listed above).

Any costimulatory domain, or portion thereof, that serves to provide a costimulatory signal is suitable for use in accordance with compositions and methods disclosed herein. In some embodiments, a chimeric antigen receptor includes a costimulatory domain, or portion thereof, from human CD28 (e.g. GenBank Accession No. P01747, e.g., from amino acids 180 to 220 of SEQ ID NO: 70). In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 70, or a fragment thereof.

```
(Amino acids 180 to 220 are underlined)
                                               SEQ ID NO: 70
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPG

PTRKHYQPYAPPRDFAAYRS
```

-continued

Exemplary Nucleic Acid Encoding Amino Acids a Human CD28 Costimulatory Domain (SEQ ID NO: 99)

```
aggagtaagaggagcaggctcctgcacagtgactacatgaacatgactcc

ccgccgccccgggcccacccgcaagcattaccagccctatgccccaccac

gcgacttcgcagcctatcgctcc
```

In some embodiments, a chimeric antigen receptor includes a costimulatory domain, or portion thereof, from human 4-1BB (e.g. GenBank Accession No. Q07011, e.g., from amino acids 214 to 255 of SEQ ID NO: 71). In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to amino acids 214 to 255 of SEQ ID NO: 75, or a portion thereof.

SEQ ID NO: 71

```
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL
```

A chimeric antigen receptor disclosed herein can include a costimulatory domain that includes a sequence of amino acids from any isoform of an endogenous mammalian (e.g., human) transmembrane polypeptide having a costimulatory domain including, e.g., an isoform of: CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides).

In some embodiments, a costimulatory domain, or portion thereof, of a chimeric antigen receptor includes a sequence of amino acids that exhibits at least 85%, 86%, 87%, 88%, 89%, 90%, 91%, 92%, 93%, 94%, 95%, 96%, 97%, 98%, 99% or more sequence identity to a costimulatory domain from one or more of a mammalian (e.g., human) CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3. In some embodiments, a costimulatory domain, or portion thereof, of a chimeric antigen receptor includes a sequence of amino acids having one or more amino acid substitutions, deletions, or additions as compared to a costimulatory domain of one or more of an endogenous mammalian (e.g., human) transmembrane polypeptide: an α chain of a T cell receptor, a β chain of the T cell receptor, a ζ chain of the T cell receptor, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides).

In some embodiments, a chimeric antigen receptor includes a costimulatory domain that is a chimeric costimulatory domain having portions of a costimulatory domain from two or more endogenous mammalian (e.g., human) transmembrane polypeptides including, without limitation, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides), such that the two or more portions of the transmembrane domains together constitute a functional costimulatory domain. In some embodiments, such a portion of a chimeric costimulatory domain can include one or more amino acid substitutions, deletions, or additions as compared to a corresponding portion of a wildtype costimulatory domain.

A costimulatory domain of a chimeric antigen receptor disclosed herein can be of any suitable length. For example, a costimulatory domain can have a length of about 20 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, or about 25 amino acids (inclusive); about 25 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, or about 30 amino acids (inclusive); about 30 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, or about 35 amino acids (inclusive); about 35 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, or about 40 amino acids (inclusive); about 40 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, or about 45 amino acids (inclusive); about 45 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, or about 50 amino acids (inclusive); about 50 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, or about 55 amino acids (inclusive); about 55 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, or about 60 amino acids (inclusive); about 60 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, or about 65 amino acids (inclusive); about 65 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, or about 70 amino acids (inclusive); about 70 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, or about 80 amino acids (inclusive); about 80 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, or about 90 amino acids (inclusive); about 90 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, or about 100 amino acids (inclusive); about 100 amino acids to about 200 amino acids, about 190 amino acids, about 180 amino acids, about 170 amino acids, about 160 amino acids, about 150 amino acids, about 140 amino acids, about 130 amino acids, about 120 amino acids, or about 110 amino acids (inclusive); about 110 amino acids to about 200 amino acids, about 190 amino acids, about 180 amino acids, about 170 amino acids, about 160 amino acids, about 150 amino acids, about 140 amino acids, about 130 amino acids, or about 120 amino acids (inclusive); about 120 amino acids to about 200 amino acids, about 190 amino acids, about 180 amino acids, about 170 amino acids, about 160 amino acids, about 150 amino acids, about 140 amino acids, or about 130 amino acids (inclusive); about 130 amino acids to about 200 amino acids, about 190 amino acids, about 180 amino acids, about 170 amino acids, about 160 amino acids, about 150 amino acids, or about 140 amino acids (inclusive); about 140 amino acids to about 200 amino acids, about 190 amino acids, about 180 amino acids, about 170 amino acids, about 160 amino acids, or about 150 amino acids (inclusive); about 150 amino acids to about 200 amino acids, about 190 amino acids, about 180 amino acids, about 170 amino acids, or about 160 amino acids (inclusive); about 160 amino acids to about 200 amino acids, about 190 amino acids, about 180 amino acids, or about 170 amino acids (inclusive); about 170 amino acids to about 200 amino acids, about 190 amino acids, or about 180 amino acids (inclusive); about 180 amino acids to about 200 amino acids or about 190 amino acids (inclusive); or about 190 amino acids to about 200 amino acids (inclusive).

In some embodiments, a chimeric antigen receptor includes two or more costimulatory domains, e.g., two, three, four, five, or more costimulatory domains. In some embodiments, the two or more costimulatory domains are identical (e.g., they have the same amino acid sequence). In some embodiments, the costimulatory domains are not identical. For example, the costimulatory domains can be selected from different endogenous mammalian (e.g., human) transmembrane polypeptides including, without limitation, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides). In some embodiments, the two or more costimulatory domains can differ from each other by one or more (e.g., two, three, four, or five) amino acid substitutions, deletions, or additions. In some embodiments, the two or more costimulatory domains exhibit at least 85%, 86%, 87%, 88%, 89%, 90%, 91%, 92%, 93%, 94%, 95%, 96%, 97%, 98%, 99% or more sequence identity to each other.

Immunoreceptor Tyrosine-Based Activation Motifs (ITAMs)

ITAMs are typically repeated (e.g., two or more times) in the cytoplasmic tails of certain cell surface proteins of the immune system, and are typically separated by between six and eight amino acids.

In some embodiments, a chimeric antigen receptor includes an ITAM, or portion thereof, from an endogenous mammalian (e.g., human) polypeptide, wherein endogenous mammalian (e.g., human) polypeptide is selected from the group of: CD3ζ (also referred to as CD3 zeta), CD3δ (CD3 delta), CD3ε (CD3 epsilon), CD3γ (CD3 gamma), DAP12, FCεR1γ (Fc epsilon receptor I gamma chain), FcRy, FcRft, to CD35, CD22, CD79A (antigen receptor complex-associated protein alpha chain), CD79B (antigen receptor complex-associated protein beta chain), and CD66d.

Any ITAM, or portion thereof, that serves to mediate signaling in an endogenous mammalian (e.g., human) transmembrane protein suitable for use in accordance with compositions and methods disclosed herein. In some embodiments, a chimeric antigen receptor includes an ITAM, or portion thereof, from human CD3 zeta (e.g. GenBank Accession No. P20963, e.g., an ITAM present in amino acids 52-164 of SEQ ID NO: 72, or a portion thereof; or SEQ ID NO: 73 or a portion thereof). In some embodiments, an ITAM comprises a sequence that is at least 80% (e.g., at least 82%, at least 84%, at least 86%, at least 88%, at least 90%, at least 92%, at least 94%, at least 96%, at least 98%, at least 99%, or 100% identical to: the sequence of amino acids 52-164 of SEQ ID NO: 72 (or a portion thereof), or the sequence of SEQ ID NO: 73 (or a portion thereof).

```
                                        SEQ ID NO: 72
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR

(Human CD3 zeta signaling domain)
                                        SEQ ID NO: 73
LRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR

(cDNA encoding human CD3 zeta signaling domain
of SEQ ID NO: 73)
                                        SEQ ID NO: 74
ctgagagtgaagttcagcaggagcgcagacgcccccgcgtaccagcaggg

ccagaaccagctctataacgagctcaatctaggacgaagagaggagtacg

atgttttggacaagagacgtggccgggaccctgagatggggggaaagccg

agaaggaagaaccctcaggaaggcctgtacaatgaactgcagaaagataa

gatggcggaggcctacagtgagattgggatgaaaggcgagcgccggaggg

gcaaggggcacgatggcctttaccagggtctcagtacagccaccaaggac

acctacgacgcccttcacatgcaggccctgccccctcgc
```

As will be appreciated by those of ordinary skill in the art, certain polypeptides have two or more isoforms that differ at least in their primary polypeptide sequence. For example, different isoforms can be generated as a result of alternative splicing. A chimeric antigen receptor disclosed herein can include an ITAM that includes a sequence of amino acids from any isoform of an endogenous mammalian transmembrane polypeptide having an ITAM including, e.g., a mammalian (e.g., human) isoform of: CD3ζ, CD3D, CD3E, CD3G, DAP12, FCER1G, FcRy, FcRft, CD35, CD22, CD79A, CD79B, or CD66d.

In some embodiments, an ITAM, or portion thereof, of a chimeric antigen receptor includes a sequence of amino acids having one or more (e.g., two, three, four, or five) amino acid substitutions, deletions, or additions as compared to an ITAM of one or more of an ITAM in an endogenous mammalian (e.g., human) transmembrane protein, such as, CD3ζ, CD3D, CD3E, CD3G, DAP12, FCER1G, FcRy, FcRft, CD35, CD22, CD79A, CD79B, or CD66d. For example, the tyrosine and leucine or isoleucine of an ITAM could be retained, while the two amino acids separating them could be replaced with different amino acids.

In some embodiments, a chimeric antigen receptor includes an ITAM that is a chimeric ITAM having portions of an ITAM from two or more endogenous mammalian (e.g., human) transmembrane polypeptides including, without limitation, CD3ζ, CD3D, CD3E, CD3G, DAP12, FCER1G, FcRy, FcRft, CD35, CD22, CD79A, CD79B, or CD66d (including, without limitation, a mammalian or human homolog of any of these polypeptides), such that the two or more ITAM portions together constitute a functional ITAM. In some embodiments, such a portion of a chimeric ITAM can include one or more amino acid substitutions, deletions, or additions as compared to a corresponding portion of a wild type ITAM.

In some embodiments, a chimeric antigen receptor includes two or more ITAMs, e.g., two, three, four, five, or more ITAMs. In some embodiments, the two or more ITAMs are identical (e.g., they have the same amino acid sequence). In some embodiments, the two or more ITAMs are not identical. For example, the ITAMs can be selected from different endogenous mammalian (e.g., human) transmembrane polypeptides including, without limitation, CD3ζ, CD3D, CD3E, CD3G, DAP12, FCER1G, FcRy, FcRft, CD35, CD22, CD79A, CD79B (including, without limitation, a mammalian or human homolog of any of these polypeptides). In some embodiments, the two or more ITAMs can differ from each other by one or more amino acid substitutions, deletions, or additions.

CAR-Linker Sequences

Any two neighboring domains of a chimeric antigen receptor can be separated by a linker sequence (e.g., any of the exemplary linker sequences described herein or known in the art).

In some embodiments, the linker sequence between the antigen-binding domain and the transmembrane domain can be 1 amino acid to about 250 amino acids, 1 amino acid to about 240 amino acids, 1 amino acid to about 230 amino acids, 1 amino acid to about 220 amino acids, 1 amino acid to about 210 amino acids, 1 amino acid to about 200 amino acids, 1 amino acid to about 190 amino acids, 1 amino acid to about 180 amino acids, 1 amino acid to about 170 amino acids, 1 amino acid to about 160 amino acids, 1 amino acid to about 150 amino acids, 1 amino acid to about 140 amino acids, 1 amino acid to about 130 amino acids, 1 amino acid to about 120 amino acids, 1 amino acid to about 110 amino acids, 1 amino acid to about 100 amino acids, 1 amino acid to about 95 amino acids, 1 amino acid to about 90 amino acids, 1 amino acid to about 85 amino acids, 1 amino acid to about 80 amino acids, 1 amino acid to about 75 amino acids, 1 amino acid to about 70 amino acids, 1 amino acid to about 65 amino acids, 1 amino acid to about 60 amino acids, 1 amino acid to about 55 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 20 amino acids, 1 amino acid to about 15 amino acids, 1 amino acid to about 10 amino acids, 1 amino acid to about 5 amino acids, about 5 amino acids to about 250 amino acids, about 5 amino acids to about 240 amino acids, about 5 amino acids to about 230 amino acids, about 5 amino acids to about 220 amino acids, about 5 amino acids to about 210 amino acids, about 5 amino acids to about 200 amino acids, about 5 amino acids to about 190 amino acids, about 5 amino acids to about 180 amino acids, about 5 amino acids to about 170 amino acids, about 5 amino acids to about 160 amino acids, about 5 amino acids to about 150 amino acids, about 5 amino acids to about 140 amino acids, about 5 amino acids to about 130 amino acids, about 5 amino acids to about 120 amino acids, about 5 amino acids to about 110 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 250 amino acids, about 10 amino acids to about 240 amino acids, about 10 amino acids to about 230 amino acids, about 10 amino acids to about 220 amino acids, about 10 amino acids to about 210 amino acids, about 10 amino acids to about 200 amino acids, about 10 amino acids to about 190 amino acids, about 10 amino acids to about 180 amino acids, about 10 amino acids to about 170 amino acids, about 10 amino acids to about 160 amino acids, about 10 amino acids to about 150 amino acids, about 10 amino acids to about 140 amino acids, about 10 amino acids to about 130 amino acids, about 10 amino acids to about 120 amino acids, about 10 amino acids to about 110 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 250 amino acids, about 15 amino acids to about 240 amino acids, about 15 amino acids to about 230 amino acids, about 15 amino acids to about 220 amino acids, about 15 amino acids to about 210 amino acids, about 15 amino acids to about 200 amino acids, about 15 amino acids to about 190 amino acids, about 15 amino acids to about 180 amino acids, about 15 amino acids to about 170 amino acids, about 15 amino acids to about 160 amino acids, about 15 amino acids to about 150 amino acids, about 15 amino acids to about 140 amino acids, about 15 amino acids to about 130 amino acids, about 15 amino acids to about 120 amino acids, about 15 amino acids to about 110 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 250 amino acids, about 20 amino acids to about 240 amino acids, about 20 amino acids to about 230 amino acids, about 20 amino acids to 220 amino acids, about 20 amino acids to about 210 amino acids, about 20 amino acids to about 200 amino acids, about 20 amino acids to about 190 amino acids, about 20 amino acids to about 180 amino acids, about 20 amino acids to about 170 amino acids, about 20 amino acids to about 160 amino acids, about 20 amino acids to about 150 amino acids, about 20 amino acids to about 140 amino acids, about 20 amino acids to about 130 amino acids, about 20 amino acids to about 120 amino acids, about 20 amino acids to about 110 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 250 amino acids, about 25 amino acids to about 240 amino acids, about 25 amino acids to about 230 amino acids, about 25 amino acids to about 220 amino acids, about 25 amino acids to about 210 amino acids, about 25 amino acids to about 200 amino acids, about 25 amino acids to about 190 amino acids, about 25 amino acids to about 180 amino acids, about 25 amino acids to about 170 amino acids, about 25 amino acids to about 160 amino acids, about 25 amino acids to about 150 amino acids, about 25 amino acids to about 140 amino acids, about 25 amino acids to about 130 amino acids, about 25 amino acids to about 120 amino acids, about 25 amino acids to about 110 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 250 amino acids, about 30 amino acids to about 240 amino acids, about 30 amino acids to about 230 amino acids, about 30 amino acids to about 220 amino acids, about 30 amino acids to about 210 amino acids, about 30 amino acids to about 200 amino acids, about 30 amino acids to about 190 amino acids, about 30 amino acids to about 180 amino acids, about 30 amino acids to about 170 amino acids, about 30 amino acids to about 160 amino acids, about 30 amino acids to about 150 amino acids, about 30 amino acids to about 140 amino acids, about 30 amino acids to about 130 amino acids, about 30 amino acids to about 120 amino acids, about 30 amino acids to about 110 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 250 amino acids, about 35 amino acids to about 240 amino acids, about 35 amino acids to about 230 amino acids, about 35 amino acids to about 220 amino acids, about 35 amino acids to about 210 amino acids, about 35 amino acids to about 200 amino acids, about 35 amino acids to about 190 amino acids, about 35 amino acids to about 180 amino acids, about 35 amino acids to about 170 amino acids, about 35 amino acids to about 160 amino acids, about 35 amino acids to about 150 amino acids, about 35 amino acids to about 140 amino acids, about 35 amino acids to about 130 amino acids, about 35 amino acids to about 120 amino acids, about 35 amino acids to about 110 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 250 amino acids, about 40 amino acids to about 240 amino acids, about 40 amino acids to about 230 amino acids, about 40 amino acids to about 220 amino acids, about 40 amino acids to about 210 amino acids, about 40 amino acids to about 200 amino acids, about 40 amino acids to about 190 amino acids, about 40 amino acids to about 180 amino acids, about 40 amino acids to about 170 amino acids, about 40 amino acids to about 160 amino acids, about 40 amino acids to about 150 amino acids, about 40 amino acids to about 140 amino acids, about 40 amino acids to about 130 amino acids, about 40 amino acids to about 120 amino acids, about 40 amino acids to about 110 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 250 amino acids, about 45 amino acids to about 240 amino acids, about 45 amino acids to about 230 amino acids, about 45 amino acids to about 220 amino acids, about 45 amino acids to about 210 amino acids, about 45 amino acids to about 200 amino acids, about 45 amino acids to about 190 amino acids, about 45 amino acids to about 180 amino acids, about 45 amino acids to about 170 amino acids, about 45 amino acids to about 160 amino acids, about 45 amino acids to about 150 amino acids, about 45 amino acids to about 140 amino acids, about 45 amino acids to about 130 amino acids, about 45 amino acids to about 120 amino acids, about 45 amino acids to about 110 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 250 amino acids, about 50 amino acids to about 240 amino acids, about 50 amino acids to about 230 amino acids, about 50 amino acids to about 220 amino acids, about 50 amino acids to about 210 amino acids, about 50 amino acids to about 200 amino acids, about 50 amino acids to about 190 amino acids, about 50 amino acids to about 180 amino acids, about 50 amino acids to about 170 amino acids, about 50 amino acids to about 160 amino acids, about 50 amino acids to about 150 amino acids, about 50 amino acids to about 140 amino acids, about 50 amino acids to about 130 amino acids, about 50 amino acids to about 120 amino acids, about 50 amino acids to about 110 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 250 amino acids, about 55 amino acids to about 240 amino acids, about 55 amino acids to about 230 amino acids, about 55 amino acids to about 220 amino acids, about 55 amino acids to about 210 amino acids, about 55 amino acids to about 200 amino acids, about 55 amino acids to about 190 amino acids, about 55 amino acids to about 180 amino acids, about 55 amino acids to about 170 amino acids, about 55 amino acids to about 160 amino acids, about 55 amino acids to about 150 amino acids, about 55 amino acids to about 140 amino acids, about 55 amino acids to about 130 amino acids, about 55 amino acids to about 120 amino acids, about 55 amino acids to about 110 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 250 amino acids, about 60 amino acids to about 240 amino acids, about 60 amino acids to about 230 amino acids, about 60 amino acids to about 220 amino acids, about 60 amino acids to about 210 amino acids, about 60 amino acids to about 200 amino acids, about 60 amino acids to about 190 amino acids, about 60 amino acids to about 180 amino acids, about 60 amino acids to about 170 amino acids, about 60 amino acids to about 160 amino acids, about 60 amino acids to about 150 amino acids, about 60 amino acids to about 140 amino acids, about 60 amino acids to about 130 amino acids, about 60 amino acids to about 120 amino acids, about 60 amino acids to about 110 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 250 amino acids, about 65 amino acids to about 240 amino acids, about 65 amino acids to about 230 amino acids, about 65 amino acids to about 220 amino acids, about 65 amino acids to about 210 amino acids, about 65 amino acids to about 200 amino acids, about 65 amino acids to about 190 amino acids, about 65 amino acids to about 180 amino acids, about 65 amino acids to about 170 amino acids, about 65 amino acids to about 160 amino acids, about 65 amino acids to about 150 amino acids, about 65 amino acids to about 140 amino acids, about 65 amino acids to about 130 amino acids, about 65 amino acids to about 120 amino acids, about 65 amino acids to about 110 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 250 amino acids, about 70 amino acids to about 240 amino acids, about 70 amino acids to about 230 amino acids, about 70 amino acids to about 220 amino acids, about 70 amino acids to about 210 amino acids, about 70 amino acids to about 200 amino acids, about 70 amino acids to about 190 amino acids, about 70 amino acids to about 180 amino acids, about 70 amino acids to about 170 amino acids, about 70 amino acids to about 160 amino acids, about 70 amino acids to about 150 amino acids, about 70 amino acids to about 140 amino acids, about 70 amino acids to about 130 amino acids, about 70 amino acids to about 120 amino acids, about 70 amino acids to about 110 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 250 amino acids, about 75 amino acids to about 240 amino acids, about 75 amino acids to about 230 amino acids, about 75 amino acids to about 220 amino acids, about 75 amino acids to about 210 amino acids, about 75 amino acids to about 200 amino acids, about 75 amino acids to about 190 amino acids, about 75 amino acids to about 180 amino acids, about 75 amino acids to about 170 amino acids, about 75 amino acids to about 160 amino acids, about 75 amino acids to about 150 amino acids, about 75 amino acids to about 140 amino acids, about 75 amino acids to about 130 amino acids, about 75 amino acids to about 120 amino acids, about 75 amino acids to about 110 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 250 amino acids, about 80 amino acids to about 240 amino acids, about 80 amino acids to about 230 amino acids, about 80 amino acids to about 220 amino acids, about 80 amino acids to about 210 amino acids, about 80 amino acids to about 200 amino acids, about 80 amino acids to about 190 amino acids, about 80 amino acids to about 180 amino acids, about 80 amino acids to about 170 amino acids, about 80 amino acids to about 160 amino acids, about 80 amino acids to about 150 amino acids, about 80 amino acids to about 140 amino acids, about 80 amino acids to about 130 amino acids, about 80 amino acids to about 120 amino acids, about 80 amino acids to about 110 amino acids, about 80 amino acids to about 100 amino acids, about 80 amino acids to about 95 amino acids, about 80 amino acids to about 90 amino acids, about 80 amino acids to about 85 amino acids, about 85 amino acids to about 250 amino acids, about 85 amino acids to about 240 amino acids, about 85 amino acids to about 230 amino acids, about 85 amino acids to about 220 amino acids, about 85 amino acids to about 210 amino acids, about 85 amino acids to about 200 amino acids, about 85 amino acids to about 190 amino acids, about 85 amino acids to about 180 amino acids, about 85 amino acids to about 170 amino acids, about 85 amino acids to about 160 amino acids, about 85 amino acids to about 150 amino acids, about 85 amino acids to about 140 amino acids, about 85 amino acids to about 130 amino acids, about 85 amino acids to about 120 amino acids, about 85 amino acids to about 110 amino acids, about 85 amino acids to about 100 amino acids, about 85 amino acids to about 95 amino acids, about 85 amino acids to about 90 amino acids, about 90 amino acids to about 250 amino acids, about 90 amino acids to about 240 amino acids, about 90 amino acids to about 230 amino acids, about 90 amino acids to about 220 amino acids, about 90 amino acids to about 210 amino acids, about 90 amino acids to about 200 amino acids, about 90 amino acids to about 190 amino acids, about 90 amino acids to about 180 amino acids, about 90 amino acids to about 170 amino acids, about 90 amino acids to about 160 amino acids, about 90 amino acids to about 150 amino acids, about 90 amino acids to about 140 amino acids, about 90 amino acids to about 130 amino acids, about 90 amino acids to about 120 amino acids, about 90 amino acids to about 110 amino acids, about 90 amino acids to about 100 amino acids, about 90 amino acids to about 95 amino acids, about 95 amino acids to about 250 amino acids, about 95 amino acids to about 240 amino acids, about 95 amino acids to about 230 amino acids, about 95 amino acids to about 220 amino acids, about 95 amino acids to about 210 amino acids, about 95 amino acids to about 200 amino acids, about 95 amino acids to about 190 amino acids, about 95 amino acids to about 180 amino acids, about 95 amino acids to about 170 amino acids, about 95 amino acids to about 160 amino acids, about 95 amino acids to about 150 amino acids, about 95 amino acids to about 140 amino acids, about 95 amino acids to about 130 amino acids, about 95 amino acids to about 120 amino acids, about 95 amino acids to about 110 amino acids, about 95 amino acids to about 100 amino acids, about 100 amino acids to about 250 amino acids, about 100 amino acids to about 240 amino acids, about 100 amino acids to about 230 amino acids, about 100 amino acids to about 220 amino acids, about 100 amino acids to about 210 amino acids, about 100 amino acids to about 200 amino acids, about 100 amino acids to about 190 amino acids, about 100 amino acids to about 180 amino acids, about 100 amino acids to about 170 amino acids, about 100 amino acids to about 160 amino acids, about 100 amino acids to about 150 amino acids, about 100 amino acids to about 140 amino acids, about 100 amino acids to about 130 amino acids, about 100 amino acids to about 120 amino acids, about 100 amino acids to about 110 amino acids, about 120 amino acids to about 250 amino acids, about 120 amino acids to about 240 amino acids, about 120 amino acids to about 230 amino acids, about 120 amino acids to about 220 amino acids, about 120 amino acids to about 210 amino acids, about 120 amino acids to about 200 amino acids, about 120 amino acids to about 190 amino acids, about 120 amino acids to about 180 amino acids, about 120 amino acids to about 170 amino acids, about 120 amino acids to about 160 amino acids, about 120 amino acids to about 150 amino acids, about 120 amino acids to about 140 amino acids, about 120 amino acids to about 130 amino acids, about 130 amino acids to about 250 amino acids, about 130 amino acids to about 240 amino acids, about 130 amino acids to about 230 amino acids, about 130 amino acids to about 220 amino acids, about 130 amino acids to about 210 amino acids, about 130 amino acids to about 200 amino acids, about 130 amino acids to about 190 amino acids, about 130 amino acids to about 180 amino acids, about 130 amino acids to about 170 amino acids, about 130 amino acids to about 160 amino acids, about 130 amino acids to about 150 amino acids, about 130 amino acids to about 140 amino acids, about 140 amino acids to about 250 amino acids, about 140 amino acids to about 240 amino acids, about 140 amino acids to about 230 amino acids, about 140 amino acids to about 220 amino acids, about 140 amino acids to about 210 amino acids, about 140 amino acids to about 200 amino acids, about 140 amino acids to about 190 amino acids, about 140 amino acids to about 180 amino acids, about 140 amino acids to about 170 amino acids, about 140 amino acids to about 160 amino acids, about 140 amino acids to about 150 amino acids, about 150 amino acids to about 250 amino acids, about 150 amino acids to about 240 amino acids, about 150 amino acids to about 230 amino acids, about 150 amino acids to about 220 amino acids, about 150 amino acids to about 210 amino acids, about 150 amino acids to about 200 amino acids, about 150 amino acids to about 190 amino acids, about 150 amino acids to about 180 amino acids, about 150 amino acids to about 170 amino acids, about 150 amino acids to about 160 amino acids, about 160 amino acids to about 250 amino acids, about 160 amino acids to about 240 amino acids, about 160 amino acids to about 230 amino acids, about 160 amino acids to about 220 amino acids, about 160 amino acids to about 210 amino acids, about 160 amino acids to about 200 amino acids, about 160 amino acids to about 190 amino acids, about 160 amino acids to about 180 amino acids, about 160 amino acids to about 170 amino acids, about 170 amino acids to about 250 amino acids, about 170 amino acids to about 240 amino acids, about 170 amino acids to about 230 amino acids, about 170 amino acids to about 220 amino acids, about 170 amino acids to about 210 amino acids, about 170 amino acids to about 200 amino acids, about 170 amino acids to about 190 amino acids, about 170 amino acids to about 180 amino acids, about 180 amino acids to about 250 amino acids, about 180 amino acids to about 240 amino acids, about 180 amino acids to about 230 amino acids, about 180 amino acids to about 220 amino acids, about 180 amino acids to about 210 amino acids, about 180 amino acids to about 200 amino acids, about 180 amino acids to about 190 amino acids, about 190 amino acids to about 250 amino acids, about 190 amino acids to about 240 amino acids, about 190 amino acids to about 230 amino acids, about 190 amino acids to about 220 amino acids, about 190 amino acids to about 210 amino acids, about 190 amino acids to about 200 amino acids, about 200 amino acids to about 250 amino acids, about 200 amino acids to about 240 amino acids, about 200 amino acids to about 230 amino acids, about 200 amino acids to 220 amino acids, about 200 amino acids to about 210 amino acids, about 210 amino acids to about 250 amino acids, about 210 amino acids to about 240 amino acids, about 210 amino acids to about 230 amino acids, about 210 amino acids to about 220 amino acids, about 220 amino acids to about 250 amino acids, about 220 amino acids to about 240 amino acids, about 220 amino acids to about 230 amino acids, about 230 amino acids to about 250 amino acids, about 230 amino acids to about 240 amino acids, or about 240 amino acids to about 250 amino acids.

In some embodiments, a linker sequence between the antigen-binding domain and the transmembrane domain can be or can include one or more of an IgG1, IgG2, IgG3, or IgG4 CH1, CH2, and CH3 domain. In some embodiments, the linker between the antigen-binding domain and the transmembrane domain can be or can include CH2-CH3 human IgG1 domains. In some embodiments, the CH2-CH3 human IgG1 domains have a sequence of:

```
                                      (SEQ ID NO: 75)
AEPKSPDKTHTCPPCPAPPVAGPSVFLFPPKPKDTLMIARTPEVTCWVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGKKD.
```

In some embodiments, the linker sequence between the antigen-binding domain and the transmembrane domain can be or include a portion of the human CD8 extracellular sequence that is proximal to the human CD8 transmembrane domain. For example, the linker sequence between the antigen-binding domain and the transmembrane domain can be or include human CD8 sequence of

```
                                      (SEQ ID NO: 76)
TTTPAPRPPTPAPTIASQPLSLRPEACRPAAGGAVHTRGLDFACDI.
```

In some embodiments, the linker sequence between the antigen-binding domain and the transmembrane domain can be or include a human IgG1 hinge sequence. In some embodiments, the human IgG1 hinge sequence is

```
                                      (SEQ ID NO: 77)
                 AEPKSPDKTHTCPPCPKDPK.
```

In some embodiments, a linker sequence (e.g., any of the linker sequences described herein or known in the art) can be present between the transmembrane domain and a costimulatory domain. In some embodiments, a linker sequence (e.g., any of the linker sequences described herein or known in the art) can be present between the costimulatory domain and the ITAM.

Nucleic Acids

Also provided herein are nucleic acids that encode any of the variety of polypeptides having a transmembrane domain of an alpha chain of interleukin-7 receptor having one or more amino acid modifications, chimeric transmembrane proteins, or other proteins described herein.

Vectors

Provided herein are vectors that include any of the nucleic acids that encode any of the variety of polypeptides having a transmembrane domain of an alpha chain of interleukin-7 receptor having one or more amino acid modifications, chimeric transmembrane proteins, or other proteins provided herein. A "vector" according to the present disclosure is a polynucleotide capable of inducing the expression of a recombinant protein (e.g., a chimeric transmembrane protein, a protein, and/or a chimeric antigen receptor) in a mammalian cell. A vector provided herein can be, e.g., in circular or linearized form. Non-limiting examples of vectors include plasmids, SV40 vectors, adenoviral viral vectors, and adeno-associated virus (AAV) vectors. Non-limiting examples of vectors include lentiviral vectors or retroviral vectors, e.g., gamma-retroviral vectors. See, e.g., Carlens et al., *Exp. Hematol.* 28(10:1137-1146, 2000; Park et al., *Trends Biotechnol.* 29(11):550-557, 2011; and Alonso-Camino et al., *Mol. Ther. Nucleic Acids* 2:e93, 2013. Non-limiting examples of retroviral vectors include those derived from Moloney murine leukemia virus, myeloproliferative sarcoma virus, murine embryonic stem cell virus, murine stem cell virus, spleen focus forming virus, or adeno-associated virus. Non-limiting examples of retroviral vectors are described in, e.g., U.S. Pat. Nos. 5,219,740 and 6,207,453; Miller et al., *BioTechniques* 7:980-990, 1989; *Miller, Human Gene Therapy* 1:5-14, 1990; Scarpa et al., *Virology* 180:849-852, 1991; Burns et al., *Proc. Natl. Acad. Sci. U.S.A.* 90:8033-8037, 1993; and Boris-Lawrie et al., *Cur. Opin. Genet. Develop.* 3:102-109, 1993. Exemplary lentiviral vectors are described in, e.g., Wang et al., *J. Immunother.* 35(9):689-701, 2003; Cooper et al., *Blood* 101:1637-1644, 2003; Verhoeyen et al., *Methods Mol. Biol.* 506:97-114, 2009; and Cavalieri et al., *Blood* 102(2):497-505, 2003.

Exemplary vectors, in which any of the nucleic acids provided herein can be inserted, are described in, e.g., Ausubel et al., Eds. "Current Protocols in Molecular Biology" Current Protocols, 1993; and Sambrook et al., Eds. "Molecular Cloning: A Laboratory Manual," 2nd ed., Cold Spring Harbor Press, 1989.

In some embodiments, the vectors further include a promoter sequence and/or enhancer sequence operably linked to any of the nucleic acids described herein. Non-limiting examples of promoters include promoters from human cytomegalovirus (CMV), mouse phosphoglycerate kinase 1, polyoma adenovirus, thyroid stimulating hormone α, vimentin, simian virus 40 (SV40), tumor necrosis factor, β-globin, α-fetoprotein, γ-globin, β-interferon, γ-glutamyl transferase, human ubiquitin C (UBC), mouse mammary tumor virus (MMTV), Rous sarcoma virus, glyceraldehyde-3-phosphate dehydrogenase, β-actin, metallothionein II (MT II), amylase, human EF1α, cathepsin, MI muscarinic receptor, retroviral LTR (e.g. human T-cell leukemia virus HTLV), AAV ITR, interleukin-2, collagenase, platelet-derived growth factor, adenovirus E2, stromelysin, murine MX, rat insulin, glucose regulated protein 78, human immunodeficiency virus, glucose regulated protein 94, α-2-macroglobulin, MHC class I, HSP70, proliferin, immunoglobulin light chain, T-cell receptor, HLA DQα, HLA DQβ, interleukin-2 receptor, MHC class II, prealbumin (transthyretin), elastase I, albumin, c-fos, neural cell adhesion molecule (NCAM), H2B histone, rat growth hormone, human serum amyloid (SAA), muscle creatinine kinase, troponin I (TN I), and Gibbon Ape Leukemia Virus (GALV). In some embodiments, the promoter may be an inducible promoter or a constitutive promoter. Additional examples of promoters are known in the art.

In some examples, the vectors provided herein further include a poly(A) sequence, which is operably linked and positioned 3' to the sequence encoding the chimeric transmembrane protein, the protein, or the chimeric antigen receptor. Non-limiting examples of a poly(A) sequence include those derived from bovine growth hormone (Woychik et al., *Proc. Natl. Acad. Sci. U.S.A.* 81(13): 3944-3948, 1984, and U.S. Pat. No. 5,122,458), mouse-β-globin, mouse-α-globin (Orkin et al., *EMBO J.* 4(2): 453-456, 1985), human collagen, polyoma virus (Batt et al., *Mol. Cell Biol.* 15(9):4783-4790, 1995), the Herpes simplex virus thymidine kinase gene (HSV TK), IgG heavy chain gene polyadenylation signal (U.S. Patent Application Publication No. 2006/0040354), human growth hormone (hGH) (Szymanski et al., *Mol. Therapy* 15(7):1340-1347, 2007), SV40 poly(A) site, e.g., SV40 late and early poly(A) site (Schek et al., *Mol. Cell Biol.* 12(12):5386-5393, 1992). In some embodiments, the poly(A) sequence includes a highly conserved upstream element (AATAAA). The this AATAAA sequence can, e.g., be substituted with other hexanucleotide sequences with homology to AATAAA which are capable of signaling polyadenylation, including, e.g., ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, and AATAAG. See, e.g., WO 06012414 A2).

A poly(A) sequence can, e.g., be a synthetic polyadenylation site. See, e.g., Levitt el al, *Genes Dev.* 3(7): 1019-1025, 1989). In some examples, a poly(A) to sequence can be the polyadenylation signal of soluble neuropilin-1: AAATAAAATACGAAATG (SEQ ID NO: 78). Additional examples of poly(A) sequences are known in the art. Additional examples and aspects of vectors are also known in the art.

In some embodiments of any of the vectors described herein, the vector can further include a sequence encoding a chimeric antigen receptor. In some embodiments, the chimeric antigen receptor can bind specifically to a tumor antigen (e.g., a tumor antigen selected from the group of glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin). In some embodiments, the chimeric antigen receptor comprises one or more co-stimulatory signaling domains selected from the group of 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, B7-H3, DAP-10, and DAP-12. In some examples of any of the vectors described herein, the vector is a lentiviral or an adenoviral vector.

Also provided herein are sets of vectors that include a first vector that includes a sequence that encodes any of the chimeric transmembrane proteins described herein (e.g., any of the vectors that includes a sequence that encodes any of the chimeric transmembrane proteins described herein), and a second vector that includes a sequence that encodes a chimeric antigen receptor (e.g., any of the chimeric antigen receptors described herein). In some embodiments, one or both of the first vector and the second vector is a lentiviral or an adenoviral vector. In some embodiments, the second vector further includes a promoter sequence and/or an enhancer sequence that is operably linked to the sequence encoding the chimeric antigen receptor. In some embodiments, the second vector further includes a poly(A) sequence operably linked to the sequence encoding the chimeric antigen receptor.

Methods of Introducing a Nucleic Acid or Vectors into a Mammalian Cell

A variety of different methods known in the art can be used to introduce any of the nucleic acids and vectors disclosed herein into a mammalian cell (e.g., any of the mammalian cells described herein, e.g., any of the T cells (e.g., human T cells) described herein). Non-limiting examples of methods that can be used to introduce a nucleic acid or vector into a mammalian cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection. Additional methods of introducing a nucleic acid or vector into a mammalian cell are known in the art.

Mammalian Cells

Also provided herein are mammalian cells that include any of the nucleic acids or vectors described herein. Also provided herein are mammalian cells that include any of the sets of vectors described herein.

In some embodiments, the mammalian cell is previously obtained from a subject (e.g., a human subject, e.g., a human subject identified or diagnosed as having a cancer) or is a daughter cell of a mammalian cell that was previously obtained from a subject (e.g., a human subject, e.g., a human subject identified or diagnosed as having a cancer). In some embodiments, the mammalian cell is an immune cell. In some embodiments, the mammalian cell is a human cell.

Non-limiting examples of immune cells include a T cell (e.g., a human T cell). Non limiting examples of T cells (e.g., human T cells) include, e.g., an immature thymocyte, a peripheral blood lymphocyte, a helper T cell, a naïve T cell, a pluripotent $T_H$ cell precursor, a lymphoid progenitor cell, a $T_{reg}$ cell, a memory T cell, a $T_H17$ cell, a $T_H22$ cell, a $T_H9$ cell, a $T_H2$ cell, a $T_H1$ cell, a $T_H3$ cell, γδ T cell, an αβ T cell, a regulatory T cell (Treg cell), and a tumor-infiltrating T cell. Additional examples of a T cell (e.g., a human T cell) include a $CD8^+$ T cell, a $CD4^+$ T cell, a memory T cell, a Treg cell, natural killer cell, B cell, and a monocyte. Additional examples of mammalian cells include a mast cell, a macrophage, a neutrophil, a dendritic cell, a basophil, an eosinophil, and a natural killer cell.

Compositions and Kits

Also provided herein are compositions (e.g., pharmaceutical compositions) that include any of the nucleic acids, vectors, sets of nucleic acids, sets of vectors, or mammalian cells described herein. For example, provided herein is a composition that includes any of the nucleic acids or sets of nucleic acids described herein, or any of the vectors or sets of vectors provided herein, and a pharmaceutically acceptable solvent or carrier.

In some embodiments, a composition can be any of the mammalian cells described herein (e.g., any of the mammalian cells described herein previously obtained from a subject, e.g., a subject identified or diagnosed as having a cancer) comprising a nucleic acid encoding any of the chimeric transmembrane proteins and/or any of the chimeric antigen receptors described herein. In a composition including any of the mammalian cells described herein, the composition can further include a cell culture medium or a pharmaceutically acceptable buffer (e.g., phosphate-buffered saline). A composition that includes any of the mammalian cells described herein can be formulated for intravenous or intraarterial administration.

Also provided are kits that include one or more of any of the compositions (e.g., pharmaceutical compositions) described herein. In some embodiments, a kit can further include instructions for performing any of the methods described herein.

Methods of Treating a Cancer in a Subject

Also provided herein are methods of treating a cancer in a subject (e.g., a human, a mouse, a rabbit, a rat, a horse, a dog, a monkey, or an ape) that include administering a therapeutically effective amount of any of the mammalian cells including a nucleic acid encoding a polypeptide having a transmembrane domain of an alpha chain of interleukin-7 receptor having one or more amino acid modifications as described herein, a chimeric transmembrane protein as described herein, or both (and optionally a nucleic acid including any of the chimeric antigen receptors described herein). In some examples of these methods, the mammalian cell is a T cell (e.g., a CD8+ T cell, a CD4+ T cell, a memory T cell, a Treg cell, and a natural killer T cell). In some examples, the mammalian cell (e.g., any of the mammalian cells described herein) is a mammalian cell previously obtained from a subject (e.g., a subject that has been identified or diagnosed as having a cancer, e.g., any of the cancers described herein). Some embodiments of these methods further include obtaining the mammalian cell from the subject.

Some embodiments of these methods further include introducing a nucleic acid encoding a single-chain chimeric antigen receptor described herein or a multi-chain chimeric antigen receptor described herein into a mammalian cell (e.g., any of the mammalian cells described herein or known in the art) to generate the mammalian cell that is administered to the subject.

Non-limiting examples of cancer that can be treated using any of the methods provided herein include: hepatocellular carcinoma, acute lymphoblastic leukemia, acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastric cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, gastric cancer, testicular cancer, throat cancer, thyroid cancer, urethral cancer, uterine cancer, vaginal cancer, and vulvar cancer.

In some embodiments of any of these methods, the methods result in a decrease in the tumor burden (e.g., a decrease in tumor mass and/or volume of a solid tumor) in a subject. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) reduction in the tumor burden in a subject (e.g., as compared to the tumor burden in the subject prior to treatment).

In some embodiments, the methods result in a decrease in the rate of progression of a cancer in the subject. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) reduction in the rate of progression of a cancer in a subject (e.g., as compared to the rate of progression of a cancer in the subject prior to treatment or in a control subject or a control population of subjects having the same cancer and administered no treatment or a different treatment).

In some embodiments of any of these methods, the methods result in an increase in the time of survival of a cancer in a subject. For example, any of the methods described herein can result in an about 1% to about 800% (e.g., about 1% to about 750%, about 700%, about 650%, about 600%, about 550%, about 500%, about 450%, about 400%, about 350%, about 300%, about 250%, about 200%, about 150%, about 100%, about 80%, about 60%, about 40%, about 20%, about 10%, or about 5% (inclusive); about 5% to about 800%, about 750%, about 700%, about 650%, about 600%, about 550%, about 500%, about 450%, about 400%, about 350%, about 300%, about 250%, about 200%, about 150%, about 100%, about 80%, about 60%, about 40%, about 20%, or about 10% (inclusive); about 10% to about 800%, about 750%, about 700%, about 650%, about 600%, about 550%, about 500%, about 450%, about 400%, about 350%, about 300%, about 250%, about 200%, about 150%, about 100%, about 80%, about 60%, about 40%, or about 20% (inclusive); about 20% to about 800%, about 750%, about 700%, about 650%, about 600%, about 550%, about 500%, about 450%, about 400%, about 350%, about 300%, about 250%, about 200%, about 150%, about 100%, about 80%, about 60%, or about 40% (inclusive); about 40% to about 800%, about 750%, about 700%, about 650%, about 600%, about 550%, about 500%, about 450%, about 400%, about 350%, about 300%, about 250%, about 200%, about 150%, about 100%, about 80%, or about 60% (inclusive); about 60% to about 800%, about 750%, about 700%, about 650%, about 600%, about 550%, about 500%, about 450%, about 400%, about 350%, about 300%, about 250%, about 200%, about 150%, about 100%, about 80% (inclusive); about 80% to about 800%, about 750%, about 700%, about 650%, about 600%, about 550%, about 500%, about 450%, about 400%, about 350%, about 300%, about 250%, about 200%, about 150%, or about 100% (inclusive); about 100% to about 800%, about 750%, about 700%, about 650%, about 600%, about 550%, about 500%, about 450%, about 400%, about 350%, about 300%, about 250%, about 200%, or about 150% (inclusive); about 150% to about 800%, about 750%, about 700%, about 650%, about 600%, about 550%, about 500%, about 450%, about 400%, about 350%, about 300%, about 250%, or about 200% (inclusive); about 200% to about 800%, about 750%, about 700%, about 650%, about 600%, about 550%, about 500%, about 450%, about 400%, about 350%, about 300%, or about 250% (inclusive); about 250% to about 800%, about 750%, about 700%, about 650%, about 600%, about 550%, about 500%, about 450%, about 400%, about 350%, or about 300% (inclusive); about 300% to about 800%, about 750%, about 700%, about 650%, about 600%, about 550%, about 500%, about 450%, about 400%, or about 350% (inclusive); about 350% to about 800%, about 750%, about 700%, about 650%, about 600%, about 550%, about 500%, about 450%, or about 400% (inclusive); about 400% to about 800%, about 750%, about 700%, about 650%, about 600%, about 550%, about 500%, or about 450% (inclusive); about 450% to about 800%, about 750%, about 700%, about 650%, about 600%, about 550%, or about 500% (inclusive); about 500% to about 800%, about 750%, about 700%, about 650%, about 600%, or about 550% (inclusive); about 550% to about 800%, about 750%, about 700%, about 650%, or about 600% (inclusive); about 600% to about 800%, about 750%, about 700%, or about 650% (inclusive); about 650% to about 800%, about 750%, or about 700% (inclusive); about 700% to about 800% or about 750% (inclusive); or about 750% to about 800% (inclusive)) increase in the time of survival of a cancer in a subject (e.g., as compared to the time of survival for a control subject or a population of control subjects having the same cancer and receiving no treatment or a different treatment).

Also provided herein are methods of inducing cell death in a cancer cell in a subject in need thereof that include administering to the subject a therapeutically effective amount of any of the mammalian cells described herein.

Also provided herein are methods of decreasing the risk of developing a metastasis or an additional metastasis in a subject having a cancer that include administering to the subject a therapeutically effective amount of any of the mammalian cells described herein. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) decrease in the risk of developing a metastasis or an additional metastasis in the subject (e.g., as compared to the risk of developing a metastasis or an additional metastasis in a control subject or a control population of subjects having the same cancer and administered no treatment or a different treatment).

EXAMPLES

The invention is further described in the following examples, which do not limit the scope of the invention described in the claims.

Figure 3:
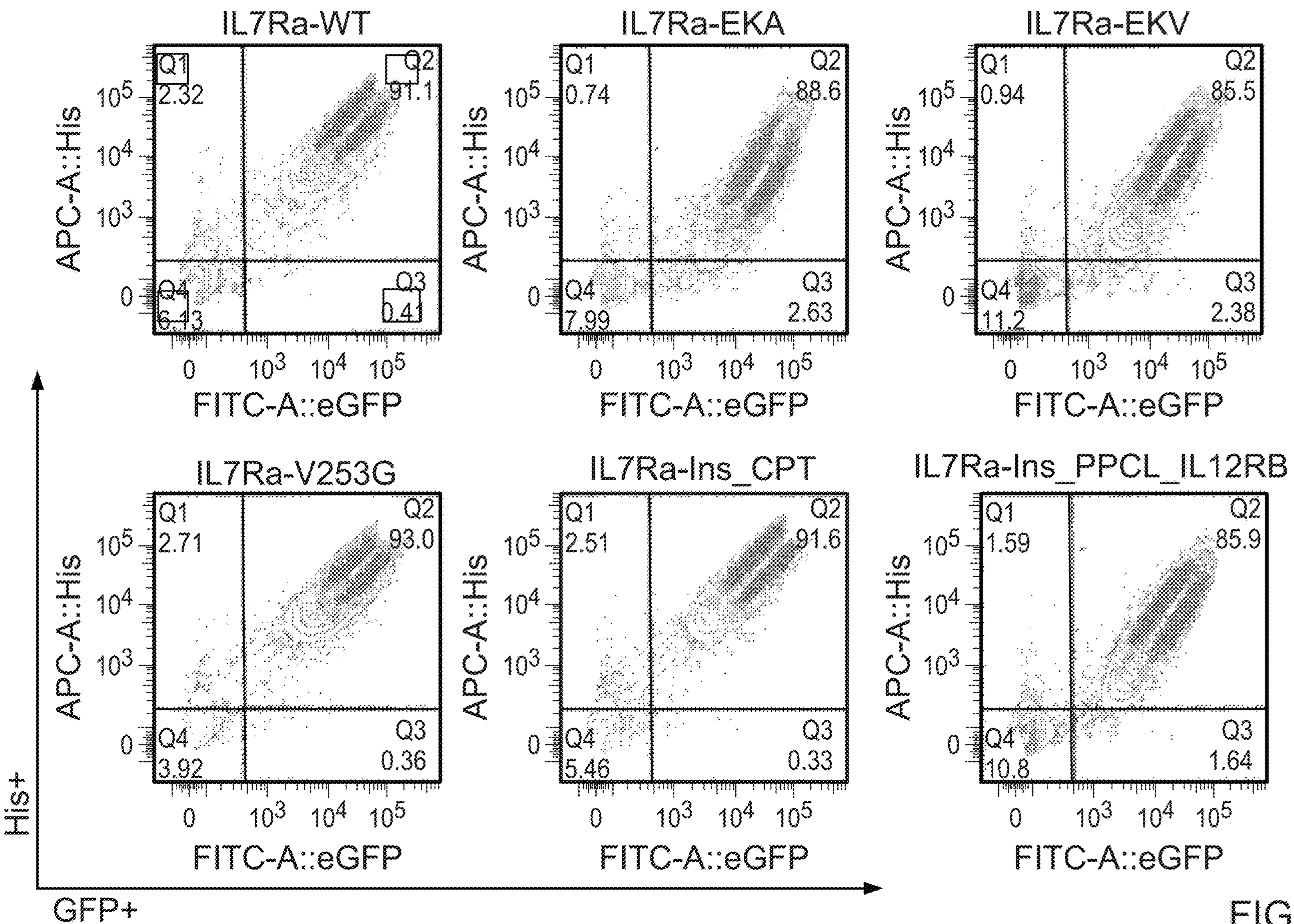
FIG. 3 is a set of flow cytometric data showing the expression of modified IL7Rα proteins on the surface of primary T cells. The data shown are from day 6 post-activation.

Example 1. Modified IL7Rα Proteins Express on the Surface of Primary T Cells Primary T cells were stained with a fluorochrome conjugated antibody against an N-terminal His tag to detect the surface expression of the mutated IL7Rα proteins. Briefly, up to $1\times10^6$ cells were harvested 72 hours post transduction with lentiviral vectors and incubated with anti-His (APC; 1:100) in PBS+2% FBS (FACS Buffer) for 30 minutes at 4° C. Flow cytometry was performed using BD LSRII Fortessa instruments and analyzed using FlowJo V10 software (FIG. 3, data shown are from day 6 post-activation). Detection of GFP (FITC) by flow cytometry was used as a surrogate for expression, since GFP gene is encoded within the same transgene as the IL7Ra mutant proteins and separated by a T2A self cleaving peptide sequence. Detection of GFP and surface detection of His tag was linear.

Figure 4:
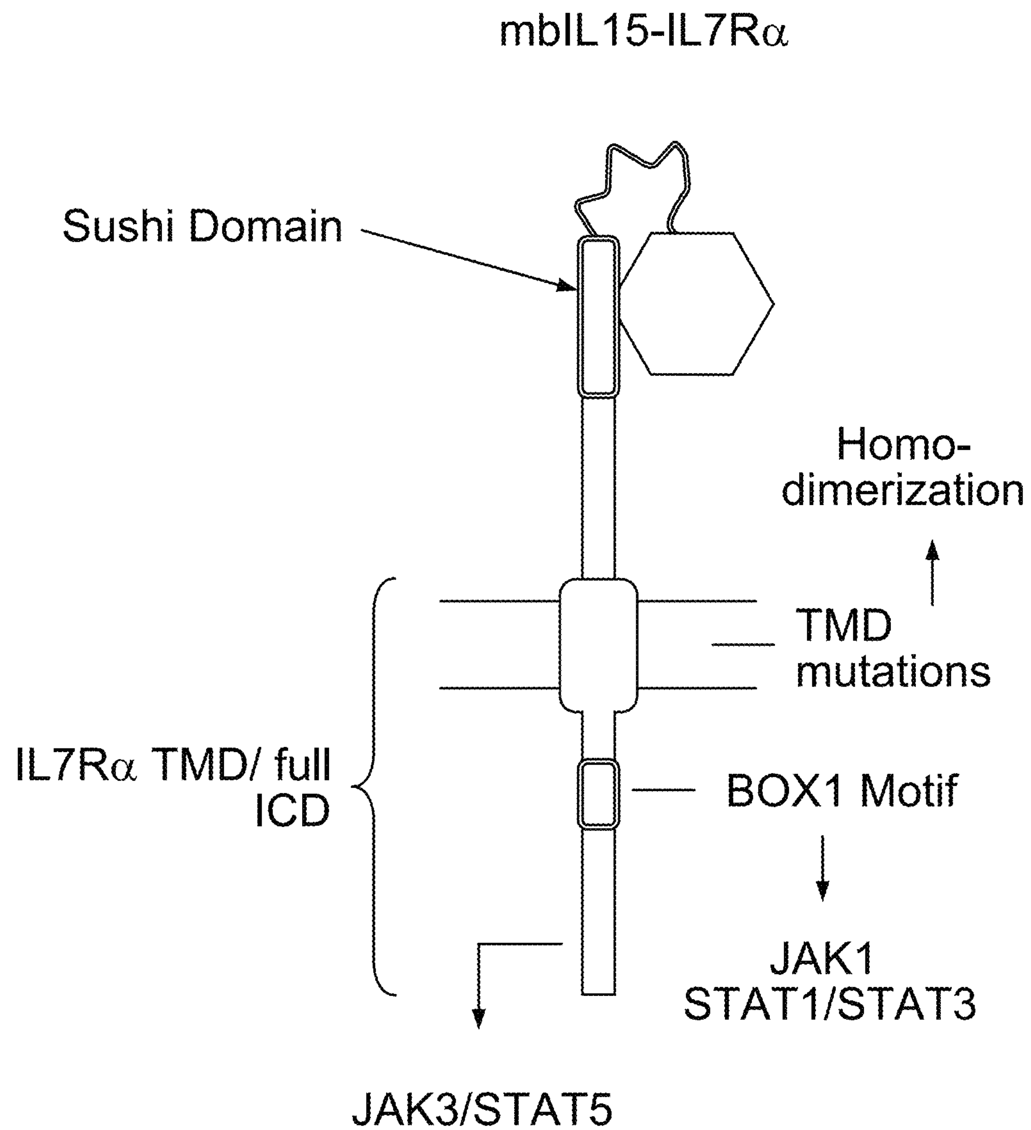
FIG. 4 is a schematic diagram of an exemplary chimeric transmembrane protein. The relevant motifs are indicated, along with the mechanism of signaling activation. The IL15Rα sushi domain is indicated by the arrow.

Example 2. Chimeric Transmembrane Proteins Express on the Surface of Primary T Cells mbIL15-IL17Rα-WT is a chimeric transmembrane protein having wildtype IL7Rα transmembrane and intracellular domains, an IL15Rα extracellular domain (including a sushi domain), a linker, and an IL15 polypeptide domain (See schematic of the construct shown in FIG. 4). mbIL15-IL17Rα-Ins_PPCL is a chimeric transmembrane protein having an wildtype IL7Rα intracellular domain, an IL7Rα transmembrane domain with an insertion of the sequence of PPCL between amino acid position 4 and 5 of mature wildtype IL7Rα, an IL15Rα extracellular domain (including a sushi domain), a linker, and an IL15 polypeptide domain.

Figure 5:
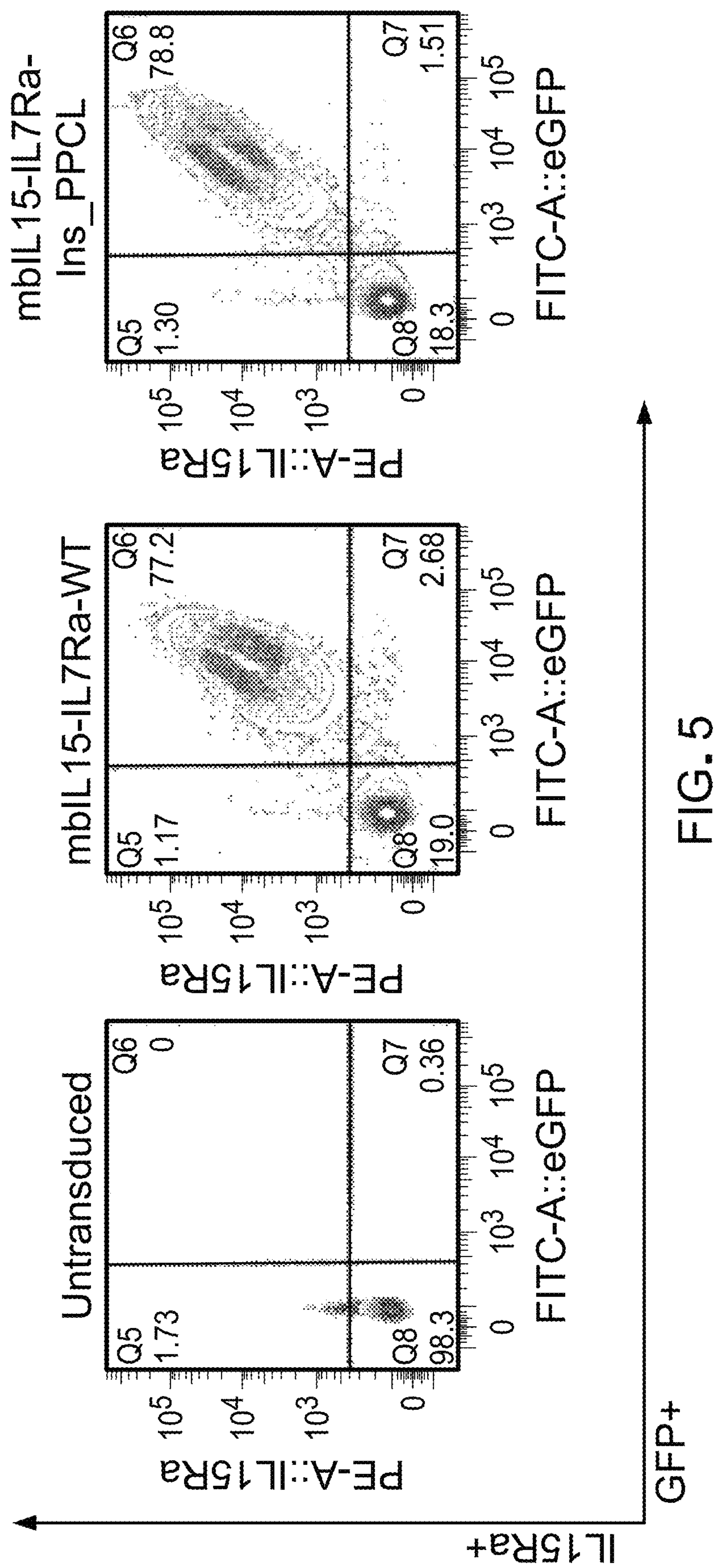
FIG. 5 is a set of flow cytometric data showing the expression of chimeric transmembrane proteins on the surface of primary T cells. The data shown are from day 6 post-activation.

Primary T cells were stained with a fluorochrome conjugated antibody against IL15Rα to detect the surface expression of the chimeric mbIL15 proteins. Briefly, up to $1\times10^6$ cells were harvested 72 hours post transduction with lentiviral vectors and incubated with anti-IL15Rα (APC; 1:100) in PBS+2% FBS (FACS Buffer) for 30 minutes at 4° C. Flow cytometry was performed using BD LSRII Fortessa instruments and analyzed using FlowJo V10 software (FIG. 5, data shown are from day 6 post-activation). Detection of GFP (FITC) by flow cytometry was used as a surrogate for expression, since GFP gene is encoded within the same transgene as the IL7Rα mutants and chimeric mbIL15 proteins and separated by a T2A self cleaving peptide sequence. Detection of GFP and surface expression of IL15Rα was linear.

Example 3. T Cells Expressing IL7 Mutant Receptors Maintain High Expression of CD62L (Tscm and Tcm Populations) and Variable Expression of CD25

Figures 6A, 6B:
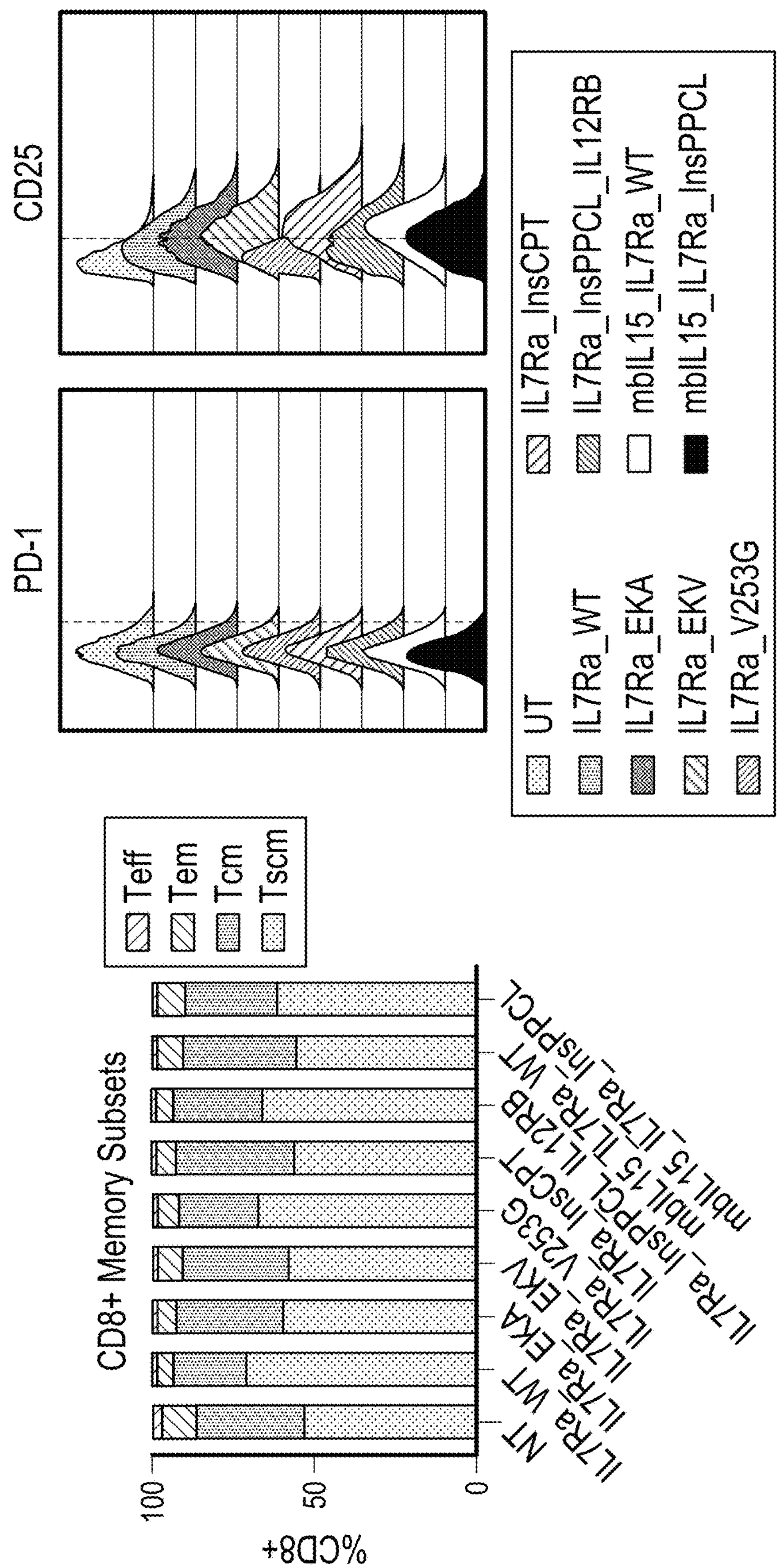
FIG. 6A is a graph showing the percentage of different types of $CD8^+$ T cells when primary human T cells were transduced with lentiviral vectors to express one of the specific IL7Rα proteins or one of the specific chimeric membrane proteins shown.
FIG. 6B is a set of two graphs of flow cytometry data showing the expression of PD-1 (left graph) or CD25 (right graph) in primary human T cells expressing different IL7Rα mutant proteins and chimeric transmembrane proteins in primary human T cells at day 15 post-activation.

Primary human T cells were transduced with lentiviral vectors to express one of the specific IL7Rα proteins or one of the specific chimeric membrane proteins shown on the x-axis of FIG. 6A. Briefly, up to $1\times10^6$ cells were harvested at each time point and incubated with anti-Myc (PE; 1:100), anti-CD4 (BV785; 1:200), anti-CD8 (PE; 1:200), anti-CD45RO (APC; 1:200), and anti-CD62L (BV605; 1:200) antibodies in PBS+2% FBS (FACS Buffer) for 30 minutes at 4° C. The relative expression levels of CD45RO and CD62L were used to determine the differentiation status of the cells. Teff=effector T cells. Tem=effector memory T cells. Tcm=central memory T cells. Tscm=stem cell memory T cells. FIG. 6A shows the percentage of different types of CD8+ T cells when the primary human T cells were transduced with the indicated proteins.

The expression of PD-1 (FIG. 6B, left graph) or CD25 (FIG. 6B, right graph) in primary human T cells expressing different IL7Rα mutant proteins and chimeric transmembrane proteins were assessed at 15 days post-activation. Briefly, up to $1\times10^6$ cells were harvested at each time point and incubated with anti-Myc (PE; 1:100), anti-CD25 (BV421; 1:100), anti-CD4 (BV785; 1:200), anti-CD8 (PE; 1:200), anti-CD45RO (APC; 1:200), anti-CD62L (BV605; 1:200), and anti-PD1 (PE-Cy7; 1:200) antibodies in PBS+2% FBS (FACS Buffer) for 30 minutes at 4° C. Untransduced ("UT") control T-cells provide basal level of PD-1 and CD25 expression.

Example 4. IL7Rα Transmembrane Domain Mutations Induce Phosphorylation of STATS in Primary T Cells The levels of phosphorylated STATS in primary human T cells left untransduced ("UT") or transduced with lentivirus encoding one of the specific IL7Rα proteins or one of the specific chimeric membrane proteins showed in FIG. 7A were assessed by Western blotting (top Western blot). Whole cell lysates were prepared from T-cells following 16-20 hours under serum/cytokine starved conditions 14 days post activation. UT T cells stimulated with 100 ng/ml soluble IL2 for 15 min serve as a positive control (+ stim), while unstimulated UT cells (– stim) provide basal phospho/protein levels. A control protein (alpha tubulin) was also assessed by Western blotting (bottom Western blot).

Figure 7B:
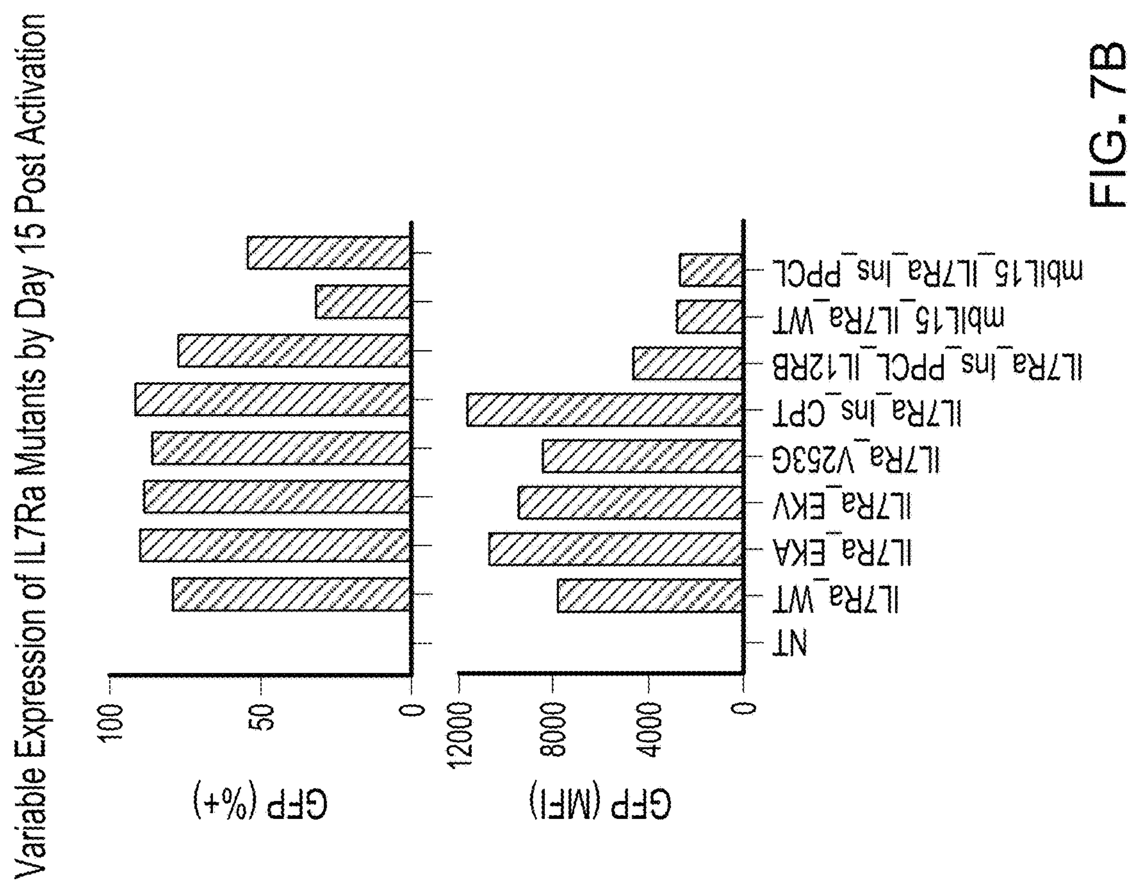
FIG. 7B is a set of two bar graphs showing the expression of various IL7Rα mutant proteins and chimeric transmembrane proteins in primary human T cells at day 15 post-activation.
Figure 7A:
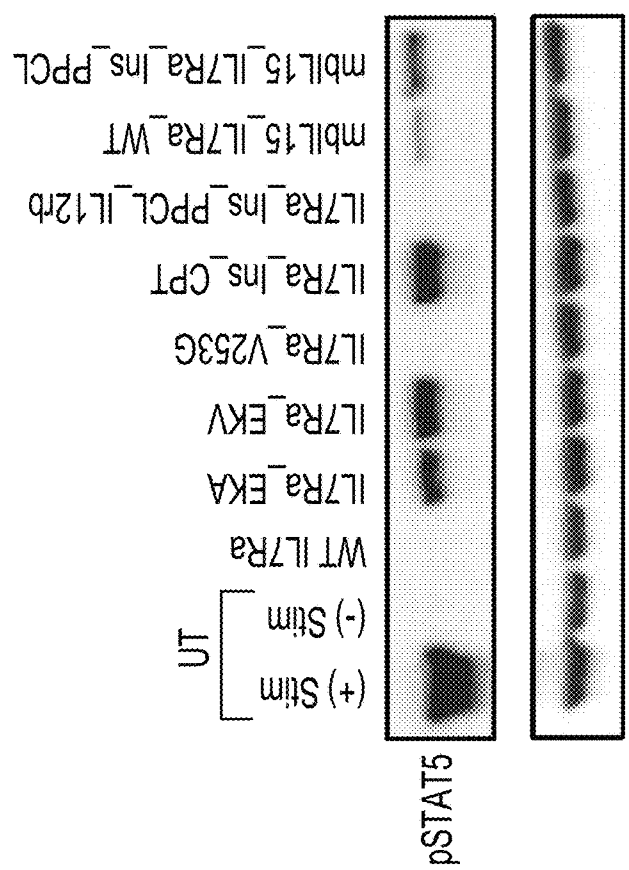
FIG. 7A is an immunoblot showing the level of phosphorylated STATS in primary human T cells left untransduced ("UT") or transduced with lentiviral encoding one of the specific IL7Rα proteins or one of the specific chimeric membrane proteins shown.

The expression of various IL7Rα mutant proteins and chimeric transmembrane proteins in primary human T cells was assessed at day 15 post-activation (FIG. 7B). GFP data is show as % expression (top bar graph) and mean fluorescence intensity (bottom bar graph). Detection of GFP expression by flow cytometry was used to track the relative numbers of cells expressing the various IL7Rα mutants or chimeric transmembrane proteins over a 14-day culture period (cells transduced on day 1 post activation).

Figures 8A, 8B:
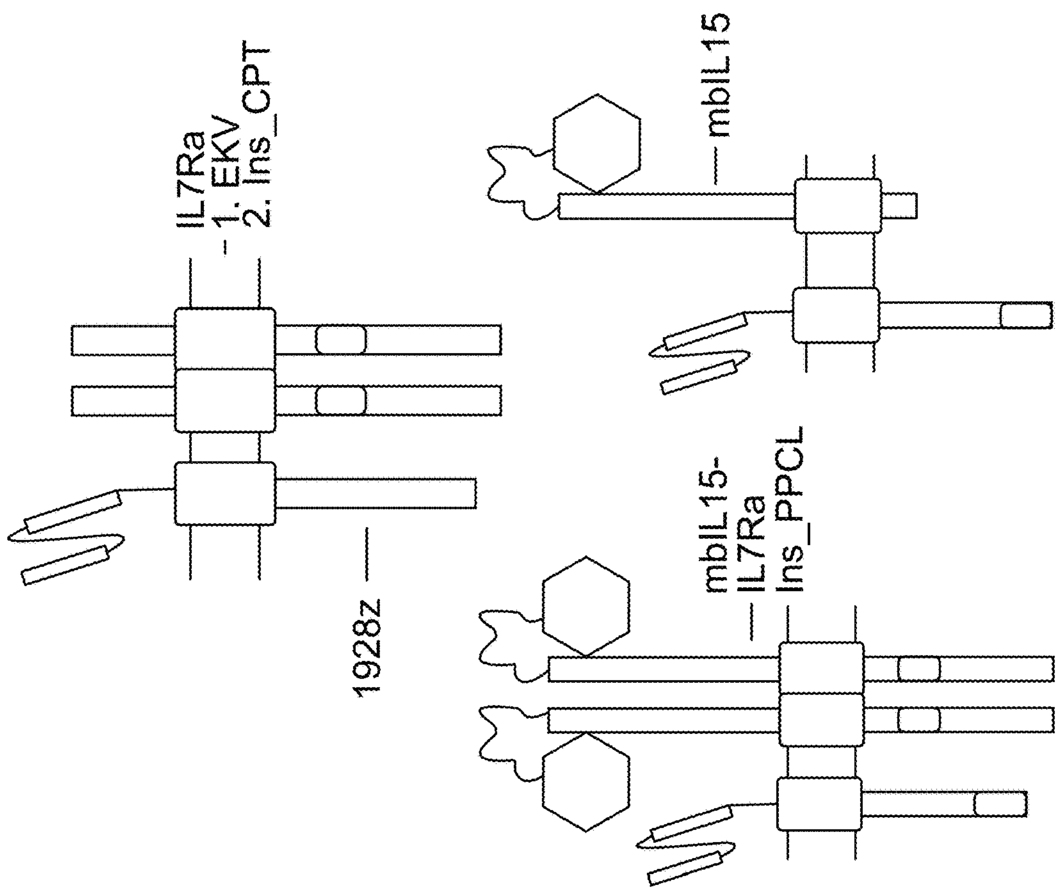
FIG. 8A shows schematic diagrams of IL7Rα mutant expression constructs and a 1928z chimeric antigen receptor expression construct that were used to co-infect primary T-cells.
FIG. 8B shows diagrammatically the 1928z chimeric antigen receptor being co-expressed at the T-cell surface with EKV or Ins_CPT IL7Rα mutant proteins, the mbIL15-17Rα Ins_PPCL chimeric transmembrane protein, or the mbIL15 chimeric transmembrane protein.

Example 5. IL7Rα Transmembrane Domain Mutations Co-Infect Primary T-Cells with CD19 CAR The expression of the CD19 CAR (1928z chimeric antigen receptor), EKV or Ins_CPT IL7Rα mutant proteins, the mbIL15-17Rα Ins_PPCL chimeric transmembrane protein, and the mbIL15 protein on the surface of primary T cells was assessed. FIGS. 8A and 8B show schematically the constructs and their co-expression on primary T cells.

Figure 8C:
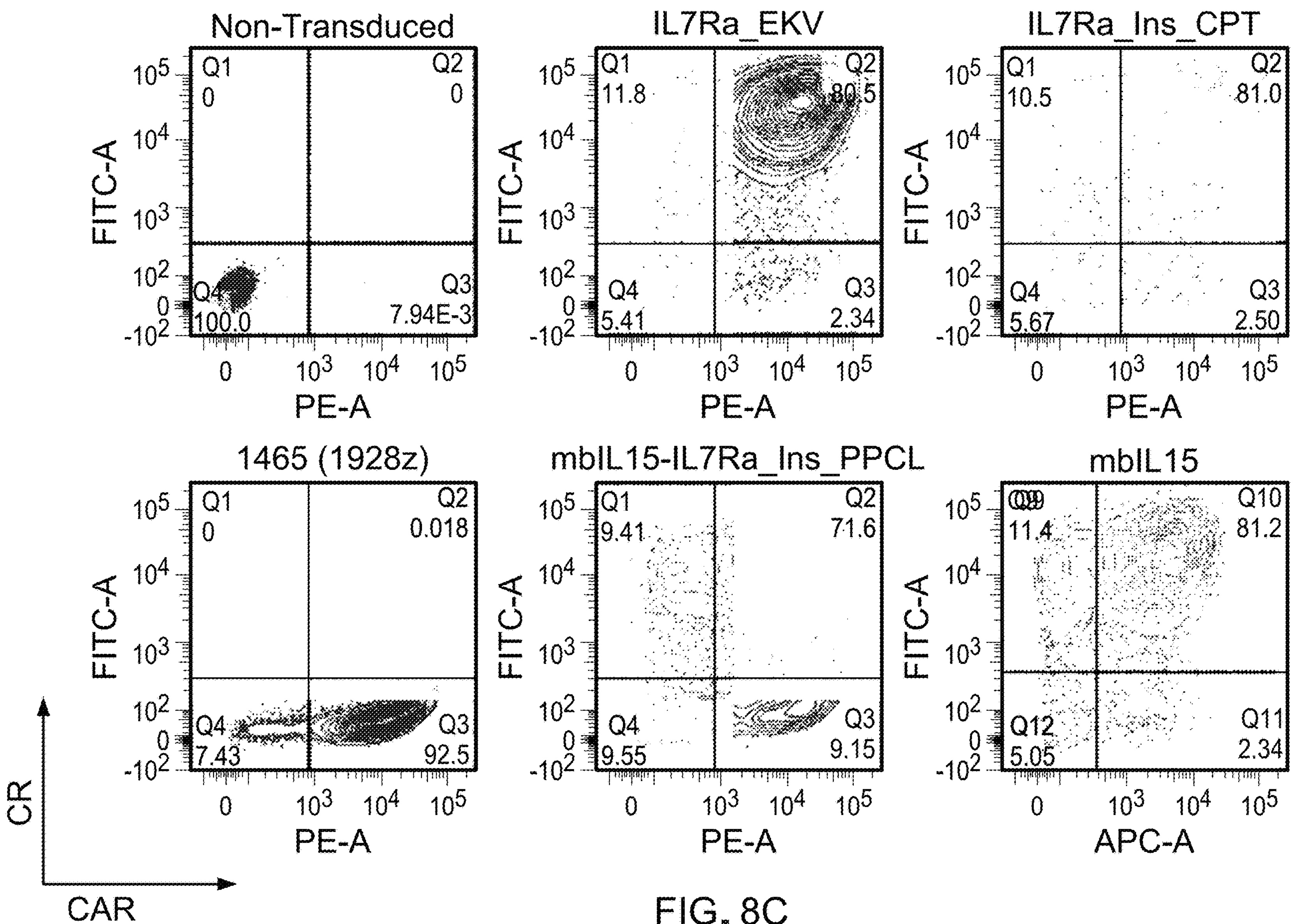
FIG. 8C is a set of flow cytometric data showing the expression of the 1928z chimeric antigen receptor, EKV or Ins_CPT IL7Rα mutant proteins, the mbIL15-17Rα Ins_PPCL chimeric transmembrane protein, and the mbIL15 protein on the surface of primary T cells. The data shown are from day 6 post-activation.

Primary T cells were either stained with fluorochrome conjugated antibodies against the His and Myc tags present at the N-terminus of the IL7Rα mutants and CAR, respectively, or stained with an anti-IL15Rα antibody to detect the surface expression of the chimeric mbIL15 proteins. Briefly, up to $1\times10^6$ cells were harvested 72 hours post transduction with lentiviral vectors and incubated with anti-His (APC; 1:100), or anti-IL15Rα (APC; 1:100) and anti-Myc (PE; 1:100) antibodies in PBS+2% FBS (FACS Buffer) for 30 minutes at 4° C. Flow cytometry was performed using BD LSRII Fortessa instruments and analyzed using FlowJo V10 software (FIG. 8C, data shown are from day 6 post-activation). GFP is expressed within the same transgene as the IL7Rα mutants and chimeric mbIL15 proteins, detection of GFP (FITC) by flow cytometry can be used as a surrogate for expression. A double positive (Myc-PE+, FITC) population demonstrates co-expression of both proteins on primary human T-cells.

Figure 8D:
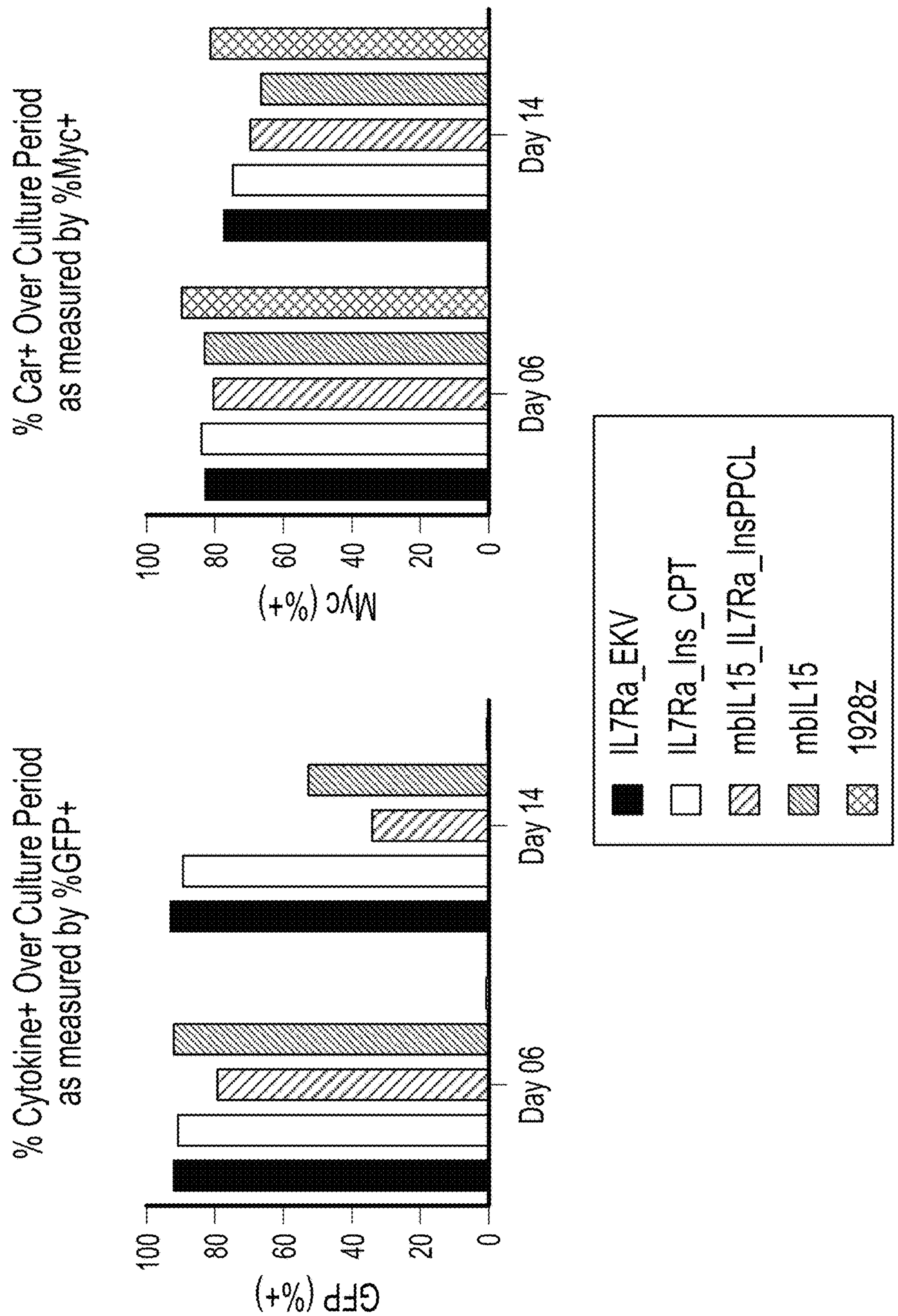
FIG. 8D is a set of two graphs showing that the number of cells expressing mbIL15-IL7Rα_Ins_PPCL and mbIL15 decreased from day 6 to day 14 in culture, while the number of cell expressing IL7Rα_EKV, IL7Rα_Ins_CPT, and the 1928z chimeric antigen receptor remained relatively constant over the same period.

The number of cells expressing mbIL15-IL7Rα_Ins_PPCL and mbIL15 decreased from day 6 to day 14 in culture (FIG. 8D). In contrast, the number of cells expressing IL7Rα_EKV, IL7Rα_Ins_CPT, and the 1928z chimeric antigen receptor remained relatively constant over the same period. Detection of GFP expression and N-terminal Myc tag (Myc-PE; 1:100 in FACS Buffer for 30 min) by flow cytometry was used to track the relative numbers of cells expressing the various IL7Rα mutants or chimeric transmembrane proteins and CD19 CAR, respectively, over a 14 day culture period (cells transduced on day 1 post activation).

Figure 9:
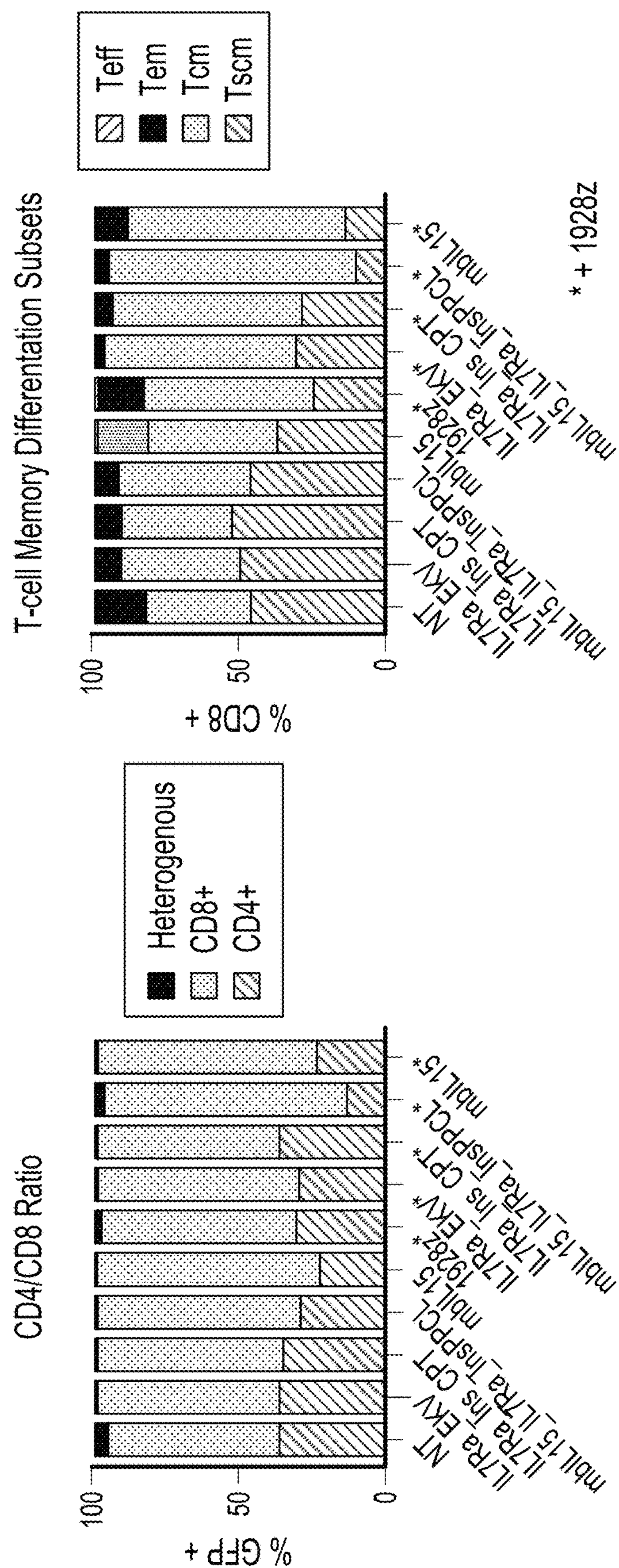
FIG. 9 is a set of two graphs showing that CAR T-cells expressing various IL7Rα mutants and chimeric transmembrane proteins maintain less differentiated memory phenotype at day 14 post activation.
Figure 10:
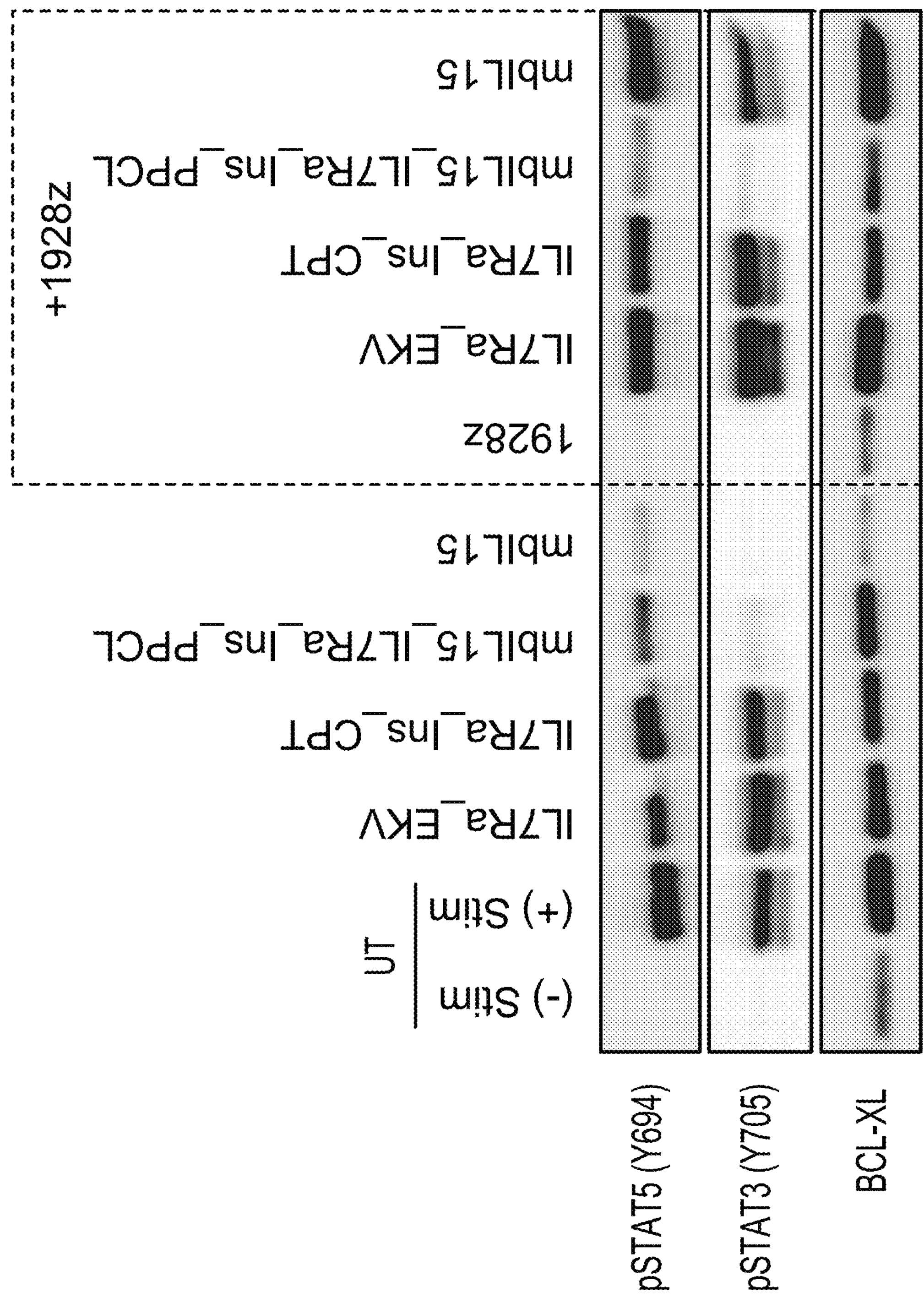
FIG. 10 is a set of immunoblots showing the levels of phosphorylated STATS and STAT3 and total protein level of BCL-XL in primary human T cells left untransduced or transduced with lentiviral vectors encoding one of the specific IL7Rα proteins or one of the specific chimeric transmembrane proteins with and without CAR (1928z).

CAR T-cells expressing various IL7Ra mutants and chimeric transmembrane proteins maintain less differentiated memory phenotype at day 14-post activation (FIG. 9). Briefly, up to $1\times10^6$ cells were harvested 14 days post activation and incubated with anti-Myc (FITC; 1:100), anti-CD4 (BV785; 1:200), anti-CD8 (PE; 1:200), anti-CD45RO (APC; 1:200), and anti CD62L (BV605; 1:200) antibodies in PBS+2% FBS (FACS Buffer) for 30 minutes at 4° C. Flow cytometry was performed using BD LSRII Fortessa instruments and analyzed using FlowJo V10 software. T-cell memory subset populations (CD62L vs CD45RO) were gated on Myc+, CD8+ populations. Teff=effector T cells. Tem=effector memory T cells. Tcm=central memory T cells. Tscm=stem cell memory T cells.

The levels of phosphorylated STATS and STAT3 and total protein level of BCL-XL in primary human T cells left untransduced or transduced with lentiviral vectors encoding one of the IL7Rα proteins shown or one of the chimeric transmembrane proteins shown (with and without CAR) was assessed. Whole cell lysates were prepared from T-cells following 16-20 hr under serum/cytokine starved conditions 14 days post activation. UT T cells stimulated with 100 ng/ml soluble IL2 for 15 min serve as a positive control (+ stim), while unstimulated-UT cells (− stim) provide basal phospho/protein levels.

Figure 11A:
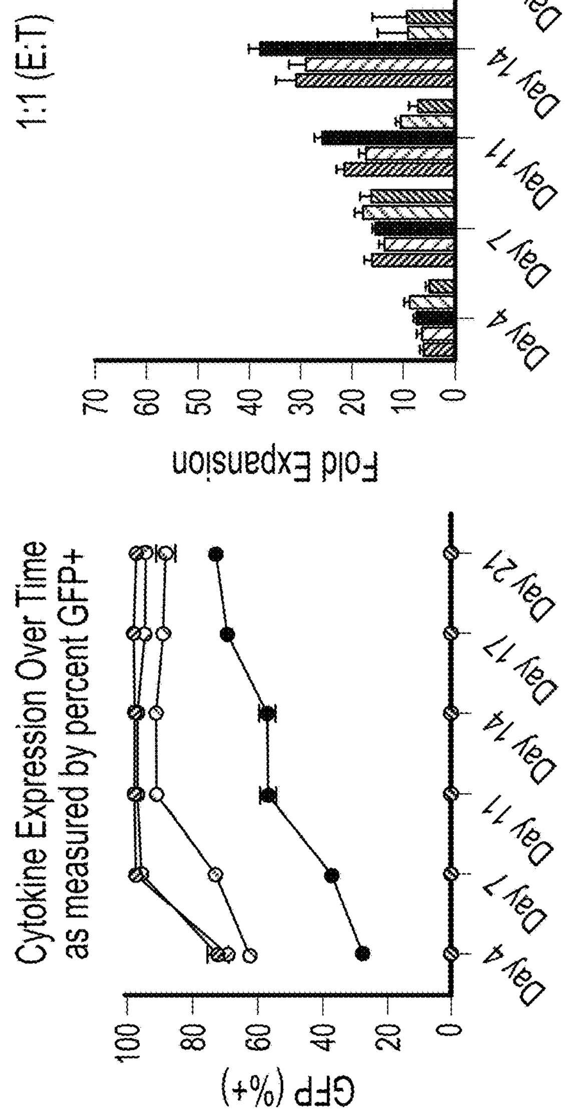
FIG. 11A is a line graph showing the expansion of cells that express the various IL7Rα mutants and FIG. 11B is a bar graph showing fold expansion of CAR-T cells over 21 days of serial encounter with Nalm6 target cells; together
Figure 11B:
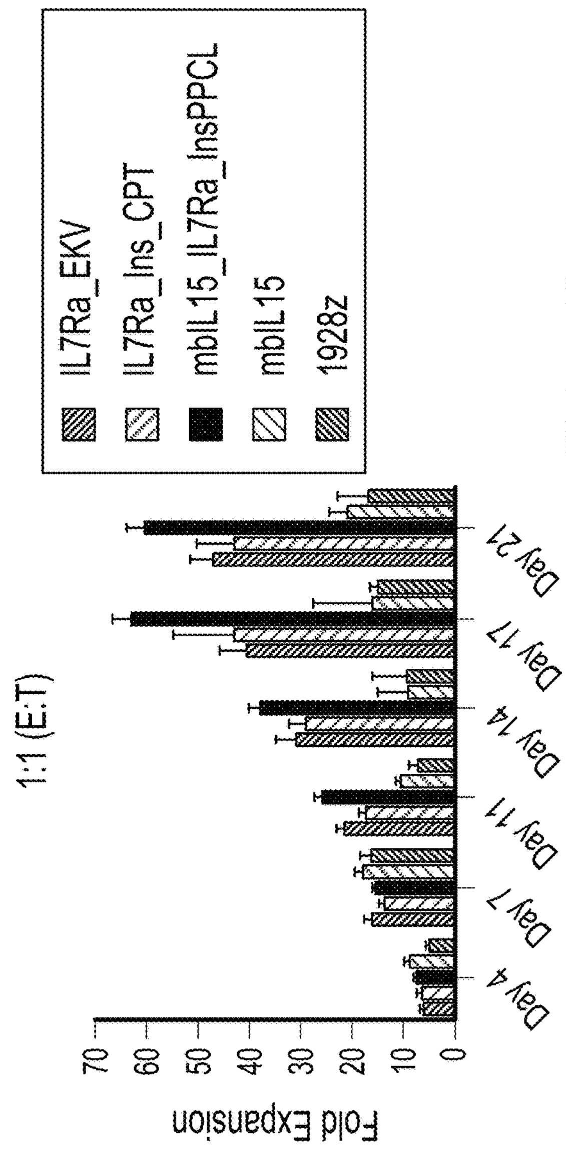

Example 6. CAR-T Cells Expressing IL7Rα Mutants Demonstrate Superior Expansion to Control CAR-T Cells Upon Serial Exposure to Antigen The expansion of CAR T-cells expressing IL7Rα mutants compared to control CAR upon serial exposure to antigen at a 1:1 ratio effector to target (E:T) ratio was assessed. At day 14 post activation, $5\times10^5$ CAR+ T-cells were plated against $5\times10^5$ Nalm6 B-cells on day 0 in each well of a GRex 24-well plate. Cells were plated in triplicate repeats. Nalm6 B cells and fresh cell culture media were added back to culture plates on days 4, 7, 11, 14, and 17 at a 1:1 ratio based to the number of CAR+ cells in each well as calculated by flow cytometry. All cells expressing IL7Rα mutants maintained 100% lysis of tumor cells throughout the 21 day assay relative to untransduced and tumor alone controls. Fold expansion of CAR+ T-cells was determined by flow cytometric analysis on days 4, 7, 11, 17, and 21. Briefly, up to $1\times10^6$ cells were harvested at each time point and incubated with anti-Myc (PE; 1:100), anti-CD3 (BV421; 1:100), anti-CD4 (BV785; 1:200), anti-CD8 (PE; 1:200), anti-CD45RO (APC; 1:200), anti-CD62L (BV605; 1:200), and anti-PD1 (PE-Cy7; 1:200) antibodies in PBS+2% FBS (FACS Buffer) for 30 minutes at 4° C. Counting beads (50 μl, 123 Count™ eBeads, Thermo Fisher Scientific) were added to each tube directly prior to flow cytometric analysis allowing for quantification of cell numbers in each condition. These numbers were used to track CAR+ expansion rates and to determine the number of Nalm6 target cells to add back to each well at a 1:1 E:T ratio. These data show that CAR T-cells expressing IL7Rα mutants demonstrate superior expansion compared to control CAR upon serial exposure to antigen at a 1:1 ratio effector to target (E:T) ratio (FIGS. 11A and 11B).

Percent lysis of CD19+ Nalm6 B-cells (FIG. 12A) and CD19-K562 cells (FIG. 12B) in a luciferase-based overnight killing assay was assessed. T-cells taken from the end of a 21-day serial killing assay (as described herein) and a Nalm6 or CD19-K562 cell line engineered to express firefly-luciferase (fLuc+). $1\times10^4$ Nalm6 or K562 cells were plated per well, and T-cells were plated according to % CAR+ at various E:T ratios. Cell lysis was measured based on relative light unit (RLU) intensity of live Nalm6 B- or K652 cells, and normalized to Nalm6 K562 alone controls.

Figure 12A:
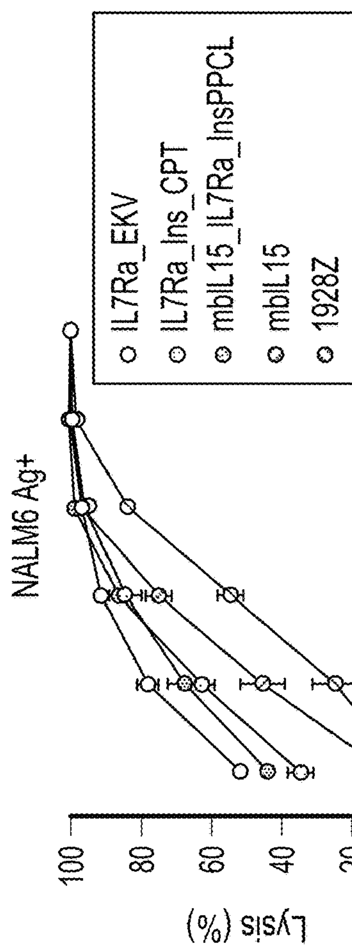
FIG. 12A is a line graph showing percent lysis of CD19+ Nalm6 B-cells in a luciferase-based overnight killing assay.

T-cells expressing IL7Rα mutants demonstrate superior killing of CD19+ Nalm6 B-cells over control CD19 CAR at low E:T ratios following 22 days of serial antigen encounter (FIG. 12A). As expected, donor and age matched (day 35 post activation) UT T-cells did not survive 21 day serial killing assay, therefore were not assayed here.

Figure 12B:
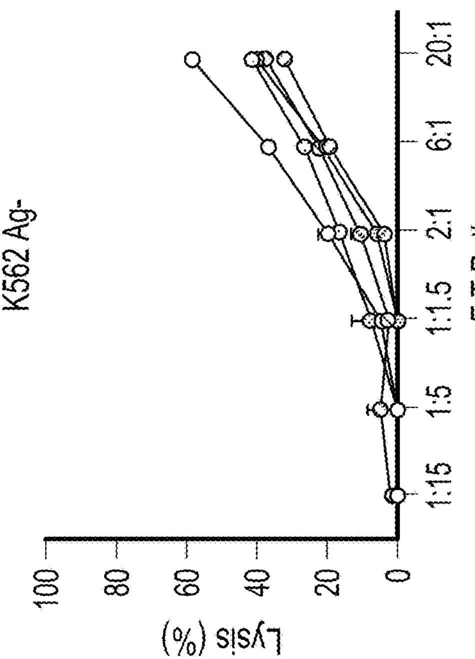
FIG. 12B is a line graph showing percent lysis of CD19- K562 cells in a luciferase-based overnight killing assay.

CAR T-cells expressing IL7Rα_EKV demonstrated increased off-target cytotoxicity against CD19-K562 at high E:T ratios (20:1 and 6:1), while CAR-T cells expressing other cytokine receptor variants demonstrated comparable off-target cytotoxicity to control CAR (FIG. 12B).

Figure 13:
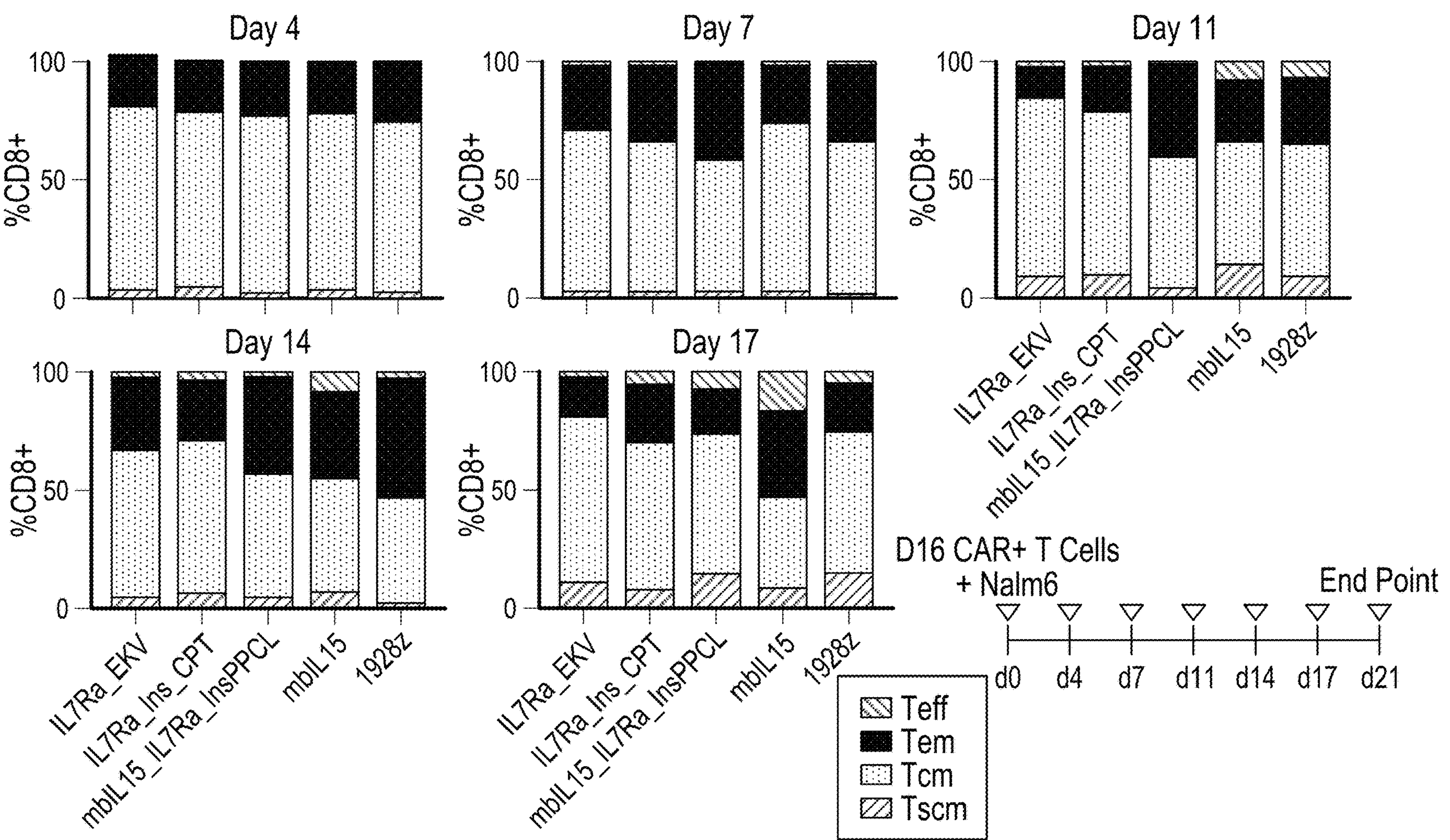
FIG. 13 is a set of bar graphs showing that CAR T-cells expressing IL7Rα mutants maintained a less differentiated memory phenotype at day 14 following serial exposure to antigen.

The memory type differentiation of CAR-T cells expressing IL7Rα mutants at day 14 following serial exposure to antigen was assessed (FIG. 13). Nalm6 B-cells were added to cell culture on days 0, 4, 7, 11, 14, 17, and 21. Teff=effector T cells. Tem=effector memory T cells. Tcm=central memory T cells. Tscm=stem cell memory T cells. Briefly, up to $1\times10^6$ cells were harvested at each time point and incubated with anti-Myc (PE; 1:100), anti-CD3 (BV421; 1:100), anti-CD4 (BV785; 1:200), anti-CD8 (PE; 1:200), anti-CD45RO (APC; 1:200), anti-CD62L (BV605; 1:200), and anti-PD1 (PE-Cy7; 1:200) antibodies in PBS+2% FBS (FACS Buffer) for 30 minutes at 4° C. These data show that CAR T-cells expressing IL7Rα mutants maintained a less differentiated memory phenotype at day 14 following serial exposure to antigen.

Figures 14A, 14B:
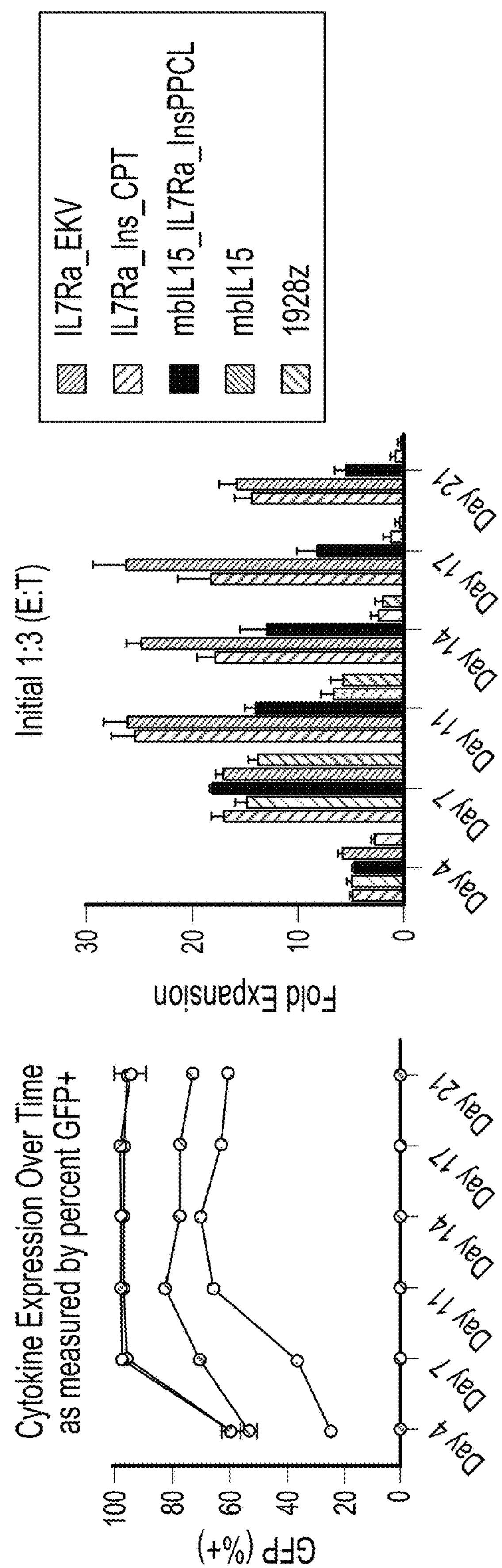
FIG. 14A is a line graph showing the expansion of cells expressing the various IL7Rα mutants and FIG. 14B is a bar graph showing fold expansion of CAR-T cells over 21 days following single encounter with antigen at a 1:3 E:T ratio; together

Example 7. CAR-T Cells Expressing IL7Rα Mutants Demonstrate Superior Expansion to Control CAR-T Cells Upon Single Exposure to Antigen Expansion of CAR T-cells expressing IL7Rα mutants compared to control CAR upon a single exposure to target at a 1:3 E:T ratio was assessed (FIGS. 14A and 14B). At day 14 post activation, $5\times10^5$ CAR+ T-cells were plated against $1.5\times10^6$ Nalm6 B-cells on day 0 in each well of a GRex 24-well plate. Cells were plated in triplicate repeats. All cells maintained 100% lysis of tumor cells throughout the 21 day assay relative to untransduced and tumor alone controls. Fold expansion of CAR+ T-cells was determined by flow cytometric analysis on days 4, 7, 11, 17, and 21. Briefly, up to $1\times10^6$ cells were harvested at each time point and incubated with anti-Myc (PE; 1:100), anti-CD3 (BV421; 1:100), anti-CD4 (BV785; 1:200), anti-CD8 (PE; 1:200), anti-CD45RO (APC; 1:200), anti-CD62L (BV605; 1:200), and anti-PD1 (PE-Cy7; 1:200) antibodies in PBS+2% FBS (FACS Buffer) for 30 minutes at 4° C. Counting beads (50 µl, 123Count™ eBeads) were added to each tube directly prior to analysis allowing for quantification of cell numbers in each condition. These data show that CAR T-cells expressing IL7Rα mutants demonstrate superior expansion to control CAR upon a single exposure to target.

Figure 15:
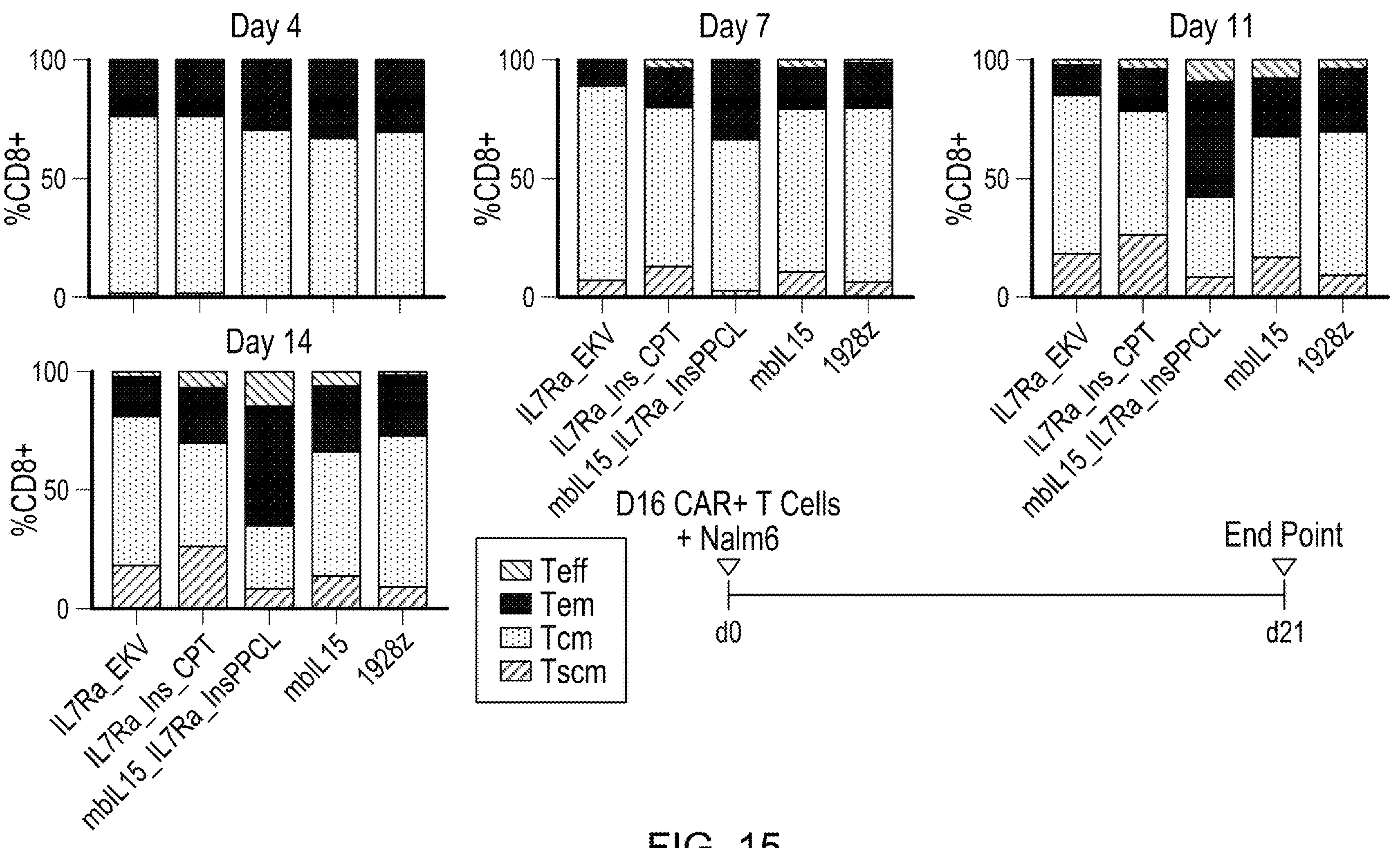
FIG. 15 is a set of bar graphs showing that CAR T-cells expressing IL7Rα mutants maintained a less differentiated memory phenotype at day 14 following single exposure to antigen.

The memory type differentiation of CAR-T cells expressing IL7Rα mutants at day 14 following serial exposure to antigen was assessed (FIG. 15). Nalm6 B-cells were added to cell culture on day 0. Briefly, up to $1\times10^6$ cells were harvested at each time point and incubated with anti-Myc (PE; 1:100), anti-CD3 (BV421; 1:100), anti-CD4 (BV785; 1:200), anti-CD8 (PE; 1:200), anti-CD45RO (APC; 1:200), anti-CD62L (BV605; 1:200), and anti-PD1 (PE-Cy7; 1:200) antibodies in PBS+2% FBS (FACS Buffer) for 30 minutes at 4° C. These data show that that CAR T-cells expressing IL7Rα mutants maintained a less differentiated memory phenotype at day 14 following single exposure to antigen. Teff=effector T cells. Tem=effector memory T cells. Tcm=central memory T cells. Tscm=stem cell memory T cells.

Example 8. CD19 CAR+IL7Ra CPT, MCP or PPCL In Vivo Test with Nalm6 Tumor $CD19^+$ Acute Lymphoblastic Leukemia (ALL) cell line Nalm6 was purchased from ATCC and transduced with luciferase to allow for bioluminescent imaging. $0.5\times10^6$ Nalm6_luc cells were implanted into NOD-SCID IL2Rgamma$^{null}$ (NSG) mice on the first day of the experiment. On day 6 (and every three to four days thereafter) animals were injected intraperitoneally with D-luciferin (150 mg/kg of 15 mg/mL substrate from Promega) and bioluminescence (BLI) was measured on an IVIS S5 Lumina (PerkinElmer, MA) imager. Images were analyzed using Living Image 4.3.1 (PerkinElmer, MA) to quantify whole body, fixed volume ROI, and total flux (photons/sec) was calculated and shown in Table 1 below. On day 6 of the experiment, animals were also divided into groups of six animals (with the exception of vehicle group for which there were only three animals) and dosed with non-transduced T cells or T cells carrying CD19 CAR alone, CD19 CAR+IL7RαCPT, CD19 CAR+IL7RαMCP, or CD19 CAR+IL7RαPPCL. All animals receiving CAR T cells received the stress test dose of $0.1\times10^6$ CAR T cells, and all animals received the same total number of T cells.

The protein and DNA sequences for each of the CD19 CAR, CD19 CAR+IL7RαCPT, CD19 CAR+IL7RαMCP, or CD19 CAR+IL7RαPPCL used in these experiments are shown below.

```
CD19 CAR DNA
                                                        (SEQ ID NO: 100)
GAACAGAAGCTGATAAGTGAGGAGGACTTGgacatccagatgacccagaccaccagcagc

ctgagcgccagcctgggcgatagagtgaccatcagctgcagagccagccaggacatcagcaagtacctgaactggtatc

agcagaaacccgacggcaccgtgaagctgctgatctaccacaccagcagactgcacagcggcgtgcccagcagattttc

tggcagcggctccggcaccgactacagcctgaccatctccaacctggaacaggaagatatcgctacctacttctgtcagca

aggcaacaccctgccctacaccttcggcggaggcaccaagctggaaatcacaggcggcggaggatctggcggaggcg

gaagtggcggagggggatctgaagtgaaactgcaggaaagcggccctggcctggtggccccatctcagtctctgagcgt

gacctgtaccgtgtccggcgtgtccctgcctgactatggcgtgtcctggatcagacagcccccagaaagggcctggaat

ggctgggagtgatctggggcagcgagacaacctactacaacagcgccctgaagtcccggctgaccatcatcaaggacaa

ctccaagagccaggtgttcctgaagatgaacagcctgcagaccgacgacaccgccatctactactgcgccaagcactact

actacggcggcagctacgccatggactactggggccagggcacaagcgtgaccgtgtctagcgggtccCTAGAC

AATGAGAAGAGCAATGGAACCATTATCCATGTGAAAGGGAAACACCTTTG

TCCAAGTCCCCTATTTCCCGGACCTTCTAAGCCCTTTTGGGTGCTGGTGGT

GGTTGGTGGAGTCCTGGCTTGCTATAGCTTGCTAGTAACAGTGGCCTTTAT

TATTTTCTGGGTGAGGAGTAAGAGGAGCAGGCTCCTGCACAGTGACTACA

TGAACATGACTCCCCGCCGCCCCGGGCCCACCCGCAAGCATTACCAGCCC

TATGCCCCACCACGCGACTTCGCAGCCTATCGCTCCCTGAGAGTGAAGTTC

AGCAGGAGCGCAGACGCCCCCGCGTACCAGCAGGGCCAGAACCAGCTCT

ATAACGAGCTCAATCTAGGACGAAGAGAGGAGTACGATGTTTTGGACAAG

AGgCGTGGCCGGGACCCTGAGATGGGGGGAAAGCCGAGAAGGAAGAACC

CTCAGGAAGGCCTGTACAATGAACTGCAGAAAGATAAGATGGCGGAGGC

CTACAGTGAGATTGGGATGAAAGGCGAGCGCCGGAGGGGCAAGGGGCAC
```

-continued

GATGGCCTTTACCAGGGTCTCAGTACAGCCACCAAGGACACCTACGACGC

CCTTCACATGCAGGCCCTGCCCCCTCGCT

CD19 CAR Protein (SEQ ID NO: 101)

EQKLISEEDLDIQMTQTTSSLSASLGDRVTISCRASQDISKYLNWYQQKPDGT

VKLLIYHTSRLHSGVPSRFSGSGSGTDYSLTISNLEQEDIATYFCQQGNTLPYT

FGGGTKLEITGGGGSGGGGSGGGGSEVKLQESGPGLVAPSQSLSVTCTVSGV

SLPDYGVSWIRQPPRKGLEWLGVIWGSETTYYNSALKSRLTIIKDNSKSQVFL

KMNSLQTDDTAIYYCAKHYYYGGSYAMDYWGQGTSVTVSSGSLDNEKSNG

TIIHVKGKHLCPSPLFPGPSKPFWVLVVVGGVLACYSLLVTVAFIIFWVRSKRS

RLLHSDYMNMTPRRPGPTRKHYQPYAPPRDFAAYRSLRVKFSRSADAPAYQ

QGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR

CD19 CAR + IL7RA_CPT DNA (SEQ ID NO: 102)

GAACAGAAGCTGATAAGTGAGGAGGACTTGgacatccagatgacccagaccaccagcagc ctgagcgccagcctgggcgatagagtgaccatcagctgcagagccagccaggacatcagcaagtacctgaactggtatc agcagaaacccgacggcaccgtgaagctgctgatctaccacaccagcagactgcacagcggcgtgcccagcagattttc tggcagcggctccggcaccgactacagcctgaccatctccaacctggaacaggaagatatcgctacctacttctgtcagca aggcaacaccctgccctacaccttcggcggaggcaccaagctggaaatcacaggcggcggaggatctggcggaggcg gaagtggcggagggggatctgaagtgaaactgcaggaaagcggccctggcctggtggccccatctcagtctctgagcgt gacctgtaccgtgtccggcgtgtccctgcctgactatggcgtgtcctggatcagacagcccccccagaaagggcctggaat ggctgggagtgatctggggcagcgagacaacctactacaacagcgccctgaagtcccggctgaccatcatcaaggacaa ctccaagagccaggtgttcctgaagatgaacagcctgcagaccgacgacaccgccatctactactgcgccaagcactact actacggcggcagctacgccatggactactggggccagggcacaagcgtgaccgtgtctagcgggtccCTAGAC

AATGAGAAGAGCAATGGAACCATTATCCATGTGAAAGGGAAACACCTTTG

TCCAAGTCCCCTATTTCCCGGACCTTCTAAGCCCTTTTGGGTGCTGGTGGT

GGTTGGTGGAGTCCTGGCTTGCTATAGCTTGCTAGTAACAGTGGCCTTTAT

TATTTTCTGGGTGAGGAGTAAGAGGAGCAGGCTCCTGCACAGTGACTACA

TGAACATGACTCCCCGCCGCCCCGGGCCCACCCGCAAGCATTACCAGCCC

TATGCCCCACCACGCGACTTCGCAGCCTATCGCTCCCTGAGAGTGAAGTTC

AGCAGGAGCGCAGACGCCCCCGCGTACCAGCAGGGCCAGAACCAGCTCT

ATAACGAGCTCAATCTAGGACGAAGAGAGGAGTACGATGTTTTGGACAAG

AGgCGTGGCCGGGACCCTGAGATGGGGGGAAAGCCGAGAAGGAAGAACC

CTCAGGAAGGCCTGTACAATGAACTGCAGAAAGATAAGATGGCGGAGGC

CTACAGTGAGATTGGGATGAAAGGCGAGCGCCGGAGGGGCAAGGGGCAC

GATGGCCTTTACCAGGGTCTCAGTACAGCCACCAAGGACACCTACGACGC

CCTTCACATGCAGGCCCTGCCCCCTCGCCGGAAGAGAAGAGGCAAGCCCA

TCCCCAACCCACTGCTGGGCCTGGATAGCACCTCCGGAAGCGGAGAGGGC

AGAGGCTCTCTGCTGACCTGCGGCGACGTGGAAGAGAACCCAGGgCCCAT

GCTCCTGCTCGTGACTTCACTTCTTCTCTGTGAACTCCCACACCCCGCGTTT

TTGCTTATCCCTcatcatcaccatcaccacGGCGAGAGCGGCTACGCCCAGAACGGC

GACCTGGAGGACGCCGAGCTGGACGACTACAGCTTCAGCTGCTACAGCCA

-continued

GCTGGAGGTGAACGGCAGCCAGCACAGCCTGACCTGCGCCTTCGAGGACC

CCGACGTGAACATCACCAACCTGGAGTTCGAGATCTGCGGCGCCCTGGTG

GAGGTGAAGTGCCTGAACTTCAGGAAGCTGCAGGAGATCTACTTCATCGA

GACCAAGAAGTTCCTGCTGATCGGCAAGAGCAACATCTGCGTGAAGGTGG

GCGAGAAGAGCCTGACCTGCAAGAAGATCGACCTGACCACCATCGTGAA

GCCCGAGGCCCCCTTCGACCTGAGCGTGGTGTACAGGGAGGGCGCCAACG

ACTTCGTGGTGACCTTCAACACCAGCCACCTGCAGAAGAAGTACGTGAAG

GTGCTGATGCACGACGTGGCCTACAGGCAGGAGAAGGACGAGAACAAGT

GGACCCACGTGAACCTGAGCAGCACCAAGCTGACCCTGCTGCAGAGGAA

GCTGCAGCCCGCCGCCATGTACGAGATCAAGGTGAGGAGCATCCCCGACC

ACTACTTCAAGGGCTTCTGGAGCGAGTGGAGCCCCAGCTACTACTTCAGG

ACCCCCGAGATCAACAACAGCAGCGGCGAGATGGACCCCATCCTGCTGAC

CTGCCCCACCATCAGCATCCTGAGCTTCTTCAGCGTGGCCCTGCTGGTGAT

CCTGGCCTGCGTGCTGTGGAAGAAGAGGATCAAGCCCATCGTGTGGCCCA

GCCTGCCCGACCACAAGAAGACCCTGGAGCACCTGTGTAAGAAGCCCAG

GAAGAACCTGAACGTGAGCTTCAACCCCGAGAGCTTCCTGGACTGCCAGA

TCCACAGGGTGGACGACATCCAGGCCAGGGACGAGGTGGAGGGCTTCCTG

CAGGACACCTTCCCCCAGCAGCTGGAGGAGAGCGAGAAGCAGAGGCTGG

GCGGCGACGTGCAGAGCCCCAACTGCCCCAGCGAGGACGTGGTGATCACC

CCCGAGAGCTTCGGCAGGGACAGCAGCCTGACCTGCCTGGCCGGCAACGT

GAGCGCCTGCGACGCCCCCATCCTGAGCAGCAGCAGGAGCCTGGACTGCA

GGGAGAGCGGCAAGAACGGCCCCCACGTGTACCAGGACCTGCTGCTGAG

CCTGGGCACCACCAACAGCACCCTGCCACCCCCCTTCAGCCTGCAGAGCG

GCATCCTGACCCTGAACCCCGTGGCCCAGGGCCAGCCCATCCTGACCAGC

CTGGGCAGCAACCAGGAGGAGGCCTACGTGACCATGAGCAGCTTCTACCA

GAACCAG

CD19 CAR + IL7RA_CPT Protein (SEQ ID NO: 103)

EQKLISEEDLDIQMTQTTSSLSASLGDRVTISCRASQDISKYLNWYQQKPDGT

VKLLIYHTSRLHSGVPSRFSGSGSGTDYSLTISNLEQEDIATYFCQQGNTLPYT

FGGGTKLEITGGGGSGGGGSGGGGSEVKLQESGPGLVAPSQSLSVTCTVSGV

SLPDYGVSWIRQPPRKGLEWLGVIWGSETTYYNSALKSRLTIIKDNSKSQVFL

KMNSLQTDDTAIYYCAKHYYYGGSYAMDYWGQGTSVTVSSGSLDNEKSNG

TIIHVKGKHLCPSPLFPGPSKPFWVLVVVGGVLACYSLLVTVAFIIFWVRSKRS

RLLHSDYMNMTPRRPGPTRKHYQPYAPPRDFAAYRSLRVKFSRSADAPAYQ

QGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPRRK

RRGKPIPNPLLGLDSTSGSGEGRGSLLTCGDVEENPGPMLLLVTSLLLCELPHP

AFLLIPHHHHHHGESGYAQNGDLEDAELDDYSFSCYSQLEVNGSQHSLTCAF

EDPDVNITNLEFEICGALVEVKCLNFRKLQEIYFIETKKFLLIGKSNICVKVGEK

SLTCKKIDLTTIVKPEAPFDLSVVYREGANDFVVTFNTSHLQKKYVKVLMHD

-continued

VAYRQEKDENKWTHVNLSSTKLTLLQRKLQPAAMYEIKVRSIPDHYFKGFW

SEWSPSYYFRTPEINNSSGEMDPILLTCPTISILSFFSVALLVILACVLWKKRIKP

IVWPSLPDHKKTLEHLCKKPRKNLNVSFNPESFLDCQIHRVDDIQARDEVEGF

LQDTFPQQLEESEKQRLGGDVQSPNCPSEDVVITPESFGRDSSLTCLAGNVSA

CDAPILSSSRSLDCRESGKNGPHVYQDLLLSLGTTNSTLPPPFSLQSGILTLNPV

AQGQPILTSLGSNQEEAYVTMSSFYQNQ

CD19CAR + IL7RaMCP DNA (SEQ ID NO: 104)

GAACAGAAGCTGATAAGTGAGGAGGACTTGgacatccagatgacccagaccaccagcagc ctgagcgccagcctgggcgatagagtgaccatcagctgcagagccagccaggacatcagcaagtacctgaactggtatc agcagaaacccgacggcaccgtgaagctgctgatctaccacaccagcagactgcacagcggcgtgcccagcagattttc tggcagcggctccggcaccgactacagcctgaccatctccaacctggaacaggaagatatcgctacctacttctgtcagca aggcaacaccctgccctacaccttcggcggaggcaccaagctggaaatcacaggcggcggaggatctggcggaggcg gaagtggcggaggggggatctgaagtgaaactgcaggaaagcggccctggcctggtggccccatctcagtctctgagcgt gacctgtaccgtgtccggcgtgtccctgcctgactatggcgtgtcctggatcagacagcccccagaaagggcctggaat ggctgggagtgatctggggcagcgagacaacctactacaacagcgccctgaagtcccggctgaccatcatcaaggacaa ctccaagagccaggtgttcctgaagatgaacagcctgcagaccgacgacaccgccatctactactgcgccaagcactact actacggcggcagctacgccatggactactggggccagggcacaagcgtgaccgtgtctagcgggtccCTAGAC

AATGAGAAGAGCAATGGAACCATTATCCATGTGAAAGGGAAACACCTTTG

TCCAAGTCCCCTATTTCCCGGACCTTCTAAGCCCTTTTGGGTGCTGGTGGT

GGTTGGTGGAGTCCTGGCTTGCTATAGCTTGCTAGTAACAGTGGCCTTTAT

TATTTTCTGGGTGAGGAGTAAGAGGAGCAGGCTCCTGCACAGTGACTACA

TGAACATGACTCCCCGCCGCCCCGGGCCCACCCGCAAGCATTACCAGCCC

TATGCCCCACCACGCGACTTCGCAGCCTATCGCTCCCTGAGAGTGAAGTTC

AGCAGGAGCGCAGACGCCCCCGCGTACCAGCAGGGCCAGAACCAGCTCT

ATAACGAGCTCAATCTAGGACGAAGAGAGGAGTACGATGTTTTGGACAAG

AGgCGTGGCCGGGACCCTGAGATGGGGGGAAAGCCGAGAAGGAAGAACC

CTCAGGAAGGCCTGTACAATGAACTGCAGAAAGATAAGATGGCGGAGGC

CTACAGTGAGATTGGGATGAAAGGCGAGCGCCGGAGGGGCAAGGGGCAC

GATGGCCTTTACCAGGGTCTCAGTACAGCCACCAAGGACACCTACGACGC

CCTTCACATGCAGGCCCTGCCCCCTCGCCGGAAGAGAAGAGGCAAGCCCA

TCCCCAACCCACTGCTGGGCCTGGATAGCACCTCCGGAAGCGGAGAGGGC

AGAGGCTCTCTGCTGACCTGCGGCGACGTGGAAGAGAACCCAGGgCCCAT

GCTCCTGCTCGTGACTTCACTTCTTCTCTGTGAACTCCCACACCCCGCGTTT

TTGCTTATCCCTcatcatcaccatcaccacGGCGAGAGCGGCTACGCCCAGAACGGC

GACCTGGAGGACGCCGAGCTGGACGACTACAGCTTCAGCTGCTACAGCCA

GCTGGAGGTGAACGGCAGCCAGCACAGCCTGACCTGCGCCTTCGAGGACC

CCGACGTGAACATCACCAACCTGGAGTTCGAGATCTGCGGCGCCCTGGTG

GAGGTGAAGTGCCTGAACTTCAGGAAGCTGCAGGAGATCTACTTCATCGA

GACCAAGAAGTTCCTGCTGATCGGCAAGAGCAACATCTGCGTGAAGGTGG

GCGAGAAGAGCCTGACCTGCAAGAAGATCGACCTGACCACCATCGTGAA

GCCCGAGGCCCCCTTCGACCTGAGCGTGGTGTACAGGGAGGGCGCCAACG

-continued

ACTTCGTGGTGACCTTCAACACCAGCCACCTGCAGAAGAAGTACGTGAAG

GTGCTGATGCACGACGTGGCCTACAGGCAGGAGAAGGACGAGAACAAGT

GGACCCACGTGAACCTGAGCAGCACCAAGCTGACCCTGCTGCAGAGGAA

GCTGCAGCCCGCCGCCATGTACGAGATCAAGGTGAGGAGCATCCCCGACC

ACTACTTCAAGGGCTTCTGGAGCGAGTGGAGCCCCAGCTACTACTTCAGG

ACCCCCGAGATCAACAACAGCAGCGGCGAGATGGACCCCATCCTGCTGAT

GTGCCCCACCATCAGCATCCTGAGCTTCTTCAGCGTGGCCCTGCTGGTGAT

CCTGGCCTGCGTGCTGTGGAAGAAGAGGATCAAGCCCATCGTGTGGCCCA

GCCTGCCCGACCACAAGAAGACCCTGGAGCACCTGTGTAAGAAGCCCAG

GAAGAACCTGAACGTGAGCTTCAACCCCGAGAGCTTCCTGGACTGCCAGA

TCCACAGGGTGGACGACATCCAGGCCAGGGACGAGGTGGAGGGCTTCCTG

CAGGACACCTTCCCCCAGCAGCTGGAGGAGAGCGAGAAGCAGAGGCTGG

GCGGCGACGTGCAGAGCCCCAACTGCCCCAGCGAGGACGTGGTGATCACC

CCCGAGAGCTTCGGCAGGGACAGCAGCCTGACCTGCCTGGCCGGCAACGT

GAGCGCCTGCGACGCCCCCATCCTGAGCAGCAGCAGGAGCCTGGACTGCA

GGGAGAGCGGCAAGAACGGCCCCCACGTGTACCAGGACCTGCTGCTGAG

CCTGGGCACCACCAACAGCACCCTGCCACCCCCCTTCAGCCTGCAGAGCG

GCATCCTGACCCTGAACCCCGTGGCCCAGGGCCAGCCCATCCTGACCAGC

CTGGGCAGCAACCAGGAGGAGGCCTACGTGACCATGAGCAGCTTCTACCA

GAACCAG

CD19CAR + IL7RaMCP Protein (SEQ ID NO: 105)

EQKLISEEDLDIQMTQTTSSLSASLGDRVTISCRASQDISKYLNWYQQKPDGT

VKLLIYHTSRLHSGVPSRFSGSGSGTDYSLTISNLEQEDIATYFCQQGNTLPYT

FGGGTKLEITGGGGSGGGGSGGGGSEVKLQESGPGLVAPSQSLSVTCTVSGV

SLPDYGVSWIRQPPRKGLEWLGVIWGSETTYYNSALKSRLTIIKDNSKSQVFL

KMNSLQTDDTAIYYCAKHYYYGGSYAMDYWGQGTSVTVSSGSLDNEKSNG

TIIHVKGKHLCPSPLFPGPSKPFWVLVVVGGVLACYSLLVTVAFIIFWVRSKRS

RLLHSDYMNMTPRRPGPTRKHYQPYAPPRDFAAYRSLRVKFSRSADAPAYQ

QGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPRRK

RRGKPIPNPLLGLDSTSGSGEGRGSLLTCGDVEENPGPMLLLVTSLLLCELPHP

AFLLIPHHHHHHGESGYAQNGDLEDAELDDYSFSCYSQLEVNGSQHSLTCAF

EDPDVNITNLEFEICGALVEVKCLNFRKLQEIYFIETKKFLLIGKSNICVKVGEK

SLTCKKIDLTTIVKPEAPFDLSVVYREGANDFVVTFNTSHLQKKYVKVLMHD

VAYRQEKDENKWTHVNLSSTKLTLLQRKLQPAAMYEIKVRSIPDHYFKGFW

SEWSPSYYFRTPEINNSSGEMDPILLMCPTISILSFFSVALLVILACVLWKKRIK

PIVWPSLPDHKKTLEHLCKKPRKNLNVSFNPESFLDCQIHRVDDIQARDEVEG

FLQDTFPQQLEESEKQRLGGDVQSPNCPSEDVVITPESFGRDSSLTCLAGNVS

ACDAPILSSSRSLDCRESGKNGPHVYQDLLLSLGTTNSTLPPPFSLQSGILTLNP

VAQGQPILTSLGSNQEEAYVTMSSFYQNQ

CD19CAR + IL7RaPPCL DNA (SEQ ID NO: 106)

GAACAGAAGCTGATAAGTGAGGAGGACTTGgacatccagatgacccagaccaccagcagc ctgagcgccagcctgggcgatagagtgaccatcagctgcagagccagccaggacatcagcaagtacctgaactggtatc agcagaaacccgacggcaccgtgaagctgctgatctaccacaccagcagactgcacagcggcgtgcccagcagattttc tggcagcggctccggcaccgactacagcctgaccatctccaacctggaacaggaagatatcgctacctacttctgtcagca aggcaacaccctgccctacaccttcggcggaggcaccaagctggaaatcacaggcggcggaggatctggcggaggcg gaagtggcggagggggatctgaagtgaaactgcaggaaagcggccctggcctggtggccccatctcagtctctgagcgt gacctgtaccgtgtccggcgtgtccctgcctgactatggcgtgtcctggatcagacagcccccagaaagggcctggaat ggctgggagtgatctggggcagcgagacaacctactacaacagcgccctgaagtcccggctgaccatcatcaaggacaa ctccaagagccaggtgttcctgaagatgaacagcctgcagaccgacgacaccgccatctactactgcgccaagcactact actacggcggcagctacgccatggactactggggccagggcacaagcgtgaccgtgtctagcgggtccCTAGAC

AATGAGAAGAGCAATGGAACCATTATCCATGTGAAAGGGAAACACCTTTG

TCCAAGTCCCCTATTTCCCGGACCTTCTAAGCCCTTTTGGGTGCTGGTGGT

GGTTGGTGGAGTCCTGGCTTGCTATAGCTTGCTAGTAACAGTGGCCTTTAT

TATTTTCTGGGTGAGGAGTAAGAGGAGCAGGCTCCTGCACAGTGACTACA

TGAACATGACTCCCCGCCGCCCCGGGCCCACCCGCAAGCATTACCAGCCC

TATGCCCCACCACGCGACTTCGCAGCCTATCGCTCCCTGAGAGTGAAGTTC

AGCAGGAGCGCAGACGCCCCCGCGTACCAGCAGGGCCAGAACCAGCTCT

ATAACGAGCTCAATCTAGGACGAAGAGAGGAGTACGATGTTTTGGACAAG

AGgCGTGGCCGGGACCCTGAGATGGGGGGAAAGCCGAGAAGGAAGAACC

CTCAGGAAGGCCTGTACAATGAACTGCAGAAAGATAAGATGGCGGAGGC

CTACAGTGAGATTGGGATGAAAGGCGAGCGCCGGAGGGGCAAGGGGCAC

GATGGCCTTTACCAGGGTCTCAGTACAGCCACCAAGGACACCTACGACGC

CCTTCACATGCAGGCCCTGCCCCCTCGCCGGAAGAGAAGAGGCAAGCCCA

TCCCCAACCCACTGCTGGGCCTGGATAGCACCTCCGGAAGCGGAGAGGGC

AGAGGCTCTCTGCTGACCTGCGGCGACGTGGAAGAGAACCCAGGgCCCAT

GCTCCTGCTCGTGACTTCACTTCTTCTCTGTGAACTCCCACACCCCGCGTTT

TTGCTTATCCCTcatcatcaccatcaccacGGCGAGAGCGGCTACGCCCAGAACGGC

GACCTGGAGGACGCCGAGCTGGACGACTACAGCTTCAGCTGCTACAGCCA

GCTGGAGGTGAACGGCAGCCAGCACAGCCTGACCTGCGCCTTCGAGGACC

CCGACGTGAACATCACCAACCTGGAGTTCGAGATCTGCGGCGCCCTGGTG

GAGGTGAAGTGCCTGAACTTCAGGAAGCTGCAGGAGATCTACTTCATCGA

GACCAAGAAGTTCCTGCTGATCGGCAAGAGCAACATCTGCGTGAAGGTGG

GCGAGAAGAGCCTGACCTGCAAGAAGATCGACCTGACCACCATCGTGAA

GCCCGAGGCCCCCTTCGACCTGAGCGTGGTGTACAGGGAGGGCGCCAACG

ACTTCGTGGTGACCTTCAACACCAGCCACCTGCAGAAGAAGTACGTGAAG

GTGCTGATGCACGACGTGGCCTACAGGCAGGAGAAGGACGAGAACAAGT

GGACCCACGTGAACCTGAGCAGCACCAAGCTGACCCTGCTGCAGAGGAA

GCTGCAGCCCGCCGCCATGTACGAGATCAAGGTGAGGAGCATCCCCGACC

ACTACTTCAAGGGCTTCTGGAGCGAGTGGAGCCCCAGCTACTACTTCAGG

ACCCCCGAGATCAACAACAGCAGCGGCGAGATGGACCCCATCCTGCTGCC

-continued

ACCCTGTTTAACCATCAGCATCCTGAGCTTCTTCAGCGTGGCCCTGCTGGT

GATCCTGGCCTGCGTGCTGTGGAAGAAGAGGATCAAGCCCATCGTGTGGC

CCAGCCTGCCCGACCACAAGAAGACCCTGGAGCACCTGTGTAAGAAGCCC

AGGAAGAACCTGAACGTGAGCTTCAACCCCGAGAGCTTCCTGGACTGCCA

GATCCACAGGGTGGACGACATCCAGGCCAGGGACGAGGTGGAGGGCTTC

CTGCAGGACACCTTCCCCCAGCAGCTGGAGGAGAGCGAGAAGCAGAGGC

TGGGCGGCGACGTGCAGAGCCCCAACTGCCCCAGCGAGGACGTGGTGATC

ACCCCCGAGAGCTTCGGCAGGGACAGCAGCCTGACCTGCCTGGCCGGCAA

CGTGAGCGCCTGCGACGCCCCCATCCTGAGCAGCAGCAGGAGCCTGGACT

GCAGGGAGAGCGGCAAGAACGGCCCCCACGTGTACCAGGACCTGCTGCT

GAGCCTGGGCACCACCAACAGCACCCTGCCACCCCCCTTCAGCCTGCAGA

GCGGCATCCTGACCCTGAACCCCGTGGCCCAGGGCCAGCCCATCCTGACC

AGCCTGGGCAGCAACCAGGAGGAGGCCTACGTGACCATGAGCAGCTTCTA

CCAGAACCAG

CD19CAR + IL7RaPPCL Protein (SEQ ID NO: 107)

EQKLISEEDLDIQMTQTTSSLSASLGDRVTISCRASQDISKYLNWYQQKPDGT

VKLLIYHTSRLHSGVPSRFSGSGSGTDYSLTISNLEQEDIATYFCQQGNTLPYT

FGGGTKLEITGGGGSGGGGSGGGGSEVKLQESGPGLVAPSQSLSVTCTVSGV

SLPDYGVSWIRQPPRKGLEWLGVIWGSETTYYNSALKSRLTIIKDNSKSQVFL

KMNSLQTDDTAIYYCAKHYYYGGSYAMDYWGQGTSVTVSSGSLDNEKSNG

TIIHVKGKHLCPSPLFPGPSKPFWVLVVVGGVLACYSLLVTVAFIIFWVRSKRS

RLLHSDYMNMTPRRPGPTRKHYQPYAPPRDFAAYRSLRVKFSRSADAPAYQ

QGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPRRK

RRGKPIPNPLLGLDSTSGSGEGRGSLLTCGDVEENPGPMLLLVTSLLLCELPHP

AFLLIPHHHHHHGESGYAQNGDLEDAELDDYSFSCYSQLEVNGSQHSLTCAF

EDPDVNITNLEFEICGALVEVKCLNFRKLQEIYFIETKKFLLIGKSNICVKVGEK

SLTCKKIDLTTIVKPEAPFDLSVVYREGANDFVVTFNTSHLQKKYVKVLMHD

VAYRQEKDENKWTHVNLSSTKLTLLQRKLQPAAMYEIKVRSIPDHYFKGFW

SEWSPSYYFRTPEINNSSGEMDPILLPPCLTISILSFFSVALLVILACVLWKKRIK

PIVWPSLPDHKKTLEHLCKKPRKNLNVSFNPESFLDCQIHRVDDIQARDEVEG

FLQDTFPQQLEESEKQRLGGDVQSPNCPSEDVVITPESFGRDSSLTCLAGNVS

ACDAPILSSSRSLDCRESGKNGPHVYQDLLLSLGTTNSTLPPPFSLQSGILTLNP

VAQGQPILTSLGSNQEEAYVTMSSFYQNQ

Tumor growth delay and the percentage of increase in life span was calculated as described below.

Tumor growth delay (TGD, or T-C)—TGD is a group endpoint. Tumor growth delay is expressed in units of days and is calculated from the median times it took the mice in a group to reach a specified tumor burden (time to evaluation size, TES). It was calculated as:

TGD=median TES treated−median TES control

Where control is UT T cells.

The % Increase in lifespan (ILS)−% ILS is a group endpoint. It was calculated as:

$$\%ILS=\left\{\frac{[(\text{median Treated Lifespan})-(\text{medium Control Lifespan})]}{\text{median Control Lifespan}}\right\}*100$$

Figure 17:
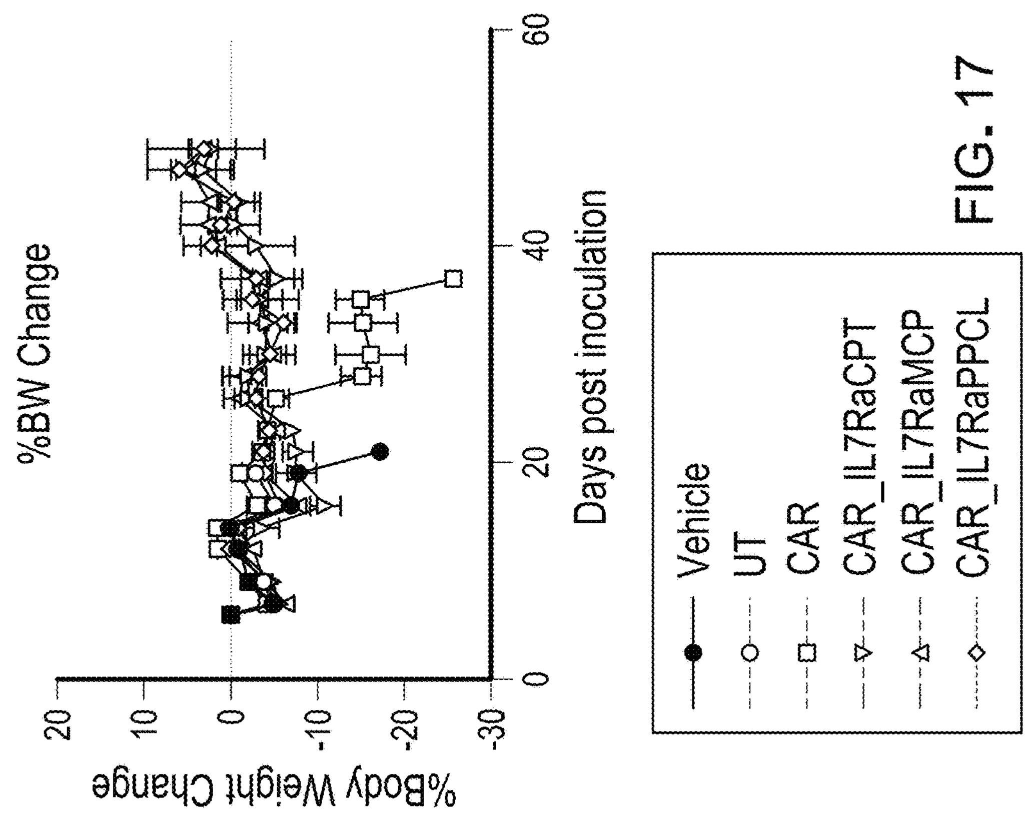
FIG. 17 is the change in body weight over time in NOD-SCID IL2Rgamma$^{null}$ mice administered $0.5\times10^6$ Nalm6_luc cells on day 1, followed by administration of $0.1\times10^6$ cells non-transduced T cells, or T cells carrying CD19 CAR alone, CD19 CAR+IL7RaCPT, CD19 CAR+IL7RaMCP, or CD19 CAR+IL7RaPPCL. The data shown are the mean+/−standard deviation.
Figure 16:
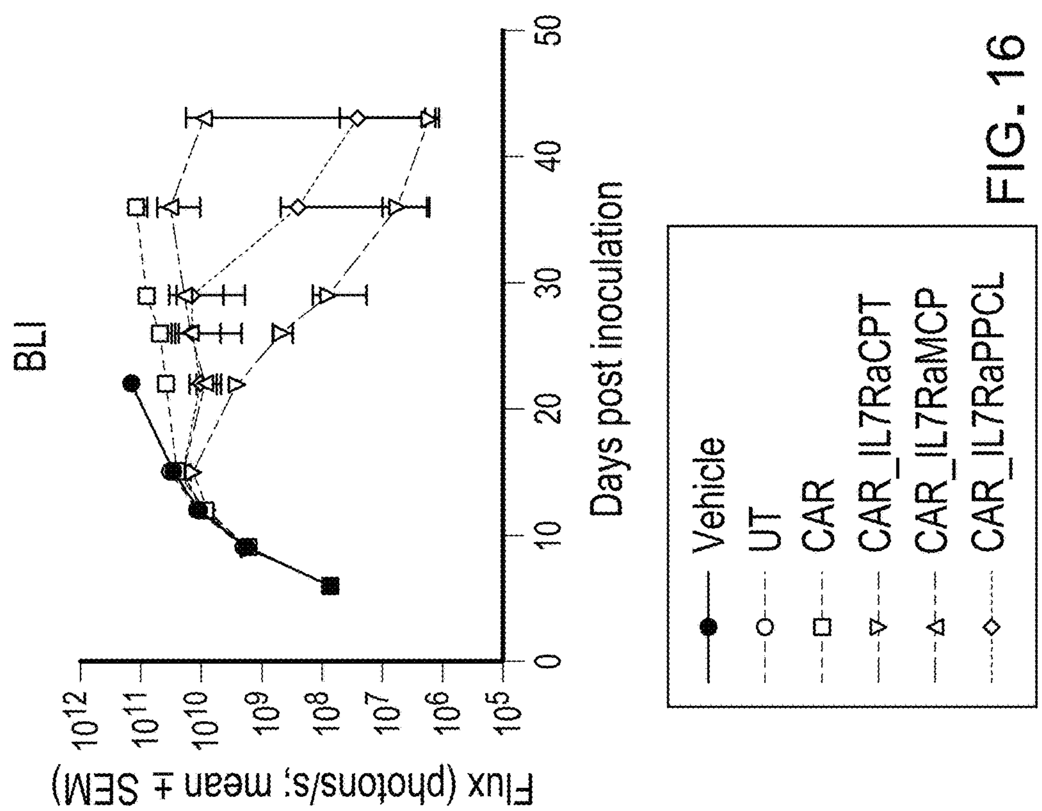
FIG. 16 is the measured flux (photons/second) over time in NOD-SCID IL2Rgamma$^{null}$ mice administered $0.5\times10^6$ Nalm6_luc cells on day 1, followed by administration of $0.1\times10^6$ cells non-transduced T cells, or T cells carrying CD19 CAR alone, CD19 CAR+IL7RaCPT, CD19 CAR+IL7RaMCP, or CD19 CAR+IL7RaPPCL. The data shown are the mean+/−standard deviation.
Figure 18:
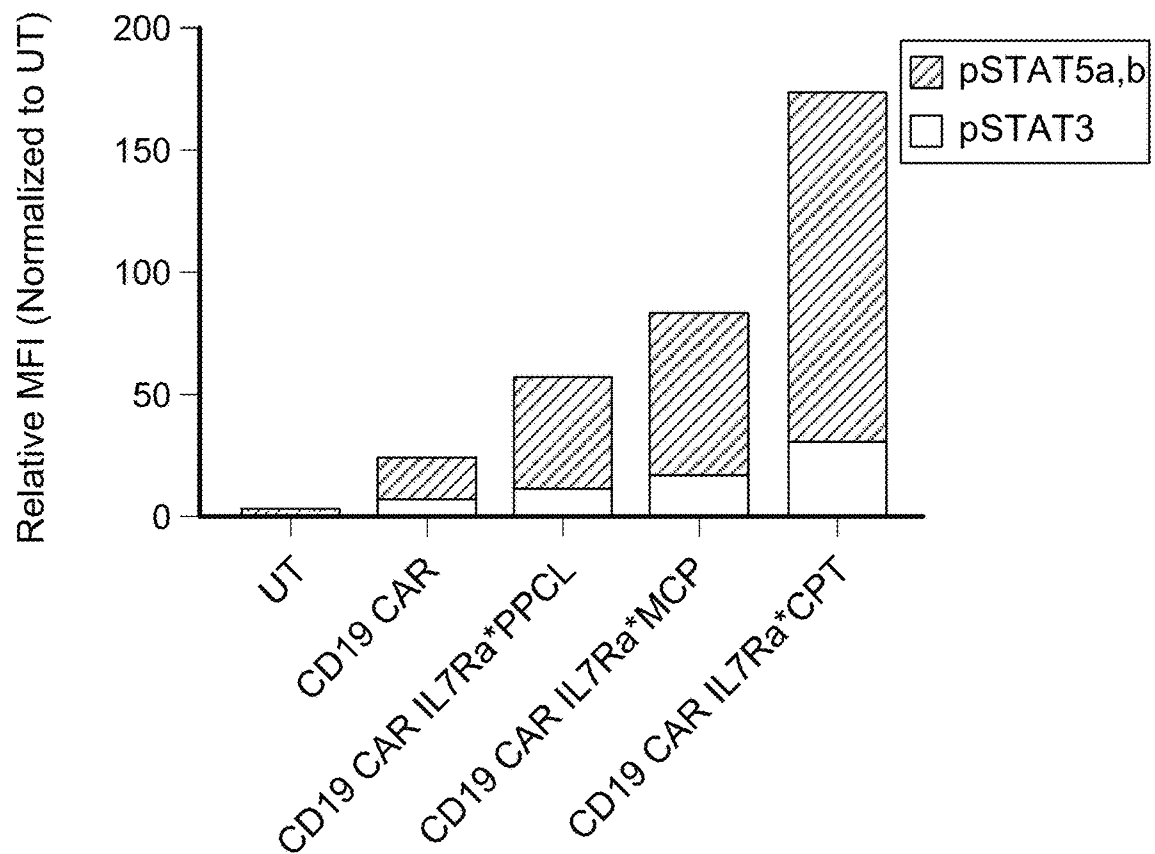
FIG. 18 is the relative mean fluorescence intensity (MFI) of pSTAT5a,b and pSTAT3 in non-transduced T cells, or T cells carrying CD19 CAR alone, CD19 CAR+IL7RaCPT, CD19 CAR+IL7RaMCP, or CD19 CAR+IL7RaPPCL. The mean fluorescence insensity data are compared to the mean fluorescence intensity measured in non-transduced T cells.

The data from these experiments are shown in FIGS. 16-18. Non-transduced T-cells had no anti-cancer activity. At the stress test dose of $0.1\times10^6$ cells, CD19 CAR alone increased life span of animals by 68.8%, but no increase in tumor growth delay. Treatment with CD19 CAR+IL7RaCPT was most efficacious with 175% increase in life span relative to vehicle treatment, and tumor growth delay >29.2 days. Treatment with CD19 CAR+IL7RaMCP and CD19 CAR+IL7RaPPT were both efficacious and increased life span >175% each with tumor growth delay of >22.0 and >17.9 days respectively.

TABLE 1

| Days post inoculation | | | | | | |
|---|---|---|---|---|---|---|
| | VEHICLE | | | | | |
| 6 | 113000000 | 49300000 | 63300000 | | | |
| 9 | 2800000000 | 1120000000 | 1460000000 | | | |
| 12 | 1.29E+10 | 9630000000 | 10400000000 | | | |
| 15 | 3.57E+10 | 20300000000 | 31400000000 | | | |
| 22 | 1.48E+11 | | | | | |
| 26 | | | | | | |
| 29 | | | | | | |
| 36 | | | | | | |
| 43 | | | | | | |
| | NONTRANSDUCED | | | | | |
| 6 | 64500000 | 54500000 | 112000000 | 62900000 | 79500000 | 82200000 |
| 9 | 1950000000 | 1340000000 | 2690000000 | 1750000000 | 2690000000 | 1710000000 |
| 12 | 8620000000 | 6800000000 | 22000000000 | 1.17E+10 | 1.27E+10 | 9370000000 |
| 15 | 3.72E+10 | 34200000000 | 54800000000 | 2.74E+10 | 3.66E+10 | 1.11E+10 |
| 22 | | | | | | |
| 26 | | | | | | |
| 29 | | | | | | |
| 36 | | | | | | |
| 43 | | | | | | |
| | CD19 CAR | | | | | |
| 6 | 84800000 | 61600000 | 68500000 | 110000000 | 54800000 | 77900000 |
| 9 | 1620000000 | 1320000000 | 1690000000 | 2450000000 | 1260000000 | 1370000000 |
| 12 | 8790000000 | 6760000000 | 10700000000 | 7700000000 | 8000000000 | 1.14E+10 |
| 15 | 3.44E+10 | 7770000000 | 28300000000 | 2.99E+10 | 2.25E+10 | 3.42E+10 |
| 22 | 3.14E+10 | 21900000000 | 33600000000 | 8.93E+10 | 3.12E+10 | 3.18E+10 |
| 26 | 1.67E+10 | 27300000000 | 28200000000 | 1.36E+11 | 4.9E+10 | 4.02E+10 |
| 29 | 1.21E+11 | 63500000000 | 83100000000 | 1.05E+11 | 8.4E+10 | 4.71E+10 |
| 36 | 1.72E+11 | | 84000000000 | | | |
| 43 | | | | | | |
| | CD19 CAR + IL7RaCPT | | | | | |
| 6 | 68600000 | 88400000 | 107000000 | 59900000 | 76800000 | 55900000 |
| 9 | 2390000000 | 1510000000 | 1820000000 | 762000000 | 1740000000 | 1370000000 |
| 12 | 8220000000 | 8260000000 | 9080000000 | 5280000000 | 8400000000 | 5540000000 |
| 15 | 1.79E+10 | 16200000000 | 14200000000 | 1.14E+10 | 1.07E+10 | 1.56E+10 |
| 22 | 3620000000 | 3550000000 | 1740000000 | 1890000000 | 1360000000 | 3490000000 |
| 26 | 690000000 | 495000000 | 147000000 | 220000000 | 126000000 | 1350000000 |
| 29 | 28300000 | 38700000 | 6530000 | 5090000 | 14300000 | 401000000 |
| 36 | 3460000 | 1170000 | 1730000 | 1070000 | 938000 | 26400000 |
| 43 | 2550000 | 953000 | | 873000 | 797000 | 3340000 |
| | CD19 CAR + IL7RaMCP | | | | | |
| 6 | 69600000 | 58600000 | 90700000 | 74800000 | 100000000 | 55900000 |
| 9 | 1870000000 | 1950000000 | 1990000000 | 1110000000 | 2620000000 | 1010000000 |
| 12 | 1.03E+10 | 6350000000 | 11500000000 | 1.32E+10 | 1.38E+10 | 5740000000 |
| 15 | 1.69E+10 | 16100000000 | 25700000000 | 3.07E+10 | 1.86E+10 | 1.38E+10 |
| 22 | 1770000000 | 5900000000 | 24700000000 | 5390000000 | 8260000000 | 7520000000 |
| 26 | 115000000 | 1970000000 | 80200000000 | 5300000 | 182000000 | 9760000000 |

TABLE 1-continued

| Days post inoculation | | | | | | |
|---|---|---|---|---|---|---|
| 29 | 2340000 | 1260000000 | 90800000000 | 2130000 | 2900000 | 2.31E+10 |
| 36 | 2990000 | 2770000 | 1.33E+11 | 1890000 | 2230000 | 6.85E+10 |
| 43 | 1240000 | 1510000 | | 978000 | 1330000 | 4.58E+10 |
| | CD19 CAR + IL7RaPPCL | | | | | |
| 6 | 74000000 | 100000000 | 97400000 | 74700000 | 56700000 | 56200000 |
| 9 | 1890000000 | 1980000000 | 3170000000 | 1000000000 | 998000000 | 811000000 |
| 12 | 1.12E+10 | 11700000000 | 16100000000 | 6850000000 | 7990000000 | 9090000000 |
| 15 | 1.98E+10 | 23300000000 | 21200000000 | 1.3E+10 | 1.92E+10 | 2.52E+10 |
| 22 | 4300000000 | 18800000000 | 36000000000 | 1290000000 | 2610000000 | 1580000000 |
| 26 | 1440000000 | 14100000000 | 62400000000 | 3110000 | 446000000 | 8730000000 |
| 29 | 66500000 | 8210000000 | 75200000000 | 1570000 | 428000000 | 1530000000 |
| 36 | 2780000 | 47600000 | 1480000000 | 659000 | 1550000 | 2990000 |
| 43 | 1400000 | 4250000 | 150000000 | 1020000 | 1440000 | 2140000 |

Example 9. In Vitro Serial Killing Experiment with GPC3 CAR+IL7RaCPT

An equal number of GPC3 CAR positive T cells and GPC3 CAR+IL7Rα CPT positive T-cells were co-cultured with Hep3B target cells from American Type Culture Company (ATCC, Manassas, Va.) ($0.5\times10^6$ CAR T cells co-cultured with $0.5\times10^6$ Hep3B target cells). The IL7Ra CPT protein is the same as described in Example 8. Target cells were added two-times per week every three to four days (at a 1:1 CAR T cell to target Hep3B cell ratio) for 35 days and the number of CAR T cells was measured by counting beads and flow cytometry. The target cells were added until day 35 and the number of CART cells after day 35 were measured once a week. The CAR T cells numbers are shown in Table 2 below.

The protein and DNA sequences for the GPC3 CAR and the GPC3 CAR+IL7RαCPT are shown below.

GPC3 CAR DNA
(SEQ ID NO: 108)

GATATCGTGATGACCCAGAGCCCCGACTCTTTAGCTGTGTCTTTAGGAGA
GAGGGCCACAATCAACTGCAAGAGCAGCCAGAGCCTCCTCTACAGCAGCA
ACCAGAAGAACTATTTAGCTTGGTACCAGCAAAAGCCCGGCCAGCCCCCC
AAGCTGCTGATCTACTGGGCCAGCAGCAGAGAGAGCGGCGTGCCCGATAG
ATTCAGCGGAAGCGGCTCCGGCACAGATTTCACCCTCACCATTAGCTCTT
TACAAGCTGAGGACGTGGCCGTGTACTACTGCCAGCAGTACTACAACTAC
CCTTTAACCTTCGGCCAAGGTACCAAGCTGGAGATCAAGGGCTCCACATC
CGGATCCGGCAAGCCCGGTAGCGGAGAAGGCAGCACAAAGGGAGAGGTGC
AGCTGGTGGAGAGCGGAGGCGGACTGGTCCAGCCCGGTGGATCTTTAAGG
CTGTCTTGTGCCGCCAGCGGCTTTACCTTTAACAAGAACGCTATGAACTG
GGTGAGGCAAGCTCCCGGTAAGGGTTTAGAGTGGGTGGGTCGTATTCGTA
ATAAGACCAACAACTACGCCACCTACTATGCCGACTCCGTGAAGGCTCGT
TTCACCATCTCTCGTGACGACAGCAAGAACAGCCTCTATTTACAGATGAA
CTCTTTAAAGACCGAGGACACCGCCGTGTACTATTGCGTGGCTGGCAACT
CCTTCGCCTACTGGGGCCAAGGCACTTTAGTGACCGTGAGCTCCgggtcc
ACCACGACGCCAGCGCCGCGACCACCAACACCGGCGCCCACCATCGCGTC
GCAGCCCCTGTCCCTGCGCCCAGAGGCGTGCCGGCCAgcggcggggggcg -continued cagTGCACACGAGGGGGCTGGACTTCGCCTGTGATATCTACATCTGGGCG
CCCTTGGCCGGGACTTGTGGGGTCCTTCTCCTGTCACTGGTTATCACCCT
TTACTGCAAACGGGGCAGAAAGAAACTCCTGTATATATTCAAACAACCAT
TTATGAGACCAGTACAAACTACTCAAGAGGAAGATGGCTGTAGCTGCCGA
TTTCCAGAAGAAGAAGAAGGAGGATGTGAACTGAGAGTGAAGTTCAGCAG
GAGCGCAGACGCCCCCGCGTACCAGCAGGGCCAGAACCAGCTCTATAACG
AGCTCAATCTAGGACGAAGAGAGGAGTACGATGTTTTGGACAAGAGgCGT
GGCCGGGACCCTGAGATGGGGGGAAAGCCGAGAAGGAAGAACCCTCAGGA
AGGCCTGTACAATGAACTGCAGAAAGATAAGATGGCGGAGGCCTACAGTG
AGATTGGGATGAAAGGCGAGCGCCGGAGGGGCAAGGGGCACGATGGCCTT
TACCAGGGTCTCAGTACAGCCACCAAGGACACCTACGACGCCCTTCACAT
GCAGGCCCTGCCCCCTCGC GPC3 CAR Protein
(SEQ ID NO: 109)

DIVMTQSPDSLAVSLGERATINCKSSQSLLYSSNQKNYLAWYQQKPGQPP
KLLIYWASSRESGVPDRFSGSGSGTDFTLTISSLQAEDVAVYYCQQYYNY
PLTFGQGTKLEIKGSTSGSGKPGSGEGSTKGEVQLVESGGGLVQPGGSLR
LSCAASGFTFNKNAMNWVRQAPGKGLEWVGRIRNKTNNYATYYADSVKAR
FTISRDDSKNSLYLQMNSLKTEDTAVYYCVAGNSFAYWGQGTLVTVSSGS
TTTPAPRPPTPAPTIASQPLSLRPEACRPAAGGAVHTRGLDFACDIYIWA
PLAGTCGVLLLSLVITLYCKRGRKKLLYIFKQPFMRPVQTTQEEDGCSCR
FPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR

GPC3CAR + IL7RaCPT
(SEQ ID NO: 110)

GATATCGTGATGACCCAGAGCCCCGACTCTTTAGCTGTGTCTTTAGGAGA
GAGGGCCACAATCAACTGCAAGAGCAGCCAGAGCCTCCTCTACAGCAGCA
ACCAGAAGAACTATTTAGCTTGGTACCAGCAAAAGCCCGGCCAGCCCCCC
AAGCTGCTGATCTACTGGGCCAGCAGCAGAGAGAGCGGCGTGCCCGATAG
ATTCAGCGGAAGCGGCTCCGGCACAGATTTCACCCTCACCATTAGCTCTT

-continued

TACAAGCTGAGGACGTGGCCGTGTACTACTGCCAGCAGTACTACAACTAC

CCTTTAACCTTCGGCCAAGGTACCAAGCTGGAGATCAAGGGCTCCACATC

CGGATCCGGCAAGCCCGGTAGCGGAGAAGGCAGCACAAAGGGAGAGGTGC

AGCTGGTGGAGAGCGGAGGCGGACTGGTCCAGCCCGGTGGATCTTTAAGG

CTGTCTTGTGCCGCCAGCGGCTTTACCTTTAACAAGAACGCTATGAACTG

GGTGAGGCAAGCTCCCGGTAAGGGTTTAGAGTGGGTGGGTCGTATTCGTA

ATAAGACCAACAACTACGCCACCTACTATGCCGACTCCGTGAAGGCTCGT

TTCACCATCTCTCGTGACGACAGCAAGAACAGCCTCTATTTACAGATGAA

CTCTTTAAAGACCGAGGACACCGCCGTGTACTATTGCGTGGCTGGCAACT

CCTTCGCCTACTGGGGCCAAGGCACTTTAGTGACCGTGAGCTCCgggtcc

ACCACGACGCCAGCGCCGCGACCACCAACACCGGCGCCCACCATCGCGTC

GCAGCCCCTGTCCCTGCGCCCAGAGGCGTGCCGGCCAgcggcgggggcg cagTGCACACGAGGGGGCTGGACTTCGCCTGTGATATCTACATCTGGGCG

CCCTTGGCCGGGACTTGTGGGGTCCTTCTCCTGTCACTGGTTATCACCCT

TTACTGCAAACGGGGCAGAAAGAAACTCCTGTATATATTCAAACAACCAT

TTATGAGACCAGTACAAACTACTCAAGAGGAAGATGGCTGTAGCTGCCGA

TTTCCAGAAGAAGAAGAAGGAGGATGTGAACTGAGAGTGAAGTTCAGCAG

GAGCGCAGACGCCCCCGCGTACCAGCAGGGCCAGAACCAGCTCTATAACG

AGCTCAATCTAGGACGAAGAGAGGAGTACGATGTTTTGGACAAGAGgCGT

GGCCGGGACCCTGAGATGGGGGGAAAGCCGAGAAGGAAGAACCCTCAGGA

AGGCCTGTACAATGAACTGCAGAAAGATAAGATGGCGGAGGCCTACAGTG

AGATTGGGATGAAAGGCGAGCGCCGGAGGGGCAAGGGGCACGATGGCCTT

TACCAGGGTCTCAGTACAGCCACCAAGGACACCTACGACGCCCTTCACAT

GCAGGCCCTGCCCCCTCGCgggtcCGGAGAGGGCAGAGGCTCTCTGCTGA

CCTGCGGCGACGTGGAAGAGAACCCAGGgCCCATGCTCCTGCTCGTGACT

TCACTTCTTCTCTGTGAACTCCCACACCCCGCGTTTTTGCTTATCCCTca tcatcaccatcaccacGGCGAGAGCGGCTACGCCCAGAACGGCGACCTGG

AGGACGCCGAGCTGGACGACTACAGCTTCAGCTGCTACAGCCAGCTGGAG

GTGAACGGCAGCCAGCACAGCCTGACCTGCGCCTTCGAGGACCCCGACGT

GAACATCACCAACCTGGAGTTCGAGATCTGCGGCGCCCTGGTGGAGGTGA

AGTGCCTGAACTTCAGGAAGCTGCAGGAGATCTACTTCATCGAGACCAAG

AAGTTCCTGCTGATCGGCAAGAGCAACATCTGCGTGAAGGTGGGCGAGAA

GAGCCTGACCTGCAAGAAGATCGACCTGACCACCATCGTGAAGCCCGAGG

CCCCCTTCGACCTGAGCGTGGTGTACAGGGAGGGCGCCAACGACTTCGTG

GTGACCTTCAACACCAGCCACCTGCAGAAGAAGTACGTGAAGGTGCTGAT

GCACGACGTGGCCTACAGGCAGGAGAAGGACGAGAACAAGTGGACCCACG

TGAACCTGAGCAGCACCAAGCTGACCCTGCTGCAGAGGAAGCTGCAGCCC

GCCGCCATGTACGAGATCAAGGTGAGGAGCATCCCCGACCACTACTTCAA

GGGCTTCTGGAGCGAGTGGAGCCCCAGCTACTACTTCAGGACCCCCGAGA

TCAACAACAGCAGCGGCGAGATGGACCCCATCCTGCTGACCTGCCCCACC

ATCAGCATCCTGAGCTTCTTCAGCGTGGCCCTGCTGGTGATCCTGGCCTG

CGTGCTGTGGAAGAAGAGGATCAAGCCCATCGTGTGGCCCAGCCTGCCCG

ACCACAAGAAGACCCTGGAGCACCTGTGTAAGAAGCCCAGGAAGAACCTG

AACGTGAGCTTCAACCCCGAGAGCTTCCTGGACTGCCAGATCCACAGGGT

GGACGACATCCAGGCCAGGGACGAGGTGGAGGGCTTCCTGCAGGACACCT

TCCCCCAGCAGCTGGAGGAGAGCGAGAAGCAGAGGCTGGGCGGCGACGTG

CAGAGCCCCAACTGCCCCAGCGAGGACGTGGTGATCACCCCCGAGAGCTT

CGGCAGGGACAGCAGCCTGACCTGCCTGGCCGGCAACGTGAGCGCCTGCG

ACGCCCCCATCCTGAGCAGCAGCAGGAGCCTGGACTGCAGGGAGAGCGGC

AAGAACGGCCCCCACGTGTACCAGGACCTGCTGCTGAGCCTGGGCACCAC

CAACAGCACCCTGCCACCCCCCTTCAGCCTGCAGAGCGGCATCCTGACCC

TGAACCCCGTGGCCCAGGGCCAGCCCATCCTGACCAGCCTGGGCAGCAAC

CAGGAGGAGGCCTACGTGACCATGAGCAGCTTCTACCAGAACCAG

GPC3CAR + IL7RaCPT Protein (SEQ ID NO: 111)

DIVMTQSPDSLAVSLGERATINCKSSQSLLYSSNQKNYLAWYQQKPGQPP

KLLIYWASSRESGVPDRFSGSGSGTDFTLTISSLQAEDVAVYYCQQYYNY

PLTFGQGTKLEIKGSTSGSGKPGSGEGSTKGEVQLVESGGGLVQPGGSLR

LSCAASGFTFNKNAMNWVRQAPGKGLEWVGRIRNKTNNYATYYADSVKAR

FTISRDDSKNSLYLQMNSLKTEDTAVYYCVAGNSFAYWGQGTLVTVSSGS

TTTPAPRPPTPAPTIASQPLSLRPEACRPAAGGAVHTRGLDFACDIYIWA

PLAGTCGVLLLSLVITLYCKRGRKKLLYIFKQPFMRPVQTTQEEDGCSCR

FPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGL

YQGLSTATKDTYDALHMQALPPRGSGEGRGSLLTCGDVEENPGPMLLLVT

SLLLCELPHPAFLLIPHHHHHHGESGYAQNGDLEDAELDDYSFSCYSQLE

VNGSQHSLTCAFEDPDVNITNLEFEICGALVEVKCLNFRKLQEIYFIETK

KFLLIGKSNICVKVGEKSLTCKKIDLTTIVKPEAPFDLSVVYREGANDFV

VTFNTSHLQKKYVKVLMHDVAYRQEKDENKWTHVNLSSTKLTLLQRKLQP

AAMYEIKVRSIPDHYFKGFWSEWSPSYYFRTPEINNSSGEMDPILLTCPT

ISILSFFSVALLVILACVLWKKRIKPIVWPSLPDHKKTLEHLCKKPRKNL

NVSFNPESFLDCQIHRVDDIQARDEVEGFLQDTFPQQLEESEKQRLGGDV

QSPNCPSEDVVITPESFGRDSSLTCLAGNVSACDAPILSSSRSLDCRESG

KNGPHVYQDLLLSLGTTNSTLPPPFSLQSGILTLNPVAQGQPILTSLGSN

QEEAYVTMSSFYQNQ

Figure 19:
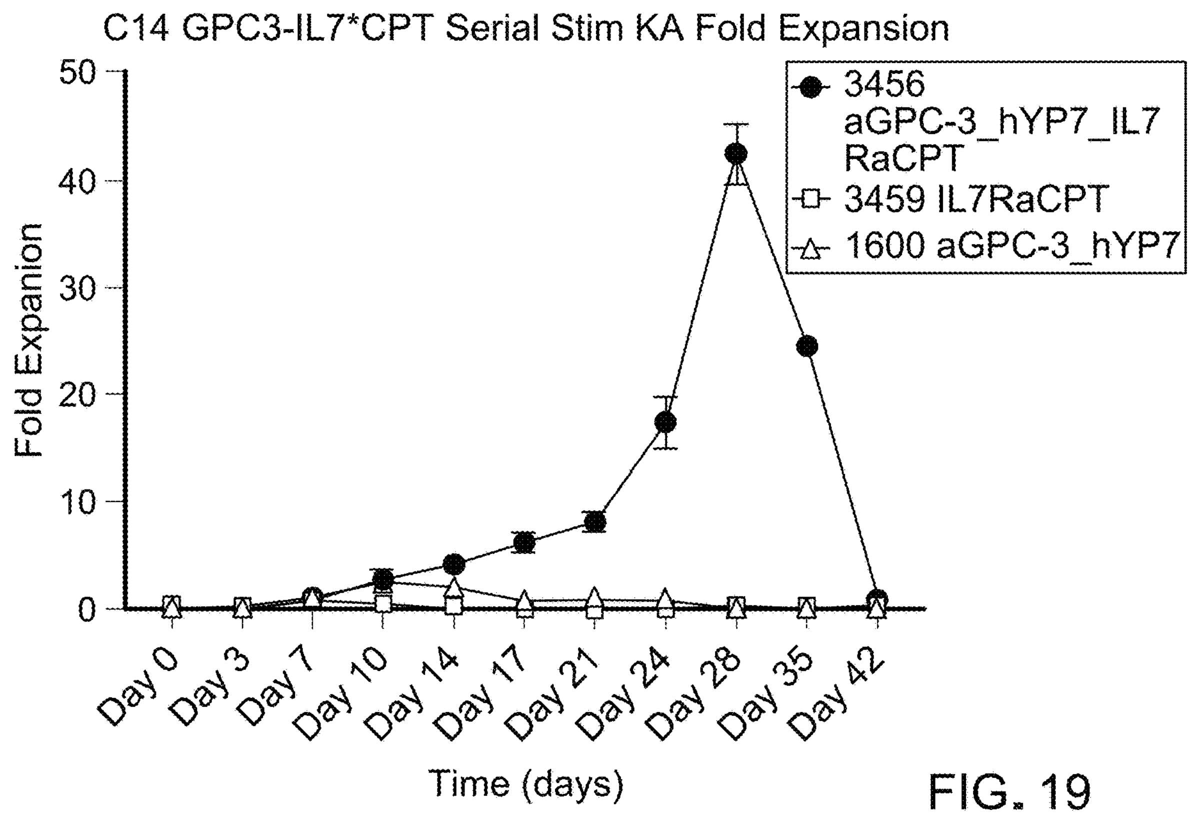
FIG. 19 is a graph showing the fold-expansion of GPC3 CAR positive T cells and GPC3 CAR+IL7Ra CPT positive T-cells co-cultured with Hep3B target cells from American Type Culture Company (ATCC, Manassas, Va.) ($0.5\times10^6$ CAR T cells co-cultured with $0.5\times10^6$ Hep3B target cells) over time (as described in Example 9).

The data from this experiment is shown in FIG. 19. GPC3 CAR T cells peaked in their expansion on day 10 with a maximal 2.4-fold above the starting cell density. GPC3 CAR T cells that also express IL7Rα CPT expanded up to 40-fold over baseline by day 28 and only stopped expanding after day 31 when targets were no longer added.

TABLE 2

| Days of Co-culture | IL7RaCPT | | | GPC3 CAR | | | GPC3 CAR + IL7RaCPT | | |
|---|---|---|---|---|---|---|---|---|---|
| 0 | 5.00E+05 | 5.00E+05 | 5.00E+05 | 5.00E+05 | 5.00E+05 | 5.00E+05 | 5.00E+05 | 5.00E+05 | 5.00E+05 |
| 3 | 6.53E+04 | 6.38E+04 | 6.43E+04 | 2.12E+04 | 1.90E+04 | 2.10E+04 | 1.33E+04 | 1.63E+04 | 1.71E+04 |
| 7 | 2.64E+05 | 2.89E+05 | 2.99E+05 | 6.16E+05 | 5.53E+05 | 5.25E+05 | 4.64E+05 | 4.88E+05 | 4.20E+05 |
| 10 | 2.09E+05 | 2.35E+05 | 2.73E+05 | 1.37E+06 | 1.19E+06 | 1.09E+06 | 1.08E+06 | 1.81E+06 | 1.40E+06 |
| 14 | 5.49E+04 | 6.72E+04 | 5.60E+04 | 1.29E+06 | 1.13E+06 | 8.15E+05 | 2.10E+06 | 2.06E+06 | 2.03E+06 |
| 17 | 1.58E+04 | 1.86E+04 | 2.05E+05 | 4.64E+05 | 3.65E+05 | 3.01E+05 | 3.51E+06 | 3.08E+06 | 2.81E+06 |
| 21 | 1.26E+04 | 9.37E+03 | 1.00E+04 | 6.30E+05 | 4.60E+05 | 3.99E+05 | 4.51E+06 | 3.94E+06 | 3.62E+06 |
| 24 | 8.21E+03 | 5.62E+03 | 4.18E+03 | 5.24E+05 | 2.30E+05 | 2.05E+05 | 9.75E+06 | 8.95E+06 | 7.39E+06 |
| 28 | 3.66E+04 | 3.41E+04 | 2.78E+04 | 1.68E+05 | 9.67E+04 | 1.26E+05 | 2.00E+07 | 2.28E+07 | 2.11E+07 |
| 35 | 4.44E+03 | 2.01E+03 | 9.94E+02 | 6.14E+04 | 4.68E+04 | 4.42E+04 | 1.24E+07 | 1.24E+07 | 1.22E+07 |
| 42 | 2.59E+03 | 1.97E+02 | 3.13E+02 | 1.40E+02 | 1.45E+02 | 9.93E+01 | 4.86E+05 | 5.42E+05 | 3.30E+05 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A protein comprising a transmembrane domain of an alpha chain of interleukin-7 receptor, with one or more modifications, wherein the transmembrane domain with one or more modification comprises the sequence of SEQ ID NO: 2 or SEQ ID NO: 4.

2. The protein of claim 1, wherein the protein further comprises an intracellular domain of an alpha chain of interleukin-7 receptor.

3. The protein of claim 2, wherein the intracellular domain comprises a sequence of SEQ ID NO: 45.

4. The protein of claim 1, wherein the protein further comprises an extracellular domain of an alpha chain of interleukin-7 receptor.

5. The protein of claim 4, wherein the extracellular domain comprises a sequence of SEQ ID NO: 11.

6. The protein of claim 1, further comprising an extracellular interleukin-15 domain; and an extracellular sushi domain from an alpha chain of interleukin-15 receptor.

7. The protein of claim 6, wherein the extracellular interleukin-15 domain comprises a sequence of SEQ ID NO: 22 or SEQ ID NO: 24.

8. The protein of claim 6, wherein the extracellular sushi domain of the alpha chain of interleukin-15 receptor comprises SEQ ID NO: 36 or SEQ ID NO: 37.

9. A nucleic acid encoding a protein of claim 1.

10. A vector comprising the nucleic acid of claim 9.

11. The vector of claim 10, further comprising a promoter operably linked to the nucleic acid, and optionally, an enhancer sequence operably linked to the nucleic acid.

12. The vector of claim 10, further comprising a sequence encoding a chimeric antigen receptor which binds specifically to a tumor antigen.

13. The vector of claim 12, wherein the tumor antigen is selected from the group consisting of: glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin $\alpha5\beta1$, integrin $\alpha v\beta3$, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin.

14. The vector of claim 12, wherein the chimeric antigen receptor comprises one or more co-stimulatory signaling domains selected from the group consisting of: 4-1BB, CD27, OX40, CD40, CD28, GITR, CD2, CDS, ICAM-1, CD11a, Lck, TNFR-I, TNFR-II, FasR, CD30, ICOS, LIGHT, NKG2C, B7-H3, DAP-10, and DAP-12.

15. The vector of claim 10, wherein the vector is a lentiviral or an adenoviral vector.

16. A mammalian cell comprising a vector of claim 10.

17. The mammalian cell of claim 16, wherein the mammalian cell is an immune cell.

18. The mammalian cell of claim 17, wherein the immune cell is selected from the group consisting of: a CD4+ T cell, a CD8+ T cell, a B cell, a monocyte, a natural killer cell, a dendritic cell, a macrophage, a regulatory T cell, and a helper T cell.

19. A pharmaceutical composition comprising a vector of claim 10 and a pharmaceutically acceptable carrier.

20. A pharmaceutical composition comprising a mammalian cell of claim 16.

* * * * *

SEQUENCE LISTING

<160> NUMBER OF SEQ ID NOS: 111

<210> SEQ ID NO 1
<211> LENGTH: 25
<212> TYPE: PRT
<213> ORGANISM: Homo sapiens

<400> SEQUENCE: 1

Pro Ile Leu Leu Thr Ile Ser Ile Leu Ser Phe Phe Ser Val Ala Leu
1 5 10 15

Leu Val Ile Leu Ala Cys Val Leu Trp
20 25

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic IL7RA EKA sequence

<400> SEQUENCE: 2

Pro Ile Leu Leu Thr Ile Ser Ile Leu Ser Phe Phe Ser Val Glu Lys
1 5 10 15

Ala Val Ile Leu Ala Cys Val Leu Trp
20 25

<210> SEQ ID NO 3
<211> LENGTH: 75
<212> TYPE: DNA
<213> ORGANISM: Artificial Sequence
<220> FEATURE:
<223> OTHER INFORMATION: Description of Artificial Sequence: Synthetic IL7RA EKA sequence

<400> SEQUENCE: 3
cccatcctgc tgaccatcag catcctgagc ttcttcagcg tggagaaggt ggtgatcctg 60
gcctgcgtgc tgtgg 75

<210> SEQ ID NO 4
<211> LENGTH: 25
<212> TYPE: PRT
<213> ORGANISM: Artificial Sequence

```
<220> FEATURE:
<223> OTHER INFORMATION: Description of Artificial Sequence: Synthetic
      IL7RA EKV sequence

<400> SEQUENCE: 4

Pro Ile Leu Leu Thr Ile Ser Ile Leu Ser Phe Phe Ser Val Glu Lys
1               5                   10                  15

Val Val Ile Leu Ala Cys Val Leu Trp
            20                  25


<210> SEQ ID NO 5
<211> LENGTH: 75
<212> TYPE: DNA
<213> ORGANISM: Artificial Sequence
<220> FEATURE:
<223> OTHER INFORMATION: Description of Artificial Sequence: Synthetic
      IL7RA EKV sequence

<400> SEQUENCE: 5

cccatcctgc tgaccatcag catcctgagc ttcttcagcg tggagaaggt ggtgatcctg     60

gcctgcgtgc tgtgg                                                      75


<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      IL7RA CPT insert sequence

<400> SEQUENCE: 6

Pro Ile Leu Leu Thr Cys Pro Thr Ile Ser Ile Leu Ser Phe Phe Ser
1               5                   10                  15

Val Ala Leu Leu Val Ile Leu Ala Cys Val Leu Trp
            20                  25


<210> SEQ ID NO 7
<211> LENGTH: 84
<212> TYPE: DNA
<213> ORGANISM: Artificial Sequence
<220> FEATURE:
<223> OTHER INFORMATION: Description of Artificial Sequence: Synthetic
      IL7RA CPT insert sequence

<400> SEQUENCE: 7

cccatcctgc tgacctgccc caccatcagc atcctgagct tcttcagcgt ggccctgctg     60

gtgatcctgg cctgcgtgct gtgg                                            84


<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      IL7RA PPCL insert sequence

<400> SEQUENCE: 8

Pro Ile Leu Leu Pro Pro Cys Leu Thr Ile Ser Ile Leu Ser Phe Phe
1               5                   10                  15

Ser Val Ala Leu Leu Val Ile Leu Ala Cys Val Leu Trp
            20                  25


<210> SEQ ID NO 9
<211> LENGTH: 87
```

```
<212> TYPE: DNA
<213> ORGANISM: Artificial Sequence
<220> FEATURE:
<223> OTHER INFORMATION: Description of Artificial Sequence: Synthetic
      IL7RA PPCL insert sequence

<400> SEQUENCE: 9

cccatcctgc tgccaccctg tttaaccatc agcatcctga gcttcttcag cgtggccctg     60

ctggtgatcc tggcctgcgt gctgtgg                                         87


<210> SEQ ID NO 10
<211> LENGTH: 22
<212> TYPE: PRT
<213> ORGANISM: Homo sapiens

<400> SEQUENCE: 10

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 11
<211> LENGTH: 220
<212> TYPE: PRT
<213> ORGANISM: Homo sapiens

<400> SEQUENCE: 11

Gly Glu Ser Gly Tyr Ala Gln Asn Gly Asp Leu Glu Asp Ala Glu Leu
1               5                   10                  15

Asp Asp Tyr Ser Phe Ser Cys Tyr Ser Gln Leu Glu Val Asn Gly Ser
            20                  25                  30

Gln His Ser Leu Thr Cys Ala Phe Glu Asp Pro Asp Val Asn Ile Thr
        35                  40                  45

Asn Leu Glu Phe Glu Ile Cys Gly Ala Leu Val Glu Val Lys Cys Leu
    50                  55                  60

Asn Phe Arg Lys Leu Gln Glu Ile Tyr Phe Ile Glu Thr Lys Lys Phe
65                  70                  75                  80

Leu Leu Ile Gly Lys Ser Asn Ile Cys Val Lys Val Gly Glu Lys Ser
                85                  90                  95

Leu Thr Cys Lys Lys Ile Asp Leu Thr Thr Ile Val Lys Pro Glu Ala
            100                 105                 110

Pro Phe Asp Leu Ser Val Val Tyr Arg Glu Gly Ala Asn Asp Phe Val
        115                 120                 125

Val Thr Phe Asn Thr Ser His Leu Gln Lys Lys Tyr Val Lys Val Leu
    130                 135                 140

Met His Asp Val Ala Tyr Arg Gln Glu Lys Asp Glu Asn Lys Trp Thr
145                 150                 155                 160

His Val Asn Leu Ser Ser Thr Lys Leu Thr Leu Leu Gln Arg Lys Leu
                165                 170                 175

Gln Pro Ala Ala Met Tyr Glu Ile Lys Val Arg Ser Ile Pro Asp His
            180                 185                 190

Tyr Phe Lys Gly Phe Trp Ser Glu Trp Ser Pro Ser Tyr Tyr Phe Arg
        195                 200                 205

Thr Pro Glu Ile Asn Asn Ser Ser Gly Glu Met Asp
    210                 215                 220


<210> SEQ ID NO 12
<211> LENGTH: 660
```

<212> TYPE: DNA
<213> ORGANISM: Homo sapiens

<400> SEQUENCE: 12

```
ggcgagagcg gctacgccca gaacggcgac ctggaggacg ccgagctgga cgactacagc     60

ttcagctgct acagccagct ggaggtgaac ggcagccagc acagcctgac ctgcgccttc    120

gaggaccccg acgtgaacat caccaacctg gagttcgaga tctgcggcgc cctggtggag    180

gtgaagtgcc tgaacttcag gaagctgcag gagatctact tcatcgagac caagaagttc    240

ctgctgatcg gcaagagcaa catctgcgtg aaggtgggcg agaagagcct gacctgcaag    300

aagatcgacc tgaccaccat cgtgaagccc gaggcccccct tcgacctgag cgtggtgtac    360

agggagggcg ccaacgactt cgtggtgacc ttcaacacca gccacctgca gaagaagtac    420

gtgaaggtgc tgatgcacga cgtggcctac aggcaggaga aggacgagaa caagtggacc    480

cacgtgaacc tgagcagcac caagctgacc ctgctgcaga ggaagctgca gcccgccgcc    540

atgtacgaga tcaaggtgag gagcatcccc gaccactact tcaagggctt ctggagcgag    600

tggagcccca gctactactt caggaccccc gagatcaaca acagcagcgg cgagatggac    660
```

<210> SEQ ID NO 13
<211> LENGTH: 219
<212> TYPE: PRT
<213> ORGANISM: Mus musculus

<400> SEQUENCE: 13

```
Glu Ser Gly Asn Ala Gln Asp Gly Asp Leu Glu Asp Ala Asp Ala Asp
1               5                   10                  15

Asp His Ser Phe Trp Cys His Ser Gln Leu Glu Val Asp Gly Ser Gln
            20                  25                  30

His Leu Leu Thr Cys Ala Phe Asn Asp Ser Asp Ile Asn Thr Ala Asn
        35                  40                  45

Leu Glu Phe Gln Ile Cys Gly Ala Leu Leu Arg Val Lys Cys Leu Thr
    50                  55                  60

Leu Asn Lys Leu Gln Asp Ile Tyr Phe Ile Lys Thr Ser Glu Phe Leu
65                  70                  75                  80

Leu Ile Gly Ser Ser Asn Ile Cys Val Lys Leu Gly Gln Lys Asn Leu
                85                  90                  95

Thr Cys Lys Asn Met Ala Ile Asn Thr Ile Val Lys Ala Glu Ala Pro
            100                 105                 110

Ser Asp Leu Lys Val Val Tyr Arg Lys Glu Ala Asn Asp Phe Leu Val
        115                 120                 125

Thr Phe Asn Ala Pro His Leu Lys Lys Lys Tyr Leu Lys Lys Val Lys
    130                 135                 140

His Asp Val Ala Tyr Arg Pro Ala Arg Gly Glu Ser Asn Trp Thr His
145                 150                 155                 160

Val Ser Leu Phe His Thr Arg Thr Thr Ile Pro Gln Arg Lys Leu Arg
                165                 170                 175

Pro Lys Ala Met Tyr Glu Ile Lys Val Arg Ser Ile Pro His Asn Asp
            180                 185                 190

Tyr Phe Lys Gly Phe Trp Ser Glu Trp Ser Pro Ser Ser Thr Phe Glu
        195                 200                 205

Thr Pro Glu Pro Lys Asn Gln Gly Gly Trp Asp
    210                 215
```

<210> SEQ ID NO 14

<211> LENGTH: 657
<212> TYPE: DNA
<213> ORGANISM: Mus musculus

<400> SEQUENCE: 14

```
gaaagtggaa atgcccagga tggagaccta gaagatgcag acgcggacga tcactccttc     60

tggtgccaca gccagttgga agtggatgga agtcaacatt tattgacttg tgcttttaat    120

gactcagaca tcaacacagc taatctggaa tttcaaatat gtggggctct tttacgagtg    180

aaatgcctaa ctcttaacaa gctgcaagat atatatttta taaagacatc agaattctta    240

ctgattggta gcagcaatat atgtgtgaag cttggacaaa agaatttaac ttgcaaaaat    300

atggctataa acacaatagt taaagccgag gctccctctg acctgaaagt cgtttatcgc    360

aaagaagcaa atgatttttt ggtgacattt aatgcacctc acttgaaaaa gaaatattta    420

aaaaaagtaa agcatgatgt ggcctaccgc ccagcaaggg gtgaaagcaa ctggacgcat    480

gtatctttat tccacacaag aacaacaatc ccacagagaa aactacgacc aaaagcaatg    540

tatgaaatca aagtccgatc cattccccat aacgattact tcaaaggctt ctggagcgag    600

tggagtccaa gttctacctt cgaaactcca gaacccaaga atcaaggagg atgggat       657
```

<210> SEQ ID NO 15
<211> LENGTH: 219
<212> TYPE: PRT
<213> ORGANISM: Mus musculus

<400> SEQUENCE: 15

```
Glu Ser Gly Asn Ala Gln Asp Gly Asp Leu Glu Asp Ala Asp Ala Asp
1               5                   10                  15

Asp His Ser Phe Trp Cys His Ser Gln Leu Glu Val Asp Gly Ser Gln
            20                  25                  30

His Leu Leu Thr Cys Ala Phe Asn Asp Ser Asp Ile Asn Thr Ala Asn
        35                  40                  45

Leu Glu Phe Gln Ile Cys Gly Ala Leu Leu Arg Val Lys Cys Leu Thr
    50                  55                  60

Leu Asn Lys Leu Gln Asp Ile Tyr Phe Ile Lys Thr Ser Glu Phe Leu
65                  70                  75                  80

Leu Ile Gly Ser Ser Asn Ile Cys Val Lys Leu Gly Gln Lys Asn Leu
                85                  90                  95

Thr Cys Lys Asn Met Ala Ile Asn Thr Ile Val Lys Ala Glu Ala Pro
            100                 105                 110

Ser Asp Leu Lys Val Val Tyr Arg Lys Glu Ala Asn Asp Phe Leu Val
        115                 120                 125

Thr Phe Asn Ala Pro His Leu Lys Lys Lys Tyr Leu Lys Lys Val Lys
    130                 135                 140

His Asp Val Ala Tyr Arg Pro Ala Arg Gly Glu Ser Asn Trp Thr His
145                 150                 155                 160

Val Ser Leu Phe His Thr Arg Thr Thr Ile Pro Gln Arg Lys Leu Arg
                165                 170                 175

Pro Lys Ala Met Tyr Glu Ile Lys Val Arg Ser Ile Pro His Asn Asp
            180                 185                 190

Tyr Phe Lys Gly Phe Trp Ser Glu Trp Ser Pro Ser Ser Thr Phe Glu
        195                 200                 205

Thr Pro Glu Pro Lys Asn Gln Gly Gly Trp Asp
    210                 215
```

<210> SEQ ID NO 16
<211> LENGTH: 657
<212> TYPE: DNA
<213> ORGANISM: Mus musculus

<400> SEQUENCE: 16
gaaagtggaa atgcccagga tggagaccta gaagatgcag acgcggacga tcactccttc 60
tggtgccaca gccagttgga agtggatgga agtcaacatt tattgacttg tgcttttaat 120
gactcagaca tcaacacagc taatctggaa tttcaaatat gtggggctct tttacgagtg 180
aaatgcctaa ctcttaacaa gctgcaagat atatatttta taaagacatc agaattctta 240
ctgattggta gcagcaatat atgtgtgaag cttggacaaa agaatttaac ttgcaaaaat 300
atggctataa acacaatagt taaagccgag gctccctctg acctgaaagt cgtttatcgc 360
aaagaagcaa atgatttttt ggtgacattt aatgcacctc acttgaaaaa gaaatattta 420
aaaaaagtaa agcatgatgt ggcctaccgc ccagcaaggg gtgaaagcaa ctggacgcat 480
gtatctttat tccacacaag aacaacaatc ccacagagaa aactacgacc aaaagcaatg 540
tatgaaatca aagtccgatc cattccccat aacgattact tcaaaggctt ctggagcgag 600
tggagtccaa gttctacctt cgaaactcca gaacccaaga atcaaggagg atgggat 657

<210> SEQ ID NO 17
<211> LENGTH: 535
<212> TYPE: PRT
<213> ORGANISM: Artificial Sequence
<220> FEATURE:
<223> OTHER INFORMATION: Description of Artificial Sequence: Synthetic
Exemplary chimeric transmembrane protein sequence

<400> SEQUENCE: 17

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser Ser Gly Gly Gly Ser Gly Gly Gly Gly Ser Gly Gly Gly Gly
115 120 125

Ser Gly Gly Gly Gly Ser Gly Gly Gly Ser Leu Gln Ile Thr Cys Pro
130 135 140

Pro Pro Met Ser Val Glu His Ala Asp Ile Trp Val Lys Ser Tyr Ser
145 150 155 160

Leu Tyr Ser Arg Glu Arg Tyr Ile Cys Asn Ser Gly Phe Lys Arg Lys
165 170 175

Ala Gly Thr Ser Ser Leu Thr Glu Cys Val Leu Asn Lys Ala Thr Asn
180 185 190

Val Ala His Trp Thr Thr Pro Ser Leu Lys Cys Ile Arg Asp Pro Ala
195 200 205

```
Leu Val His Gln Arg Pro Ala Pro Pro Ser Thr Val Thr Thr Ala Gly
    210                 215                 220

Val Thr Pro Gln Pro Glu Ser Leu Ser Pro Ser Gly Lys Glu Pro Ala
225                 230                 235                 240

Ala Ser Ser Pro Ser Ser Asn Asn Thr Ala Ala Thr Thr Ala Ala Ile
                245                 250                 255

Val Pro Gly Ser Gln Leu Met Pro Ser Lys Ser Pro Ser Thr Gly Thr
            260                 265                 270

Thr Glu Ile Ser Ser His Glu Ser Ser His Gly Thr Pro Ser Gln Thr
        275                 280                 285

Thr Ala Lys Asn Trp Glu Leu Thr Ala Ser Ala Ser His Gln Pro Pro
    290                 295                 300

Gly Val Tyr Pro Gln Gly His Ser Asp Thr Thr Pro Ile Leu Leu Thr
305                 310                 315                 320

Ile Ser Leu Leu Ser Phe Phe Ser Val Ala Leu Leu Val Ile Leu Ala
                325                 330                 335

Cys Val Leu Trp Lys Lys Arg Ile Lys Pro Ile Val Trp Pro Ser Leu
            340                 345                 350

Pro Asp His Lys Lys Thr Leu Glu His Leu Cys Lys Lys Pro Arg Lys
        355                 360                 365

Asn Leu Asn Val Ser Phe Asn Pro Glu Ser Phe Leu Asp Cys Gln Ile
    370                 375                 380

His Arg Val Asp Asp Ile Gln Ala Arg Asp Glu Val Glu Gly Phe Leu
385                 390                 395                 400

Gln Asp Thr Phe Pro Gln Gln Leu Glu Glu Ser Glu Lys Gln Arg Leu
                405                 410                 415

Gly Gly Asp Val Gln Ser Pro Asn Cys Pro Ser Glu Asp Val Val Ile
            420                 425                 430

Thr Pro Glu Ser Phe Gly Arg Asp Ser Ser Leu Thr Cys Leu Ala Gly
        435                 440                 445

Asn Val Ser Ala Cys Asp Ala Pro Ile Leu Ser Ser Ser Arg Ser Leu
    450                 455                 460

Asp Cys Arg Glu Ser Gly Lys Asn Gly Pro His Val Tyr Gln Asp Leu
465                 470                 475                 480

Leu Leu Ser Leu Gly Thr Thr Asn Ser Thr Leu Pro Pro Pro Phe Ser
                485                 490                 495

Leu Gln Ser Gly Ile Leu Thr Leu Asn Pro Val Ala Gln Gly Gln Pro
            500                 505                 510

Ile Leu Thr Ser Leu Gly Ser Asn Gln Glu Glu Ala Tyr Val Thr Met
        515                 520                 525

Ser Ser Phe Tyr Gln Asn Gln
    530                 535
```

```
<210> SEQ ID NO 18
<211> LENGTH: 1605
<212> TYPE: DNA
<213> ORGANISM: Artificial Sequence
<220> FEATURE:
<223> OTHER INFORMATION: Description of Artificial Sequence: Synthetic
      Exemplary chimeric transmembrane sequence

<400> SEQUENCE: 18

aactgggtga atgtgatcag cgacctgaag aagatcgagg atctgatcca gagcatgcac     60

attgatgcca ccctgtacac agaatctgat gtgcacccta gctgtaaagt gaccgccatg    120

aagtgtttc tgctggagct gcaggtgatt tctctggaaa gcggagatgc ctctatccac    180
```

```
gacacagtgg agaatctgat catcctggcc aacaatagcc tgagcagcaa tggcaatgtg    240
acagagtctg gctgtaagga gtgtgaggag ctggaggaga agaacatcaa ggagtttctg    300
cagagctttg tgcacatcgt gcagatgttc atcaatacaa gcagcggtgg gggctcaggc    360
ggaggaggct ctggcggagg cggaagcggg ggagggggct caggcggcgg gtccttgcag    420
attacatgcc ctcctccaat gtctgtggag cacgccgata tttgggtgaa gtcctacagc    480
ctgtacagca gagagagata catctgcaac agcggcttta agagaaaggc cggcacctct    540
tctctgacag agtgcgtgct gaataaggcc acaaatgtgg cccactggac aacacctagc    600
ctgaagtgca ttagagatcc tgccctggtc caccagaggc ctgcccctcc atctacagtg    660
acaacagccg gagtgacacc tcagcctgaa tctctgagcc cttctggaaa agaacctgcc    720
gccagctctc ctagctctaa taataccgcc gccacaacag ccgccattgt gcctggatct    780
cagctgatgc ctagcaagtc tcctagcaca ggcacaacag agatcagcag ccacgaatct    840
tctcacggaa caccttctca gaccaccgcc aagaattggg agctgacagc ctctgcctct    900
caccagcctc caggagtgta tcctcagggc cactctgata caacacccat cctgctgacc    960
atcagcatcc tgagcttctt cagcgtggcc ctgctggtga tcctggcctg cgtgctgtgg   1020
aagaagagga tcaagcccat cgtgtggccc agcctgcccg accacaagaa gaccctggag   1080
cacctgtgta agaagcccag gaagaacctg aacgtgagct tcaaccccga gagcttcctg   1140
gactgccaga tccacagggt ggacgacatc caggccaggg acgaggtgga gggcttcctg   1200
caggacacct tcccccagca gctggaggag agcgagaagc agaggctggg cggcgacgtg   1260
cagagcccca actgccccag cgaggacgtg gtgatcaccc ccgagagctt cggcagggac   1320
agcagcctga cctgcctggc cggcaacgtg agcgcctgcg acgcccccat cctgagcagc   1380
agcaggagcc tggactgcag gg agagcggc aagaacggcc cccacgtgta ccaggacctg   1440
ctgctgagcc tgggcaccac caacagcacc ctgccacccc ccttcagcct gcagagcggc   1500
atcctgaccc tgaaccccgt ggcccagggc cagcccatcc tgaccagcct gggcagcaac   1560
caggaggagg cctacgtgac catgagcagc ttctaccaga accag                   1605
```

```
<210> SEQ ID NO 19
<211> LENGTH: 539
<212> TYPE: PRT
<213> ORGANISM: Artificial Sequence
<220> FEATURE:
<223> OTHER INFORMATION: Description of Artificial Sequence: Synthetic
      Exemplary chimeric transmembrane protein sequence

<400> SEQUENCE: 19

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
```

-continued

```
            100                 105                 110

Thr Ser Ser Gly Gly Gly Ser Gly Gly Gly Gly Ser Gly Gly Gly Gly
        115                 120                 125

Ser Gly Gly Gly Gly Ser Gly Gly Gly Ser Leu Gln Ile Thr Cys Pro
    130                 135                 140

Pro Pro Met Ser Val Glu His Ala Asp Ile Trp Val Lys Ser Tyr Ser
145                 150                 155                 160

Leu Tyr Ser Arg Glu Arg Tyr Ile Cys Asn Ser Gly Phe Lys Arg Lys
                165                 170                 175

Ala Gly Thr Ser Ser Leu Thr Glu Cys Val Leu Asn Lys Ala Thr Asn
            180                 185                 190

Val Ala His Trp Thr Thr Pro Ser Leu Lys Cys Ile Arg Asp Pro Ala
        195                 200                 205

Leu Val His Gln Arg Pro Ala Pro Pro Ser Thr Val Thr Thr Ala Gly
    210                 215                 220

Val Thr Pro Gln Pro Glu Ser Leu Ser Pro Ser Gly Lys Glu Pro Ala
225                 230                 235                 240

Ala Ser Ser Pro Ser Ser Asn Asn Thr Ala Ala Thr Thr Ala Ala Ile
                245                 250                 255

Val Pro Gly Ser Gln Leu Met Pro Ser Lys Ser Pro Ser Thr Gly Thr
            260                 265                 270

Thr Glu Ile Ser Ser His Glu Ser Ser His Gly Thr Pro Ser Gln Thr
        275                 280                 285

Thr Ala Lys Asn Trp Glu Leu Thr Ala Ser Ala Ser His Gln Pro Pro
    290                 295                 300

Gly Val Tyr Pro Gln Gly His Ser Asp Thr Thr Pro Ile Leu Leu Pro
305                 310                 315                 320

Pro Cys Leu Thr Ile Ser Ile Leu Ser Phe Phe Ser Val Ala Leu Leu
                325                 330                 335

Val Ile Leu Ala Cys Val Leu Trp Lys Lys Arg Ile Lys Pro Ile Val
            340                 345                 350

Trp Pro Ser Leu Pro Asp His Lys Lys Thr Leu Glu His Leu Cys Lys
        355                 360                 365

Lys Pro Arg Lys Asn Leu Asn Val Ser Phe Asn Pro Glu Ser Phe Leu
    370                 375                 380

Asp Cys Gln Ile His Arg Val Asp Asp Ile Gln Ala Arg Asp Glu Val
385                 390                 395                 400

Glu Gly Phe Leu Gln Asp Thr Phe Pro Gln Gln Leu Glu Glu Ser Glu
                405                 410                 415

Lys Gln Arg Leu Gly Gly Asp Val Gln Ser Pro Asn Cys Pro Ser Glu
            420                 425                 430

Asp Val Val Ile Thr Pro Glu Ser Phe Gly Arg Asp Ser Ser Leu Thr
        435                 440                 445

Cys Leu Ala Gly Asn Val Ser Ala Cys Asp Ala Pro Ile Leu Ser Ser
    450                 455                 460

Ser Arg Ser Leu Asp Cys Arg Glu Ser Gly Lys Asn Gly Pro His Val
465                 470                 475                 480

Tyr Gln Asp Leu Leu Leu Ser Leu Gly Thr Thr Asn Ser Thr Leu Pro
                485                 490                 495

Pro Pro Phe Ser Leu Gln Ser Gly Ile Leu Thr Leu Asn Pro Val Ala
            500                 505                 510

Gln Gly Gln Pro Ile Leu Thr Ser Leu Gly Ser Asn Gln Glu Glu Ala
        515                 520                 525
```

Tyr Val Thr Met Ser Ser Phe Tyr Gln Asn Gln
530 535

<210> SEQ ID NO 20
<211> LENGTH: 1617
<212> TYPE: DNA
<213> ORGANISM: Artificial Sequence
<220> FEATURE:
<223> OTHER INFORMATION: Description of Artificial Sequence: Synthetic Exemplary chimeric transmembrane sequence

<400> SEQUENCE: 20
aactgggtga atgtgatcag cgacctgaag aagatcgagg atctgatcca gagcatgcac 60
attgatgcca ccctgtacac agaatctgat gtgcacccta gctgtaaagt gaccgccatg 120
aagtgttttc tgctggagct gcaggtgatt tctctggaaa gcggagatgc ctctatccac 180
gacacagtgg agaatctgat catcctggcc aacaatagcc tgagcagcaa tggcaatgtg 240
acagagtctg gctgtaagga gtgtgaggag ctggaggaga agaacatcaa ggagtttctg 300
cagagctttg tgcacatcgt gcagatgttc atcaatacaa gcagcggtgg gggctcaggc 360
ggaggaggct ctggcggagg cggaagcggg ggagggggct caggcggcgg gtccttgcag 420
attacatgcc ctcctccaat gtctgtggag cacgccgata tttgggtgaa gtcctacagc 480
ctgtacagca gagagagata catctgcaac agcggcttta agagaaaggc cggcacctct 540
tctctgacag agtgcgtgct gaataaggcc acaaatgtgg cccactggac aacacctagc 600
ctgaagtgca ttagagatcc tgccctggtc caccagaggc ctgcccctcc atctacagtg 660
acaacagccg gagtgacacc tcagcctgaa tctctgagcc cttctggaaa agaacctgcc 720
gccagctctc ctagctctaa taataccgcc gccacaacag ccgccattgt gcctggatct 780
cagctgatgc ctagcaagtc tcctagcaca ggcacaacag agatcagcag ccacgaatct 840
tctcacggaa caccttctca gaccaccgcc aagaattggg agctgacagc ctctgcctct 900
caccagcctc caggagtgta tcctcagggc cactctgata caacacccat cctgctgcca 960
ccctgtttaa ccatcagcat cctgagcttc ttcagcgtgg ccctgctggt gatcctggcc 1020
tgcgtgctgt ggaagaagag gatcaagccc atcgtgtggc ccagcctgcc cgaccacaag 1080
aagaccctgg agcacctgtg taagaagccc aggaagaacc tgaacgtgag cttcaacccc 1140
gagagcttcc tggactgcca gatccacagg gtggacgaca tccaggccag ggacgaggtg 1200
gagggcttcc tgcaggacac cttcccccag cagctggagg agagcgagaa gcagaggctg 1260
ggcggcgacg tgcagagccc caactgcccc agcgaggacg tggtgatcac ccccgagagc 1320
ttcggcaggg acagcagcct gacctgcctg gccggcaacg tgagcgcctg cgacgccccc 1380
atcctgagca gcagcaggag cctggactgc agggagagcg gcaagaacgg cccccacgtg 1440
taccaggacc tgctgctgag cctgggcacc accaacagca ccctgccacc ccccttcagc 1500
ctgcagagcg gcatcctgac cctgaacccc gtggcccagg gccagcccat cctgaccagc 1560
ctgggcagca accaggagga ggcctacgtg accatgagca gcttctacca gaaccag 1617

<210> SEQ ID NO 21
<211> LENGTH: 18
<212> TYPE: PRT
<213> ORGANISM: Homo sapiens

<400> SEQUENCE: 21

Met Asp Trp Thr Trp Ile Leu Phe Leu Val Ala Ala Ala Thr Arg Val
1 5 10 15

His Ser

<210> SEQ ID NO 22
<211> LENGTH: 114
<212> TYPE: PRT
<213> ORGANISM: Homo sapiens

<400> SEQUENCE: 22

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 23
<211> LENGTH: 342
<212> TYPE: DNA
<213> ORGANISM: Homo sapiens

<400> SEQUENCE: 23

```
aactgggtga atgtaataag tgatttgaaa aaaattgaag atcttattca atctatgcat      60

attgatgcta ctttatatac ggaaagtgat gttcacccca gttgcaaagt aacagcaatg     120

aagtgctttc tcttggagtt acaagttatt tcacttgagt ccggagatgc aagtattcat     180

gatacagtag aaaatctgat catcctagca aacaacagtt tgtcttctaa tgggaatgta     240

acagaatctg gatgcaaaga atgtgaggaa ctggaggaaa aaaatattaa agaatttttg     300

cagagttttg tacatattgt ccaaatgttc atcaacactt ct                        342
```

<210> SEQ ID NO 24
<211> LENGTH: 135
<212> TYPE: PRT
<213> ORGANISM: Homo sapiens

<400> SEQUENCE: 24

```
Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95
```

```
Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135


<210> SEQ ID NO 25
<211> LENGTH: 408
<212> TYPE: DNA
<213> ORGANISM: Homo sapiens

<400> SEQUENCE: 25

atggtattgg gaaccataga tttgtgcagc tgtttcagtg cagggcttcc taaaacagaa      60

gccaactggg tgaatgtaat aagtgatttg aaaaaaattg aagatcttat tcaatctatg     120

catattgatg ctactttata tacggaaagt gatgttcacc ccagttgcaa agtaacagca     180

atgaagtgct ttctcttgga gttacaagtt atttcacttg agtccggaga tgcaagtatt     240

catgatacag tagaaaatct gatcatccta gcaaacaaca gtttgtcttc taatgggaat     300

gtaacagaat ctggatgcaa agaatgtgag gaactggagg aaaaaaatat taaagaattt     360

ttgcagagtt ttgtacatat tgtccaaatg ttcatcaaca cttcttga                  408


<210> SEQ ID NO 26
<211> LENGTH: 114
<212> TYPE: PRT
<213> ORGANISM: Mus musculus

<400> SEQUENCE: 26

Asn Trp Ile Asp Val Arg Tyr Asp Leu Glu Lys Ile Glu Ser Leu Ile
1               5                   10                  15

Gln Ser Ile His Ile Asp Thr Thr Leu Tyr Thr Asp Ser Asp Phe His
            20                  25                  30

Pro Ser Cys Lys Val Thr Ala Met Asn Cys Phe Leu Leu Glu Leu Gln
        35                  40                  45

Val Ile Leu His Glu Tyr Ser Asn Met Thr Leu Asn Glu Thr Val Arg
    50                  55                  60

Asn Val Leu Tyr Leu Ala Asn Ser Thr Leu Ser Ser Asn Lys Asn Val
65                  70                  75                  80

Ala Glu Ser Gly Cys Lys Glu Cys Glu Glu Leu Glu Glu Lys Thr Phe
                85                  90                  95

Thr Glu Phe Leu Gln Ser Phe Ile Arg Ile Val Gln Met Phe Ile Asn
            100                 105                 110

Thr Ser


<210> SEQ ID NO 27
<211> LENGTH: 342
<212> TYPE: DNA
<213> ORGANISM: Mus musculus

<400> SEQUENCE: 27

aactggatag atgtaagata tgacctggag aaaattgaaa gccttattca atctattcat      60

attgacacca ctttatacac tgacagtgac tttcatccca gttgcaaagt tactgcaatg     120

aactgctttc tcctggaatt gcaggttatt ttacatgagt acagtaacat gactcttaat     180

gaaacagtaa gaaacgtgct ctaccttgca aacagcactc tgtcttctaa caagaatgta     240
```

```
gcagaatctg gctgcaagga atgtgaggag ctggaggaga aaaccttcac agagtttttg    300

caaagcttta tacgcattgt ccaaatgttc atcaacacgt cc                       342


<210> SEQ ID NO 28
<211> LENGTH: 114
<212> TYPE: PRT
<213> ORGANISM: Mus musculus

<400> SEQUENCE: 28

Asn Trp Ile Asp Val Arg Tyr Asp Leu Glu Lys Ile Glu Ser Leu Ile
1               5                   10                  15

Gln Ser Ile His Ile Asp Thr Thr Leu Tyr Thr Asp Ser Asp Phe His
            20                  25                  30

Pro Ser Cys Lys Val Thr Ala Met Asn Cys Phe Leu Leu Glu Leu Gln
        35                  40                  45

Val Ile Leu His Glu Tyr Ser Asn Met Thr Leu Asn Glu Thr Val Arg
    50                  55                  60

Asn Val Leu Tyr Leu Ala Asn Ser Thr Leu Ser Ser Asn Lys Asn Val
65                  70                  75                  80

Ala Glu Ser Gly Cys Lys Glu Cys Glu Glu Leu Glu Glu Lys Thr Phe
                85                  90                  95

Thr Glu Phe Leu Gln Ser Phe Ile Arg Ile Val Gln Met Phe Ile Asn
            100                 105                 110

Thr Ser


<210> SEQ ID NO 29
<211> LENGTH: 342
<212> TYPE: DNA
<213> ORGANISM: Mus musculus

<400> SEQUENCE: 29

aactggatag atgtaagata tgacctggag aaaattgaaa gccttattca atctattcat     60

attgacacca ctttatacac tgacagtgac tttcatccca gttgcaaagt tactgcaatg    120

aactgctttc tcctggaatt gcaggttatt ttacatgagt acagtaacat gactcttaat    180

gaaacagtaa gaaacgtgct ctaccttgca aacagcactc tgtcttctaa caagaatgta    240

gcagaatctg gctgcaagga atgtgaggag ctggaggaga aaaccttcac agagtttttg    300

caaagcttta tacgcattgt ccaaatgttc atcaacacgt cc                       342


<210> SEQ ID NO 30
<211> LENGTH: 439
<212> TYPE: PRT
<213> ORGANISM: Homo sapiens

<400> SEQUENCE: 30

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Ile Thr Asn
        35                  40                  45

Leu Glu Phe Glu Ile Cys Gly Ala Leu Val Glu Val Lys Cys Leu Asn
    50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Glu Lys Ser Leu
```

```
                85                  90                  95

Thr Cys Lys Lys Ile Asp Leu Thr Thr Ile Val Lys Pro Glu Ala Pro
            100                 105                 110

Phe Asp Leu Ser Val Val Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
        195                 200                 205

Pro Glu Ile Asn Asn Ser Ser Gly Glu Met Asp Pro Ile Leu Leu Thr
    210                 215                 220

Ile Ser Ile Leu Ser Phe Phe Ser Val Ala Leu Leu Val Ile Leu Ala
225                 230                 235                 240

Cys Val Leu Trp Lys Lys Arg Ile Lys Pro Ile Val Trp Pro Ser Leu
                245                 250                 255

Pro Asp His Lys Lys Thr Leu Glu His Leu Cys Lys Lys Pro Arg Lys
            260                 265                 270

Asn Leu Asn Val Ser Phe Asn Pro Glu Ser Phe Leu Asp Cys Gln Ile
        275                 280                 285

His Arg Val Asp Asp Ile Gln Ala Arg Asp Glu Val Glu Gly Phe Leu
    290                 295                 300

Gln Asp Thr Phe Pro Gln Gln Leu Glu Glu Ser Glu Lys Gln Arg Leu
305                 310                 315                 320

Gly Gly Asp Val Gln Ser Pro Asn Cys Pro Ser Glu Asp Val Val Ile
                325                 330                 335

Thr Pro Glu Ser Phe Gly Arg Asp Ser Ser Leu Thr Cys Leu Ala Gly
            340                 345                 350

Asn Val Ser Ala Cys Asp Ala Pro Ile Leu Ser Ser Ser Arg Ser Leu
        355                 360                 365

Asp Cys Arg Glu Ser Gly Lys Asn Gly Pro His Val Tyr Gln Asp Leu
    370                 375                 380

Leu Leu Ser Leu Gly Thr Thr Asn Ser Thr Leu Pro Pro Pro Phe Ser
385                 390                 395                 400

Leu Gln Ser Gly Ile Leu Thr Leu Asn Pro Val Ala Gln Gly Gln Pro
                405                 410                 415

Ile Leu Thr Ser Leu Gly Ser Asn Gln Glu Glu Ala Tyr Val Thr Met
            420                 425                 430

Ser Ser Phe Tyr Gln Asn Gln
        435
```

<210> SEQ ID NO 31
<211> LENGTH: 1317
<212> TYPE: DNA
<213> ORGANISM: Homo sapiens

<400> SEQUENCE: 31

```
gaaagtggct atgctcaaaa tggagacttg gaagatgcag aactggatga ctactcattc      60

tcatgctata gccagttgga agtgaatgga tcgcagcact cactgacctg tgcttttgag     120
```

```
gacccagatg tcaacatcac caatctggaa tttgaaatat gtggggccct cgtggaggta    180

aagtgcctga atttcaggaa actacaagag atatatttca tcgagacaaa gaaattctta    240

ctgattggaa agagcaatat atgtgtgaag gttggagaaa agagtctaac ctgcaaaaaa    300

atagacctaa ccactatagt taaacctgag gctccttttg acctgagtgt cgtctatcgg    360

gaaggagcca atgactttgt ggtgacattt aatacatcac acttgcaaaa gaagtatgta    420

aaagttttaa tgcacgatgt agcttaccgc caggaaaagg atgaaaacaa atggacgcat    480

gtgaatttat ccagcacaaa gctgacactc ctgcagagaa agctccaacc ggcagcaatg    540

tatgagatta aagttcgatc catccctgat cactatttta aaggcttctg gagtgaatgg    600

agtccaagtt attacttcag aactccagag atcaataata gctcagggga gatggatcct    660

atcttactaa ccatcagcat tttgagtttt ttctctgtcg ctctgttggt catcttggcc    720

tgtgtgttat ggaaaaaaag gattaagcct atcgtatggc ccagtctccc cgatcataag    780

aagactctgg aacatctttg taagaaacca agaaaaaatt taaatgtgag tttcaatcct    840

gaaagtttcc tggactgcca gattcatagg gtggatgaca ttcaagctag agatgaagtg    900

gaaggttttc tgcaagatac gtttcctcag caactagaag aatctgagaa gcagaggctt    960

ggaggggatg tgcagagccc caactgccca tctgaggatg tagtcatcac tccagaaagc   1020

tttggaagag attcatccct cacatgcctg gctgggaatg tcagtgcatg tgacgcccct   1080

attctctcct cttccaggtc cctagactgc agggagagtg gcaagaatgg gcctcatgtg   1140

taccaggacc tcctgcttag ccttgggact acaaacagca cgctgccccc tccatttttct  1200

ctccaatctg gaatcctgac attgaaccca gttgctcagg gtcagcccat tcttacttcc   1260

ctgggatcaa atcaagaaga agcatatgtc accatgtcca gcttctacca aaaccag      1317
```

```
<210> SEQ ID NO 32
<211> LENGTH: 439
<212> TYPE: PRT
<213> ORGANISM: Mus musculus

<400> SEQUENCE: 32

Glu Ser Gly Asn Ala Gln Asp Gly Asp Leu Glu Asp Ala Asp Ala Asp
1               5                   10                  15

Asp His Ser Phe Trp Cys His Ser Gln Leu Glu Val Asp Gly Ser Gln
            20                  25                  30

His Leu Leu Thr Cys Ala Phe Asn Asp Ser Asp Ile Asn Thr Ala Asn
        35                  40                  45

Leu Glu Phe Gln Ile Cys Gly Ala Leu Leu Arg Val Lys Cys Leu Thr
    50                  55                  60

Leu Asn Lys Leu Gln Asp Ile Tyr Phe Ile Lys Thr Ser Glu Phe Leu
65                  70                  75                  80

Leu Ile Gly Ser Ser Asn Ile Cys Val Lys Leu Gly Gln Lys Asn Leu
                85                  90                  95

Thr Cys Lys Asn Met Ala Ile Asn Thr Ile Val Lys Ala Glu Ala Pro
            100                 105                 110

Ser Asp Leu Lys Val Val Tyr Arg Lys Glu Ala Asn Asp Phe Leu Val
        115                 120                 125

Thr Phe Asn Ala Pro His Leu Lys Lys Lys Tyr Leu Lys Lys Val Lys
    130                 135                 140

His Asp Val Ala Tyr Arg Pro Ala Arg Gly Glu Ser Asn Trp Thr His
145                 150                 155                 160
```

```
Val Ser Leu Phe His Thr Arg Thr Thr Ile Pro Gln Arg Lys Leu Arg
                165                 170                 175

Pro Lys Ala Met Tyr Glu Ile Lys Val Arg Ser Ile Pro His Asn Asp
            180                 185                 190

Tyr Phe Lys Gly Phe Trp Ser Glu Trp Ser Pro Ser Ser Thr Phe Glu
        195                 200                 205

Thr Pro Glu Pro Lys Asn Gln Gly Gly Trp Asp Pro Val Leu Pro Ser
    210                 215                 220

Val Thr Ile Leu Ser Leu Phe Ser Val Phe Leu Leu Val Ile Leu Ala
225                 230                 235                 240

His Val Leu Trp Lys Lys Arg Ile Lys Pro Val Val Trp Pro Ser Leu
                245                 250                 255

Pro Asp His Lys Lys Thr Leu Glu Gln Leu Cys Lys Lys Pro Lys Thr
            260                 265                 270

Ser Leu Asn Val Ser Phe Asn Pro Glu Ser Phe Leu Asp Cys Gln Ile
        275                 280                 285

His Glu Val Lys Gly Val Glu Ala Arg Asp Glu Val Glu Ser Phe Leu
    290                 295                 300

Pro Asn Asp Leu Pro Ala Gln Pro Glu Glu Leu Glu Thr Gln Gly His
305                 310                 315                 320

Arg Ala Ala Val His Ser Ala Asn Arg Ser Pro Glu Thr Ser Val Ser
                325                 330                 335

Pro Pro Glu Thr Val Arg Arg Glu Ser Pro Leu Arg Cys Leu Ala Arg
            340                 345                 350

Asn Leu Ser Thr Cys Asn Ala Pro Pro Leu Leu Ser Ser Arg Ser Pro
        355                 360                 365

Asp Tyr Arg Asp Gly Asp Arg Asn Arg Pro Pro Val Tyr Gln Asp Leu
    370                 375                 380

Leu Pro Asn Ser Gly Asn Thr Asn Val Pro Val Pro Val Pro Gln Pro
385                 390                 395                 400

Leu Pro Phe Gln Ser Gly Ile Leu Ile Pro Val Ser Gln Arg Gln Pro
                405                 410                 415

Ile Ser Thr Ser Ser Val Leu Asn Gln Glu Glu Ala Tyr Val Thr Met
            420                 425                 430

Ser Ser Phe Tyr Gln Asn Lys
        435
```

<210> SEQ ID NO 33
<211> LENGTH: 1317
<212> TYPE: DNA
<213> ORGANISM: Mus musculus

<400> SEQUENCE: 33

```
gaaagtggaa atgcccagga tggagaccta gaagatgcag acgcggacga tcactccttc      60

tggtgccaca gccagttgga agtggatgga agtcaacatt tattgacttg tgcttttaat     120

gactcagaca tcaacacagc taatctggaa tttcaaatat gtggggctct tttacgagtg     180

aaatgcctaa ctcttaacaa gctgcaagat atatatttta taaagacatc agaattctta     240

ctgattggta gcagcaatat atgtgtgaag cttggacaaa agaatttaac ttgcaaaaat     300

atggctataa acacaatagt taaagccgag gctccctctg acctgaaagt cgtttatcgc     360

aaagaagcaa atgatttttt ggtgacattt aatgcacctc acttgaaaaa gaaatattta     420

aaaaaagtaa agcatgatgt ggcctaccgc ccagcaaggg gtgaaagcaa ctggacgcat     480

gtatctttat tccacacaag aacaacaatc ccacagagaa aactacgacc aaaagcaatg     540
```

```
tatgaaatca aagtccgatc cattccccat aacgattact tcaaaggctt ctggagcgag    600

tggagtccaa gttctacctt cgaaactcca gaacccaaga atcaaggagg atgggatcct    660

gtcttgccaa gtgtcaccat tctgagtttg ttctctgtgt ttttgttggt catcttagcc    720

catgtgctat ggaaaaaaag gattaaacct gtcgtatggc ctagtctccc cgatcataag    780

aaaactctgg aacaactatg taagaagcca aaaacgagtc tgaatgtgag tttcaatccc    840

gaaagtttcc tggactgcca gattcatgag gtgaaaggcg ttgaagccag ggacgaggtg    900

gaaagttttc tgcccaatga tcttcctgca cagccagagg agttggagac acagggacac    960

agagccgctg tacacagtgc aaaccgctcg cctgagactt cagtcagccc accagaaaca   1020

gttagaagag agtcaccctt aagatgcctg gctagaaatc tgagtacctg caatgcccct   1080

ccactccttt cctctaggtc ccctgactac agagatggtg acagaaatag gcctcctgtg   1140

tatcaagact tgctgccaaa ctctggaaac acaaatgtcc ctgtccctgt ccctcaacca   1200

ttgcctttcc agtcgggaat cctgatacca gtttctcaga gacagcccat ctccacttcc   1260

tcagtactga atcaagaaga agcgtatgtc accatgtcta gtttttacca aaacaaa      1317
```

<210> SEQ ID NO 34
<211> LENGTH: 266
<212> TYPE: PRT
<213> ORGANISM: Mus musculus

<400> SEQUENCE: 34

```
Glu Ser Gly Asn Ala Gln Asp Gly Asp Leu Glu Asp Ala Asp Ala Asp
1               5                   10                  15

Asp His Ser Phe Trp Cys His Ser Gln Leu Glu Val Asp Gly Ser Gln
            20                  25                  30

His Leu Leu Thr Cys Ala Phe Asn Asp Ser Asp Ile Asn Thr Ala Asn
        35                  40                  45

Leu Glu Phe Gln Ile Cys Gly Ala Leu Leu Arg Val Lys Cys Leu Thr
    50                  55                  60

Leu Asn Lys Leu Gln Asp Ile Tyr Phe Ile Lys Thr Ser Glu Phe Leu
65                  70                  75                  80

Leu Ile Gly Ser Ser Asn Ile Cys Val Lys Leu Gly Gln Lys Asn Leu
                85                  90                  95

Thr Cys Lys Asn Met Ala Ile Asn Thr Ile Val Lys Ala Glu Ala Pro
            100                 105                 110

Ser Asp Leu Lys Val Val Tyr Arg Lys Glu Ala Asn Asp Phe Leu Val
        115                 120                 125

Thr Phe Asn Ala Pro His Leu Lys Lys Lys Tyr Leu Lys Lys Val Lys
    130                 135                 140

His Asp Val Ala Tyr Arg Pro Ala Arg Gly Glu Ser Asn Trp Thr His
145                 150                 155                 160

Val Ser Leu Phe His Thr Arg Thr Thr Ile Pro Gln Arg Lys Leu Arg
                165                 170                 175

Pro Lys Ala Met Tyr Glu Ile Lys Val Arg Ser Ile Pro His Asn Asp
            180                 185                 190

Tyr Phe Lys Gly Phe Trp Ser Glu Trp Ser Pro Ser Ser Thr Phe Glu
        195                 200                 205

Thr Pro Glu Pro Lys Asn Gln Gly Gly Trp Asp Pro Val Leu Pro Ser
    210                 215                 220

Val Thr Ile Leu Ser Leu Phe Ser Val Phe Leu Leu Val Ile Leu Ala
225                 230                 235                 240
```

```
His Val Leu Trp Lys Lys Arg Ile Lys Pro Val Val Trp Pro Ser Leu
                245                 250                 255

Pro Asp His Lys Lys Thr Leu Glu Gln Leu
            260                 265
```

<210> SEQ ID NO 35
<211> LENGTH: 861
<212> TYPE: DNA
<213> ORGANISM: Mus musculus

<400> SEQUENCE: 35

```
atgatggctc tgggtagagc tttcgctata gttttctgct taattcaagc tgtttctgga     60

gaaagtggaa atgcccagga tggagaccta gaagatgcag acgcggacga tcactccttc    120

tggtgccaca gccagttgga agtggatgga agtcaacatt tattgacttg tgcttttaat    180

gactcagaca tcaacacagc taatctggaa tttcaaatat gtggggctct tttacgagtg    240

aaatgcctaa ctcttaacaa gctgcaagat atatatttta taaagacatc agaattctta    300

ctgattggta gcagcaatat atgtgtgaag cttggacaaa agaatttaac ttgcaaaaat    360

atggctataa acacaatagt taaagccgag gctccctctg acctgaaagt cgtttatcgc    420

aaagaagcaa atgatttttt ggtgacattt aatgcacctc acttgaaaaa gaaatattta    480

aaaaaagtaa agcatgatgt ggcctaccgc ccagcaaggg gtgaaagcaa ctggacgcat    540

gtatctttat tccacacaag aacaacaatc ccacagagaa aactacgacc aaaagcaatg    600

tatgaaatca aagtccgatc cattccccat aacgattact tcaaaggctt ctggagcgag    660

tggagtccaa gttctacctt cgaaactcca gaacccaaga atcaaggagg atgggatcct    720

gtcttgccaa gtgtcaccat tctgagtttg ttctctgtgt tttgttggt catcttagcc    780

catgtgctat ggaaaaaaag gattaaacct gtcgtatggc ctagtctccc cgatcataag    840

aaaactctgg aacaactata g                                              861
```

<210> SEQ ID NO 36
<211> LENGTH: 62
<212> TYPE: PRT
<213> ORGANISM: Homo sapiens

<400> SEQUENCE: 36

```
Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys Ile
    50                  55                  60
```

<210> SEQ ID NO 37
<211> LENGTH: 62
<212> TYPE: PRT
<213> ORGANISM: Homo sapiens

<400> SEQUENCE: 37

```
Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30
```

```
Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys Ile
    50                  55                  60


<210> SEQ ID NO 38
<211> LENGTH: 62
<212> TYPE: PRT
<213> ORGANISM: Mus musculus

<400> SEQUENCE: 38

Cys Pro Pro Pro Val Ser Ile Glu His Ala Asp Ile Arg Val Lys Asn
1               5                   10                  15

Tyr Ser Val Asn Ser Arg Glu Arg Tyr Val Cys Asn Ser Gly Phe Lys
            20                  25                  30

Arg Lys Ala Gly Thr Ser Thr Leu Ile Glu Cys Val Ile Asn Lys Asn
        35                  40                  45

Thr Asn Val Ala His Trp Thr Thr Pro Ser Leu Lys Cys Ile
    50                  55                  60


<210> SEQ ID NO 39
<211> LENGTH: 62
<212> TYPE: PRT
<213> ORGANISM: Mus musculus

<400> SEQUENCE: 39

Cys Pro Pro Pro Val Ser Ile Glu His Ala Asp Ile Arg Val Lys Asn
1               5                   10                  15

Tyr Ser Val Asn Ser Arg Glu Arg Tyr Val Cys Asn Ser Gly Phe Lys
            20                  25                  30

Arg Lys Ala Gly Thr Ser Thr Leu Ile Glu Cys Val Ile Asn Lys Asn
        35                  40                  45

Thr Asn Val Ala His Trp Thr Thr Pro Ser Leu Lys Cys Ile
    50                  55                  60


<210> SEQ ID NO 40
<211> LENGTH: 59
<212> TYPE: PRT
<213> ORGANISM: Gallus gallus

<400> SEQUENCE: 40

Cys Pro Arg Leu Ser Thr Thr Glu Phe Ala Asp Val Ala Ala Glu Thr
1               5                   10                  15

Tyr Pro Leu Lys Thr Lys Leu Arg Tyr Glu Cys Asp Ser Gly Tyr Arg
            20                  25                  30

Arg Arg Ser Gly Asn Thr Leu Thr Ile Arg Cys Gln Asn Val Ser Gly
        35                  40                  45

Thr Ala Ser Trp Val His Asp Glu Leu Val Cys
    50                  55


<210> SEQ ID NO 41
<211> LENGTH: 175
<212> TYPE: PRT
<213> ORGANISM: Homo sapiens

<400> SEQUENCE: 41

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30
```

```
Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175


<210> SEQ ID NO 42
<211> LENGTH: 25
<212> TYPE: PRT
<213> ORGANISM: Mus musculus

<400> SEQUENCE: 42

Pro Val Leu Pro Ser Val Thr Ile Leu Ser Leu Phe Ser Val Phe Leu
1               5                   10                  15

Leu Val Ile Leu Ala His Val Leu Trp
            20                  25


<210> SEQ ID NO 43

<400> SEQUENCE: 43

000


<210> SEQ ID NO 44
<211> LENGTH: 25
<212> TYPE: PRT
<213> ORGANISM: Macaca fascicularis

<400> SEQUENCE: 44

Pro Ile Leu Leu Thr Ile Ser Leu Leu Ser Phe Phe Ser Val Ala Leu
1               5                   10                  15

Leu Val Ile Leu Ala Cys Val Leu Trp
            20                  25


<210> SEQ ID NO 45
<211> LENGTH: 195
<212> TYPE: PRT
<213> ORGANISM: Homo sapiens

<400> SEQUENCE: 45

Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45
```

```
Asp Ile Gln Ala Arg Asp Glu Val Glu Gly Phe Leu Gln Asp Thr Phe
    50                  55                  60

Pro Gln Gln Leu Glu Glu Ser Glu Lys Gln Arg Leu Gly Gly Asp Val
65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Ser Arg Ser Leu Asp Cys Arg Glu
        115                 120                 125

Ser Gly Lys Asn Gly Pro His Val Tyr Gln Asp Leu Leu Leu Ser Leu
    130                 135                 140

Gly Thr Thr Asn Ser Thr Leu Pro Pro Pro Phe Ser Leu Gln Ser Gly
145                 150                 155                 160

Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Gln
        195
```

<210> SEQ ID NO 46
<211> LENGTH: 195
<212> TYPE: PRT
<213> ORGANISM: Mus musculus

<400> SEQUENCE: 46

```
Lys Lys Arg Ile Lys Pro Val Val Trp Pro Ser Leu Pro Asp His Lys
1               5                   10                  15

Lys Thr Leu Glu Gln Leu Cys Lys Lys Pro Lys Thr Ser Leu Asn Val
            20                  25                  30

Ser Phe Asn Pro Glu Ser Phe Leu Asp Cys Gln Ile His Glu Val Lys
        35                  40                  45

Gly Val Glu Ala Arg Asp Glu Val Glu Ser Phe Leu Pro Asn Asp Leu
    50                  55                  60

Pro Ala Gln Pro Glu Glu Leu Glu Thr Gln Gly His Arg Ala Ala Val
65                  70                  75                  80

His Ser Ala Asn Arg Ser Pro Glu Thr Ser Val Ser Pro Pro Glu Thr
                85                  90                  95

Val Arg Arg Glu Ser Pro Leu Arg Cys Leu Ala Arg Asn Leu Ser Thr
            100                 105                 110

Cys Asn Ala Pro Pro Leu Leu Ser Ser Arg Ser Pro Asp Tyr Arg Asp
        115                 120                 125

Gly Asp Arg Asn Arg Pro Pro Val Tyr Gln Asp Leu Leu Pro Asn Ser
    130                 135                 140

Gly Asn Thr Asn Val Pro Val Pro Val Pro Gln Pro Leu Pro Phe Gln
145                 150                 155                 160

Ser Gly Ile Leu Ile Pro Val Ser Gln Arg Gln Pro Ile Ser Thr Ser
                165                 170                 175

Ser Val Leu Asn Gln Glu Glu Ala Tyr Val Thr Met Ser Ser Phe Tyr
            180                 185                 190

Gln Asn Lys
        195
```

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
Linker sequence

<400> SEQUENCE: 47

Ser Gly Gly Ser
1

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
Linker sequence

<400> SEQUENCE: 48

Ser Gly Gly Gly Ser
1 5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
Linker sequence

<400> SEQUENCE: 49

Ser Gly Gly Gly Gly Ser
1 5

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
Linker sequence

<400> SEQUENCE: 50

Ser Gly Gly Gly Gly Ser Gly Gly Gly Gly Ser Gly Gly Gly Gly
1 5 10 15

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
Linker sequence

<400> SEQUENCE: 51

Ala Ser Thr Lys Gly Pro Ser Val Phe Pro Leu Ala Pro Ser Ser Ser
1 5 10 15

Gly Ser Gly

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
Linker sequence

<400> SEQUENCE: 52

Gly Gly Gly Gly Ser Gly Gly Gly Gly Ser Gly Gly Gly Gly Ser
1 5 10 15

<210> SEQ ID NO 53
<211> LENGTH: 23
<212> TYPE: PRT
<213> ORGANISM: Artificial Sequence
<220> FEATURE:
<223> OTHER INFORMATION: Description of Artificial Sequence: Synthetic Linker sequence

<400> SEQUENCE: 53

Gly Gly Gly Ser Gly Gly Gly Gly Ser Gly Gly Gly Gly Ser Gly Gly
1 5 10 15

Gly Gly Ser Gly Gly Gly Ser
20

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic Linker sequence

<400> SEQUENCE: 54

Gly Ser Thr Ser Gly Ser Gly Lys Pro Gly Ser Gly Glu Gly Ser Thr
1 5 10 15

Lys Gly

<210> SEQ ID NO 55
<211> LENGTH: 54
<212> TYPE: DNA
<213> ORGANISM: Artificial Sequence
<220> FEATURE:
<223> OTHER INFORMATION: Description of Artificial Sequence: Synthetic Linker sequence

<400> SEQUENCE: 55
ggcagcacca gcggcagcgg caaaccgggc agcggcgaag gcagcaccaa aggc 54

<210> SEQ ID NO 56
<211> LENGTH: 25
<212> TYPE: PRT
<213> ORGANISM: Artificial Sequence
<220> FEATURE:
<223> OTHER INFORMATION: Description of Artificial Sequence: Synthetic Linker sequence

<400> SEQUENCE: 56

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 57
<211> LENGTH: 75
<212> TYPE: DNA
<213> ORGANISM: Artificial Sequence
<220> FEATURE:
<223> OTHER INFORMATION: Description of Artificial Sequence: Synthetic Linker sequence

<400> SEQUENCE: 57

```
ggcggtggtg gttctggagg cggtggcagc ggtggaggtg gctcaggagg aggaggtagc     60

ggcggcggag ggagt                                                      75


<210> SEQ ID NO 58
<211> LENGTH: 233
<212> TYPE: PRT
<213> ORGANISM: Homo sapiens

<400> SEQUENCE: 58

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Trp Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Lys Asp
225                 230


<210> SEQ ID NO 59
<211> LENGTH: 46
<212> TYPE: PRT
<213> ORGANISM: Homo sapiens

<400> SEQUENCE: 59

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45


<210> SEQ ID NO 60
<211> LENGTH: 20
<212> TYPE: PRT
```

<213> ORGANISM: Homo sapiens

<400> SEQUENCE: 60

Ala Glu Pro Lys Ser Pro Asp Lys Thr His Thr Cys Pro Pro Cys Pro
1               5                   10                  15

Lys Asp Pro Lys
            20

<210> SEQ ID NO 61
<211> LENGTH: 220
<212> TYPE: PRT
<213> ORGANISM: Homo sapiens

<400> SEQUENCE: 61

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 62
<211> LENGTH: 164
<212> TYPE: PRT
<213> ORGANISM: Homo sapiens

<400> SEQUENCE: 62

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

```
Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 63
<211> LENGTH: 23
<212> TYPE: PRT
<213> ORGANISM: Homo sapiens

<400> SEQUENCE: 63

Leu Gly Leu Leu Val Ala Gly Val Leu Val Leu Leu Val Ser Leu Gly
1               5                   10                  15

Val Ala Ile His Leu Cys Cys
            20


<210> SEQ ID NO 64
<211> LENGTH: 26
<212> TYPE: PRT
<213> ORGANISM: Homo sapiens

<400> SEQUENCE: 64

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25


<210> SEQ ID NO 65
<211> LENGTH: 25
<212> TYPE: PRT
<213> ORGANISM: Homo sapiens

<400> SEQUENCE: 65

Ala Leu Ile Val Leu Gly Gly Val Ala Gly Leu Leu Leu Phe Ile Gly
1               5                   10                  15

Leu Gly Ile Phe Phe Cys Val Arg Cys
            20                  25


<210> SEQ ID NO 66
<211> LENGTH: 23
<212> TYPE: PRT
<213> ORGANISM: Homo sapiens

<400> SEQUENCE: 66

Leu Cys Tyr Leu Leu Asp Gly Ile Leu Phe Ile Tyr Gly Val Ile Leu
1               5                   10                  15

Thr Ala Leu Phe Leu Arg Val
            20


<210> SEQ ID NO 67
```

<211> LENGTH: 26
<212> TYPE: PRT
<213> ORGANISM: Homo sapiens

<400> SEQUENCE: 67

```
Trp Val Leu Val Val Val Gly Gly Val Leu Ala Cys Tyr Ser Leu Leu
1               5                   10                  15

Val Thr Val Ala Phe Ile Ile Phe Trp Val
            20                  25
```

<210> SEQ ID NO 68
<211> LENGTH: 24
<212> TYPE: PRT
<213> ORGANISM: Homo sapiens

<400> SEQUENCE: 68

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 69
<211> LENGTH: 24
<212> TYPE: PRT
<213> ORGANISM: Homo sapiens

<400> SEQUENCE: 69

```
Ala Leu Pro Ala Ala Leu Ala Val Ile Ser Phe Leu Leu Gly Leu Gly
1               5                   10                  15

Leu Gly Val Ala Cys Val Leu Ala
            20
```

<210> SEQ ID NO 70
<211> LENGTH: 220
<212> TYPE: PRT
<213> ORGANISM: Homo sapiens

<400> SEQUENCE: 70

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
```

```
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220


<210> SEQ ID NO 71
<211> LENGTH: 255
<212> TYPE: PRT
<213> ORGANISM: Homo sapiens

<400> SEQUENCE: 71

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255


<210> SEQ ID NO 72
<211> LENGTH: 164
<212> TYPE: PRT
<213> ORGANISM: Homo sapiens

<400> SEQUENCE: 72

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
```

```
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 73
<211> LENGTH: 113
<212> TYPE: PRT
<213> ORGANISM: Homo sapiens

<400> SEQUENCE: 73

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg


<210> SEQ ID NO 74
<211> LENGTH: 339
<212> TYPE: DNA
<213> ORGANISM: Homo sapiens

<400> SEQUENCE: 74

ctgagagtga agttcagcag gagcgcagac gcccccgcgt accagcaggg ccagaaccag      60

ctctataacg agctcaatct aggacgaaga gaggagtacg atgttttgga caagagacgt     120

ggccgggacc ctgagatggg gggaaagccg agaaggaaga accctcagga aggcctgtac     180

aatgaactgc agaaagataa gatggcggag gcctacagtg agattgggat gaaaggcgag     240

cgccggaggg gcaaggggca cgatggcctt taccagggtc tcagtacagc caccaaggac     300

acctacgacg cccttcacat gcaggccctg ccccctcgc                            339
```

<210> SEQ ID NO 75
<211> LENGTH: 233
<212> TYPE: PRT
<213> ORGANISM: Homo sapiens

<400> SEQUENCE: 75

```
Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Trp Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Lys Asp
225                 230
```

<210> SEQ ID NO 76
<211> LENGTH: 46
<212> TYPE: PRT
<213> ORGANISM: Homo sapiens

<400> SEQUENCE: 76

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45
```

<210> SEQ ID NO 77
<211> LENGTH: 20
<212> TYPE: PRT
<213> ORGANISM: Homo sapiens

<400> SEQUENCE: 77

```
Ala Glu Pro Lys Ser Pro Asp Lys Thr His Thr Cys Pro Pro Cys Pro
```

1 5 10 15

Lys Asp Pro Lys
20

<210> SEQ ID NO 78
<211> LENGTH: 17
<212> TYPE: DNA
<213> ORGANISM: Homo sapiens

<400> SEQUENCE: 78
aaataaaata cgaaatg 17

<210> SEQ ID NO 79
<211> LENGTH: 28
<212> TYPE: PRT
<213> ORGANISM: Artificial Sequence
<220> FEATURE:
<223> OTHER INFORMATION: Description of Artificial Sequence: Synthetic
IL7RA MCP insert sequence

<400> SEQUENCE: 79

Pro Ile Leu Leu Thr Met Cys Pro Ile Ser Ile Leu Ser Phe Phe Ser
1 5 10 15

Val Ala Leu Leu Val Ile Leu Ala Cys Val Leu Trp
20 25

<210> SEQ ID NO 80
<211> LENGTH: 84
<212> TYPE: DNA
<213> ORGANISM: Artificial Sequence
<220> FEATURE:
<223> OTHER INFORMATION: Description of Artificial Sequence: Synthetic
IL7RA MCP insert sequence

<400> SEQUENCE: 80
cccatcctgc tgaccatgtg ccccatcagc atcctgagct tcttcagcgt ggccctgctg 60
gtgatcctgg cctgcgtgct gtgg 84

<210> SEQ ID NO 81
<211> LENGTH: 66
<212> TYPE: DNA
<213> ORGANISM: Homo sapiens

<400> SEQUENCE: 81
atgctcctgc tcgtgacttc acttcttctc tgtgaactcc cacaccccgc gtttttgctt 60
atccct 66

<210> SEQ ID NO 82
<211> LENGTH: 586
<212> TYPE: DNA
<213> ORGANISM: Homo sapiens

<400> SEQUENCE: 82
aagaagagga tcaagcccat cgtgtggccc agcctgcccg accacaagaa gaccctggag 60
cacctgtgta agaagcccag gaagaacctg aacgtgagct tcaaccccga gagcttcctg 120
gactgccaga tccacagggt ggacgacatc caggccaggg acgaggtgga gggcttcctg 180
caggacacct tcccccagca gctggaggag agcgagaagc agaggctggg cggcgacgtg 240
cagagcccca actgccccag cgaggacgtg gtgatcaccc ccgagagctt cggcagggac 300
agcagcctga cctgcctggc cggcaacgtg agcgcctgcg acgcccccat cctgagcagc 360

```
agcaggagcc tggactgcag ggagagcggc aagaacggcc cccacgtgta ccaggacctg    420

ctgctgagcc tgggcaccac caacagcacc ctgccacccc ccttcagcct gcagagcggc    480

atcctgaccc tgaaccccgt ggcccagggc cagcccatcc tgaccagcct gggcagcaac    540

caggaggagg cctacgtgac catgagcagc ttctaccaga accags                   586


<210> SEQ ID NO 83
<211> LENGTH: 538
<212> TYPE: PRT
<213> ORGANISM: Artificial Sequence
<220> FEATURE:
<223> OTHER INFORMATION: Description of Artificial Sequence: Synthetic
      Exemplary chimeric transmembrane protein sequence

<400> SEQUENCE: 83

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ser Gly Gly Gly Ser Gly Gly Gly Gly Ser Gly Gly Gly Gly
        115                 120                 125

Ser Gly Gly Gly Gly Ser Gly Gly Gly Ser Leu Gln Ile Thr Cys Pro
    130                 135                 140

Pro Pro Met Ser Val Glu His Ala Asp Ile Trp Val Lys Ser Tyr Ser
145                 150                 155                 160

Leu Tyr Ser Arg Glu Arg Tyr Ile Cys Asn Ser Gly Phe Lys Arg Lys
                165                 170                 175

Ala Gly Thr Ser Ser Leu Thr Glu Cys Val Leu Asn Lys Ala Thr Asn
            180                 185                 190

Val Ala His Trp Thr Thr Pro Ser Leu Lys Cys Ile Arg Asp Pro Ala
        195                 200                 205

Leu Val His Gln Arg Pro Ala Pro Pro Ser Thr Val Thr Thr Ala Gly
    210                 215                 220

Val Thr Pro Gln Pro Glu Ser Leu Ser Pro Ser Gly Lys Glu Pro Ala
225                 230                 235                 240

Ala Ser Ser Pro Ser Ser Asn Asn Thr Ala Ala Thr Thr Ala Ala Ile
                245                 250                 255

Val Pro Gly Ser Gln Leu Met Pro Ser Lys Ser Pro Ser Thr Gly Thr
            260                 265                 270

Thr Glu Ile Ser Ser His Glu Ser Ser His Gly Thr Pro Ser Gln Thr
        275                 280                 285

Thr Ala Lys Asn Trp Glu Leu Thr Ala Ser Ala Ser His Gln Pro Pro
    290                 295                 300

Gly Val Tyr Pro Gln Gly His Ser Asp Thr Thr Pro Ile Leu Leu Thr
305                 310                 315                 320
```

```
Cys Pro Thr Ile Ser Ile Leu Ser Phe Phe Ser Val Ala Leu Leu Val
                325                 330                 335

Ile Leu Ala Cys Val Leu Trp Lys Lys Arg Ile Lys Pro Ile Val Trp
            340                 345                 350

Pro Ser Leu Pro Asp His Lys Lys Thr Leu Glu His Leu Cys Lys Lys
        355                 360                 365

Pro Arg Lys Asn Leu Asn Val Ser Phe Asn Pro Glu Ser Phe Leu Asp
    370                 375                 380

Cys Gln Ile His Arg Val Asp Asp Ile Gln Ala Arg Asp Glu Val Glu
385                 390                 395                 400

Gly Phe Leu Gln Asp Thr Phe Pro Gln Gln Leu Glu Glu Ser Glu Lys
                405                 410                 415

Gln Arg Leu Gly Gly Asp Val Gln Ser Pro Asn Cys Pro Ser Glu Asp
            420                 425                 430

Val Val Ile Thr Pro Glu Ser Phe Gly Arg Asp Ser Ser Leu Thr Cys
        435                 440                 445

Leu Ala Gly Asn Val Ser Ala Cys Asp Ala Pro Ile Leu Ser Ser Ser
    450                 455                 460

Arg Ser Leu Asp Cys Arg Glu Ser Gly Lys Asn Gly Pro His Val Tyr
465                 470                 475                 480

Gln Asp Leu Leu Leu Ser Leu Gly Thr Thr Asn Ser Thr Leu Pro Pro
                485                 490                 495

Pro Phe Ser Leu Gln Ser Gly Ile Leu Thr Leu Asn Pro Val Ala Gln
            500                 505                 510

Gly Gln Pro Ile Leu Thr Ser Leu Gly Ser Asn Gln Glu Glu Ala Tyr
        515                 520                 525

Val Thr Met Ser Ser Phe Tyr Gln Asn Gln
    530                 535
```

<210> SEQ ID NO 84
<211> LENGTH: 1614
<212> TYPE: DNA
<213> ORGANISM: Artificial Sequence
<220> FEATURE:
<223> OTHER INFORMATION: Description of Artificial Sequence: Synthetic
Exemplary chimeric transmembrane sequence

<400> SEQUENCE: 84

```
aactgggtga atgtgatcag cgacctgaag aagatcgagg atctgatcca gagcatgcac     60

attgatgcca ccctgtacac agaatctgat gtgcacccta gctgtaaagt gaccgccatg    120

aagtgttttc tgctggagct gcaggtgatt tctctggaaa gcggagatgc ctctatccac    180

gacacagtgg agaatctgat catcctggcc aacaatagcc tgagcagcaa tggcaatgtg    240

acagagtctg gctgtaagga gtgtgaggag ctggaggaga agaacatcaa ggagtttctg    300

cagagctttg tgcacatcgt gcagatgttc atcaatacaa gcagcggtgg gggctcaggc    360

ggaggaggct ctggcggagg cggaagcggg ggagggggct caggcggcgg gtccttgcag    420

attacatgcc ctcctccaat gtctgtggag cacgccgata tttgggtgaa gtcctacagc    480

ctgtacagca gagagagata catctgcaac agcggcttta agagaaaggc cggcacctct    540

tctctgacag agtgcgtgct gaataaggcc acaaatgtgg cccactggac aacacctagc    600

ctgaagtgca ttagagatcc tgccctggtc caccagaggc ctgcccctcc atctacagtg    660

acaacagccg gagtgacacc tcagcctgaa tctctgagcc cttctggaaa agaacctgcc    720

gccagctctc ctagctctaa taataccgcc gccacaacag ccgccattgt gcctggatct    780
```

```
cagctgatgc ctagcaagtc tcctagcaca ggcacaacag agatcagcag ccacgaatct     840

tctcacggaa caccttctca gaccaccgcc aagaattggg agctgacagc ctctgcctct     900

caccagcctc caggagtgta tcctcagggc cactctgata caacacccat cctgctgacc     960

tgccccacca tcagcatcct gagcttcttc agcgtggccc tgctggtgat cctggcctgc    1020

gtgctgtgga agaagaggat caagcccatc gtgtggccca gcctgcccga ccacaagaag    1080

accctggagc acctgtgtaa gaagcccagg aagaacctga acgtgagctt caaccccgag    1140

agcttcctgg actgccagat ccacagggtg gacgacatcc aggccaggga cgaggtggag    1200

ggcttcctgc aggacacctt cccccagcag ctggaggaga gcgagaagca gaggctgggc    1260

ggcgacgtgc agagccccaa ctgccccagc gaggacgtgg tgatcacccc cgagagcttc    1320

ggcagggaca gcagcctgac ctgcctggcc ggcaacgtga gcgcctgcga cgcccccatc    1380

ctgagcagca gcaggagcct ggactgcagg gagagcggca agaacggccc ccacgtgtac    1440

caggacctgc tgctgagcct gggcaccacc aacagcaccc tgccaccccc cttcagcctg    1500

cagagcggca tcctgaccct gaaccccgtg gcccagggcc agcccatcct gaccagcctg    1560

ggcagcaacc aggaggaggc ctacgtgacc atgagcagct tctaccagaa ccag          1614


<210> SEQ ID NO 85
<211> LENGTH: 538
<212> TYPE: PRT
<213> ORGANISM: Artificial Sequence
<220> FEATURE:
<223> OTHER INFORMATION: Description of Artificial Sequence: Synthetic
      Exemplary chimeric transmembrane protein sequence

<400> SEQUENCE: 85

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ser Gly Gly Gly Ser Gly Gly Gly Gly Ser Gly Gly Gly Gly
        115                 120                 125

Ser Gly Gly Gly Gly Ser Gly Gly Gly Ser Leu Gln Ile Thr Cys Pro
    130                 135                 140

Pro Pro Met Ser Val Glu His Ala Asp Ile Trp Val Lys Ser Tyr Ser
145                 150                 155                 160

Leu Tyr Ser Arg Glu Arg Tyr Ile Cys Asn Ser Gly Phe Lys Arg Lys
                165                 170                 175

Ala Gly Thr Ser Ser Leu Thr Glu Cys Val Leu Asn Lys Ala Thr Asn
            180                 185                 190

Val Ala His Trp Thr Thr Pro Ser Leu Lys Cys Ile Arg Asp Pro Ala
        195                 200                 205

Leu Val His Gln Arg Pro Ala Pro Pro Ser Thr Val Thr Thr Ala Gly
```

```
    210                 215                 220

Val Thr Pro Gln Pro Glu Ser Leu Ser Pro Ser Gly Lys Glu Pro Ala
225                 230                 235                 240

Ala Ser Ser Pro Ser Ser Asn Asn Thr Ala Ala Thr Thr Ala Ala Ile
                245                 250                 255

Val Pro Gly Ser Gln Leu Met Pro Ser Lys Ser Pro Ser Thr Gly Thr
            260                 265                 270

Thr Glu Ile Ser Ser His Glu Ser Ser His Gly Thr Pro Ser Gln Thr
        275                 280                 285

Thr Ala Lys Asn Trp Glu Leu Thr Ala Ser Ala Ser His Gln Pro Pro
    290                 295                 300

Gly Val Tyr Pro Gln Gly His Ser Asp Thr Thr Pro Ile Leu Leu Met
305                 310                 315                 320

Cys Pro Thr Ile Ser Ile Leu Ser Phe Phe Ser Val Ala Leu Leu Val
                325                 330                 335

Ile Leu Ala Cys Val Leu Trp Lys Lys Arg Ile Lys Pro Ile Val Trp
            340                 345                 350

Pro Ser Leu Pro Asp His Lys Lys Thr Leu Glu His Leu Cys Lys Lys
        355                 360                 365

Pro Arg Lys Asn Leu Asn Val Ser Phe Asn Pro Glu Ser Phe Leu Asp
    370                 375                 380

Cys Gln Ile His Arg Val Asp Asp Ile Gln Ala Arg Asp Glu Val Glu
385                 390                 395                 400

Gly Phe Leu Gln Asp Thr Phe Pro Gln Gln Leu Glu Glu Ser Glu Lys
                405                 410                 415

Gln Arg Leu Gly Gly Asp Val Gln Ser Pro Asn Cys Pro Ser Glu Asp
            420                 425                 430

Val Val Ile Thr Pro Glu Ser Phe Gly Arg Asp Ser Ser Leu Thr Cys
        435                 440                 445

Leu Ala Gly Asn Val Ser Ala Cys Asp Ala Pro Ile Leu Ser Ser Ser
    450                 455                 460

Arg Ser Leu Asp Cys Arg Glu Ser Gly Lys Asn Gly Pro His Val Tyr
465                 470                 475                 480

Gln Asp Leu Leu Leu Ser Leu Gly Thr Thr Asn Ser Thr Leu Pro Pro
                485                 490                 495

Pro Phe Ser Leu Gln Ser Gly Ile Leu Thr Leu Asn Pro Val Ala Gln
            500                 505                 510

Gly Gln Pro Ile Leu Thr Ser Leu Gly Ser Asn Gln Glu Glu Ala Tyr
        515                 520                 525

Val Thr Met Ser Ser Phe Tyr Gln Asn Gln
    530                 535


<210> SEQ ID NO 86
<211> LENGTH: 1614
<212> TYPE: DNA
<213> ORGANISM: Artificial Sequence
<220> FEATURE:
<223> OTHER INFORMATION: Description of Artificial Sequence: Synthetic
      Exemplary chimeric transmembrane sequence

<400> SEQUENCE: 86

aactgggtga atgtgatcag cgacctgaag aagatcgagg atctgatcca gagcatgcac      60

attgatgcca ccctgtacac agaatctgat gtgcacccta gctgtaaagt gaccgccatg     120

aagtgtttc tgctggagct gcaggtgatt tctctggaaa gcggagatgc ctctatccac     180
```

```
gacacagtgg agaatctgat catcctggcc aacaatagcc tgagcagcaa tggcaatgtg    240

acagagtctg gctgtaagga gtgtgaggag ctggaggaga agaacatcaa ggagtttctg    300

cagagctttg tgcacatcgt gcagatgttc atcaatacaa gcagcggtgg gggctcaggc    360

ggaggaggct ctggcggagg cggaagcggg ggagggggct caggcggcgg gtccttgcag    420

attacatgcc ctcctccaat gtctgtggag cacgccgata tttgggtgaa gtcctacagc    480

ctgtacagca gagagagata catctgcaac agcggcttta agagaaaggc cggcacctct    540

tctctgacag agtgcgtgct gaataaggcc acaaatgtgg cccactggac aacacctagc    600

ctgaagtgca ttagagatcc tgccctggtc caccagaggc ctgcccctcc atctacagtg    660

acaacagccg gagtgacacc tcagcctgaa tctctgagcc cttctggaaa agaacctgcc    720

gccagctctc ctagctctaa taataccgcc gccacaacag ccgccattgt gcctggatct    780

cagctgatgc ctagcaagtc tcctagcaca ggcacaacag agatcagcag ccacgaatct    840

tctcacggaa caccttctca gaccaccgcc aagaattggg agctgacagc ctctgcctct    900

caccagcctc caggagtgta tcctcagggc cactctgata caacacccat cctgctgatg    960

tgccccacca tcagcatcct gagcttcttc agcgtggccc tgctggtgat cctggcctgc   1020

gtgctgtgga agaagaggat caagcccatc gtgtggccca gcctgcccga ccacaagaag   1080

accctggagc acctgtgtaa gaagcccagg aagaacctga acgtgagctt caaccccgag   1140

agcttcctgg actgccagat ccacagggtg gacgacatcc aggccaggga cgaggtggag   1200

ggcttcctgc aggacacctt cccccagcag ctggaggaga gcgagaagca gaggctgggc   1260

ggcgacgtgc agagccccaa ctgccccagc gaggacgtgg tgatcacccc cgagagcttc   1320

ggcagggaca gcagcctgac ctgcctggcc ggcaacgtga gcgcctgcga cgcccccatc   1380

ctgagcagca gcaggagcct ggactgcagg gagagcggca agaacggccc ccacgtgtac   1440

caggacctgc tgctgagcct gggcaccacc aacagcaccc tgccaccccc cttcagcctg   1500

cagagcggca tcctgaccct gaaccccgtg gcccagggcc agcccatcct gaccagcctg   1560

ggcagcaacc aggaggaggc ctacgtgacc atgagcagct tctaccagaa ccag         1614
```

```
<210> SEQ ID NO 87
<211> LENGTH: 535
<212> TYPE: PRT
<213> ORGANISM: Artificial Sequence
<220> FEATURE:
<223> OTHER INFORMATION: Description of Artificial Sequence: Synthetic
      Exemplary chimeric transmembrane protein sequence

<400> SEQUENCE: 87

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110
```

```
Thr Ser Ser Gly Gly Gly Ser Gly Gly Gly Gly Ser Gly Gly Gly Gly
        115                 120                 125

Ser Gly Gly Gly Gly Ser Gly Gly Gly Ser Leu Gln Ile Thr Cys Pro
    130                 135                 140

Pro Pro Met Ser Val Glu His Ala Asp Ile Trp Val Lys Ser Tyr Ser
145                 150                 155                 160

Leu Tyr Ser Arg Glu Arg Tyr Ile Cys Asn Ser Gly Phe Lys Arg Lys
                165                 170                 175

Ala Gly Thr Ser Ser Leu Thr Glu Cys Val Leu Asn Lys Ala Thr Asn
            180                 185                 190

Val Ala His Trp Thr Thr Pro Ser Leu Lys Cys Ile Arg Asp Pro Ala
        195                 200                 205

Leu Val His Gln Arg Pro Ala Pro Pro Ser Thr Val Thr Thr Ala Gly
    210                 215                 220

Val Thr Pro Gln Pro Glu Ser Leu Ser Pro Ser Gly Lys Glu Pro Ala
225                 230                 235                 240

Ala Ser Ser Pro Ser Ser Asn Asn Thr Ala Ala Thr Thr Ala Ala Ile
                245                 250                 255

Val Pro Gly Ser Gln Leu Met Pro Ser Lys Ser Pro Ser Thr Gly Thr
            260                 265                 270

Thr Glu Ile Ser Ser His Glu Ser Ser His Gly Thr Pro Ser Gln Thr
        275                 280                 285

Thr Ala Lys Asn Trp Glu Leu Thr Ala Ser Ala Ser His Gln Pro Pro
    290                 295                 300

Gly Val Tyr Pro Gln Gly His Ser Asp Thr Thr Pro Ile Leu Leu Thr
305                 310                 315                 320

Ile Ser Ile Leu Ser Phe Phe Ser Val Glu Lys Ala Val Ile Leu Ala
                325                 330                 335

Cys Val Leu Trp Lys Lys Arg Ile Lys Pro Ile Val Trp Pro Ser Leu
            340                 345                 350

Pro Asp His Lys Lys Thr Leu Glu His Leu Cys Lys Lys Pro Arg Lys
        355                 360                 365

Asn Leu Asn Val Ser Phe Asn Pro Glu Ser Phe Leu Asp Cys Gln Ile
    370                 375                 380

His Arg Val Asp Asp Ile Gln Ala Arg Asp Glu Val Glu Gly Phe Leu
385                 390                 395                 400

Gln Asp Thr Phe Pro Gln Gln Leu Glu Glu Ser Glu Lys Gln Arg Leu
                405                 410                 415

Gly Gly Asp Val Gln Ser Pro Asn Cys Pro Ser Glu Asp Val Val Ile
            420                 425                 430

Thr Pro Glu Ser Phe Gly Arg Asp Ser Ser Leu Thr Cys Leu Ala Gly
        435                 440                 445

Asn Val Ser Ala Cys Asp Ala Pro Ile Leu Ser Ser Ser Arg Ser Leu
    450                 455                 460

Asp Cys Arg Glu Ser Gly Lys Asn Gly Pro His Val Tyr Gln Asp Leu
465                 470                 475                 480

Leu Leu Ser Leu Gly Thr Thr Asn Ser Thr Leu Pro Pro Pro Phe Ser
                485                 490                 495

Leu Gln Ser Gly Ile Leu Thr Leu Asn Pro Val Ala Gln Gly Gln Pro
            500                 505                 510

Ile Leu Thr Ser Leu Gly Ser Asn Gln Glu Glu Ala Tyr Val Thr Met
        515                 520                 525
```

```
Ser Ser Phe Tyr Gln Asn Gln
    530                 535


<210> SEQ ID NO 88
<211> LENGTH: 1605
<212> TYPE: DNA
<213> ORGANISM: Artificial Sequence
<220> FEATURE:
<223> OTHER INFORMATION: Description of Artificial Sequence: Synthetic
      Exemplary chimeric transmembrane sequence

<400> SEQUENCE: 88

aactgggtga atgtgatcag cgacctgaag aagatcgagg atctgatcca gagcatgcac     60

attgatgcca ccctgtacac agaatctgat gtgcacccta gctgtaaagt gaccgccatg    120

aagtgtttc tgctggagct gcaggtgatt tctctggaaa gcggagatgc ctctatccac    180

gacacagtgg agaatctgat catcctggcc aacaatagcc tgagcagcaa tggcaatgtg    240

acagagtctg gctgtaagga gtgtgaggag ctggaggaga agaacatcaa ggagtttctg    300

cagagctttg tgcacatcgt gcagatgttc atcaatacaa gcagcggtgg gggctcaggc    360

ggaggaggct ctggcggagg cggaagcggg ggagggggct caggcggcgg gtccttgcag    420

attacatgcc ctcctccaat gtctgtggag cacgccgata tttgggtgaa gtcctacagc    480

ctgtacagca gagagagata catctgcaac agcggcttta agagaaaggc cggcacctct    540

tctctgacag agtgcgtgct gaataaggcc acaaatgtgg cccactggac aacacctagc    600

ctgaagtgca ttagagatcc tgccctggtc caccagaggc ctgcccctcc atctacagtg    660

acaacagccg gagtgacacc tcagcctgaa tctctgagcc cttctggaaa agaacctgcc    720

gccagctctc ctagctctaa taataccgcc gccacaacag ccgccattgt gcctggatct    780

cagctgatgc ctagcaagtc tcctagcaca ggcacaacag agatcagcag ccacgaatct    840

tctcacggaa caccttctca gaccaccgcc aagaattggg agctgacagc ctctgcctct    900

caccagcctc caggagtgta tcctcagggc cactctgata caacacccat cctgctgacc    960

atcagcatcc tgagcttctt cagcgtggag aaggccgtga tcctggcctg cgtgctgtgg   1020

aagaagagga tcaagcccat cgtgtggccc agcctgcccg accacaagaa gaccctggag   1080

cacctgtgta agaagcccag gaagaacctg aacgtgagct tcaaccccga gagcttcctg   1140

gactgccaga tccacagggt ggacgacatc caggccaggg acgaggtgga gggcttcctg   1200

caggacacct tcccccagca gctggaggag agcgagaagc agaggctggg cggcgacgtg   1260

cagagcccca actgccccag cgaggacgtg gtgatcaccc ccgagagctt cggcagggac   1320

agcagcctga cctgcctggc cggcaacgtg agcgcctgcg acgcccccat cctgagcagc   1380

agcaggagcc tggactgcag ggagagcggc aagaacggcc cccacgtgta ccaggacctg   1440

ctgctgagcc tgggcaccac caacagcacc ctgccacccc ccttcagcct gcagagcggc   1500

atcctgaccc tgaaccccgt ggcccagggc cagcccatcc tgaccagcct gggcagcaac   1560

caggaggagg cctacgtgac catgagcagc ttctaccaga accag                   1605


<210> SEQ ID NO 89
<211> LENGTH: 535
<212> TYPE: PRT
<213> ORGANISM: Artificial Sequence
<220> FEATURE:
<223> OTHER INFORMATION: Description of Artificial Sequence: Synthetic
      Exemplary chimeric transmembrane protein sequence

<400> SEQUENCE: 89
```

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ser Gly Gly Gly Ser Gly Gly Gly Gly Ser Gly Gly Gly Gly
        115                 120                 125

Ser Gly Gly Gly Gly Ser Gly Gly Gly Ser Leu Gln Ile Thr Cys Pro
    130                 135                 140

Pro Pro Met Ser Val Glu His Ala Asp Ile Trp Val Lys Ser Tyr Ser
145                 150                 155                 160

Leu Tyr Ser Arg Glu Arg Tyr Ile Cys Asn Ser Gly Phe Lys Arg Lys
                165                 170                 175

Ala Gly Thr Ser Ser Leu Thr Glu Cys Val Leu Asn Lys Ala Thr Asn
            180                 185                 190

Val Ala His Trp Thr Thr Pro Ser Leu Lys Cys Ile Arg Asp Pro Ala
        195                 200                 205

Leu Val His Gln Arg Pro Ala Pro Pro Ser Thr Val Thr Thr Ala Gly
    210                 215                 220

Val Thr Pro Gln Pro Glu Ser Leu Ser Pro Ser Gly Lys Glu Pro Ala
225                 230                 235                 240

Ala Ser Ser Pro Ser Ser Asn Asn Thr Ala Ala Thr Thr Ala Ala Ile
                245                 250                 255

Val Pro Gly Ser Gln Leu Met Pro Ser Lys Ser Pro Ser Thr Gly Thr
            260                 265                 270

Thr Glu Ile Ser Ser His Glu Ser Ser His Gly Thr Pro Ser Gln Thr
        275                 280                 285

Thr Ala Lys Asn Trp Glu Leu Thr Ala Ser Ala Ser His Gln Pro Pro
    290                 295                 300

Gly Val Tyr Pro Gln Gly His Ser Asp Thr Thr Pro Ile Leu Leu Thr
305                 310                 315                 320

Ile Ser Ile Leu Ser Phe Phe Ser Val Glu Lys Val Val Ile Leu Ala
                325                 330                 335

Cys Val Leu Trp Lys Lys Arg Ile Lys Pro Ile Val Trp Pro Ser Leu
            340                 345                 350

Pro Asp His Lys Lys Thr Leu Glu His Leu Cys Lys Lys Pro Arg Lys
        355                 360                 365

Asn Leu Asn Val Ser Phe Asn Pro Glu Ser Phe Leu Asp Cys Gln Ile
    370                 375                 380

His Arg Val Asp Asp Ile Gln Ala Arg Asp Glu Val Glu Gly Phe Leu
385                 390                 395                 400

Gln Asp Thr Phe Pro Gln Gln Leu Glu Glu Ser Glu Lys Gln Arg Leu
                405                 410                 415

Gly Gly Asp Val Gln Ser Pro Asn Cys Pro Ser Glu Asp Val Val Ile
```

```
            420                 425                 430

Thr Pro Glu Ser Phe Gly Arg Asp Ser Ser Leu Thr Cys Leu Ala Gly
        435                 440                 445

Asn Val Ser Ala Cys Asp Ala Pro Ile Leu Ser Ser Ser Arg Ser Leu
    450                 455                 460

Asp Cys Arg Glu Ser Gly Lys Asn Gly Pro His Val Tyr Gln Asp Leu
465                 470                 475                 480

Leu Leu Ser Leu Gly Thr Thr Asn Ser Thr Leu Pro Pro Pro Phe Ser
                485                 490                 495

Leu Gln Ser Gly Ile Leu Thr Leu Asn Pro Val Ala Gln Gly Gln Pro
            500                 505                 510

Ile Leu Thr Ser Leu Gly Ser Asn Gln Glu Glu Ala Tyr Val Thr Met
        515                 520                 525

Ser Ser Phe Tyr Gln Asn Gln
    530                 535


<210> SEQ ID NO 90
<211> LENGTH: 1605
<212> TYPE: DNA
<213> ORGANISM: Artificial Sequence
<220> FEATURE:
<223> OTHER INFORMATION: Description of Artificial Sequence: Synthetic
      Exemplary chimeric transmembrane sequence

<400> SEQUENCE: 90

aactgggtga atgtgatcag cgacctgaag aagatcgagg atctgatcca gagcatgcac     60

attgatgcca ccctgtacac agaatctgat gtgcacccta gctgtaaagt gaccgccatg    120

aagtgttttc tgctggagct gcaggtgatt tctctggaaa gcggagatgc ctctatccac    180

gacacagtgg agaatctgat catcctggcc aacaatagcc tgagcagcaa tggcaatgtg    240

acagagtctg gctgtaagga gtgtgaggag ctggaggaga agaacatcaa ggagtttctg    300

cagagctttg tgcacatcgt gcagatgttc atcaatacaa gcagcggtgg gggctcaggc    360

ggaggaggct ctggcggagg cggaagcggg ggagggggct caggcggcgg gtccttgcag    420

attacatgcc ctcctccaat gtctgtggag cacgccgata tttgggtgaa gtcctacagc    480

ctgtacagca gagagagata catctgcaac agcggcttta agagaaaggc cggcacctct    540

tctctgacag agtgcgtgct gaataaggcc acaaatgtgg cccactggac aacacctagc    600

ctgaagtgca ttagagatcc tgccctggtc caccagaggc ctgcccctcc atctacagtg    660

acaacagccg gagtgacacc tcagcctgaa tctctgagcc cttctggaaa agaacctgcc    720

gccagctctc ctagctctaa taataccgcc gccacaacag ccgccattgt gcctggatct    780

cagctgatgc ctagcaagtc tcctagcaca ggcacaacag agatcagcag ccacgaatct    840

tctcacggaa caccttctca gaccaccgcc aagaattggg agctgacagc ctctgcctct    900

caccagcctc caggagtgta tcctcagggc cactctgata caacacccat cctgctgacc    960

atcagcatcc tgagcttctt cagcgtggag aaggtggtga tcctggcctg cgtgctgtgg   1020

aagaagagga tcaagcccat cgtgtggccc agcctgcccg accacaagaa gaccctggag   1080

cacctgtgta agaagcccag gaagaacctg aacgtgagct tcaaccccga gagcttcctg   1140

gactgccaga tccacagggt ggacgacatc caggccaggg acgaggtgga gggcttcctg   1200

caggacacct tcccccagca gctggaggag agcgagaagc agaggctggg cggcgacgtg   1260

cagagcccca actgccccag cgaggacgtg gtgatcaccc ccgagagctt cggcagggac   1320

agcagcctga cctgcctggc cggcaacgtg agcgcctgcg acgcccccat cctgagcagc   1380
```

```
agcaggagcc tggactgcag ggagagcggc aagaacggcc cccacgtgta ccaggacctg   1440

ctgctgagcc tgggcaccac caacagcacc ctgccacccc ccttcagcct gcagagcggc   1500

atcctgaccc tgaaccccgt ggcccagggc cagcccatcc tgaccagcct gggcagcaac   1560

caggaggagg cctacgtgac catgagcagc ttctaccaga accag                   1605


<210> SEQ ID NO 91
<211> LENGTH: 54
<212> TYPE: DNA
<213> ORGANISM: Homo sapiens

<400> SEQUENCE: 91

atggattgga cctggattct gtttctggtg gccgctgcca caagagtgca cagc           54


<210> SEQ ID NO 92
<211> LENGTH: 26
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 92

Ser Gly Gly Gly Ser Gly Gly Gly Gly Ser Gly Gly Gly Gly Ser Gly
1               5                   10                  15

Gly Gly Gly Ser Gly Gly Gly Ser Leu Gln
            20                  25


<210> SEQ ID NO 93
<211> LENGTH: 22
<212> TYPE: PRT
<213> ORGANISM: Homo sapiens

<400> SEQUENCE: 93

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 94
<211> LENGTH: 66
<212> TYPE: DNA
<213> ORGANISM: Homo sapiens

<400> SEQUENCE: 94

atgcttctcc tggtgacaag ccttctgctc tgtgagttac cacacccagc attcctcctg     60

attcct                                                                66


<210> SEQ ID NO 95
<211> LENGTH: 242
<212> TYPE: PRT
<213> ORGANISM: Artificial Sequence
<220> FEATURE:
<223> OTHER INFORMATION: Description of Artificial Sequence: Synthetic
      Anti-CD19 scFv sequence

<400> SEQUENCE: 95

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30
```

```
Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

```
<210> SEQ ID NO 96
<211> LENGTH: 726
<212> TYPE: DNA
<213> ORGANISM: Artificial Sequence
<220> FEATURE:
<223> OTHER INFORMATION: Description of Artificial Sequence: Synthetic
      Anti-CD19 scFv sequence

<400> SEQUENCE: 96

gacatccaga tgacccagac caccagcagc ctgagcgcca gcctgggcga tagagtgacc      60

atcagctgca gagccagcca ggacatcagc aagtacctga actggtatca gcagaaaccc     120

gacggcaccg tgaagctgct gatctaccac accagcagac tgcacagcgg cgtgcccagc     180

agattttctg gcagcggctc cggcaccgac tacagcctga ccatctccaa cctggaacag     240

gaagatatcg ctacctactt ctgtcagcaa ggcaacaccc tgccctacac cttcggcgga     300

ggcaccaagc tggaaatcac aggcggcgga ggatctggcg gaggcggaag tggcggaggg     360

ggatctgaag tgaaactgca ggaaagcggc cctggcctgg tggccccatc tcagtctctg     420

agcgtgacct gtaccgtgtc cggcgtgtcc ctgcctgact atggcgtgtc ctggatcaga     480

cagcccccca gaaagggcct ggaatggctg ggagtgatct ggggcagcga gacaacctac     540

tacaacagcg ccctgaagtc ccggctgacc atcatcaagg acaactccaa gagccaggtg     600

ttcctgaaga tgaacagcct gcagaccgac gacaccgcca tctactactg cgccaagcac     660

tactactacg gcggcagcta cgccatggac tactggggcc agggcacaag cgtgaccgtg     720

tctagc                                                                726
```

<210> SEQ ID NO 97
<211> LENGTH: 57
<212> TYPE: PRT
<213> ORGANISM: Homo sapiens

<400> SEQUENCE: 97

```
Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro Phe Trp
            20                  25                  30

Val Leu Val Val Val Gly Gly Val Leu Ala Cys Tyr Ser Leu Leu Val
        35                  40                  45

Thr Val Ala Phe Ile Ile Phe Trp Val
    50                  55
```

<210> SEQ ID NO 98
<211> LENGTH: 171
<212> TYPE: DNA
<213> ORGANISM: Homo sapiens

<400> SEQUENCE: 98

```
ctagacaatg agaagagcaa tggaaccatt atccatgtga aagggaaaca cctttgtcca     60

agtcccctat ttcccggacc ttctaagccc ttttgggtgc tggtggtggt tggtggagtc    120

ctggcttgct atagcttgct agtaacagtg gcctttatta ttttctgggt g             171
```

<210> SEQ ID NO 99
<211> LENGTH: 123
<212> TYPE: DNA
<213> ORGANISM: Homo sapiens

<400> SEQUENCE: 99

```
aggagtaaga ggagcaggct cctgcacagt gactacatga acatgactcc ccgccgcccc     60

gggcccaccc gcaagcatta ccagccctat gccccaccac gcgacttcgc agcctatcgc    120

tcc                                                                  123
```

<210> SEQ ID NO 100
<211> LENGTH: 1396
<212> TYPE: DNA
<213> ORGANISM: Artificial Sequence
<220> FEATURE:
<223> OTHER INFORMATION: Description of Artificial Sequence: Synthetic
      CD19 CAR DNA sequence

<400> SEQUENCE: 100

```
gaacagaagc tgataagtga ggaggacttg gacatccaga tgacccagac caccagcagc     60

ctgagcgcca gcctgggcga tagagtgacc atcagctgca gagccagcca ggacatcagc    120

aagtacctga actggtatca gcagaaaccc gacggcaccg tgaagctgct gatctaccac    180

accagcagac tgcacagcgg cgtgcccagc agattttctg gcagcggctc cggcaccgac    240

tacagcctga ccatctccaa cctggaacag gaagatatcg ctacctactt ctgtcagcaa    300

ggcaacaccc tgccctacac cttcggcgga ggcaccaagc tggaaatcac aggcggcgga    360

ggatctggcg gaggcggaag tggcggaggg ggatctgaag tgaaactgca ggaaagcggc    420

cctggcctgg tggccccatc tcagtctctg agcgtgacct gtaccgtgtc cggcgtgtcc    480

ctgcctgact atggcgtgtc ctggatcaga cagcccccca gaaagggcct ggaatggctg    540

ggagtgatct ggggcagcga gacaacctac tacaacagcg ccctgaagtc ccggctgacc    600

atcatcaagg acaactccaa gagccaggtg ttcctgaaga tgaacagcct gcagaccgac    660
```

```
gacaccgcca tctactactg cgccaagcac tactactacg gcggcagcta cgccatggac    720

tactggggcc agggcacaag cgtgaccgtg tctagcgggt ccctagacaa tgagaagagc    780

aatggaacca ttatccatgt gaaagggaaa cacctttgtc caagtcccct atttcccgga    840

ccttctaagc ccttttgggt gctggtggtg gttggtggag tcctggcttg ctatagcttg    900

ctagtaacag tggcctttat tattttctgg gtgaggagta agaggagcag gctcctgcac    960

agtgactaca tgaacatgac tccccgccgc cccgggccca cccgcaagca ttaccagccc   1020

tatgccccac cacgcgactt cgcagcctat cgctccctga gagtgaagtt cagcaggagc   1080

gcagacgccc ccgcgtacca gcagggccag aaccagctct ataacgagct caatctagga   1140

cgaagagagg agtacgatgt tttggacaag aggcgtggcc gggaccctga gatgggggga   1200

aagccgagaa ggaagaaccc tcaggaaggc ctgtacaatg aactgcagaa agataagatg   1260

gcggaggcct acagtgagat tgggatgaaa ggcgagcgcc ggaggggcaa ggggcacgat   1320

ggcctttacc agggtctcag tacagccacc aaggacacct acgacgccct tcacatgcag   1380

gccctgcccc ctcgct                                                   1396
```

<210> SEQ ID NO 101
<211> LENGTH: 465
<212> TYPE: PRT
<213> ORGANISM: Artificial Sequence
<220> FEATURE:
<223> OTHER INFORMATION: Description of Artificial Sequence: Synthetic CD19 CAR DNA sequence

<400> SEQUENCE: 101

```
Glu Gln Lys Leu Ile Ser Glu Glu Asp Leu Asp Ile Gln Met Thr Gln
1               5                   10                  15

Thr Thr Ser Ser Leu Ser Ala Ser Leu Gly Asp Arg Val Thr Ile Ser
            20                  25                  30

Cys Arg Ala Ser Gln Asp Ile Ser Lys Tyr Leu Asn Trp Tyr Gln Gln
        35                  40                  45

Lys Pro Asp Gly Thr Val Lys Leu Leu Ile Tyr His Thr Ser Arg Leu
    50                  55                  60

His Ser Gly Val Pro Ser Arg Phe Ser Gly Ser Gly Ser Gly Thr Asp
65                  70                  75                  80

Tyr Ser Leu Thr Ile Ser Asn Leu Glu Gln Glu Asp Ile Ala Thr Tyr
                85                  90                  95

Phe Cys Gln Gln Gly Asn Thr Leu Pro Tyr Thr Phe Gly Gly Gly Thr
            100                 105                 110

Lys Leu Glu Ile Thr Gly Gly Gly Gly Ser Gly Gly Gly Gly Ser Gly
        115                 120                 125

Gly Gly Gly Ser Glu Val Lys Leu Gln Glu Ser Gly Pro Gly Leu Val
    130                 135                 140

Ala Pro Ser Gln Ser Leu Ser Val Thr Cys Thr Val Ser Gly Val Ser
145                 150                 155                 160

Leu Pro Asp Tyr Gly Val Ser Trp Ile Arg Gln Pro Pro Arg Lys Gly
                165                 170                 175

Leu Glu Trp Leu Gly Val Ile Trp Gly Ser Glu Thr Thr Tyr Tyr Asn
            180                 185                 190

Ser Ala Leu Lys Ser Arg Leu Thr Ile Ile Lys Asp Asn Ser Lys Ser
        195                 200                 205

Gln Val Phe Leu Lys Met Asn Ser Leu Gln Thr Asp Asp Thr Ala Ile
    210                 215                 220
```

```
Tyr Tyr Cys Ala Lys His Tyr Tyr Tyr Gly Gly Ser Tyr Ala Met Asp
225                 230                 235                 240

Tyr Trp Gly Gln Gly Thr Ser Val Thr Val Ser Ser Gly Ser Leu Asp
                245                 250                 255

Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Leu Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465
```

<210> SEQ ID NO 102
<211> LENGTH: 2928
<212> TYPE: DNA
<213> ORGANISM: Artificial Sequence
<220> FEATURE:
<223> OTHER INFORMATION: Description of Artificial Sequence: Synthetic CD19 CAR + IL7A_CPT sequence

<400> SEQUENCE: 102

```
gaacagaagc tgataagtga ggaggacttg gacatccaga tgacccagac caccagcagc     60

ctgagcgcca gcctgggcga tagagtgacc atcagctgca gagccagcca ggacatcagc    120

aagtacctga actggtatca gcagaaaccc gacggcaccg tgaagctgct gatctaccac    180

accagcagac tgcacagcgg cgtgcccagc agattttctg gcagcggctc cggcaccgac    240

tacagcctga ccatctccaa cctggaacag gaagatatcg ctacctactt ctgtcagcaa    300

ggcaacaccc tgccctacac cttcggcgga ggcaccaagc tggaaatcac aggcggcgga    360

ggatctggcg gaggcggaag tggcggaggg ggatctgaag tgaaactgca ggaaagcggc    420

cctggcctgg tggccccatc tcagtctctg agcgtgacct gtaccgtgtc cggcgtgtcc    480

ctgcctgact atggcgtgtc ctggatcaga cagcccccca gaaagggcct ggaatggctg    540

ggagtgatct ggggcagcga gacaacctac tacaacagcg ccctgaagtc ccggctgacc    600
```

```
atcatcaagg acaactccaa gagccaggtg ttcctgaaga tgaacagcct gcagaccgac    660
gacaccgcca tctactactg cgccaagcac tactactacg gcggcagcta cgccatggac    720
tactggggcc agggcacaag cgtgaccgtg tctagcgggt ccctagacaa tgagaagagc    780
aatggaacca ttatccatgt gaaagggaaa cacctttgtc caagtcccct atttcccgga    840
ccttctaagc ccttttgggt gctggtggtg gttggtggag tcctggcttg ctatagcttg    900
ctagtaacag tggcctttat tattttctgg gtgaggagta agaggagcag gctcctgcac    960
agtgactaca tgaacatgac tccccgccgc cccgggccca cccgcaagca ttaccagccc   1020
tatgccccac cacgcgactt cgcagcctat cgctccctga gagtgaagtt cagcaggagc   1080
gcagacgccc ccgcgtacca gcagggccag aaccagctct ataacgagct caatctagga   1140
cgaagagagg agtacgatgt tttggacaag aggcgtggcc gggaccctga gatgggggga   1200
aagccgagaa ggaagaaccc tcaggaaggc ctgtacaatg aactgcagaa agataagatg   1260
gcggaggcct acagtgagat tgggatgaaa ggcgagcgcc ggaggggcaa ggggcacgat   1320
ggcctttacc agggtctcag tacagccacc aaggacacct acgacgccct tcacatgcag   1380
gccctgcccc ctcgccggaa gagaagaggc aagcccatcc ccaacccact gctgggcctg   1440
gatagcacct ccggaagcgg agagggcaga ggctctctgc tgacctgcgg cgacgtggaa   1500
gagaacccag ggcccatgct cctgctcgtg acttcacttc ttctctgtga actcccacac   1560
cccgcgtttt tgcttatccc tcatcatcac catcaccacg gcgagagcgg ctacgcccag   1620
aacggcgacc tggaggacgc cgagctggac gactacagct tcagctgcta cagccagctg   1680
gaggtgaacg gcagccagca cagcctgacc tgcgccttcg aggaccccga cgtgaacatc   1740
accaacctgg agttcgagat ctgcggcgcc ctggtggagg tgaagtgcct gaacttcagg   1800
aagctgcagg agatctactt catcgagacc aagaagttcc tgctgatcgg caagagcaac   1860
atctgcgtga aggtgggcga gaagagcctg acctgcaaga agatcgacct gaccaccatc   1920
gtgaagcccg aggccccctt cgacctgagc gtggtgtaca gggagggcgc caacgacttc   1980
gtggtgacct tcaacaccag ccacctgcag aagaagtacg tgaaggtgct gatgcacgac   2040
gtggcctaca ggcaggagaa ggacgagaac aagtggaccc acgtgaacct gagcagcacc   2100
aagctgaccc tgctgcagag gaagctgcag cccgccgcca tgtacgagat caaggtgagg   2160
agcatccccg accactactt caagggcttc tggagcgagt ggagccccag ctactacttc   2220
aggacccccg agatcaacaa cagcagcggc gagatggacc ccatcctgct gacctgcccc   2280
accatcagca tcctgagctt cttcagcgtg gccctgctgg tgatcctggc ctgcgtgctg   2340
tggaagaaga ggatcaagcc catcgtgtgg cccagcctgc ccgaccacaa gaagaccctg   2400
gagcacctgt gtaagaagcc caggaagaac ctgaacgtga gcttcaaccc cgagagcttc   2460
ctggactgcc agatccacag ggtggacgac atccaggcca gggacgaggt ggagggcttc   2520
ctgcaggaca ccttccccca gcagctggag gagagcgaga agcagaggct gggcggcgac   2580
gtgcagagcc ccaactgccc cagcgaggac gtggtgatca cccccgagag cttcggcagg   2640
gacagcagcc tgacctgcct ggccggcaac gtgagcgcct gcgacgcccc catcctgagc   2700
agcagcagga gcctggactg cagggagagc ggcaagaacg gcccccacgt gtaccaggac   2760
ctgctgctga gcctgggcac caccaacagc accctgccac ccccccttcag cctgcagagc   2820
ggcatcctga ccctgaaccc cgtggcccag ggccagccca tcctgaccag cctgggcagc   2880
aaccaggagg aggcctacgt gaccatgagc agcttctacc agaaccag                 2928
```

<210> SEQ ID NO 103
<211> LENGTH: 976
<212> TYPE: PRT
<213> ORGANISM: Artificial Sequence
<220> FEATURE:
<223> OTHER INFORMATION: Description of Artificial Sequence: Synthetic
CD19 CAR + IL7A_CPT sequence

<400> SEQUENCE: 103

```
Glu Gln Lys Leu Ile Ser Glu Glu Asp Leu Asp Ile Gln Met Thr Gln
1               5                   10                  15

Thr Thr Ser Ser Leu Ser Ala Ser Leu Gly Asp Arg Val Thr Ile Ser
            20                  25                  30

Cys Arg Ala Ser Gln Asp Ile Ser Lys Tyr Leu Asn Trp Tyr Gln Gln
        35                  40                  45

Lys Pro Asp Gly Thr Val Lys Leu Leu Ile Tyr His Thr Ser Arg Leu
    50                  55                  60

His Ser Gly Val Pro Ser Arg Phe Ser Gly Ser Gly Ser Gly Thr Asp
65                  70                  75                  80

Tyr Ser Leu Thr Ile Ser Asn Leu Glu Gln Glu Asp Ile Ala Thr Tyr
                85                  90                  95

Phe Cys Gln Gln Gly Asn Thr Leu Pro Tyr Thr Phe Gly Gly Gly Thr
            100                 105                 110

Lys Leu Glu Ile Thr Gly Gly Gly Gly Ser Gly Gly Gly Gly Ser Gly
        115                 120                 125

Gly Gly Gly Ser Glu Val Lys Leu Gln Glu Ser Gly Pro Gly Leu Val
    130                 135                 140

Ala Pro Ser Gln Ser Leu Ser Val Thr Cys Thr Val Ser Gly Val Ser
145                 150                 155                 160

Leu Pro Asp Tyr Gly Val Ser Trp Ile Arg Gln Pro Pro Arg Lys Gly
                165                 170                 175

Leu Glu Trp Leu Gly Val Ile Trp Gly Ser Glu Thr Thr Tyr Tyr Asn
            180                 185                 190

Ser Ala Leu Lys Ser Arg Leu Thr Ile Ile Lys Asp Asn Ser Lys Ser
        195                 200                 205

Gln Val Phe Leu Lys Met Asn Ser Leu Gln Thr Asp Asp Thr Ala Ile
    210                 215                 220

Tyr Tyr Cys Ala Lys His Tyr Tyr Tyr Gly Gly Ser Tyr Ala Met Asp
225                 230                 235                 240

Tyr Trp Gly Gln Gly Thr Ser Val Thr Val Ser Ser Gly Ser Leu Asp
                245                 250                 255

Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Leu Arg Val Lys Phe Ser Arg Ser Ala Asp Ala Pro Ala Tyr Gln Gln
        355                 360                 365
```

```
Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg Arg Lys Arg Arg Gly Lys Pro Ile Pro Asn Pro Leu Leu Gly Leu
465                 470                 475                 480

Asp Ser Thr Ser Gly Ser Gly Glu Gly Arg Gly Ser Leu Leu Thr Cys
                485                 490                 495

Gly Asp Val Glu Glu Asn Pro Gly Pro Met Leu Leu Leu Val Thr Ser
            500                 505                 510

Leu Leu Leu Cys Glu Leu Pro His Pro Ala Phe Leu Leu Ile Pro His
        515                 520                 525

His His His His His Gly Glu Ser Gly Tyr Ala Gln Asn Gly Asp Leu
    530                 535                 540

Glu Asp Ala Glu Leu Asp Asp Tyr Ser Phe Ser Cys Tyr Ser Gln Leu
545                 550                 555                 560

Glu Val Asn Gly Ser Gln His Ser Leu Thr Cys Ala Phe Glu Asp Pro
                565                 570                 575

Asp Val Asn Ile Thr Asn Leu Glu Phe Glu Ile Cys Gly Ala Leu Val
            580                 585                 590

Glu Val Lys Cys Leu Asn Phe Arg Lys Leu Gln Glu Ile Tyr Phe Ile
        595                 600                 605

Glu Thr Lys Lys Phe Leu Leu Ile Gly Lys Ser Asn Ile Cys Val Lys
    610                 615                 620

Val Gly Glu Lys Ser Leu Thr Cys Lys Lys Ile Asp Leu Thr Thr Ile
625                 630                 635                 640

Val Lys Pro Glu Ala Pro Phe Asp Leu Ser Val Val Tyr Arg Glu Gly
                645                 650                 655

Ala Asn Asp Phe Val Val Thr Phe Asn Thr Ser His Leu Gln Lys Lys
            660                 665                 670

Tyr Val Lys Val Leu Met His Asp Val Ala Tyr Arg Gln Glu Lys Asp
        675                 680                 685

Glu Asn Lys Trp Thr His Val Asn Leu Ser Ser Thr Lys Leu Thr Leu
    690                 695                 700

Leu Gln Arg Lys Leu Gln Pro Ala Ala Met Tyr Glu Ile Lys Val Arg
705                 710                 715                 720

Ser Ile Pro Asp His Tyr Phe Lys Gly Phe Trp Ser Glu Trp Ser Pro
                725                 730                 735

Ser Tyr Tyr Phe Arg Thr Pro Glu Ile Asn Asn Ser Ser Gly Glu Met
            740                 745                 750

Asp Pro Ile Leu Leu Thr Cys Pro Thr Ile Ser Ile Leu Ser Phe Phe
        755                 760                 765

Ser Val Ala Leu Leu Val Ile Leu Ala Cys Val Leu Trp Lys Lys Arg
    770                 775                 780
```

```
Ile Lys Pro Ile Val Trp Pro Ser Leu Pro Asp His Lys Lys Thr Leu
785                 790                 795                 800

Glu His Leu Cys Lys Lys Pro Arg Lys Asn Leu Asn Val Ser Phe Asn
                805                 810                 815

Pro Glu Ser Phe Leu Asp Cys Gln Ile His Arg Val Asp Asp Ile Gln
            820                 825                 830

Ala Arg Asp Glu Val Glu Gly Phe Leu Gln Asp Thr Phe Pro Gln Gln
        835                 840                 845

Leu Glu Glu Ser Glu Lys Gln Arg Leu Gly Gly Asp Val Gln Ser Pro
    850                 855                 860

Asn Cys Pro Ser Glu Asp Val Val Ile Thr Pro Glu Ser Phe Gly Arg
865                 870                 875                 880

Asp Ser Ser Leu Thr Cys Leu Ala Gly Asn Val Ser Ala Cys Asp Ala
                885                 890                 895

Pro Ile Leu Ser Ser Ser Arg Ser Leu Asp Cys Arg Glu Ser Gly Lys
            900                 905                 910

Asn Gly Pro His Val Tyr Gln Asp Leu Leu Leu Ser Leu Gly Thr Thr
        915                 920                 925

Asn Ser Thr Leu Pro Pro Pro Phe Ser Leu Gln Ser Gly Ile Leu Thr
    930                 935                 940

Leu Asn Pro Val Ala Gln Gly Gln Pro Ile Leu Thr Ser Leu Gly Ser
945                 950                 955                 960

Asn Gln Glu Glu Ala Tyr Val Thr Met Ser Ser Phe Tyr Gln Asn Gln
                965                 970                 975
```

<210> SEQ ID NO 104
<211> LENGTH: 2928
<212> TYPE: DNA
<213> ORGANISM: Artificial Sequence
<220> FEATURE:
<223> OTHER INFORMATION: Description of Artificial Sequence: Synthetic CD19 CAR + IL7RaMCP sequence

<400> SEQUENCE: 104

```
gaacagaagc tgataagtga ggaggacttg gacatccaga tgacccagac caccagcagc     60

ctgagcgcca gcctgggcga tagagtgacc atcagctgca gagccagcca ggacatcagc    120

aagtacctga actggtatca gcagaaaccc gacggcaccg tgaagctgct gatctaccac    180

accagcagac tgcacagcgg cgtgcccagc agattttctg gcagcggctc cggcaccgac    240

tacagcctga ccatctccaa cctggaacag gaagatatcg ctacctactt ctgtcagcaa    300

ggcaacaccc tgccctacac cttcggcgga ggcaccaagc tggaaatcac aggcggcgga    360

ggatctggcg gaggcggaag tggcggaggg ggatctgaag tgaaactgca ggaaagcggc    420

cctggcctgg tggccccatc tcagtctctg agcgtgacct gtaccgtgtc cggcgtgtcc    480

ctgcctgact atggcgtgtc ctggatcaga cagcccccca gaaagggcct ggaatggctg    540

ggagtgatct ggggcagcga gacaacctac tacaacagcg ccctgaagtc ccggctgacc    600

atcatcaagg acaactccaa gagccaggtg ttcctgaaga tgaacagcct gcagaccgac    660

gacaccgcca tctactactg cgccaagcac tactactacg gcggcagcta cgccatggac    720

tactggggcc agggcacaag cgtgaccgtg tctagcgggt ccctagacaa tgagaagagc    780

aatggaacca ttatccatgt gaaagggaaa cacctttgtc caagtcccct atttcccgga    840

ccttctaagc ccttttgggt gctggtggtg gttggtggag tcctggcttg ctatagcttg    900

ctagtaacag tggcctttat tattttctgg gtgaggagta agaggagcag gctcctgcac    960
```

```
agtgactaca tgaacatgac tccccgccgc cccgggccca cccgcaagca ttaccagccc   1020

tatgccccac cacgcgactt cgcagcctat cgctccctga gagtgaagtt cagcaggagc   1080

gcagacgccc ccgcgtacca gcagggccag aaccagctct ataacgagct caatctagga   1140

cgaagagagg agtacgatgt tttggacaag aggcgtggcc gggaccctga gatgggggga   1200

aagccgagaa ggaagaaccc tcaggaaggc ctgtacaatg aactgcagaa agataagatg   1260

gcggaggcct acagtgagat tgggatgaaa ggcgagcgcc ggaggggcaa ggggcacgat   1320

ggcctttacc agggtctcag tacagccacc aaggacacct acgacgccct tcacatgcag   1380

gccctgcccc ctcgccggaa gagaagaggc aagcccatcc ccaacccact gctgggcctg   1440

gatagcacct ccggaagcgg agagggcaga ggctctctgc tgacctgcgg cgacgtggaa   1500

gagaacccag ggcccatgct cctgctcgtg acttcacttc ttctctgtga actcccacac   1560

cccgcgtttt tgcttatccc tcatcatcac catcaccacg gcgagagcgg ctacgcccag   1620

aacggcgacc tggaggacgc cgagctggac gactacagct tcagctgcta cagccagctg   1680

gaggtgaacg gcagccagca cagcctgacc tgcgccttcg aggaccccga cgtgaacatc   1740

accaacctgg agttcgagat ctgcggcgcc ctggtggagg tgaagtgcct gaacttcagg   1800

aagctgcagg agatctactt catcgagacc aagaagttcc tgctgatcgg caagagcaac   1860

atctgcgtga aggtgggcga gaagagcctg acctgcaaga agatcgacct gaccaccatc   1920

gtgaagcccg aggccccctt cgacctgagc gtggtgtaca gggagggcgc caacgacttc   1980

gtggtgacct tcaacaccag ccacctgcag aagaagtacg tgaaggtgct gatgcacgac   2040

gtggcctaca ggcaggagaa ggacgagaac aagtggaccc acgtgaacct gagcagcacc   2100

aagctgaccc tgctgcagag gaagctgcag cccgccgcca tgtacgagat caaggtgagg   2160

agcatccccg accactactt caagggcttc tggagcgagt ggagccccag ctactacttc   2220

aggacccccg agatcaacaa cagcagcggc gagatggacc ccatcctgct gatgtgcccc   2280

accatcagca tcctgagctt cttcagcgtg gccctgctgg tgatcctggc ctgcgtgctg   2340

tggaagaaga ggatcaagcc catcgtgtgg cccagcctgc ccgaccacaa gaagaccctg   2400

gagcacctgt gtaagaagcc caggaagaac ctgaacgtga gcttcaaccc cgagagcttc   2460

ctggactgcc agatccacag ggtggacgac atccaggcca gggacgaggt ggagggcttc   2520

ctgcaggaca ccttccccca gcagctggag gagagcgaga agcagaggct gggcggcgac   2580

gtgcagagcc ccaactgccc cagcgaggac gtggtgatca cccccgagag cttcggcagg   2640

gacagcagcc tgacctgcct ggccggcaac gtgagcgcct gcgacgcccc catcctgagc   2700

agcagcagga gcctggactg cagggagagc ggcaagaacg gcccccacgt gtaccaggac   2760

ctgctgctga gcctgggcac caccaacagc accctgccac cccccttcag cctgcagagc   2820

ggcatcctga ccctgaaccc cgtggcccag ggccagccca tcctgaccag cctgggcagc   2880

aaccaggagg aggcctacgt gaccatgagc agcttctacc agaaccag                2928
```

<210> SEQ ID NO 105
<211> LENGTH: 976
<212> TYPE: PRT
<213> ORGANISM: Artificial Sequence
<220> FEATURE:
<223> OTHER INFORMATION: Description of Artificial Sequence: Synthetic
      CD19 CAR + IL7RaMCP sequence

<400> SEQUENCE: 105

```
Glu Gln Lys Leu Ile Ser Glu Glu Asp Leu Asp Ile Gln Met Thr Gln
1               5                   10                  15
```

```
Thr Thr Ser Ser Leu Ser Ala Ser Leu Gly Asp Arg Val Thr Ile Ser
            20                  25                  30

Cys Arg Ala Ser Gln Asp Ile Ser Lys Tyr Leu Asn Trp Tyr Gln Gln
        35                  40                  45

Lys Pro Asp Gly Thr Val Lys Leu Leu Ile Tyr His Thr Ser Arg Leu
    50                  55                  60

His Ser Gly Val Pro Ser Arg Phe Ser Gly Ser Gly Ser Gly Thr Asp
65                  70                  75                  80

Tyr Ser Leu Thr Ile Ser Asn Leu Glu Gln Glu Asp Ile Ala Thr Tyr
                85                  90                  95

Phe Cys Gln Gln Gly Asn Thr Leu Pro Tyr Thr Phe Gly Gly Gly Thr
            100                 105                 110

Lys Leu Glu Ile Thr Gly Gly Gly Gly Ser Gly Gly Gly Gly Ser Gly
        115                 120                 125

Gly Gly Gly Ser Glu Val Lys Leu Gln Glu Ser Gly Pro Gly Leu Val
    130                 135                 140

Ala Pro Ser Gln Ser Leu Ser Val Thr Cys Thr Val Ser Gly Val Ser
145                 150                 155                 160

Leu Pro Asp Tyr Gly Val Ser Trp Ile Arg Gln Pro Pro Arg Lys Gly
                165                 170                 175

Leu Glu Trp Leu Gly Val Ile Trp Gly Ser Glu Thr Thr Tyr Tyr Asn
            180                 185                 190

Ser Ala Leu Lys Ser Arg Leu Thr Ile Ile Lys Asp Asn Ser Lys Ser
        195                 200                 205

Gln Val Phe Leu Lys Met Asn Ser Leu Gln Thr Asp Asp Thr Ala Ile
    210                 215                 220

Tyr Tyr Cys Ala Lys His Tyr Tyr Tyr Gly Gly Ser Tyr Ala Met Asp
225                 230                 235                 240

Tyr Trp Gly Gln Gly Thr Ser Val Thr Val Ser Ser Gly Ser Leu Asp
                245                 250                 255

Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Leu Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430
```

```
Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg Arg Lys Arg Arg Gly Lys Pro Ile Pro Asn Pro Leu Leu Gly Leu
465                 470                 475                 480

Asp Ser Thr Ser Gly Ser Gly Glu Gly Arg Gly Ser Leu Leu Thr Cys
                485                 490                 495

Gly Asp Val Glu Glu Asn Pro Gly Pro Met Leu Leu Leu Val Thr Ser
            500                 505                 510

Leu Leu Leu Cys Glu Leu Pro His Pro Ala Phe Leu Leu Ile Pro His
        515                 520                 525

His His His His His Gly Glu Ser Gly Tyr Ala Gln Asn Gly Asp Leu
    530                 535                 540

Glu Asp Ala Glu Leu Asp Asp Tyr Ser Phe Ser Cys Tyr Ser Gln Leu
545                 550                 555                 560

Glu Val Asn Gly Ser Gln His Ser Leu Thr Cys Ala Phe Glu Asp Pro
                565                 570                 575

Asp Val Asn Ile Thr Asn Leu Glu Phe Glu Ile Cys Gly Ala Leu Val
            580                 585                 590

Glu Val Lys Cys Leu Asn Phe Arg Lys Leu Gln Glu Ile Tyr Phe Ile
        595                 600                 605

Glu Thr Lys Lys Phe Leu Leu Ile Gly Lys Ser Asn Ile Cys Val Lys
    610                 615                 620

Val Gly Glu Lys Ser Leu Thr Cys Lys Lys Ile Asp Leu Thr Thr Ile
625                 630                 635                 640

Val Lys Pro Glu Ala Pro Phe Asp Leu Ser Val Val Tyr Arg Glu Gly
                645                 650                 655

Ala Asn Asp Phe Val Val Thr Phe Asn Thr Ser His Leu Gln Lys Lys
            660                 665                 670

Tyr Val Lys Val Leu Met His Asp Val Ala Tyr Arg Gln Glu Lys Asp
        675                 680                 685

Glu Asn Lys Trp Thr His Val Asn Leu Ser Ser Thr Lys Leu Thr Leu
    690                 695                 700

Leu Gln Arg Lys Leu Gln Pro Ala Ala Met Tyr Glu Ile Lys Val Arg
705                 710                 715                 720

Ser Ile Pro Asp His Tyr Phe Lys Gly Phe Trp Ser Glu Trp Ser Pro
                725                 730                 735

Ser Tyr Tyr Phe Arg Thr Pro Glu Ile Asn Asn Ser Ser Gly Glu Met
            740                 745                 750

Asp Pro Ile Leu Leu Met Cys Pro Thr Ile Ser Ile Leu Ser Phe Phe
        755                 760                 765

Ser Val Ala Leu Leu Val Ile Leu Ala Cys Val Leu Trp Lys Lys Arg
    770                 775                 780

Ile Lys Pro Ile Val Trp Pro Ser Leu Pro Asp His Lys Lys Thr Leu
785                 790                 795                 800

Glu His Leu Cys Lys Lys Pro Arg Lys Asn Leu Asn Val Ser Phe Asn
                805                 810                 815

Pro Glu Ser Phe Leu Asp Cys Gln Ile His Arg Val Asp Asp Ile Gln
            820                 825                 830

Ala Arg Asp Glu Val Glu Gly Phe Leu Gln Asp Thr Phe Pro Gln Gln
        835                 840                 845

Leu Glu Glu Ser Glu Lys Gln Arg Leu Gly Gly Asp Val Gln Ser Pro
```

```
    850                 855                 860

Asn Cys Pro Ser Glu Asp Val Val Ile Thr Pro Glu Ser Phe Gly Arg
865                 870                 875                 880

Asp Ser Ser Leu Thr Cys Leu Ala Gly Asn Val Ser Ala Cys Asp Ala
                885                 890                 895

Pro Ile Leu Ser Ser Ser Arg Ser Leu Asp Cys Arg Glu Ser Gly Lys
            900                 905                 910

Asn Gly Pro His Val Tyr Gln Asp Leu Leu Leu Ser Leu Gly Thr Thr
        915                 920                 925

Asn Ser Thr Leu Pro Pro Pro Phe Ser Leu Gln Ser Gly Ile Leu Thr
    930                 935                 940

Leu Asn Pro Val Ala Gln Gly Gln Pro Ile Leu Thr Ser Leu Gly Ser
945                 950                 955                 960

Asn Gln Glu Glu Ala Tyr Val Thr Met Ser Ser Phe Tyr Gln Asn Gln
                965                 970                 975


<210> SEQ ID NO 106
<211> LENGTH: 2931
<212> TYPE: DNA
<213> ORGANISM: Artificial Sequence
<220> FEATURE:
<223> OTHER INFORMATION: Description of Artificial Sequence: Synthetic
      CD19 CAR + IL7RaPPCL sequence

<400> SEQUENCE: 106

gaacagaagc tgataagtga ggaggacttg gacatccaga tgacccagac caccagcagc     60

ctgagcgcca gcctgggcga tagagtgacc atcagctgca gagccagcca ggacatcagc    120

aagtacctga actggtatca gcagaaaccc gacggcaccg tgaagctgct gatctaccac    180

accagcagac tgcacagcgg cgtgcccagc agattttctg gcagcggctc cggcaccgac    240

tacagcctga ccatctccaa cctggaacag gaagatatcg ctacctactt ctgtcagcaa    300

ggcaacaccc tgccctacac cttcggcgga ggcaccaagc tggaaatcac aggcggcgga    360

ggatctggcg gaggcggaag tggcggaggg ggatctgaag tgaaactgca ggaaagcggc    420

cctggcctgg tggccccatc tcagtctctg agcgtgacct gtaccgtgtc cggcgtgtcc    480

ctgcctgact atggcgtgtc ctggatcaga cagccccca gaaagggcct ggaatggctg     540

ggagtgatct ggggcagcga gacaacctac tacaacagcg ccctgaagtc ccggctgacc    600

atcatcaagg acaactccaa gagccaggtg ttcctgaaga tgaacagcct gcagaccgac    660

gacaccgcca tctactactg cgccaagcac tactactacg gcggcagcta cgccatggac    720

tactggggcc agggcacaag cgtgaccgtg tctagcgggt ccctagacaa tgagaagagc    780

aatggaacca ttatccatgt gaaagggaaa cacctttgtc caagtcccct atttcccgga    840

ccttctaagc ccttttgggt gctggtggtg gttggtggag tcctggcttg ctatagcttg    900

ctagtaacag tggcctttat tattttctgg gtgaggagta agaggagcag gctcctgcac    960

agtgactaca tgaacatgac tccccgccgc cccgggccca cccgcaagca ttaccagccc   1020

tatgccccac cacgcgactt cgcagcctat cgctccctga gagtgaagtt cagcaggagc   1080

gcagacgccc ccgcgtacca gcagggccag aaccagctct ataacgagct caatctagga   1140

cgaagagagg agtacgatgt tttggacaag aggcgtggcc gggaccctga gatgggggga   1200

aagccgagaa ggaagaaccc tcaggaaggc ctgtacaatg aactgcagaa agataagatg   1260

gcggaggcct acagtgagat tgggatgaaa ggcgagcgcc ggaggggcaa ggggcacgat   1320

ggcctttacc agggtctcag tacagccacc aaggacacct acgacgccct tcacatgcag   1380
```

```
gccctgcccc ctcgccggaa gagaagaggc aagcccatcc ccaacccact gctgggcctg   1440

gatagcacct ccggaagcgg agagggcaga ggctctctgc tgacctgcgg cgacgtggaa   1500

gagaacccag ggcccatgct cctgctcgtg acttcacttc ttctctgtga actcccacac   1560

cccgcgtttt tgcttatccc tcatcatcac catcaccacg gcgagagcgg ctacgcccag   1620

aacggcgacc tggaggacgc cgagctggac gactacagct tcagctgcta cagccagctg   1680

gaggtgaacg gcagccagca cagcctgacc tgcgccttcg aggaccccga cgtgaacatc   1740

accaacctgg agttcgagat ctgcggcgcc ctggtggagg tgaagtgcct gaacttcagg   1800

aagctgcagg agatctactt catcgagacc aagaagttcc tgctgatcgg caagagcaac   1860

atctgcgtga aggtgggcga gaagagcctg acctgcaaga agatcgacct gaccaccatc   1920

gtgaagcccg aggccccctt cgacctgagc gtggtgtaca gggagggcgc caacgacttc   1980

gtggtgacct tcaacaccag ccacctgcag aagaagtacg tgaaggtgct gatgcacgac   2040

gtggcctaca ggcaggagaa ggacgagaac aagtggaccc acgtgaacct gagcagcacc   2100

aagctgaccc tgctgcagag gaagctgcag cccgccgcca tgtacgagat caaggtgagg   2160

agcatccccg accactactt caagggcttc tggagcgagt ggagccccag ctactacttc   2220

aggacccccg agatcaacaa cagcagcggc gagatggacc ccatcctgct gccaccctgt   2280

ttaaccatca gcatcctgag cttcttcagc gtggccctgc tggtgatcct ggcctgcgtg   2340

ctgtggaaga agaggatcaa gcccatcgtg tggcccagcc tgcccgacca caagaagacc   2400

ctggagcacc tgtgtaagaa gcccaggaag aacctgaacg tgagcttcaa ccccgagagc   2460

ttcctggact gccagatcca cagggtggac gacatccagg ccagggacga ggtggagggc   2520

ttcctgcagg acaccttccc ccagcagctg gaggagagcg agaagcagag gctgggcggc   2580

gacgtgcaga gccccaactg ccccagcgag gacgtggtga tcacccccga gagcttcggc   2640

agggacagca gcctgacctg cctggccggc aacgtgagcg cctgcgacgc ccccatcctg   2700

agcagcagca ggagcctgga ctgcagggag agcggcaaga acggccccca cgtgtaccag   2760

gacctgctgc tgagcctggg caccaccaac agcaccctgc cacccccctt cagcctgcag   2820

agcggcatcc tgaccctgaa ccccgtggcc cagggccagc ccatcctgac cagcctgggc   2880

agcaaccagg aggaggccta cgtgaccatg agcagcttct accagaacca g            2931
```

<210> SEQ ID NO 107
<211> LENGTH: 977
<212> TYPE: PRT
<213> ORGANISM: Artificial Sequence
<220> FEATURE:
<223> OTHER INFORMATION: Description of Artificial Sequence: Synthetic CD19 CAR + IL7RaPPCL sequence

<400> SEQUENCE: 107

```
Glu Gln Lys Leu Ile Ser Glu Glu Asp Leu Asp Ile Gln Met Thr Gln
1               5                   10                  15

Thr Thr Ser Ser Leu Ser Ala Ser Leu Gly Asp Arg Val Thr Ile Ser
            20                  25                  30

Cys Arg Ala Ser Gln Asp Ile Ser Lys Tyr Leu Asn Trp Tyr Gln Gln
        35                  40                  45

Lys Pro Asp Gly Thr Val Lys Leu Leu Ile Tyr His Thr Ser Arg Leu
    50                  55                  60

His Ser Gly Val Pro Ser Arg Phe Ser Gly Ser Gly Ser Gly Thr Asp
65                  70                  75                  80
```

```
Tyr Ser Leu Thr Ile Ser Asn Leu Glu Gln Glu Asp Ile Ala Thr Tyr
                85                  90                  95

Phe Cys Gln Gln Gly Asn Thr Leu Pro Tyr Thr Phe Gly Gly Gly Thr
            100                 105                 110

Lys Leu Glu Ile Thr Gly Gly Gly Gly Ser Gly Gly Gly Gly Ser Gly
        115                 120                 125

Gly Gly Gly Ser Glu Val Lys Leu Gln Glu Ser Gly Pro Gly Leu Val
    130                 135                 140

Ala Pro Ser Gln Ser Leu Ser Val Thr Cys Thr Val Ser Gly Val Ser
145                 150                 155                 160

Leu Pro Asp Tyr Gly Val Ser Trp Ile Arg Gln Pro Pro Arg Lys Gly
                165                 170                 175

Leu Glu Trp Leu Gly Val Ile Trp Gly Ser Glu Thr Thr Tyr Tyr Asn
            180                 185                 190

Ser Ala Leu Lys Ser Arg Leu Thr Ile Ile Lys Asp Asn Ser Lys Ser
        195                 200                 205

Gln Val Phe Leu Lys Met Asn Ser Leu Gln Thr Asp Asp Thr Ala Ile
    210                 215                 220

Tyr Tyr Cys Ala Lys His Tyr Tyr Tyr Gly Gly Ser Tyr Ala Met Asp
225                 230                 235                 240

Tyr Trp Gly Gln Gly Thr Ser Val Thr Val Ser Ser Gly Ser Leu Asp
                245                 250                 255

Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Leu Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg Arg Lys Arg Arg Gly Lys Pro Ile Pro Asn Pro Leu Leu Gly Leu
465                 470                 475                 480

Asp Ser Thr Ser Gly Ser Gly Glu Gly Arg Gly Ser Leu Leu Thr Cys
                485                 490                 495

Gly Asp Val Glu Glu Asn Pro Gly Pro Met Leu Leu Leu Val Thr Ser
```

```
            500                 505                 510

Leu Leu Leu Cys Glu Leu Pro His Pro Ala Phe Leu Leu Ile Pro His
        515                 520                 525

His His His His His Gly Glu Ser Gly Tyr Ala Gln Asn Gly Asp Leu
    530                 535                 540

Glu Asp Ala Glu Leu Asp Asp Tyr Ser Phe Ser Cys Tyr Ser Gln Leu
545                 550                 555                 560

Glu Val Asn Gly Ser Gln His Ser Leu Thr Cys Ala Phe Glu Asp Pro
                565                 570                 575

Asp Val Asn Ile Thr Asn Leu Glu Phe Glu Ile Cys Gly Ala Leu Val
            580                 585                 590

Glu Val Lys Cys Leu Asn Phe Arg Lys Leu Gln Glu Ile Tyr Phe Ile
        595                 600                 605

Glu Thr Lys Lys Phe Leu Leu Ile Gly Lys Ser Asn Ile Cys Val Lys
    610                 615                 620

Val Gly Glu Lys Ser Leu Thr Cys Lys Lys Ile Asp Leu Thr Thr Ile
625                 630                 635                 640

Val Lys Pro Glu Ala Pro Phe Asp Leu Ser Val Val Tyr Arg Glu Gly
                645                 650                 655

Ala Asn Asp Phe Val Val Thr Phe Asn Thr Ser His Leu Gln Lys Lys
            660                 665                 670

Tyr Val Lys Val Leu Met His Asp Val Ala Tyr Arg Gln Glu Lys Asp
        675                 680                 685

Glu Asn Lys Trp Thr His Val Asn Leu Ser Ser Thr Lys Leu Thr Leu
    690                 695                 700

Leu Gln Arg Lys Leu Gln Pro Ala Ala Met Tyr Glu Ile Lys Val Arg
705                 710                 715                 720

Ser Ile Pro Asp His Tyr Phe Lys Gly Phe Trp Ser Glu Trp Ser Pro
                725                 730                 735

Ser Tyr Tyr Phe Arg Thr Pro Glu Ile Asn Asn Ser Ser Gly Glu Met
            740                 745                 750

Asp Pro Ile Leu Leu Pro Pro Cys Leu Thr Ile Ser Ile Leu Ser Phe
        755                 760                 765

Phe Ser Val Ala Leu Leu Val Ile Leu Ala Cys Val Leu Trp Lys Lys
    770                 775                 780

Arg Ile Lys Pro Ile Val Trp Pro Ser Leu Pro Asp His Lys Lys Thr
785                 790                 795                 800

Leu Glu His Leu Cys Lys Lys Pro Arg Lys Asn Leu Asn Val Ser Phe
                805                 810                 815

Asn Pro Glu Ser Phe Leu Asp Cys Gln Ile His Arg Val Asp Asp Ile
            820                 825                 830

Gln Ala Arg Asp Glu Val Glu Gly Phe Leu Gln Asp Thr Phe Pro Gln
        835                 840                 845

Gln Leu Glu Glu Ser Glu Lys Gln Arg Leu Gly Gly Asp Val Gln Ser
    850                 855                 860

Pro Asn Cys Pro Ser Glu Asp Val Val Ile Thr Pro Glu Ser Phe Gly
865                 870                 875                 880

Arg Asp Ser Ser Leu Thr Cys Leu Ala Gly Asn Val Ser Ala Cys Asp
                885                 890                 895

Ala Pro Ile Leu Ser Ser Ser Arg Ser Leu Asp Cys Arg Glu Ser Gly
            900                 905                 910

Lys Asn Gly Pro His Val Tyr Gln Asp Leu Leu Leu Ser Leu Gly Thr
        915                 920                 925
```

```
Thr Asn Ser Thr Leu Pro Pro Pro Phe Ser Leu Gln Ser Gly Ile Leu
    930                 935                 940

Thr Leu Asn Pro Val Ala Gln Gly Gln Pro Ile Leu Thr Ser Leu Gly
945                 950                 955                 960

Ser Asn Gln Glu Glu Ala Tyr Val Thr Met Ser Ser Phe Tyr Gln Asn
                965                 970                 975

Gln
```

```
<210> SEQ ID NO 108
<211> LENGTH: 1419
<212> TYPE: DNA
<213> ORGANISM: Artificial Sequence
<220> FEATURE:
<223> OTHER INFORMATION: Description of Artificial Sequence: Synthetic
      GPC3 CAR sequence

<400> SEQUENCE: 108

gatatcgtga tgacccagag ccccgactct ttagctgtgt ctttaggaga gagggccaca      60

atcaactgca agagcagcca gagcctcctc tacagcagca accagaagaa ctatttagct     120

tggtaccagc aaaagcccgg ccagcccccc aagctgctga tctactgggc cagcagcaga     180

gagagcggcg tgcccgatag attcagcgga agcggctccg gcacagattt caccctcacc     240

attagctctt tacaagctga ggacgtggcc gtgtactact gccagcagta ctacaactac     300

cctttaacct tcggccaagg taccaagctg gagatcaagg gctccacatc cggatccggc     360

aagcccggta gcggagaagg cagcacaaag ggagaggtgc agctggtgga gagcggaggc     420

ggactggtcc agcccggtgg atctttaagg ctgtcttgtg ccgccagcgg ctttaccttt     480

aacaagaacg ctatgaactg ggtgaggcaa gctcccggta agggtttaga gtgggtgggt     540

cgtattcgta ataagaccaa caactacgcc acctactatg ccgactccgt gaaggctcgt     600

ttcaccatct ctcgtgacga cagcaagaac agcctctatt tacagatgaa ctctttaaag     660

accgaggaca ccgccgtgta ctattgcgtg gctggcaact ccttcgccta ctggggccaa     720

ggcactttag tgaccgtgag ctccgggtcc accacgacgc cagcgccgcg accaccaaca     780

ccggcgccca ccatcgcgtc gcagcccctg tccctgcgcc cagaggcgtg ccggccagcg     840

gcggggggcg cagtgcacac gagggggctg gacttcgcct gtgatatcta catctgggcg     900

cccttggccg ggacttgtgg ggtccttctc ctgtcactgg ttatcaccct ttactgcaaa     960

cggggcagaa agaaactcct gtatatattc aaacaaccat ttatgagacc agtacaaact    1020

actcaagagg aagatggctg tagctgccga tttccagaag aagaagaagg aggatgtgaa    1080

ctgagagtga agttcagcag gagcgcagac gcccccgcgt accagcaggg ccagaaccag    1140

ctctataacg agctcaatct aggacgaaga gaggagtacg atgttttgga caagaggcgt    1200

ggccgggacc ctgagatggg gggaaagccg agaaggaaga accctcagga aggcctgtac    1260

aatgaactgc agaaagataa gatggcggag gcctacagtg agattgggat gaaaggcgag    1320

cgccggaggg gcaaggggca cgatggcctt taccagggtc tcagtacagc caccaaggac    1380

acctacgacg cccttcacat gcaggccctg ccccctcgc                           1419
```

```
<210> SEQ ID NO 109
<211> LENGTH: 473
<212> TYPE: PRT
<213> ORGANISM: Artificial Sequence
<220> FEATURE:
<223> OTHER INFORMATION: Description of Artificial Sequence: Synthetic
      GPC3 CAR sequence
```

<400> SEQUENCE: 109

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Tyr Ser
20 25 30

Ser Asn Gln Lys Asn Tyr Leu Ala Trp Tyr Gln Gln Lys Pro Gly Gln
35 40 45

Pro Pro Lys Leu Leu Ile Tyr Trp Ala Ser Ser Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Asn Tyr Pro Leu Thr Phe Gly Gln Gly Thr Lys Leu Glu Ile
100 105 110

Lys Gly Ser Thr Ser Gly Ser Gly Lys Pro Gly Ser Gly Glu Gly Ser
115 120 125

Thr Lys Gly Glu Val Gln Leu Val Glu Ser Gly Gly Gly Leu Val Gln
130 135 140

Pro Gly Gly Ser Leu Arg Leu Ser Cys Ala Ala Ser Gly Phe Thr Phe
145 150 155 160

Asn Lys Asn Ala Met Asn Trp Val Arg Gln Ala Pro Gly Lys Gly Leu
165 170 175

Glu Trp Val Gly Arg Ile Arg Asn Lys Thr Asn Asn Tyr Ala Thr Tyr
180 185 190

Tyr Ala Asp Ser Val Lys Ala Arg Phe Thr Ile Ser Arg Asp Asp Ser
195 200 205

Lys Asn Ser Leu Tyr Leu Gln Met Asn Ser Leu Lys Thr Glu Asp Thr
210 215 220

Ala Val Tyr Tyr Cys Val Ala Gly Asn Ser Phe Ala Tyr Trp Gly Gln
225 230 235 240

Gly Thr Leu Val Thr Val Ser Ser Gly Ser Thr Thr Thr Pro Ala Pro
245 250 255

Arg Pro Pro Thr Pro Ala Pro Thr Ile Ala Ser Gln Pro Leu Ser Leu
260 265 270

Arg Pro Glu Ala Cys Arg Pro Ala Ala Gly Gly Ala Val His Thr Arg
275 280 285

Gly Leu Asp Phe Ala Cys Asp Ile Tyr Ile Trp Ala Pro Leu Ala Gly
290 295 300

Thr Cys Gly Val Leu Leu Leu Ser Leu Val Ile Thr Leu Tyr Cys Lys
305 310 315 320

Arg Gly Arg Lys Lys Leu Leu Tyr Ile Phe Lys Gln Pro Phe Met Arg
325 330 335

Pro Val Gln Thr Thr Gln Glu Glu Asp Gly Cys Ser Cys Arg Phe Pro
340 345 350

Glu Glu Glu Glu Gly Gly Cys Glu Leu Arg Val Lys Phe Ser Arg Ser
355 360 365

Ala Asp Ala Pro Ala Tyr Gln Gln Gly Gln Asn Gln Leu Tyr Asn Glu
370 375 380

Leu Asn Leu Gly Arg Arg Glu Glu Tyr Asp Val Leu Asp Lys Arg Arg
385 390 395 400

Gly Arg Asp Pro Glu Met Gly Gly Lys Pro Arg Arg Lys Asn Pro Gln

```
            405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470


<210> SEQ ID NO 110
<211> LENGTH: 2895
<212> TYPE: DNA
<213> ORGANISM: Artificial Sequence
<220> FEATURE:
<223> OTHER INFORMATION: Description of Artificial Sequence: Synthetic
      GPC3 CAR + IL7aCPT sequence

<400> SEQUENCE: 110

gatatcgtga tgacccagag ccccgactct ttagctgtgt ctttaggaga gagggccaca     60

atcaactgca agagcagcca gagcctcctc tacagcagca accagaagaa ctatttagct    120

tggtaccagc aaaagcccgg ccagcccccc aagctgctga tctactgggc cagcagcaga    180

gagagcggcg tgcccgatag attcagcgga agcggctccg gcacagattt caccctcacc    240

attagctctt tacaagctga ggacgtggcc gtgtactact gccagcagta ctacaactac    300

cctttaacct tcggccaagg taccaagctg gagatcaagg gctccacatc cggatccggc    360

aagcccggta gcggagaagg cagcacaaag ggagaggtgc agctggtgga gagcggaggc    420

ggactggtcc agcccggtgg atctttaagg ctgtcttgtg ccgccagcgg ctttaccttt    480

aacaagaacg ctatgaactg ggtgaggcaa gctcccggta agggtttaga gtgggtgggt    540

cgtattcgta ataagaccaa caactacgcc acctactatg ccgactccgt gaaggctcgt    600

ttcaccatct ctcgtgacga cagcaagaac agcctctatt tacagatgaa ctctttaaag    660

accgaggaca ccgccgtgta ctattgcgtg gctggcaact ccttcgccta ctggggccaa    720

ggcactttag tgaccgtgag ctccgggtcc accacgacgc cagcgccgcg accaccaaca    780

ccggcgccca ccatcgcgtc gcagcccctg tccctgcgcc cagaggcgtg ccggccagcg    840

gcggggggcg cagtgcacac gagggggctg gacttcgcct gtgatatcta catctgggcg    900

cccttggccg ggacttgtgg ggtccttctc ctgtcactgg ttatcaccct ttactgcaaa    960

cggggcagaa agaaactcct gtatatattc aaacaaccat ttatgagacc agtacaaact   1020

actcaagagg aagatggctg tagctgccga tttccagaag aagaagaagg aggatgtgaa   1080

ctgagagtga agttcagcag gagcgcagac gcccccgcgt accagcaggg ccagaaccag   1140

ctctataacg agctcaatct aggacgaaga gaggagtacg atgttttgga caagaggcgt   1200

ggccgggacc ctgagatggg gggaaagccg agaaggaaga accctcagga aggcctgtac   1260

aatgaactgc agaaagataa gatggcggag gcctacagtg agattgggat gaaaggcgag   1320

cgccggaggg gcaaggggca cgatggcctt taccagggtc tcagtacagc caccaaggac   1380

acctacgacg cccttcacat gcaggccctg ccccctcgcg ggtccggaga gggcagaggc   1440

tctctgctga cctgcggcga cgtggaagag aacccagggc ccatgctcct gctcgtgact   1500

tcacttcttc tctgtgaact cccacacccc gcgtttttgc ttatccctca tcatcaccat   1560

caccacggcg agagcggcta cgcccagaac ggcgacctgg aggacgccga gctggacgac   1620
```

```
tacagcttca gctgctacag ccagctggag gtgaacggca gccagcacag cctgacctgc   1680

gccttcgagg accccgacgt gaacatcacc aacctggagt tcgagatctg cggcgccctg   1740

gtggaggtga agtgcctgaa cttcaggaag ctgcaggaga tctacttcat cgagaccaag   1800

aagttcctgc tgatcggcaa gagcaacatc tgcgtgaagg tgggcgagaa gagcctgacc   1860

tgcaagaaga tcgacctgac caccatcgtg aagcccgagg cccccttcga cctgagcgtg   1920

gtgtacaggg agggcgccaa cgacttcgtg gtgaccttca acaccagcca cctgcagaag   1980

aagtacgtga aggtgctgat gcacgacgtg gcctacaggc aggagaagga cgagaacaag   2040

tggacccacg tgaacctgag cagcaccaag ctgaccctgc tgcagaggaa gctgcagccc   2100

gccgccatgt acgagatcaa ggtgaggagc atccccgacc actacttcaa gggcttctgg   2160

agcgagtgga gccccagcta ctacttcagg acccccgaga tcaacaacag cagcggcgag   2220

atggacccca tcctgctgac ctgccccacc atcagcatcc tgagcttctt cagcgtggcc   2280

ctgctggtga tcctggcctg cgtgctgtgg aagaagagga tcaagcccat cgtgtggccc   2340

agcctgcccg accacaagaa gaccctggag cacctgtgta agaagcccag gaagaacctg   2400

aacgtgagct tcaaccccga gagcttcctg gactgccaga tccacagggt ggacgacatc   2460

caggccaggg acgaggtgga gggcttcctg caggacacct tcccccagca gctggaggag   2520

agcgagaagc agaggctggg cggcgacgtg cagagcccca actgccccag cgaggacgtg   2580

gtgatcaccc ccgagagctt cggcagggac agcagcctga cctgcctggc cggcaacgtg   2640

agcgcctgcg acgcccccat cctgagcagc agcaggagcc tggactgcag ggagagcggc   2700

aagaacggcc cccacgtgta ccaggacctg ctgctgagcc tgggcaccac caacagcacc   2760

ctgccacccc ccttcagcct gcagagcggc atcctgaccc tgaaccccgt ggcccagggc   2820

cagcccatcc tgaccagcct gggcagcaac caggaggagg cctacgtgac catgagcagc   2880

ttctaccaga accag                                                    2895
```

```
<210> SEQ ID NO 111
<211> LENGTH: 965
<212> TYPE: PRT
<213> ORGANISM: Artificial Sequence
<220> FEATURE:
<223> OTHER INFORMATION: Description of Artificial Sequence: Synthetic
      GPC3 CAR + IL7aCPT sequence

<400> SEQUENCE: 111

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Tyr Pro Leu Thr Phe Gly Gln Gly Thr Lys Leu Glu Ile
            100                 105                 110

Lys Gly Ser Thr Ser Gly Ser Gly Lys Pro Gly Ser Gly Glu Gly Ser
        115                 120                 125
```

```
Thr Lys Gly Glu Val Gln Leu Val Glu Ser Gly Gly Gly Leu Val Gln
    130                 135                 140

Pro Gly Gly Ser Leu Arg Leu Ser Cys Ala Ala Ser Gly Phe Thr Phe
145                 150                 155                 160

Asn Lys Asn Ala Met Asn Trp Val Arg Gln Ala Pro Gly Lys Gly Leu
                165                 170                 175

Glu Trp Val Gly Arg Ile Arg Asn Lys Thr Asn Asn Tyr Ala Thr Tyr
            180                 185                 190

Tyr Ala Asp Ser Val Lys Ala Arg Phe Thr Ile Ser Arg Asp Asp Ser
        195                 200                 205

Lys Asn Ser Leu Tyr Leu Gln Met Asn Ser Leu Lys Thr Glu Asp Thr
    210                 215                 220

Ala Val Tyr Tyr Cys Val Ala Gly Asn Ser Phe Ala Tyr Trp Gly Gln
225                 230                 235                 240

Gly Thr Leu Val Thr Val Ser Ser Gly Ser Thr Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
        275                 280                 285

Gly Leu Asp Phe Ala Cys Asp Ile Tyr Ile Trp Ala Pro Leu Ala Gly
    290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg Gly Ser Gly Glu Gly Arg Gly
465                 470                 475                 480

Ser Leu Leu Thr Cys Gly Asp Val Glu Glu Asn Pro Gly Pro Met Leu
                485                 490                 495

Leu Leu Val Thr Ser Leu Leu Leu Cys Glu Leu Pro His Pro Ala Phe
            500                 505                 510

Leu Leu Ile Pro His His His His His His Gly Glu Ser Gly Tyr Ala
        515                 520                 525

Gln Asn Gly Asp Leu Glu Asp Ala Glu Leu Asp Asp Tyr Ser Phe Ser
    530                 535                 540

Cys Tyr Ser Gln Leu Glu Val Asn Gly Ser Gln His Ser Leu Thr Cys
```

```
545                 550                 555                 560

Ala Phe Glu Asp Pro Asp Val Asn Ile Thr Asn Leu Glu Phe Glu Ile
                565                 570                 575

Cys Gly Ala Leu Val Glu Val Lys Cys Leu Asn Phe Arg Lys Leu Gln
            580                 585                 590

Glu Ile Tyr Phe Ile Glu Thr Lys Lys Phe Leu Leu Ile Gly Lys Ser
        595                 600                 605

Asn Ile Cys Val Lys Val Gly Glu Lys Ser Leu Thr Cys Lys Lys Ile
    610                 615                 620

Asp Leu Thr Thr Ile Val Lys Pro Glu Ala Pro Phe Asp Leu Ser Val
625                 630                 635                 640

Val Tyr Arg Glu Gly Ala Asn Asp Phe Val Val Thr Phe Asn Thr Ser
                645                 650                 655

His Leu Gln Lys Lys Tyr Val Lys Val Leu Met His Asp Val Ala Tyr
            660                 665                 670

Arg Gln Glu Lys Asp Glu Asn Lys Trp Thr His Val Asn Leu Ser Ser
        675                 680                 685

Thr Lys Leu Thr Leu Leu Gln Arg Lys Leu Gln Pro Ala Ala Met Tyr
    690                 695                 700

Glu Ile Lys Val Arg Ser Ile Pro Asp His Tyr Phe Lys Gly Phe Trp
705                 710                 715                 720

Ser Glu Trp Ser Pro Ser Tyr Tyr Phe Arg Thr Pro Glu Ile Asn Asn
                725                 730                 735

Ser Ser Gly Glu Met Asp Pro Ile Leu Leu Thr Cys Pro Thr Ile Ser
            740                 745                 750

Ile Leu Ser Phe Phe Ser Val Ala Leu Leu Val Ile Leu Ala Cys Val
        755                 760                 765

Leu Trp Lys Lys Arg Ile Lys Pro Ile Val Trp Pro Ser Leu Pro Asp
    770                 775                 780

His Lys Lys Thr Leu Glu His Leu Cys Lys Lys Pro Arg Lys Asn Leu
785                 790                 795                 800

Asn Val Ser Phe Asn Pro Glu Ser Phe Leu Asp Cys Gln Ile His Arg
                805                 810                 815

Val Asp Asp Ile Gln Ala Arg Asp Glu Val Glu Gly Phe Leu Gln Asp
            820                 825                 830

Thr Phe Pro Gln Gln Leu Glu Glu Ser Glu Lys Gln Arg Leu Gly Gly
        835                 840                 845

Asp Val Gln Ser Pro Asn Cys Pro Ser Glu Asp Val Val Ile Thr Pro
    850                 855                 860

Glu Ser Phe Gly Arg Asp Ser Ser Leu Thr Cys Leu Ala Gly Asn Val
865                 870                 875                 880

Ser Ala Cys Asp Ala Pro Ile Leu Ser Ser Ser Arg Ser Leu Asp Cys
                885                 890                 895

Arg Glu Ser Gly Lys Asn Gly Pro His Val Tyr Gln Asp Leu Leu Leu
            900                 905                 910

Ser Leu Gly Thr Thr Asn Ser Thr Leu Pro Pro Pro Phe Ser Leu Gln
        915                 920                 925

Ser Gly Ile Leu Thr Leu Asn Pro Val Ala Gln Gly Gln Pro Ile Leu
    930                 935                 940
```

-continued

```
Thr Ser Leu Gly Ser Asn Gln Glu Glu Ala Tyr Val Thr Met Ser Ser
945                 950                 955                 960

Phe Tyr Gln Asn Gln
                965
```